(12) United States Patent
Hatakeyama et al.

(10) Patent No.: US 10,968,175 B2
(45) Date of Patent: *Apr. 6, 2021

(54) RESIST COMPOSITION AND PATTERNING PROCESS

(71) Applicant: Shin-Etsu Chemical Co., Ltd., Tokyo (JP)

(72) Inventors: Jun Hatakeyama, Joetsu (JP); Daisuke Domon, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 156 days.

This patent is subject to a terminal disclaimer.

(21) Appl. No.: 16/142,760

(22) Filed: Sep. 26, 2018

(65) Prior Publication Data
US 2019/0113843 A1    Apr. 18, 2019

(30) Foreign Application Priority Data

Oct. 16, 2017 (JP) .............................. JP2017-200092

(51) Int. Cl.
*C07C 381/12* (2006.01)
*G03F 7/00* (2006.01)
*G03F 7/004* (2006.01)
*G03F 7/039* (2006.01)
*G03F 7/038* (2006.01)
*G03F 7/16* (2006.01)
*G03F 7/38* (2006.01)
*G03F 7/20* (2006.01)
*G03F 7/32* (2006.01)
*C08F 220/18* (2006.01)
*C08F 220/26* (2006.01)
*C08F 220/22* (2006.01)
*C08F 220/28* (2006.01)

(52) U.S. Cl.
CPC .......... *C07C 381/12* (2013.01); *C08F 220/18* (2013.01); *C08F 220/1804* (2020.02); *C08F 220/1806* (2020.02); *C08F 220/22* (2013.01); *C08F 220/26* (2013.01); *C08F 220/28* (2013.01); *G03F 7/0045* (2013.01); *G03F 7/0382* (2013.01); *G03F 7/0392* (2013.01); *G03F 7/0397* (2013.01); *G03F 7/162* (2013.01); *G03F 7/168* (2013.01); *G03F 7/2004* (2013.01); *G03F 7/2006* (2013.01); *G03F 7/2037* (2013.01); *G03F 7/322* (2013.01); *G03F 7/38* (2013.01)

(58) Field of Classification Search
CPC ...... G03F 7/0045; G03F 7/038; G03F 7/0392; G03F 7/0395; G03F 7/0397; G03F 7/0382; G03F 7/162; G03F 7/168; G03F 7/2004; G03F 7/2006; G03F 7/2037; G03F 7/322; G03F 7/38; G03F 7/028; C08F 220/18; C08F 220/1804; C08F 220/1806; C08F 220/22; C08F 220/26; C08F 220/28; C07C 381/12

See application file for complete search history.

(56) References Cited

U.S. PATENT DOCUMENTS

| | | | |
|---|---|---|---|
| 6,673,511 B1 | 1/2004 | Hatakeyama et al. | |
| 6,749,988 B2 | 6/2004 | Hatakeyama et al. | |
| 6,916,593 B2 | 7/2005 | Hatakeyama et al. | |
| 9,250,518 B2 | 2/2016 | Hatakeyama et al. | |
| 2012/0029197 A1* | 2/2012 | Mauro .................. | C07C 303/20 546/134 |
| 2015/0111157 A1* | 4/2015 | Kato ..................... | G03F 7/2041 430/285.1 |
| 2016/0116840 A1* | 4/2016 | Tsuchimura .......... | C07C 311/14 257/618 |
| 2018/0364574 A1* | 12/2018 | Hatakeyama .......... | C08F 212/14 |
| 2019/0033716 A1* | 1/2019 | Ohashi .................. | G03F 7/039 |

FOREIGN PATENT DOCUMENTS

| | | | |
|---|---|---|---|
| JP | 2001-194776 A | | 7/2001 |
| JP | 2002-226470 A | | 8/2002 |
| JP | 2002-363148 A | | 12/2002 |
| JP | 2011074064 A | * | 4/2011 |
| JP | 2015-90382 A | | 5/2015 |

OTHER PUBLICATIONS

Machine translation of JP2011074064A (no date).*
Wang et al., "Photobase generator and photo decomposable quencher for high-resolution photoresist applications," Advances in Resist Materials and Processing Technology XXVII, Proc. of SPIE vol. 7639, pp. 76390W-1 to 76390W-15 (2010).

* cited by examiner

*Primary Examiner* — Amanda C. Walke
(74) *Attorney, Agent, or Firm* — Westerman, Hattori, Daniels & Adrian, LLP

(57) ABSTRACT

A resist composition comprising a base polymer and a sulfonium or iodonium salt capable of generating a brominated benzene-containing sulfonic acid offers a high sensitivity, minimal LWR and improved CDU independent of whether it is of positive or negative tone.

18 Claims, No Drawings

RESIST COMPOSITION AND PATTERNING PROCESS

CROSS-REFERENCE TO RELATED APPLICATION

This non-provisional application claims priority under 35 U.S.C. § 119(a) on Patent Application No. 2017-200092 filed in Japan on Oct. 16, 2017, the entire contents of which are hereby incorporated by reference.

TECHNICAL FIELD

This invention relates to a resist composition and a pattern forming process.

BACKGROUND ART

To meet the demand for higher integration density and operating speed of LSIs, the effort to reduce the pattern rule is in rapid progress. The wide-spreading flash memory market and the demand for increased storage capacities drive forward the miniaturization technology. As the advanced miniaturization technology, manufacturing of microelectronic devices at the 65-nm node by the ArF lithography has been implemented in a mass scale. Manufacturing of 45-nm node devices by the next generation ArF immersion lithography is approaching to the verge of high-volume application. The candidates for the next generation 32-nm node include ultra-high NA lens immersion lithography using a liquid having a higher refractive index than water in combination with a high refractive index lens and a high refractive index resist film, EUV lithography of wavelength 13.5 nm, and double patterning version of the ArF lithography, on which active research efforts have been made.

As the pattern feature size is reduced, approaching to the diffraction limit of light, light contrast lowers. In the case of positive resist film, a lowering of light contrast leads to reductions of resolution and focus margin of hole and trench patterns. For mitigating the influence of reduced resolution of resist pattern due to a lowering of light contrast, an attempt is made to enhance the dissolution contrast of resist film.

Chemically amplified resist compositions comprising an acid generator capable of generating an acid upon exposure to light or EB include chemically amplified positive resist compositions wherein deprotection reaction takes place under the action of acid and chemically amplified negative resist compositions wherein crosslinking reaction takes place under the action of acid. Quenchers are often added to these resist compositions for the purpose of controlling the diffusion of the acid to unexposed areas to improve the contrast. The addition of quenchers is fully effective to this purpose. A number of amine quenchers were proposed as disclosed in Patent Documents 1 to 3.

With respect to the acid labile group used in (meth) acrylate polymers for the ArF lithography, deprotection reaction takes place when a photoacid generator capable of generating a sulfonic acid having fluorine substituted at α-position (referred to "α-fluorinated sulfonic acid") is used, but not when an acid generator capable of generating a sulfonic acid not having fluorine substituted at α-position (referred to "α-non-fluorinated sulfonic acid") or carboxylic acid is used. If a sulfonium or iodonium salt capable of generating an α-fluorinated sulfonic acid is combined with a sulfonium or iodonium salt capable of generating an α-non-fluorinated sulfonic acid, the sulfonium or iodonium salt capable of generating an α-non-fluorinated sulfonic acid undergoes ion exchange with the α-fluorinated sulfonic acid. Through the ion exchange, the α-fluorinated sulfonic acid thus generated by light exposure is converted back to the sulfonium or iodonium salt while the sulfonium or iodonium salt of an α-non-fluorinated sulfonic acid or carboxylic acid functions as a quencher.

Further, the sulfonium or iodonium salt capable of generating an α-non-fluorinated sulfonic acid also functions as a photodegradable quencher since it loses the quencher function by photodegradation. Non-Patent Document 1 points out that the addition of a photodegradable quencher expands the margin of a trench pattern although the structural formula is not illustrated. However, it has only a little influence on performance improvement. There is a desire to have a quencher for further improving contrast.

Patent Document 4 discloses a quencher of onium salt type which reduces its basicity through a mechanism that it generates an amino-containing carboxylic acid upon light exposure, which in turn forms a lactam in the presence of acid. Due to the mechanism that basicity is reduced under the action of acid, acid diffusion is controlled by high basicity in the unexposed region where the amount of acid generated is minimal, whereas acid diffusion is promoted due to reduced basicity of the quencher in the overexposed region where the amount of acid generated is large. This expands the difference in acid amount between the exposed and unexposed regions, from which an improvement in contrast is expected. Despite the advantage of improved contrast, the acid diffusion controlling effect is rather reduced.

As the pattern feature size is reduced, the edge roughness (LWR) of line patterns and the critical dimension uniformity (CDU) of hole patterns are regarded significant. It is pointed out that these factors are affected by the segregation or agglomeration of a base polymer and acid generator and the diffusion of generated acid. There is a tendency that as the resist film becomes thinner, LWR becomes greater. A film thickness reduction to comply with the progress of size reduction causes a degradation of LWR, which becomes a serious problem.

The EUV lithography resist must meet high sensitivity, high resolution and low LWR at the same time. As the acid diffusion distance is reduced, LWR is reduced, but sensitivity becomes lower. For example, as the PEB temperature is lowered, the outcome is a reduced LWR, but a lower sensitivity. As the amount of quencher added is increased, the outcome is a reduced LWR, but a lower sensitivity. It is necessary to overcome the tradeoff relation between sensitivity and LWR.

CITATION LIST

Patent Document 1: JP-A 2001-194776
Patent Document 2: JP-A 2002-226470
Patent Document 3: JP-A 2002-363148
Patent Document 4: JP-A 2015-090382 (U.S. Pat. No. 9,250,518)
Non-Patent Document 1: SPIE Vol. 7639 p76390 W (2010)

DISCLOSURE OF INVENTION

For the acid-catalyzed chemically amplified resist, it is desired to develop an acid generator or quencher capable of providing a high sensitivity and reducing LWR or improving CDU of hole patterns.

An object of the invention is to provide a resist composition which exhibits a high sensitivity and a reduced LWR or improved CDU, independent of whether it is of positive tone or negative tone; and a pattern forming process using the same.

The inventors have found that using a sulfonium or iodonium salt capable of generating a sulfonic acid bonded to brominated benzene ring as the acid generator or quencher, a resist material having a reduced LWR, improved CDU, high contrast, improved resolution, and wide process margin is obtainable.

In one aspect, the invention provides a resist composition comprising a base polymer and a sulfonium salt having the formula (A-1) and/or an iodonium salt having the formula (A-2).

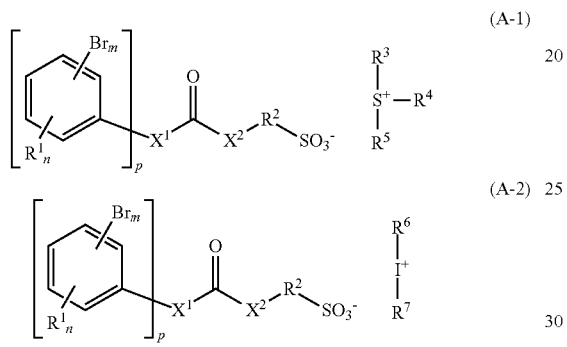

Herein $R^1$ is hydroxyl, carboxyl, $C_1$-$C_6$ alkyl, $C_1$-$C_6$ alkoxy, $C_2$-$C_6$ acyloxy, fluorine, chlorine, amino, —$NR^8$—C(=O)—$R^9$, or —$NR^8$—C(=O)—O—$R^9$, $R^8$ is hydrogen or a $C_1$-$C_6$ alkyl group, $R^9$ is a $C_1$-$C_6$ alkyl, $C_2$-$C_8$ alkenyl or $C_7$-$C_{20}$ aralkyl group. $R^2$ is a $C_2$-$C_{12}$ alkylene group in which at least one hydrogen may be substituted by a halogen other than fluorine, or a $C_6$-$C_{10}$ arylene group in which at least one hydrogen may be substituted by a $C_1$-$C_{10}$ alkyl, $C_1$-$C_{10}$ alkoxy, halogen or hydroxyl moiety. $R^3$, $R^4$ and $R^5$ are each independently fluorine, chlorine, bromine, iodine or a $C_1$-$C_{20}$ monovalent hydrocarbon group which may contain a heteroatom, any two of $R^3$, $R^4$ and $R^5$ may bond together to form a ring with the sulfur atom to which they are attached. $R^6$ and $R^7$ are each independently trifluoromethyl or a $C_1$-$C_{20}$ monovalent hydrocarbon group which may contain a heteroatom. $X^1$ is a single bond or a (p+1)-valent $C_1$-$C_{20}$ linking group which may contain an ether bond, carbonyl, ester bond, amide bond, sultone, lactam, carbonate, halogen, hydroxyl or carboxyl moiety. $X^2$ is an ether bond or —$NR^{10}$—, $R^{10}$ is hydrogen or $C_1$-$C_4$ alkyl; m is an integer of 1 to 5, preferably 2 or 3, n is an integer of 0 to 3, m+n is 1 to 5, and p is an integer of 1 to 3.

In one embodiment, the sulfonium salt and/or iodonium salt functions as a quencher. Then the resist composition further comprises an acid generator capable of generating sulfonic acid, imide acid or methide acid.

In another embodiment, the sulfonium salt and/or iodonium salt functions as an acid generator. Then the resist composition further comprises a quencher.

Typically the resist composition further comprises an organic solvent.

In a preferred embodiment, the base polymer comprises recurring units having the formula (a1) or recurring units having the formula (a2).

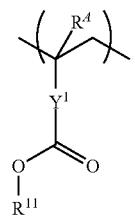

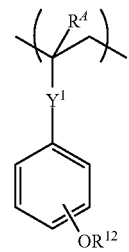

Herein $R^A$ is each independently hydrogen or methyl, $Y^1$ is a single bond, phenylene group, naphthylene group, or $C_1$-$C_{12}$ linking group containing an ester bond and/or lactone ring, $Y^2$ is a single bond or ester bond, $R^{11}$ and $R^{12}$ each are an acid labile group.

The resist composition may further comprise a dissolution inhibitor. The resist composition is typically a chemically amplified positive resist composition.

In another preferred embodiment, the base polymer is free of an acid labile group. The resist composition may further comprise a crosslinker. The composition is typically a chemically amplified negative resist composition.

Often the resist composition further comprises a surfactant.

In a preferred embodiment, the base polymer further comprises recurring units of at least one type selected from the formulae (f1) to (f3).

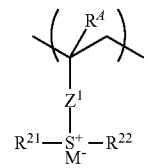

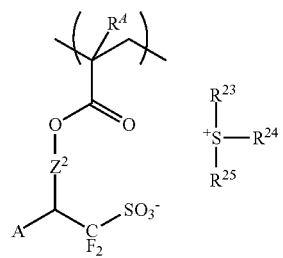

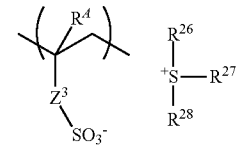

Herein $R^A$ is each independently hydrogen or methyl; $Z^1$ is a single bond, phenylene group, —O—$Z^{12}$, or —C(=O)—

$Z^{11}$-$Z^{12}$-, $Z^{11}$ is —O— or —NH—, $Z^{12}$ is a $C_1$-$C_6$ alkylene group, $C_2$-$C_6$ alkenylene group, or phenylene group, which may contain a carbonyl, ester bond, ether bond or hydroxyl moiety; $Z^2$ is a single bond, —$Z^{21}$—C(=O)—O—, —$Z^{21}$—O— or —$Z^{21}$—O—C(=O)—, $Z^{21}$ is a $C_1$-$C_{12}$ alkylene group which may contain a carbonyl, ester bond or ether bond; $Z^3$ is a single bond, methylene, ethylene, phenylene, fluorinated phenylene, —O—$Z^{32}$—, or —C(=O)—$Z^{31}$-$Z^{32}$—, $Z^{31}$ is —O— or —NH—, $Z^{32}$ is a $C_1$-$C_6$ alkylene group, phenylene group, fluorinated phenylene group, trifluoromethyl-substituted phenylene group, or $C_2$-$C_6$ alkenylene group, which may contain a carbonyl, ester bond, ether bond or hydroxyl moiety; $R^{21}$ to $R^{28}$ are each independently a $C_1$-$C_{20}$ monovalent hydrocarbon group which may contain a heteroatom, any two of $R^{23}$, $R^{24}$ and $R^{25}$ or any two of $R^{26}$, $R^{27}$ and $R^{28}$ may bond together to form a ring with the sulfur atom to which they are attached, A is hydrogen or trifluoromethyl; and $M^-$ is a non-nucleophilic counter ion.

In another aspect, the invention provides a process for forming a pattern comprising the steps of applying the resist composition defined above onto a substrate, baking to form a resist film, exposing the resist film to high-energy radiation, and developing the exposed film in a developer.

Typically, the high-energy radiation is ArF excimer laser radiation of wavelength 193 nm, KrF excimer laser radiation of wavelength 248 nm, EB, or EUV of wavelength 3 to 15 nm.

Advantageous Effects of Invention

A resist film containing a sulfonium or iodonium salt capable of generating a sulfonic acid bonded to brominated benzene ring has the advantage that the sulfonium or iodonium salt of sulfonic acid bonded to brominated benzene ring is highly effective for suppressing acid diffusion because of the high atomic weight of bromine. This contributes to low LWR and improved CDU. Upon exposure to EUV or EB, bromine is ionized to promote decomposition of an acid generator, achieving a higher sensitivity. A resist material having a high sensitivity, reduced LWR, and improved CDU is obtainable.

DESCRIPTION OF EMBODIMENTS

As used herein, the singular forms "a," "an" and "the" include plural referents unless the context clearly dictates otherwise. The notation ($C_n$-$C_m$) means a group containing from n to m carbon atoms per group. As used herein, the term "brominated" compound means a bromine-containing compound. In chemical formulae, Me stands for methyl, Ac for acetyl, and Ph for phenyl.

The abbreviations and acronyms have the following meaning.
EB: electron beam
EUV: extreme ultraviolet
Mw: weight average molecular weight
Mn: number average molecular weight
Mw/Mn: molecular weight distribution or dispersity
GPC: gel permeation chromatography
PEB: post-exposure bake
PAG: photoacid generator
LWR: line width roughness
CDU: critical dimension uniformity Resist Composition The resist composition of the invention is defined as comprising a base polymer and a sulfonium salt and/or iodonium salt of a sulfonic acid bonded to brominated benzene ring. It is noted that for simplicity's sake, the sulfonium or iodonium salt is referred to as "onium salt," and the sulfonic acid bonded to brominated benzene ring is referred to as "brominated benzene-containing sulfonic acid," hereinafter. The onium salt is an acid generator capable of generating a brominated benzene-containing sulfonic acid upon light exposure, but also functions as a quencher at the same time because it possesses a strongly basic sulfonium or iodonium. Where the acid labile group on the base polymer is a tertiary ester or tertiary ether, the brominated benzene-containing sulfonic acid does not possess a sufficient acidity to induce deprotection reaction of the acid labile group. In this case, it is recommended to separately add an acid generator capable of generating a strong acid such as α-fluorinated sulfonic acid, imide acid or methide acid, as will be described later, in order to induce deprotection reaction of the acid labile group. The acid generator capable of generating an α-fluorinated sulfonic acid, imide acid or methide acid may be either of addition type which is added to the base polymer or of bound type which is bound in the base polymer.

When a resist composition containing the onium salt capable of generating brominated benzene-containing sulfonic acid in admixture with an acid generator capable of generating a perfluoroalkylsulfonic acid or superstrong acid is exposed to radiation, brominated benzene-containing sulfonic acid and perfluoroalkylsulfonic acid generate.

Since the acid generator is not entirely decomposed, the undecomposed acid generator is present nearby. When the onium salt capable of generating brominated benzene-containing sulfonic acid co-exists with the perfluoroalkylsulfonic acid, the perfluoroalkylsulfonic acid first undergoes ion exchange with the onium salt capable of generating brominated benzene-containing sulfonic acid, whereby an onium salt of perfluoroalkylsulfonic acid is created and a brominated benzene-containing sulfonic acid is released. This is because the salt of perfluoroalkylsulfonic acid having a higher acid strength is more stable. In contrast, when an onium salt of perfluoroalkylsulfonic acid co-exists with a brominated benzene-containing sulfonic acid, no ion exchange takes place. Ion exchange takes place not only with the perfluoroalkylsulfonic acid, but also similarly with arylsulfonic acid, alkylsulfonic acid, imide acid and methide acid having a higher acid strength than the brominated benzene-containing sulfonic acid.

The brominated benzene-containing sulfonic acid has a higher molecular weight than a similar sulfonic acid bonded to unsubstituted benzene ring and thus a high ability to suppress acid diffusion. Upon exposure to high-energy radiation such as EUV or EB, bromine is ionized to generate secondary electrons. The energy of secondary electrons is transferred to the acid generator to promote its decomposition, contributing to a higher sensitivity. The effect becomes significant when the number of bromine substitution is 2 or more.

When the inventive onium salt functions as the quencher, another sulfonium or iodonium salt may be separately added to the resist composition as the quencher. Examples of the sulfonium or iodonium salt to be added as the quencher include sulfonium or iodonium salts of carboxylic acid, sulfonic acid, imide acid and saccharin. The carboxylic acid used herein may or may not be fluorinated at α-position.

Where the acid labile group on the base polymer is an acetal group, the brominated benzene-containing sulfonic acid incurs deprotection reaction of the acetal group. In this case, the onium salt capable of generating the brominated benzene-containing sulfonic acid functions as an acid generator rather than the quencher.

For the LWR improving purpose, it is effective to prevent a polymer and/or acid generator from agglomeration as indicated above. Effective means for preventing agglomeration of a polymer is by reducing the difference between hydrophobic and hydrophilic properties or by lowering the glass transition temperature (Tg) thereof. Specifically, it is effective to reduce the polarity difference between a hydrophobic acid labile group and a hydrophilic adhesive group or to lower the Tg by using a compact adhesive group like monocyclic lactone. One effective means for preventing agglomeration of an acid generator is by introducing a substituent into the triphenylsulfonium cation. In particular, with respect to a methacrylate polymer containing an alicyclic protective group and a lactone adhesive group for ArF lithography, a triphenylsulfonium composed solely of aromatic groups has a heterogeneous structure and low compatibility. As the substituent to be introduced into triphenylsulfonium, an alicyclic group or lactone similar to those used in the base polymer is regarded adequate. When lactone is introduced into a sulfonium salt which is hydrophilic, the resulting sulfonium salt becomes too hydrophilic and thus less compatible with a polymer, with a likelihood that the sulfonium salt will agglomerate. When a hydrophobic alkyl group is introduced, the sulfonium salt may be uniformly dispersed within the resist film. WO 2011/048919 discloses the technique for improving LWR by introducing an alkyl group into a sulfonium salt capable of generating an α-fluorinated sulfone imide acid.

For the LWR improving purpose, the dispersibility of the quencher is an important factor. Even when the dispersibility of the acid generator in a resist film is improved, the quencher can cause a lowering of LWR if it is unevenly distributed. In the case of a quencher of sulfonium salt type as well, an alkyl or similar substituent introduced into the triphenylsulfonium cation is effective for LWR improvement. Also a halogen atom introduced into the quencher of sulfonium salt type is effective for enhancing hydrophobic properties to improve dispersibility. The introduction of a bulky halogen atom like bromine is effective not only in the cation moiety, but also in the anion moiety of the sulfonium salt. The onium salt of brominated benzene-containing sulfonic acid wherein a bromine atom(s) is introduced into the anion moiety is effective for enhancing the dispersibility of the quencher in a resist film for reducing LWR.

The onium salt of brominated benzene-containing sulfonic acid exerts a LWR reducing effect, which may stand good either in positive and negative tone pattern formation by alkaline development or in negative tone pattern formation by organic solvent development.

Sulfonium and Iodonium Salts

The inventive resist composition contains a sulfonium salt having the formula (A-1) and/or an iodonium salt having the formula (A-2).

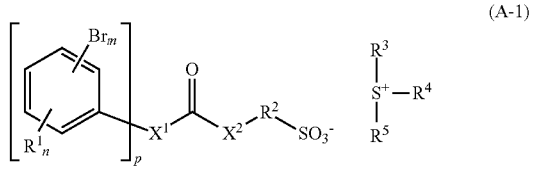
(A-1)

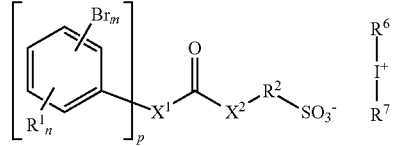
(A-2)

Herein $R^1$ is a hydroxyl group, carboxyl group, $C_1$-$C_6$ alkyl group, $C_1$-$C_6$ alkoxy group, $C_2$-$C_6$ acyloxy group, fluorine, chlorine, amino, —$NR^8$—C(=O)—$R^9$, or —$NR^8$—C(=O)—O—$R^9$, wherein $R^8$ is hydrogen or a $C_1$-$C_6$ alkyl group, and $R^9$ is a $C_1$-$C_6$ alkyl group, $C_2$-$C_8$ alkenyl group or $C_7$-$C_{20}$ aralkyl group. Examples of the alkyl group which may be straight, branched or cyclic include methyl, ethyl, n-propyl, isopropyl, cyclopropyl, n-butyl, isobutyl, sec-butyl, tert-butyl, cyclobutyl, n-pentyl, cyclopentyl, n-hexyl and cyclohexyl. Examples of the alkyl moiety in the alkoxy and acyloxy groups are as exemplified just above for the alkyl group. Examples of the alkenyl group which may be straight, branched or cyclic include vinyl, 1-propenyl and 2-propenyl. Examples of the aralkyl group include benzyl and phenethyl. Preferably, $R^1$ is fluorine, chlorine, hydroxyl, amino, $C_1$-$C_3$ alkyl, $C_1$-$C_3$ alkoxy, $C_2$-$C_4$ acyloxy or —$NR^8$—C(=O)—$R^9$.

$R^2$ is a $C_2$-$C_{12}$ alkylene group or $C_6$-$C_{10}$ arylene group. In the alkylene group, at least one (one or more or even all) hydrogen may be substituted by a halogen other than fluorine. In the arylene group, at least one (one or more or even all) hydrogen may be substituted by a $C_1$-$C_{10}$ alkyl, $C_1$-$C_{10}$ alkoxy, halogen or hydroxyl moiety. Examples of the alkyl and alkoxy groups are as exemplified above. Examples of the alkylene group which may be straight, branched or cyclic include ethylene, propane-1,2-diyl, propane-1,3-diyl, propane-2,3-diyl, butane-1,2-diyl, butane-1,3-diyl, butane-1,4-diyl, cyclohexane-1,4-diyl, adamantane-1,3-diyl, norbornane-2,3-diyl, and norbornane-2,5-diyl. Examples of the arylene group include 1,2-phenylene, 1,3-phenylene, 1,4-phenylene, 1,3-naphthylene, 1,4-naphthylene, 1,5-naphthylene, 1,6-naphthylene, 1,7-naphthylene, 1,8-naphthylene, 2,6-naphthylene, and 2,7-naphthylene. Preferably $R^2$ is a $C_2$-$C_{12}$ alkylene group.

$R^3$, $R^4$ and $R^5$ are each independently fluorine, chlorine, bromine, iodine or a $C_1$-$C_{20}$ monovalent hydrocarbon group which may contain a heteroatom. Any two of $R^3$, $R^4$ and $R^5$ may bond together to form a ring with the sulfur atom to which they are attached. The monovalent hydrocarbon group may be straight, branched or cyclic and examples thereof include $C_1$-$C_{20}$ alkyl groups, $C_2$-$C_{20}$ alkenyl groups, $C_6$-$C_{20}$ aryl groups, and $C_7$-$C_{20}$ aralkyl groups. Also included are substituted forms of the foregoing in which at least one (one or more or even all) hydrogen is substituted by hydroxyl, carboxyl, halogen, oxo, cyano, amide, nitro, sultone, sulfone moiety or sulfonium salt-containing moiety, or in which at least one carbon is substituted by an ether bond, ester bond, carbonyl moiety, carbonate moiety or sulfonic acid ester bond.

$R^6$ and $R^7$ are each independently trifluoromethyl or a $C_1$-$C_{20}$ monovalent hydrocarbon group which may contain a heteroatom. The monovalent hydrocarbon group may be straight, branched or cyclic. Preferred examples thereof include $C_6$-$C_{10}$ aryl groups, $C_2$-$C_6$ alkenyl groups, and $C_2$-$C_6$ alkynyl groups, in which at least one (one or more or even all) hydrogen may be substituted by halogen, trifluoromethyl, $C_1$-$C_{10}$ alkyl, $C_1$-$C_{10}$ alkoxy, hydroxyl, carboxyl, $C_2$-$C_{10}$ alkoxycarbonyl, nitro or cyano moiety.

$X^1$ is a single bond or a (p+1)-valent $C_1$-$C_{20}$ linking group which may contain an ether bond, carbonyl, ester bond, amide bond, sultone, lactam, carbonate, halogen, hydroxyl or carboxyl moiety.

$X^2$ is an ether bond or —$NR^{10}$—, wherein $R^{10}$ is hydrogen or $C_1$-$C_4$ alkyl.

The subscript m is an integer of 1 to 5, n is an integer of 0 to 3, m+n is 1 to 5, and p is an integer of 1 to 3.

Examples of the cation moiety in the sulfonium salt having formula (A-1) are given below, but not limited thereto.

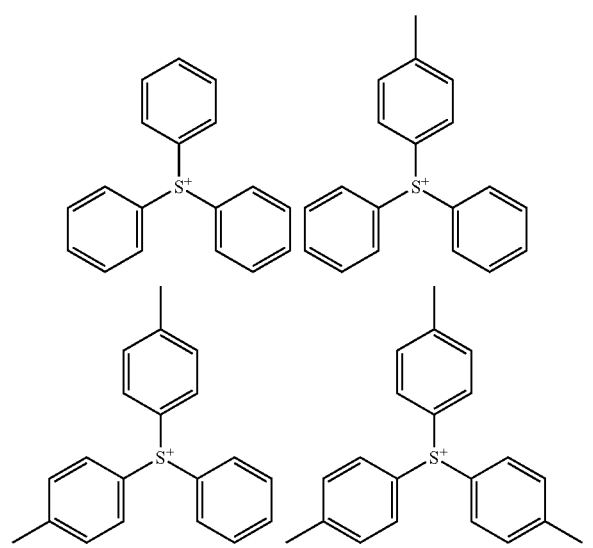
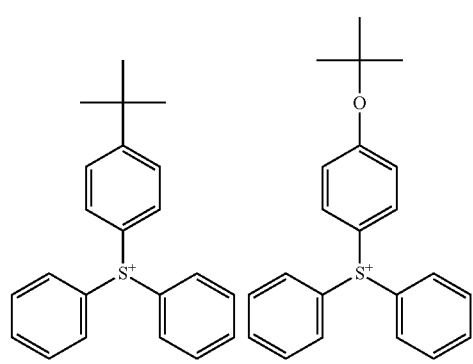
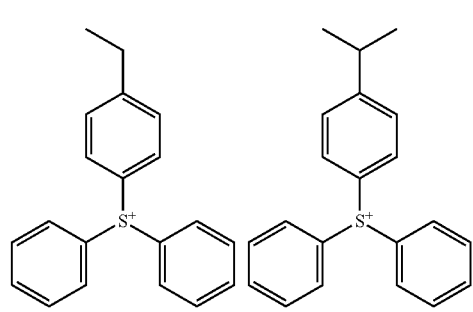
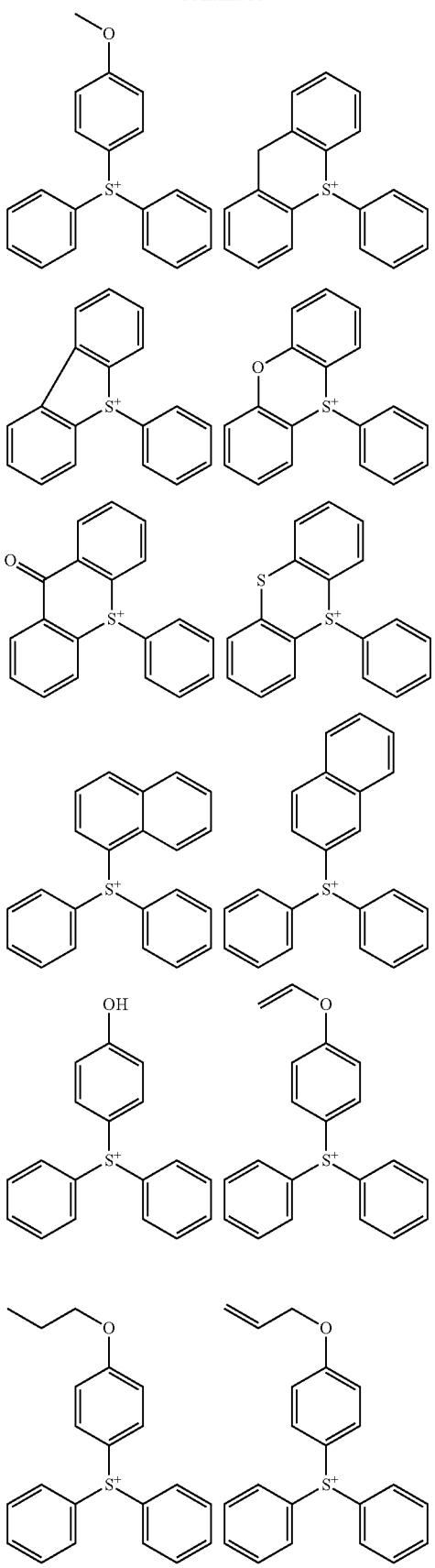

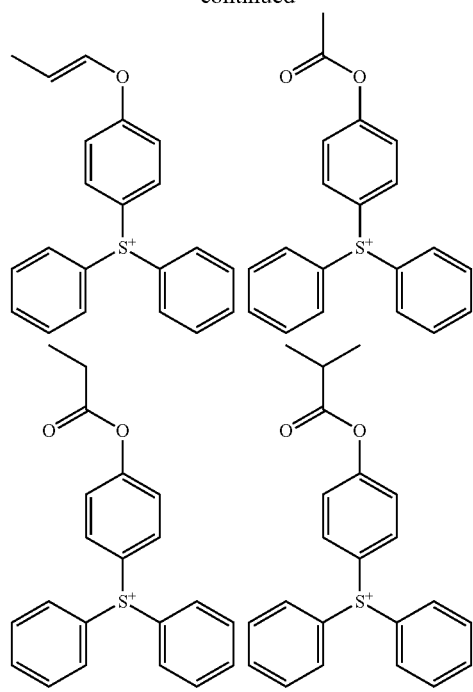
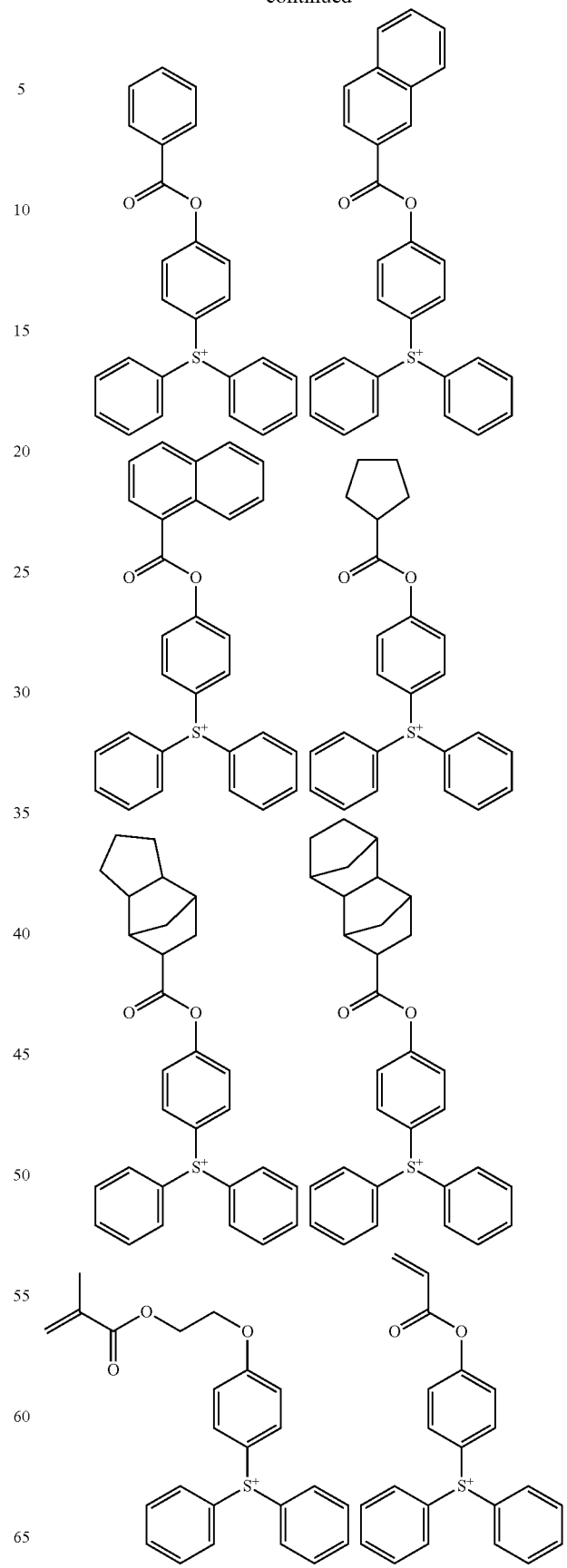

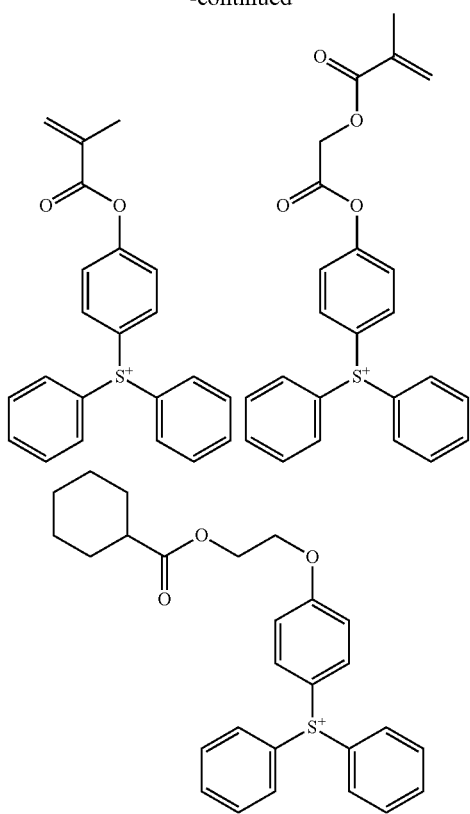
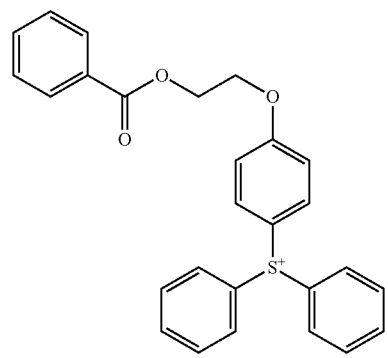
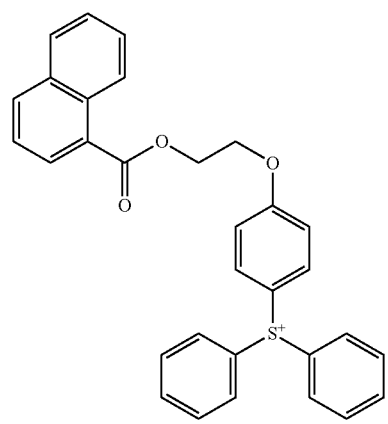
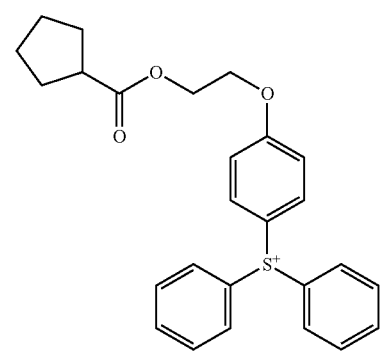
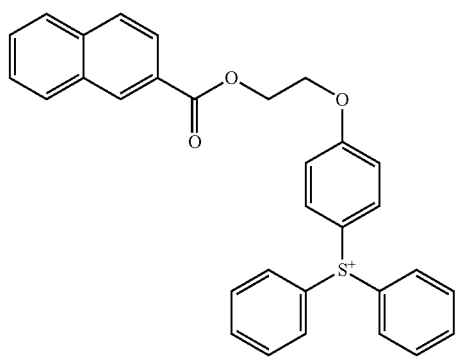
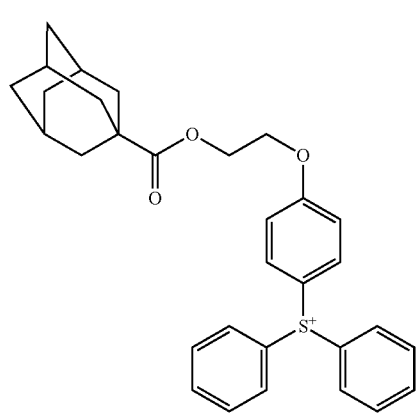
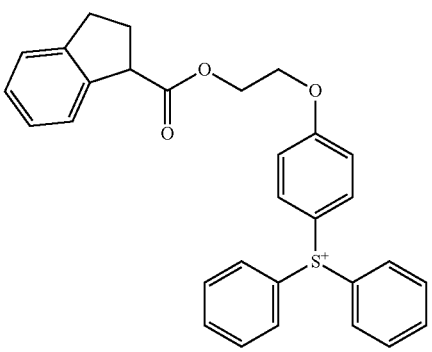

-continued
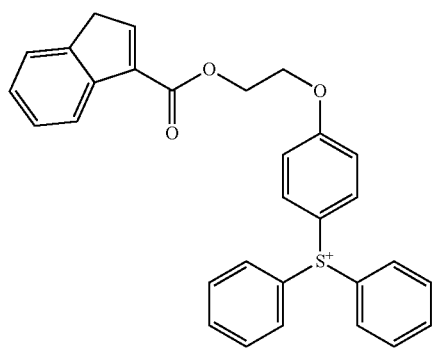
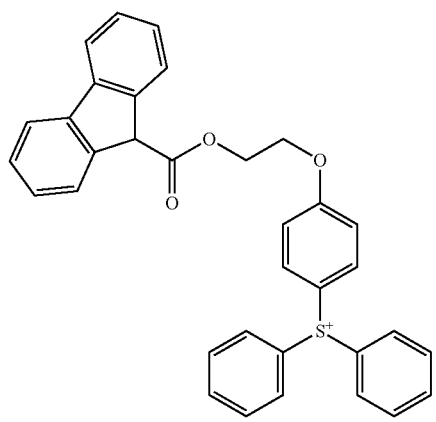
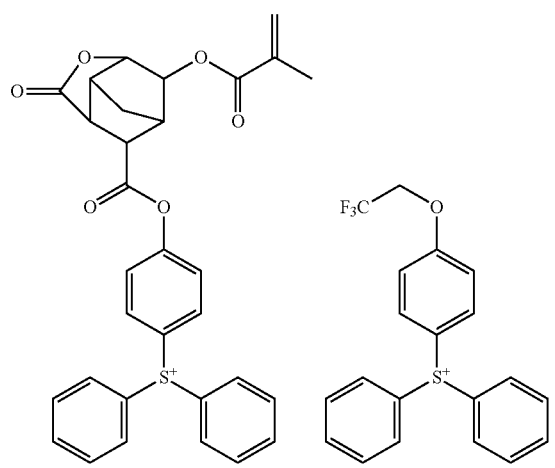
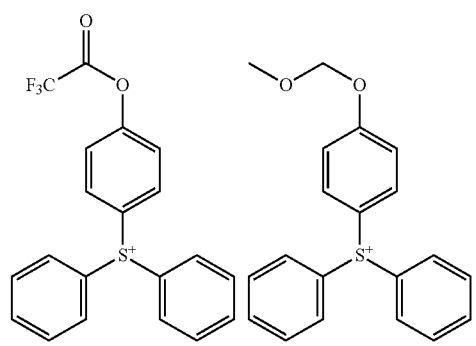
-continued
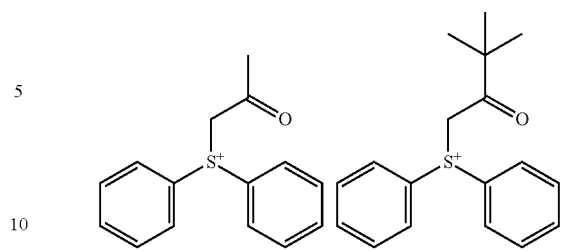
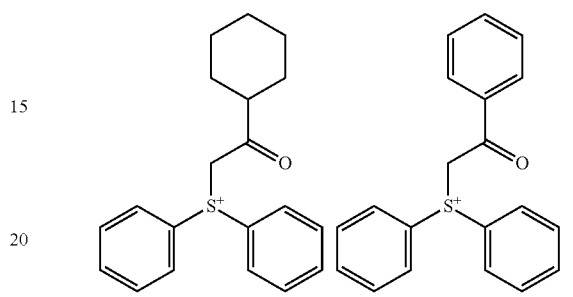
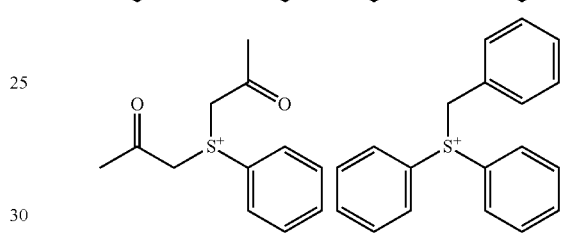
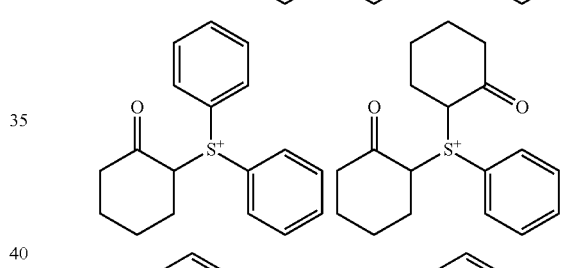
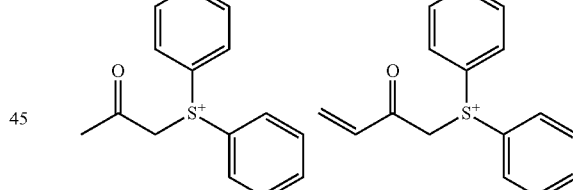
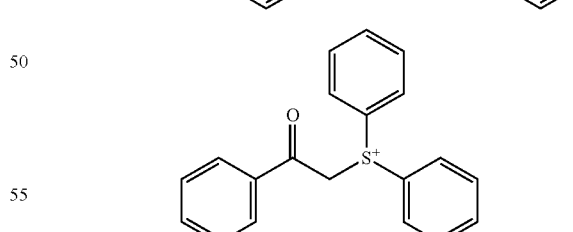
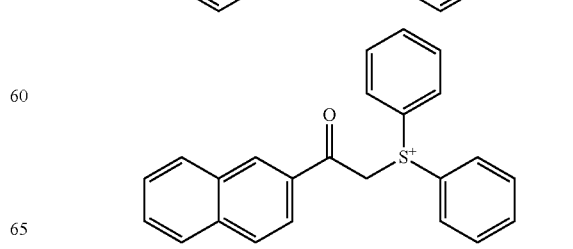

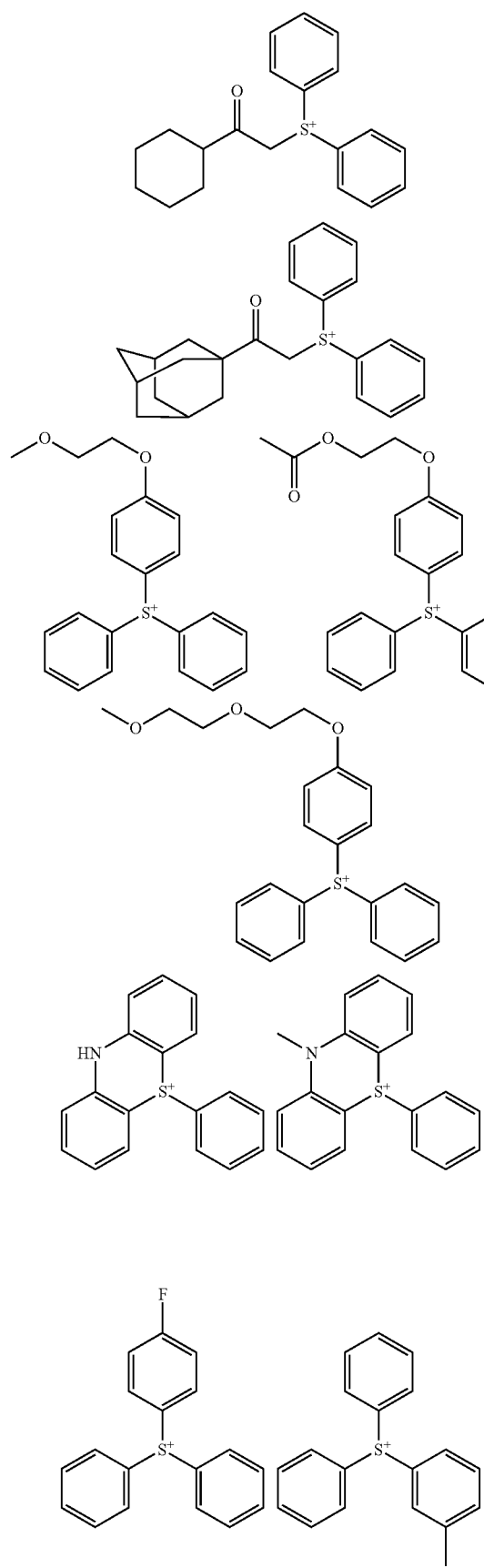
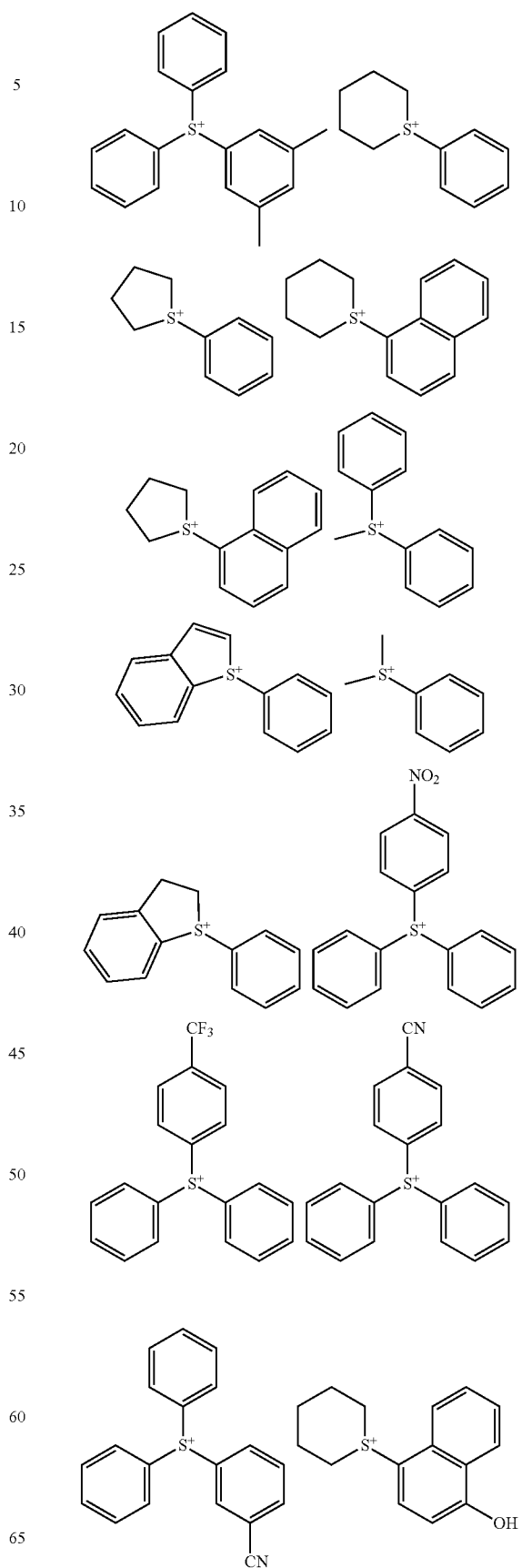

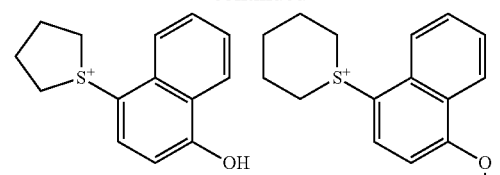
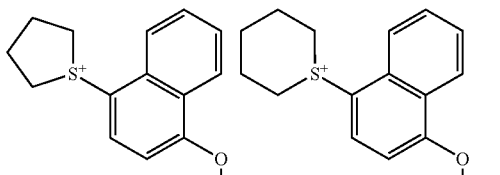
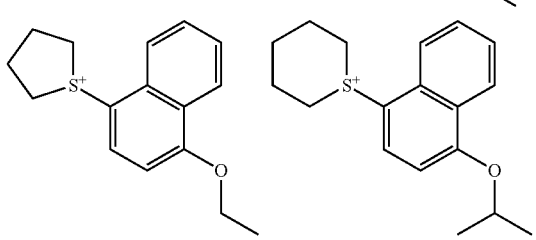
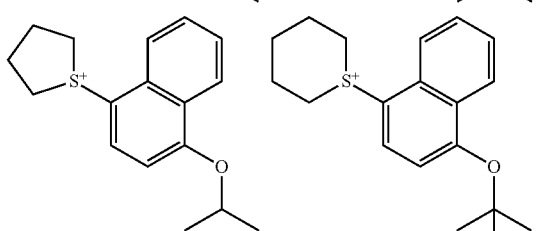
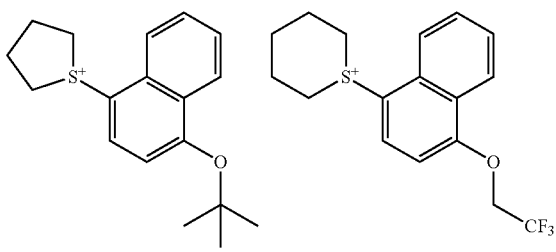
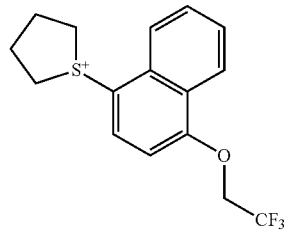
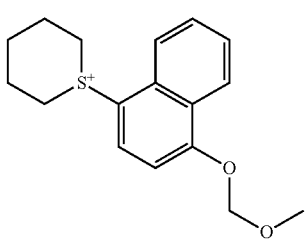
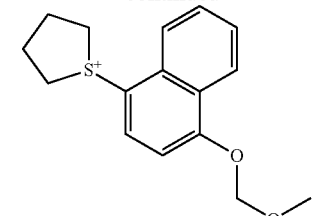
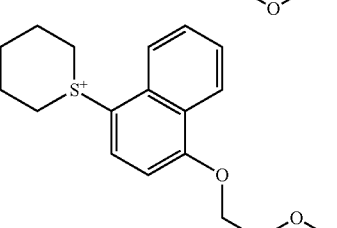
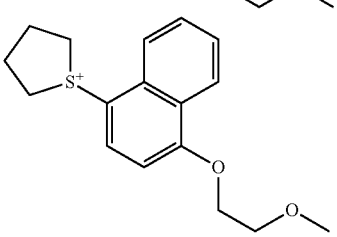
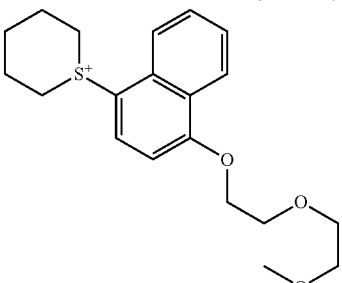
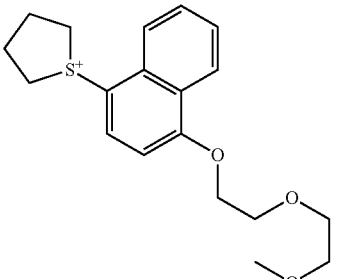
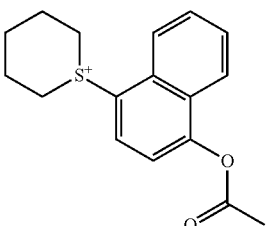
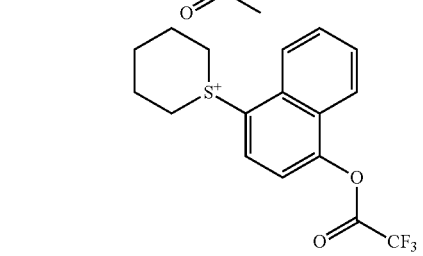

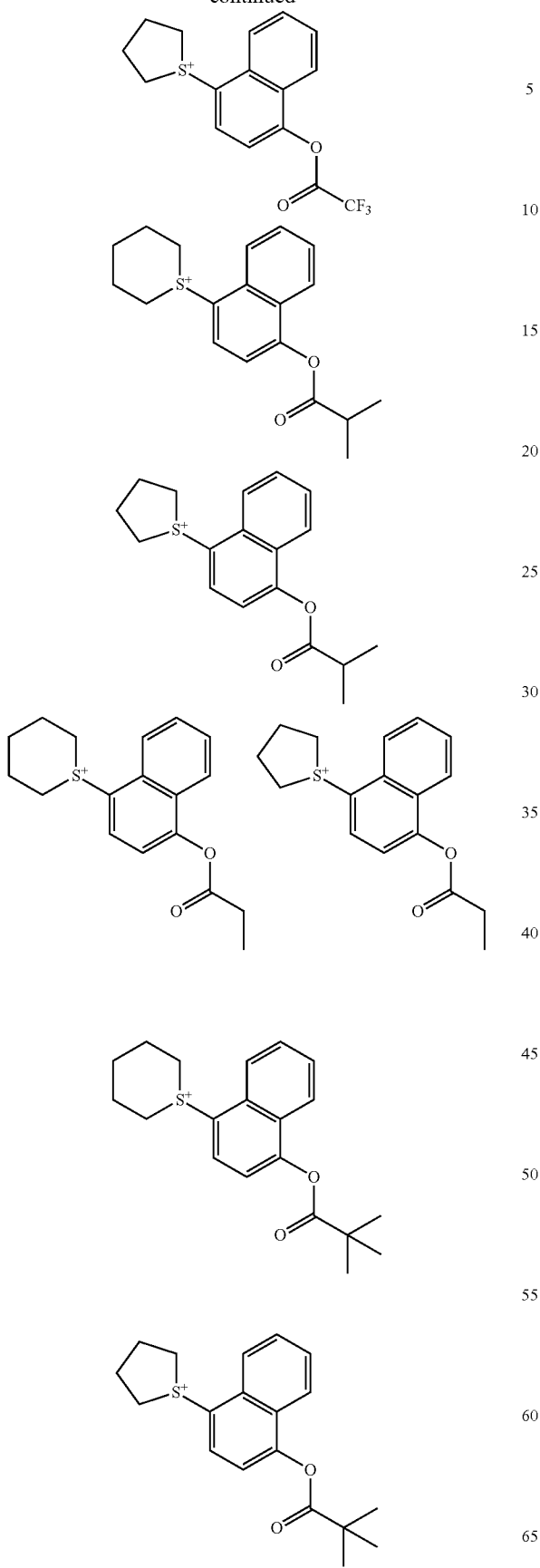
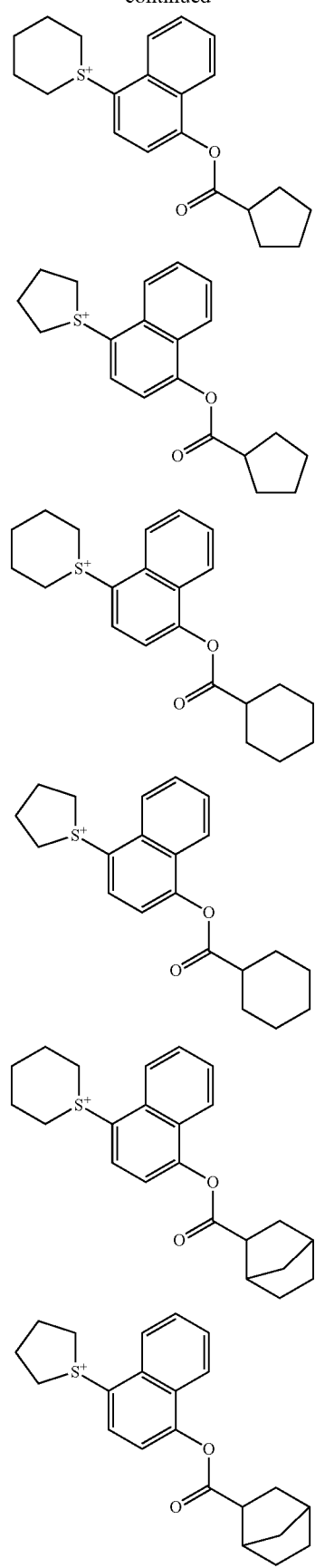

-continued
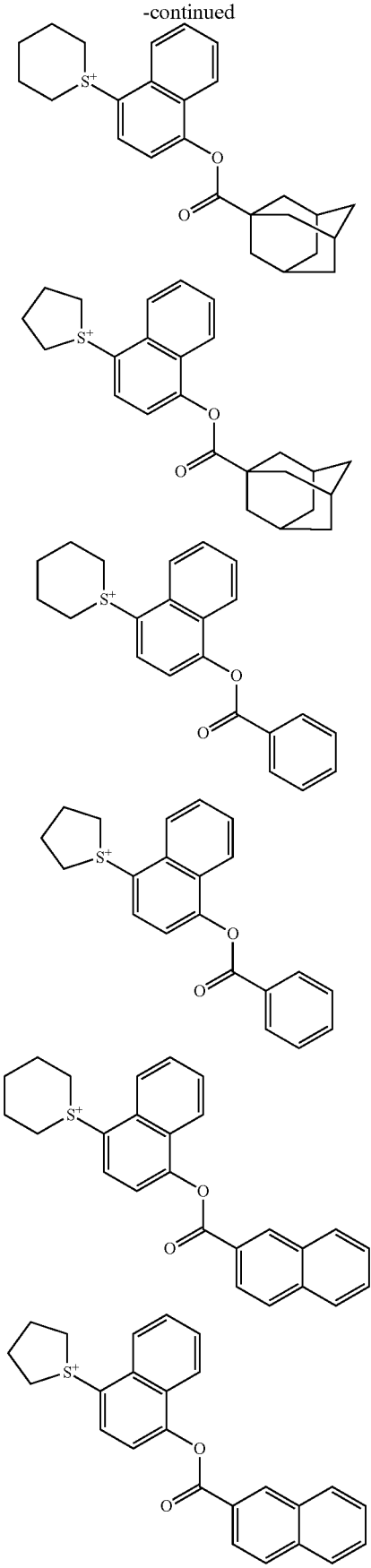
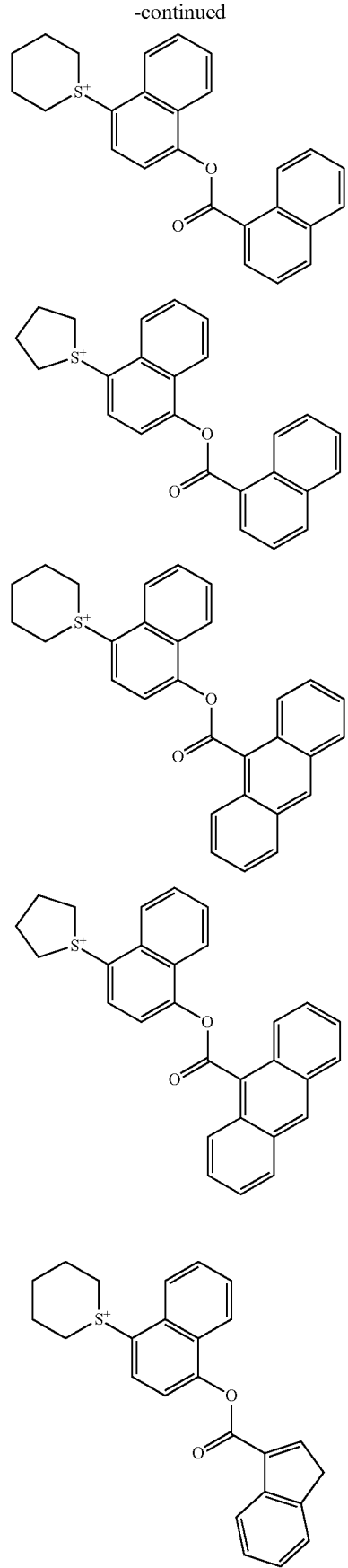

25
-continued
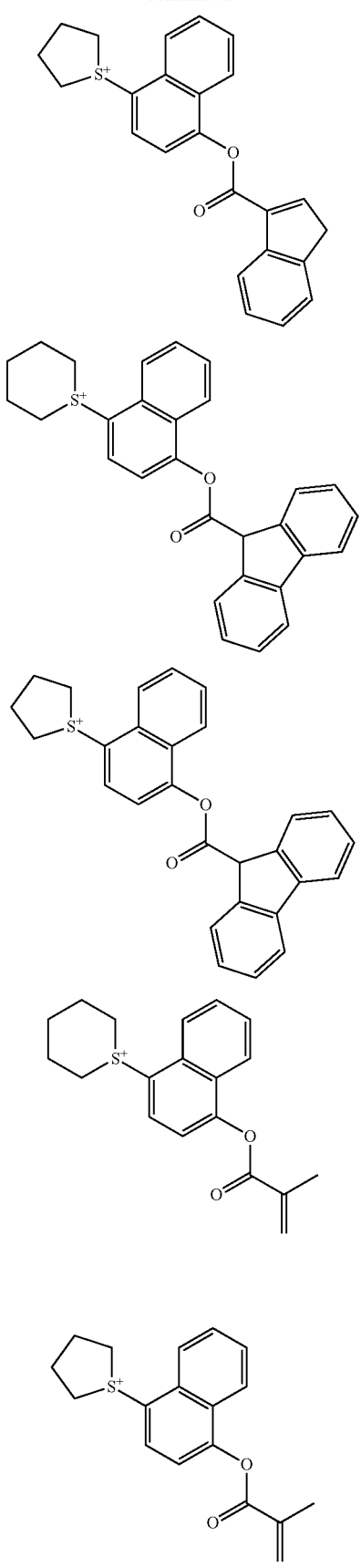
26
-continued
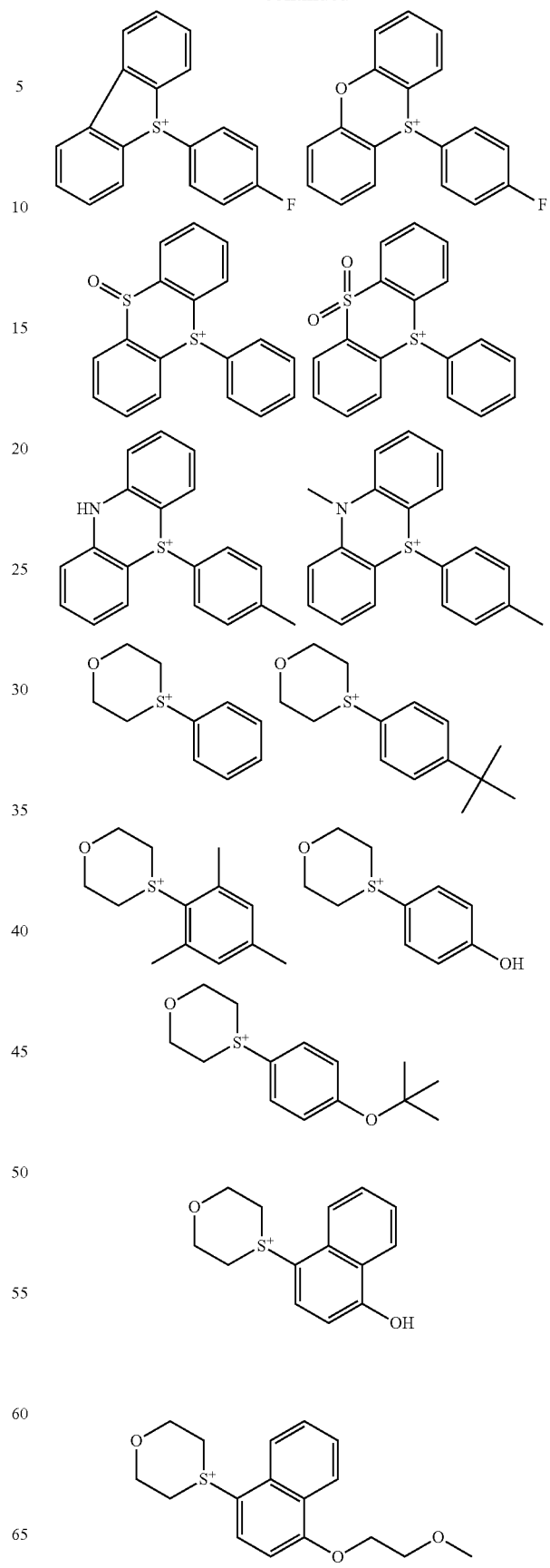

-continued
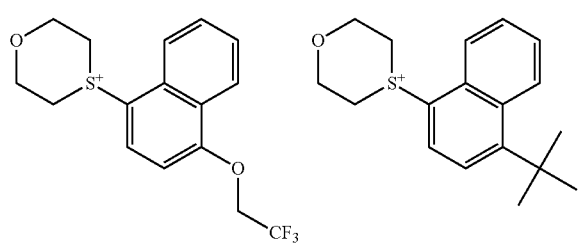
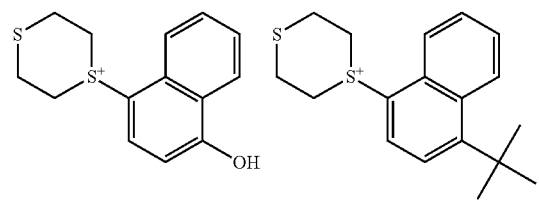
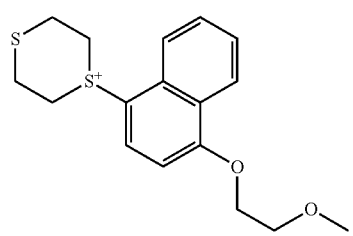
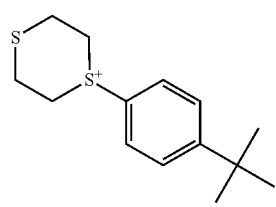
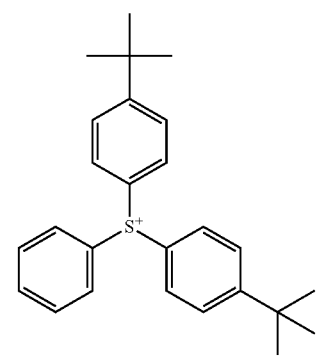
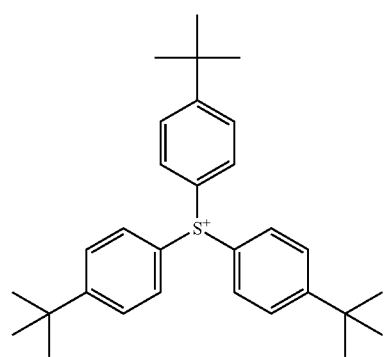
-continued
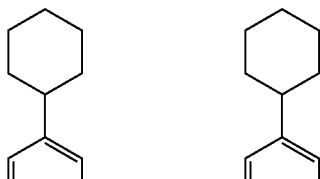
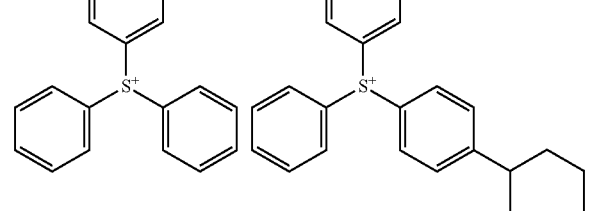
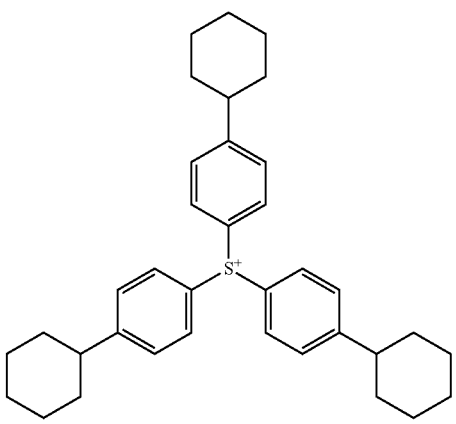
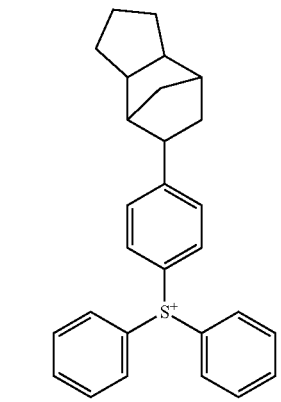

29
-continued
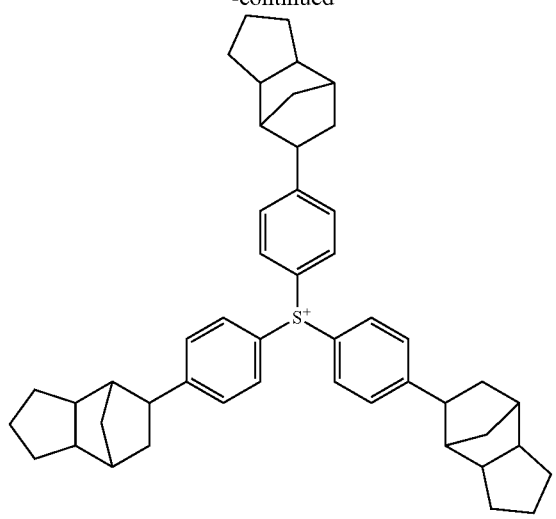
30
-continued
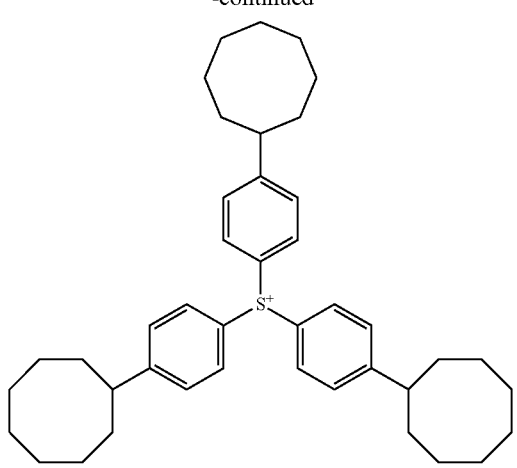
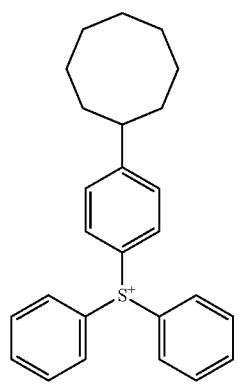
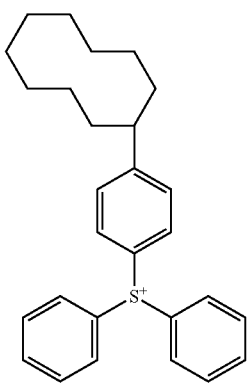
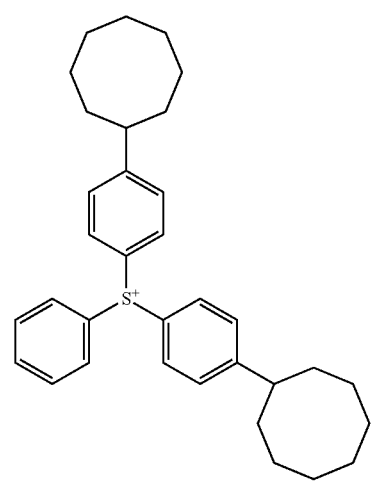
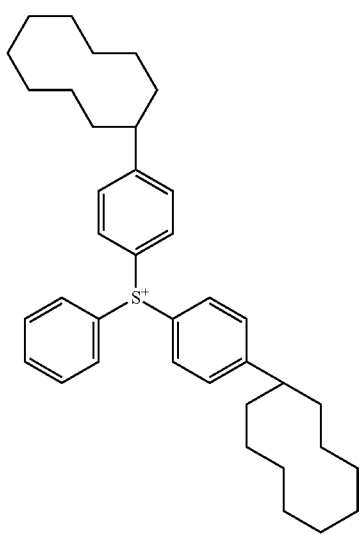

31
-continued
32
-continued
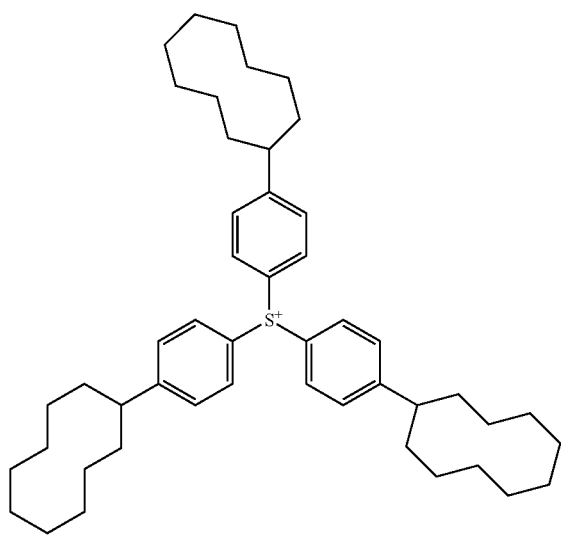
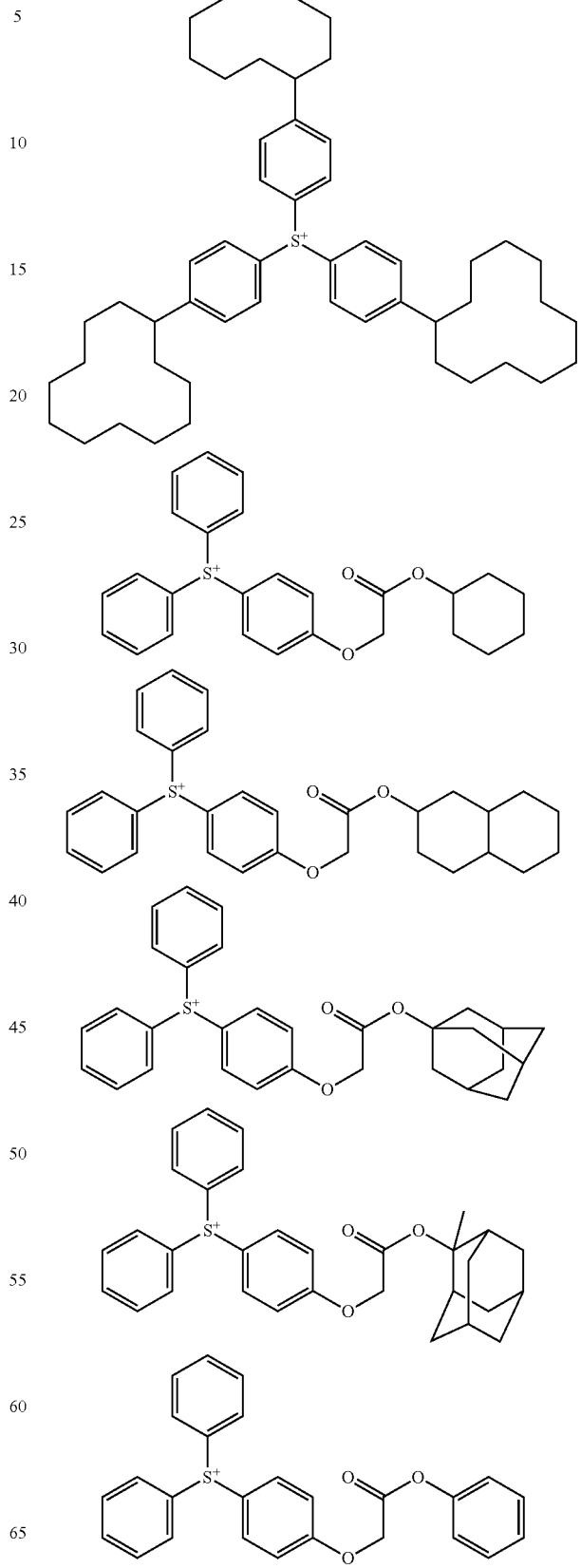

-continued
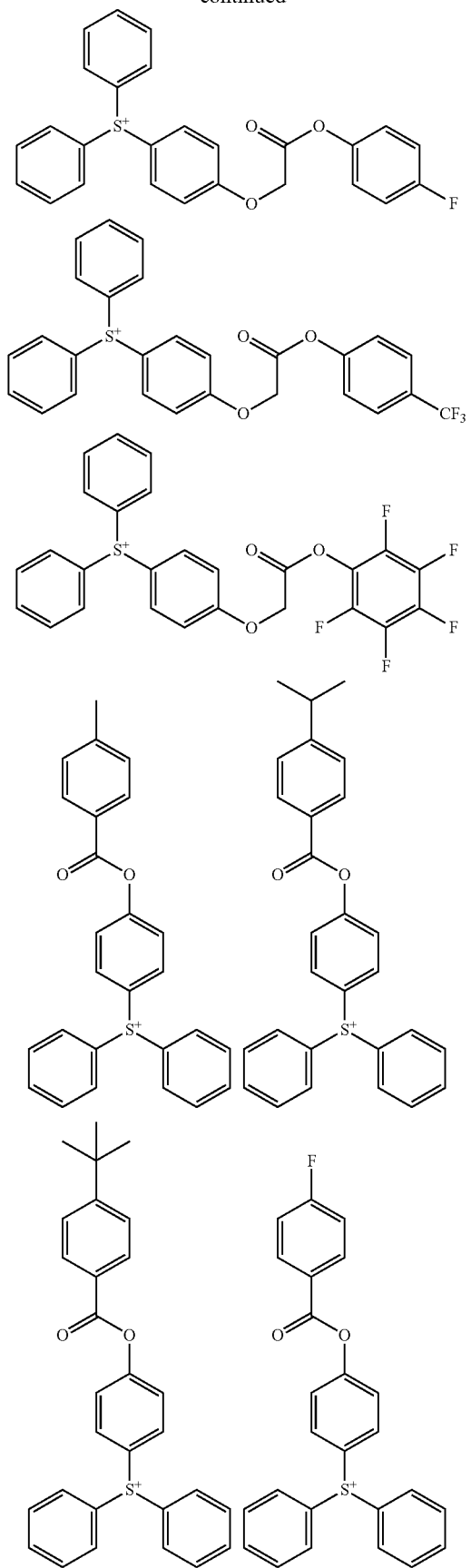
-continued
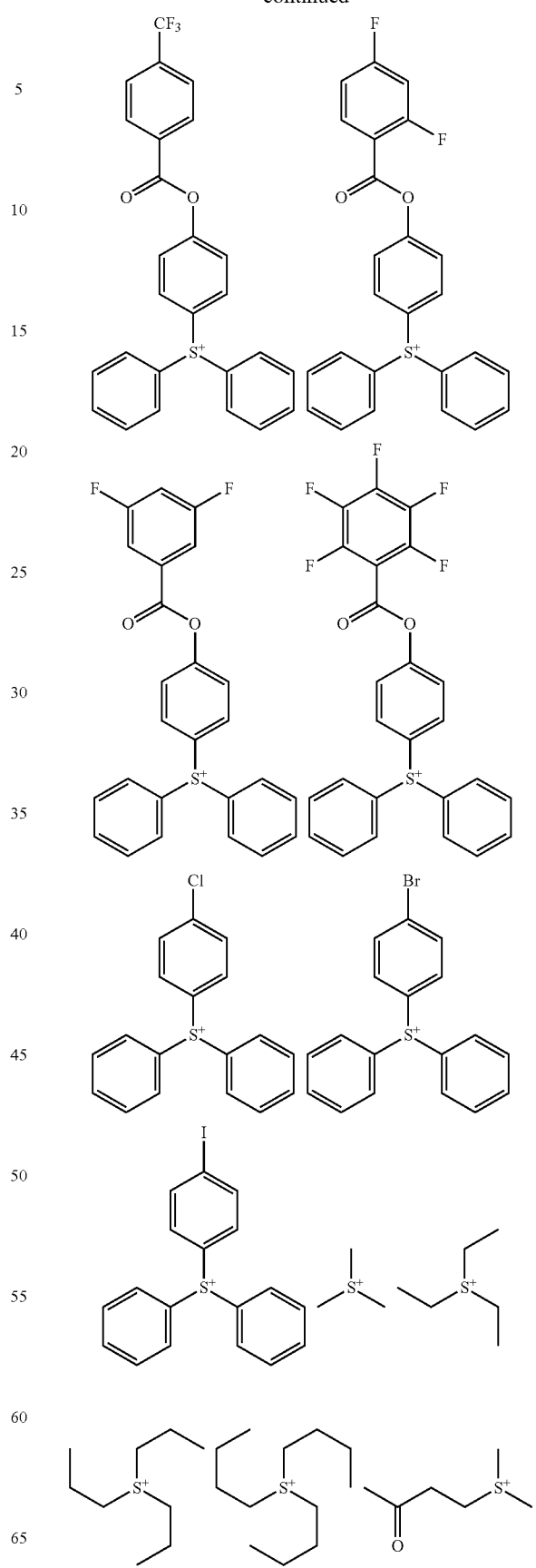

35
-continued
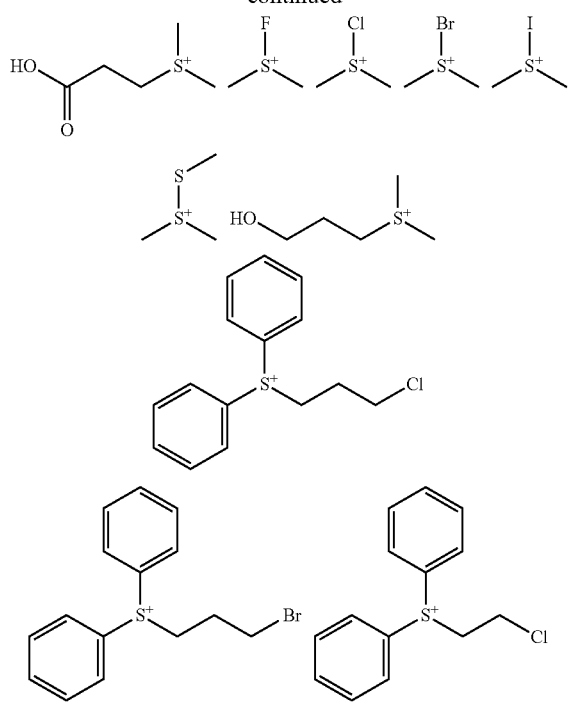
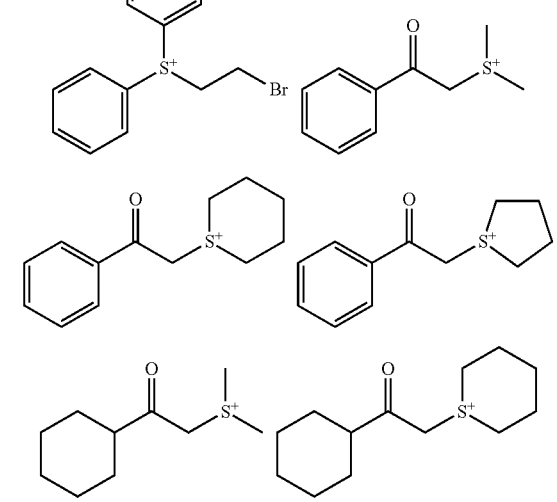
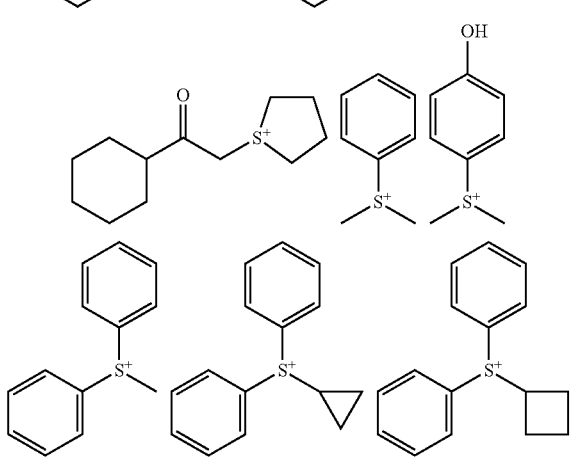
36
-continued
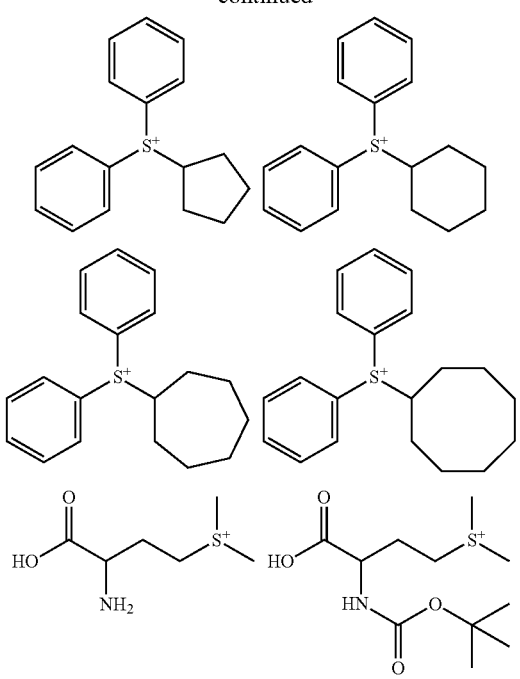
Examples of the cation moiety in the iodonium salt having formula (A-2) are given below, but not limited thereto.
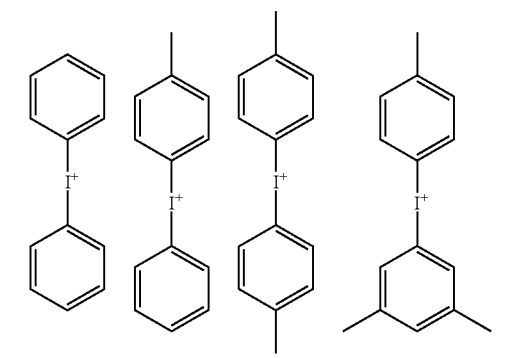
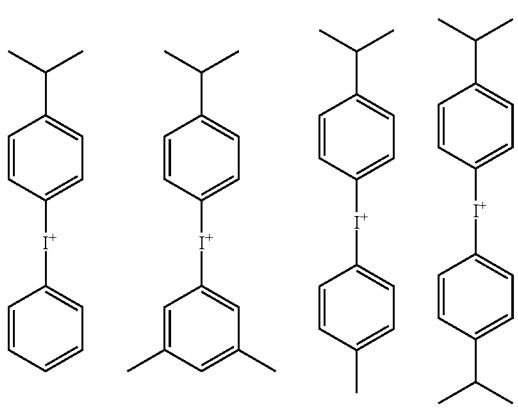

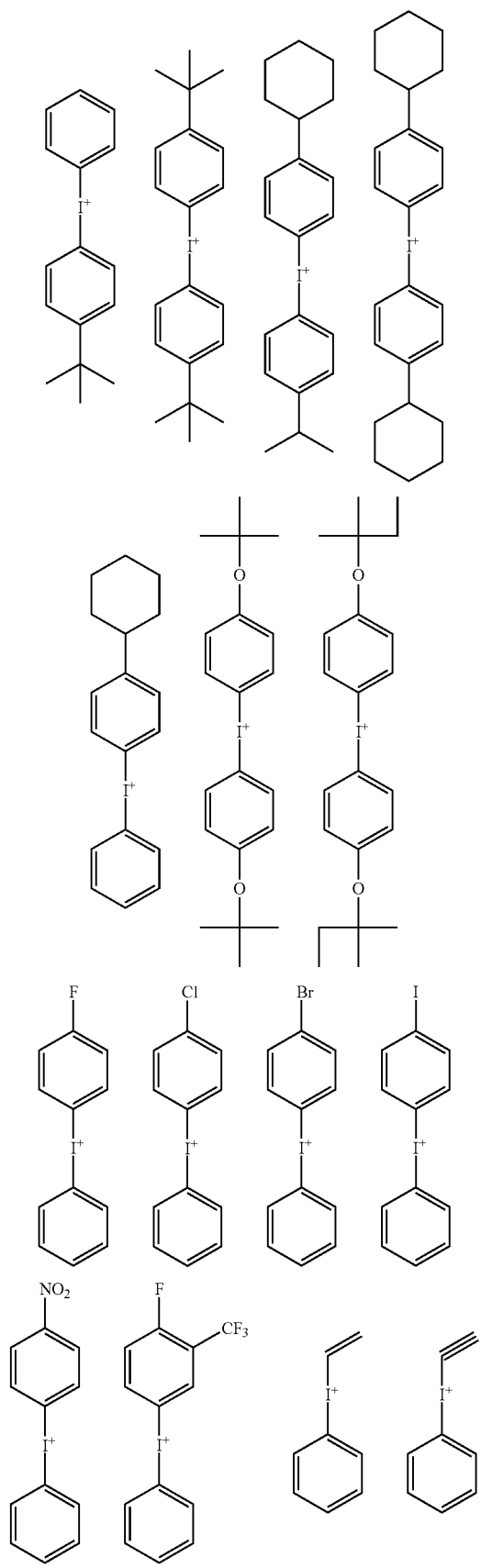
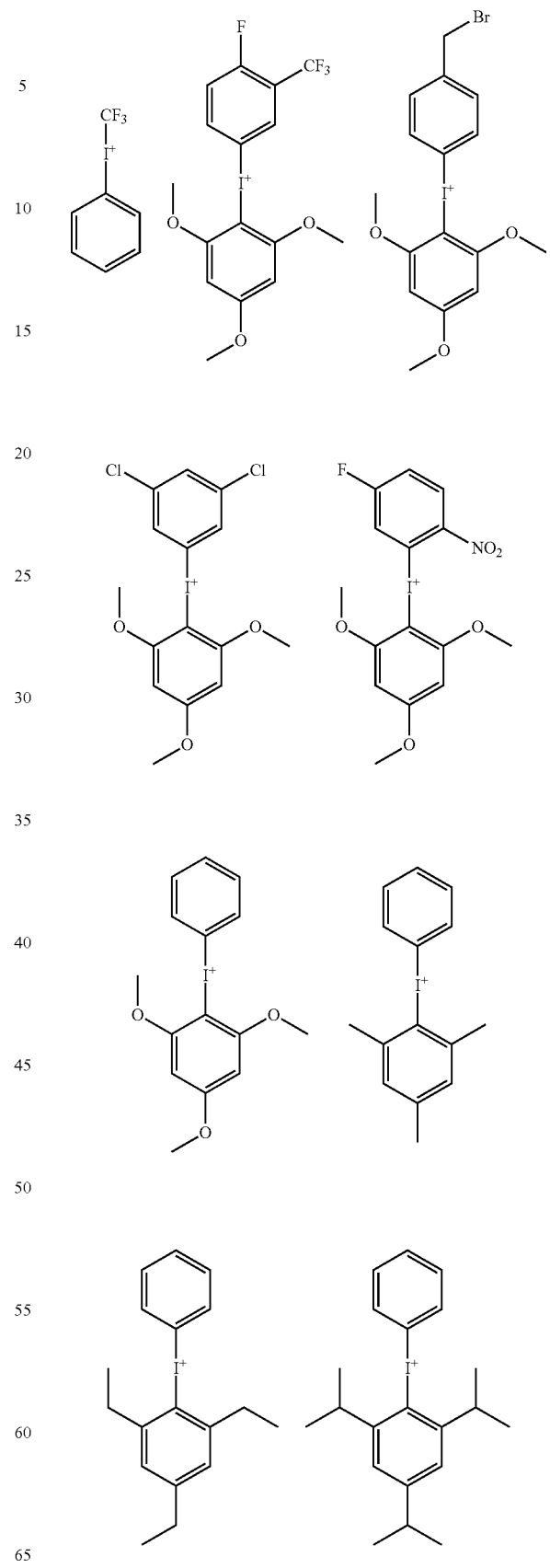

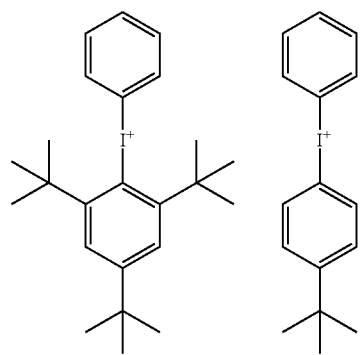
Examples of the anion moiety in the sulfonium salt having formula (A-1) and the iodonium salt having formula (A-2) are given below, but not limited thereto.
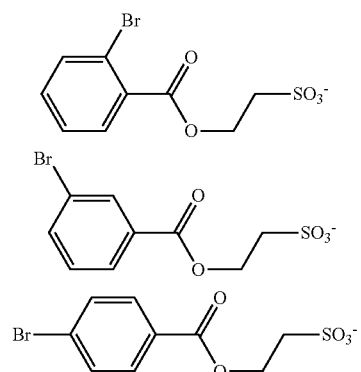
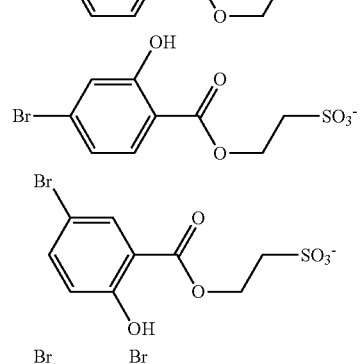
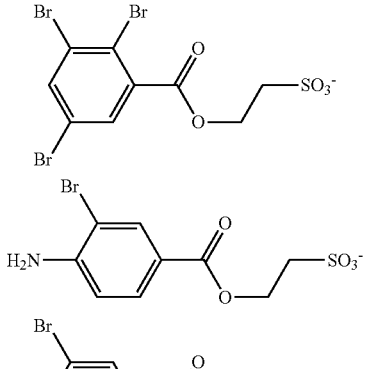
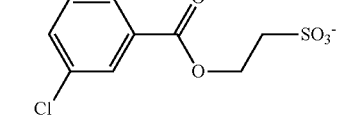
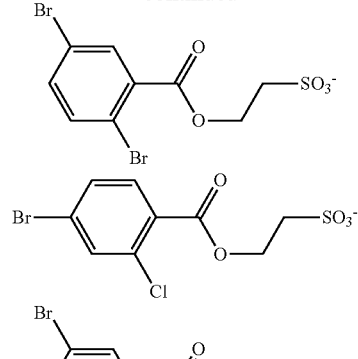
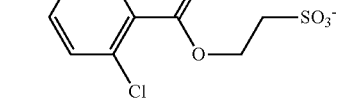
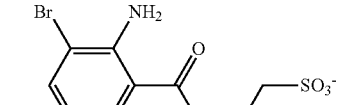
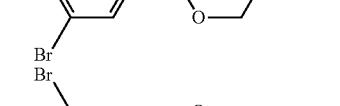
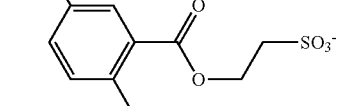
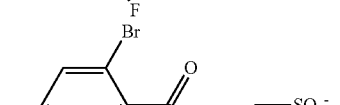
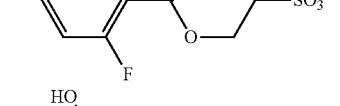
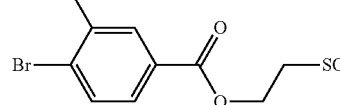
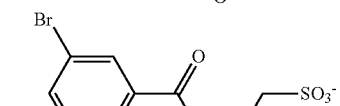
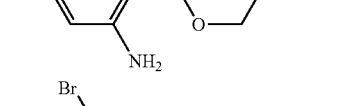
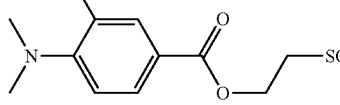
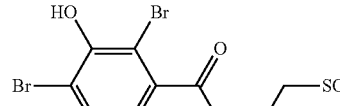
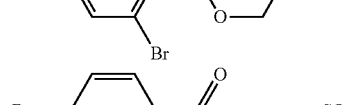
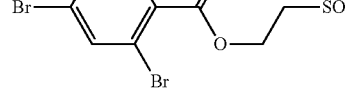

-continued
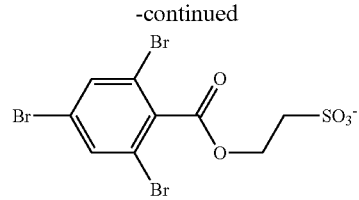
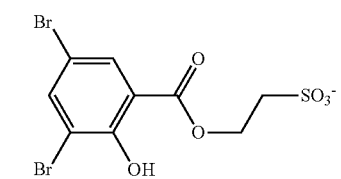
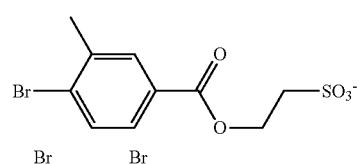
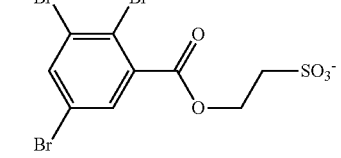
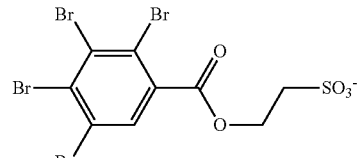
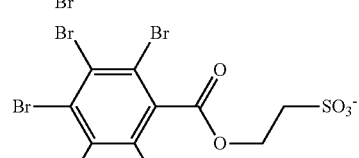
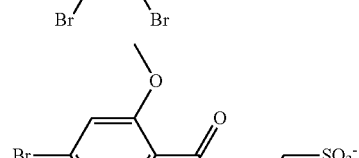
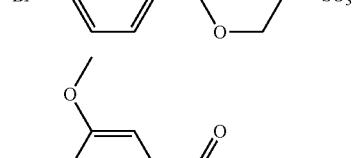
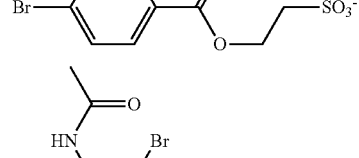
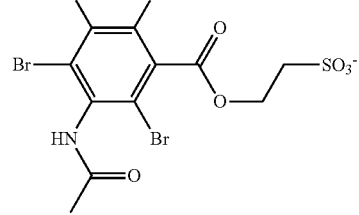
-continued
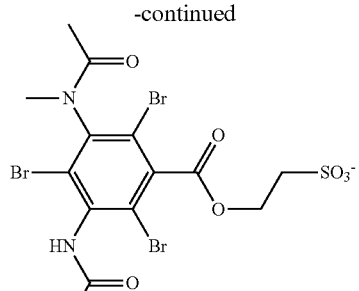
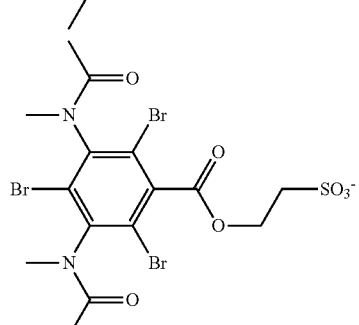
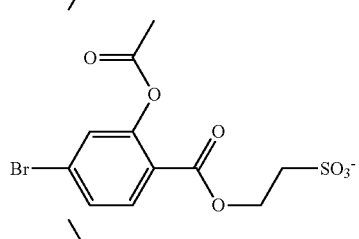
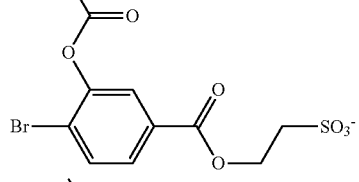
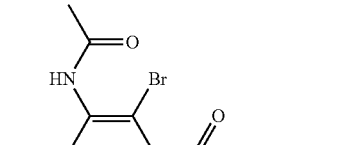
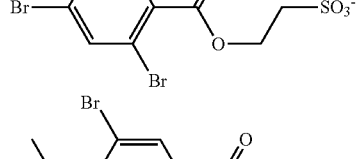
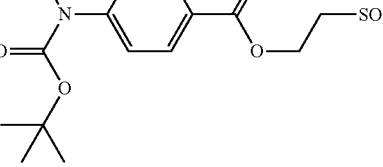
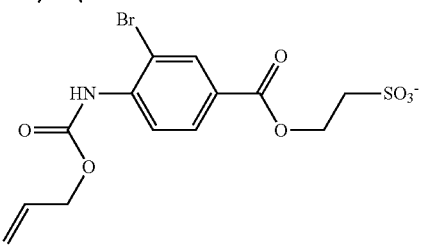

43
-continued
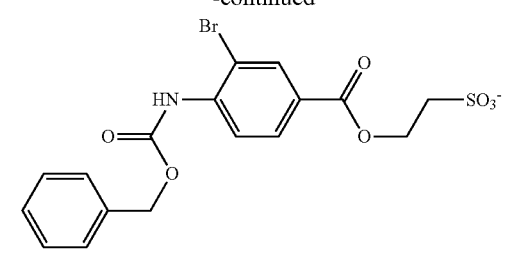
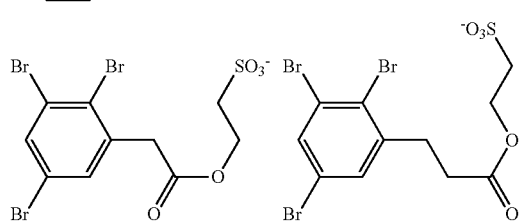
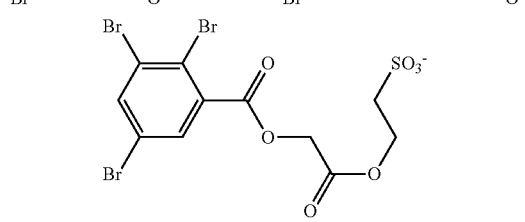
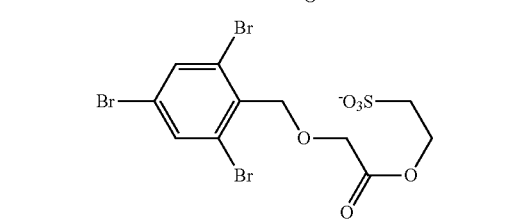
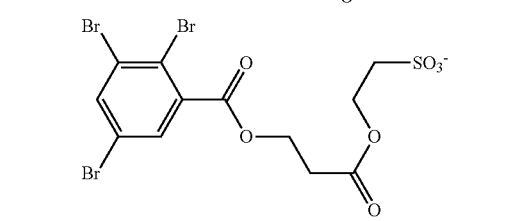
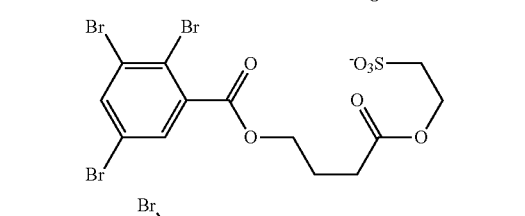
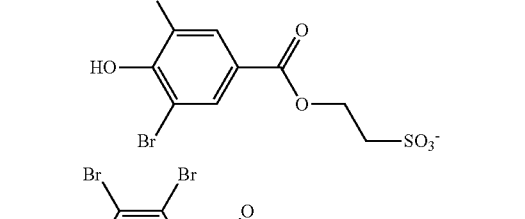
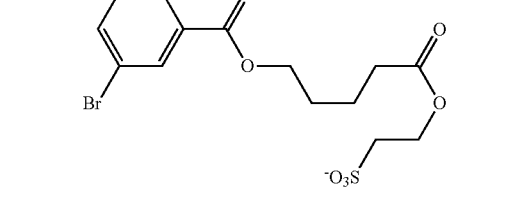
44
-continued
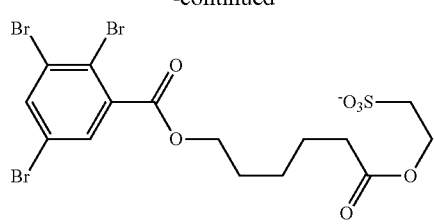
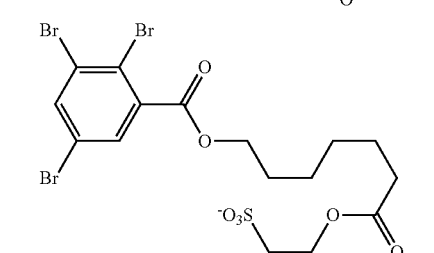
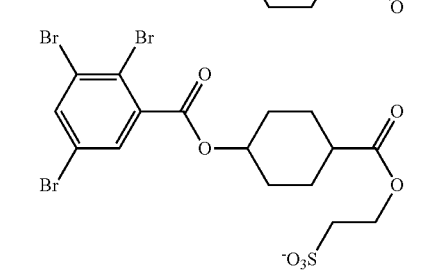
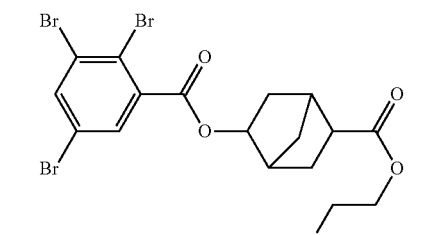
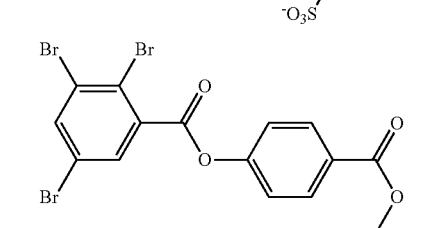
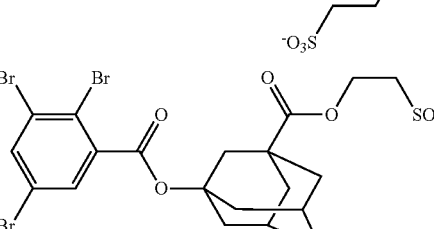
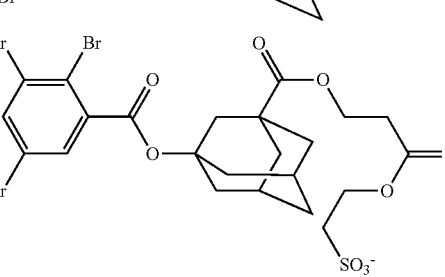

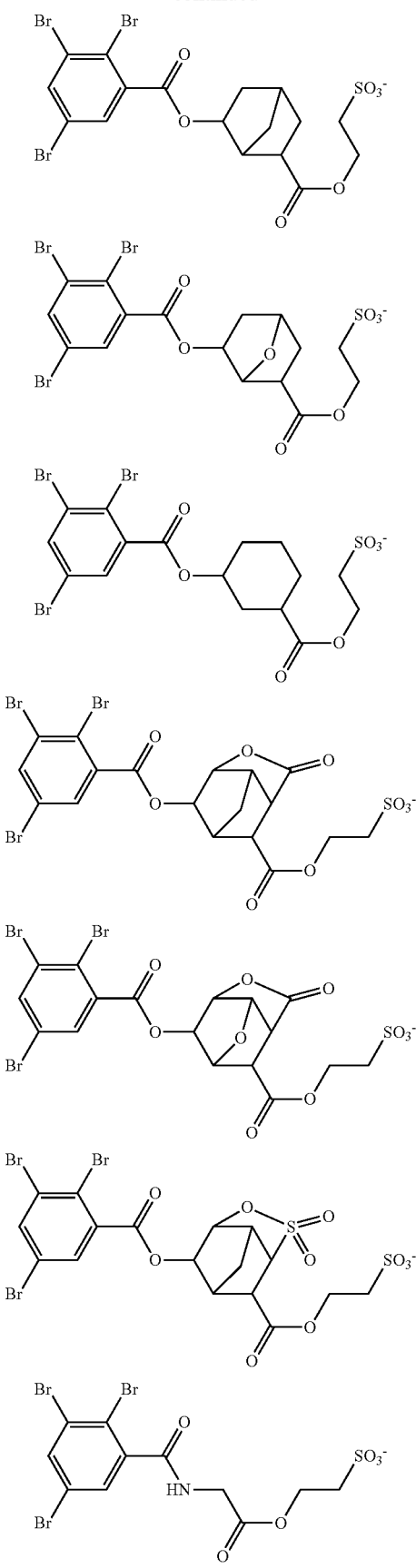
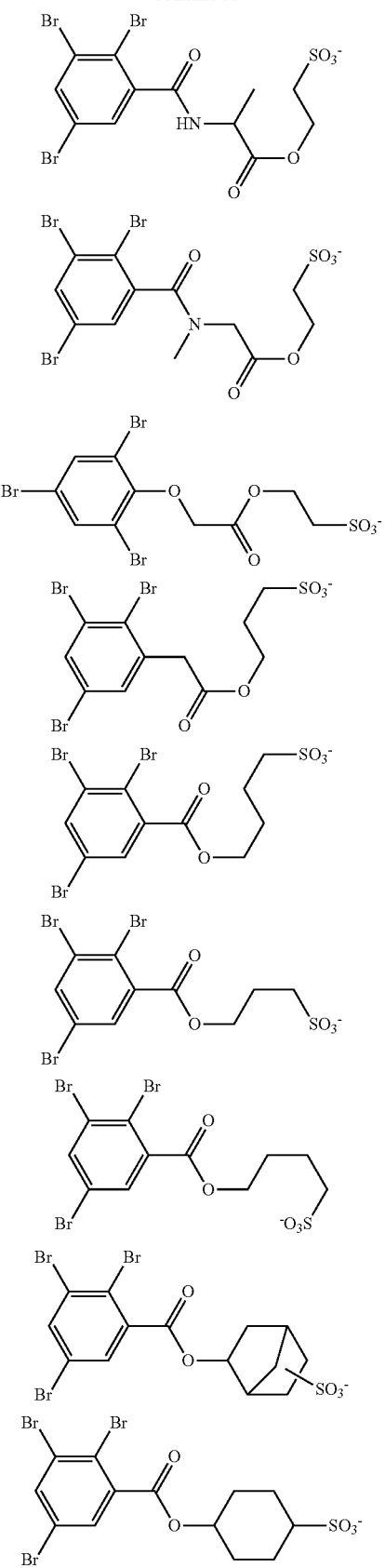

47
-continued
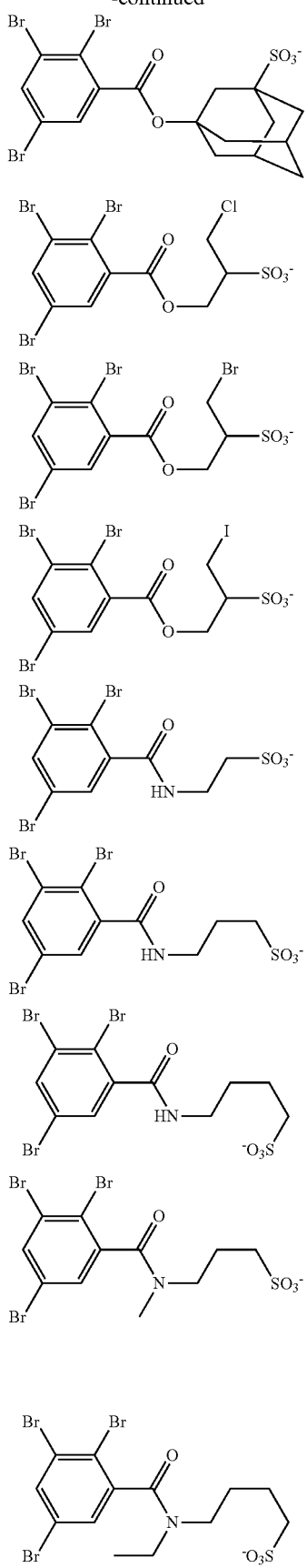
48
-continued
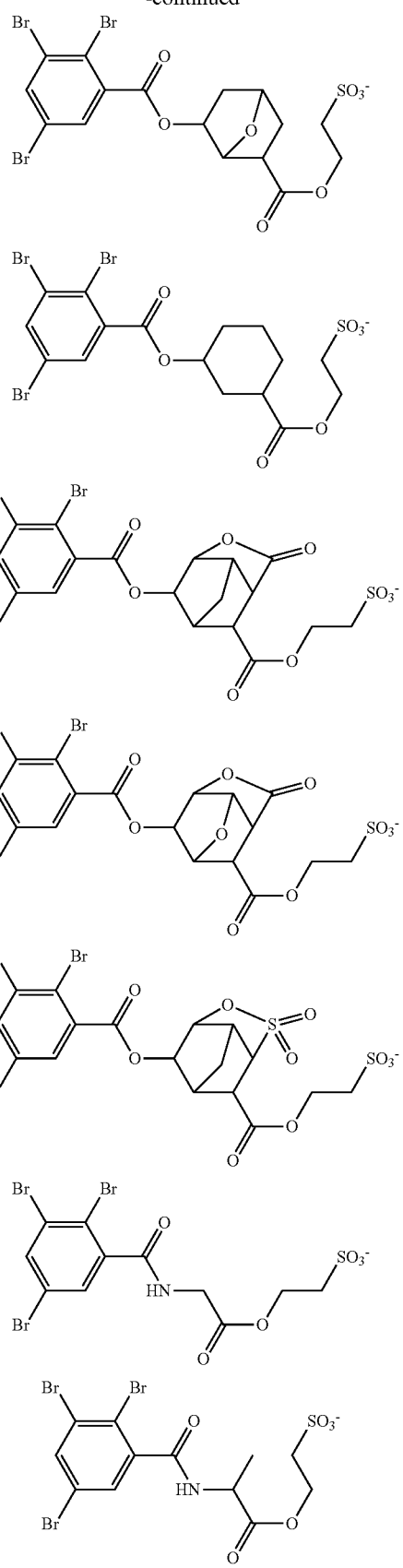

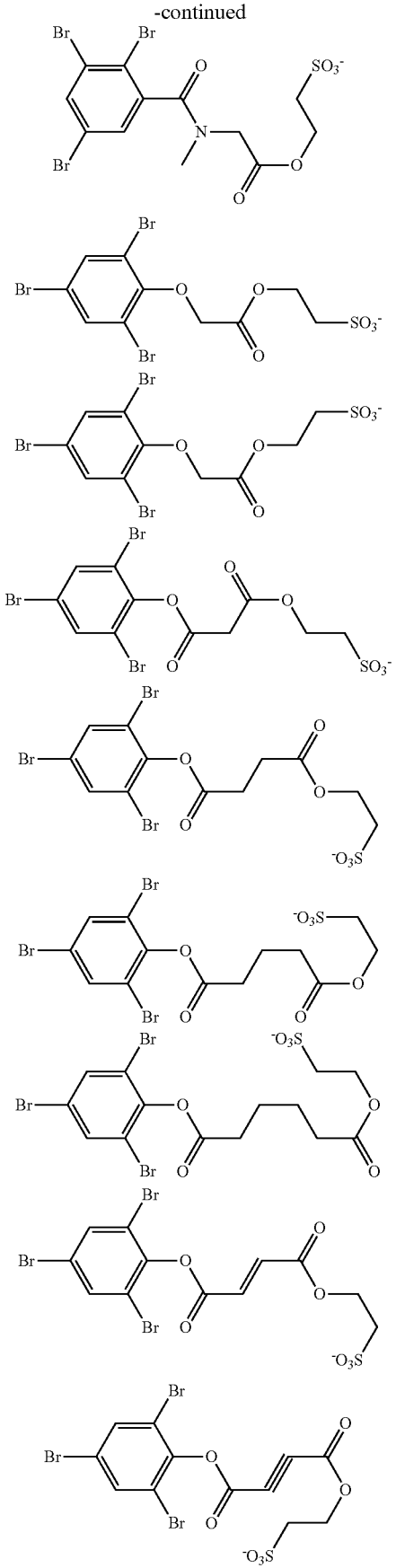
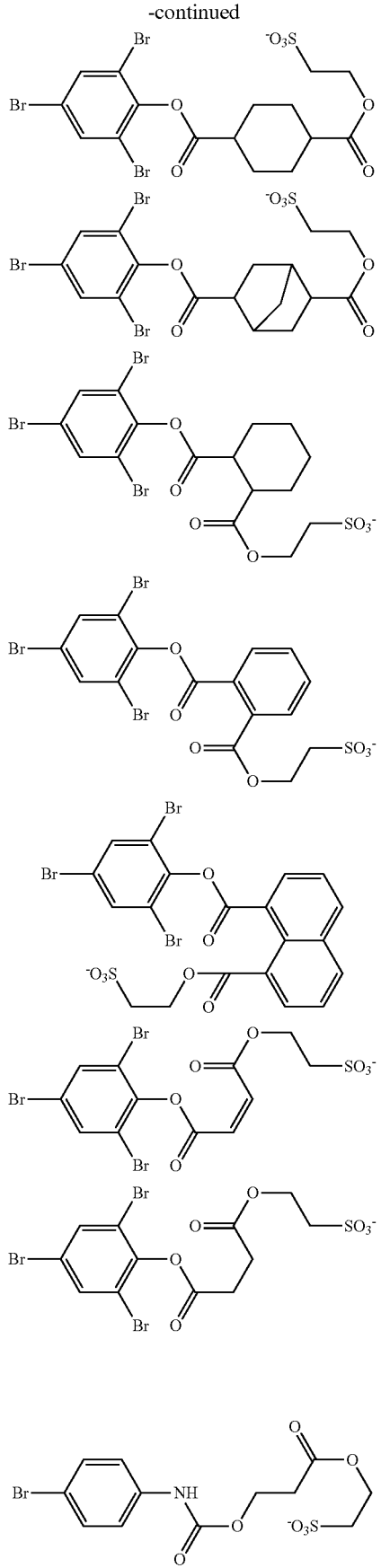

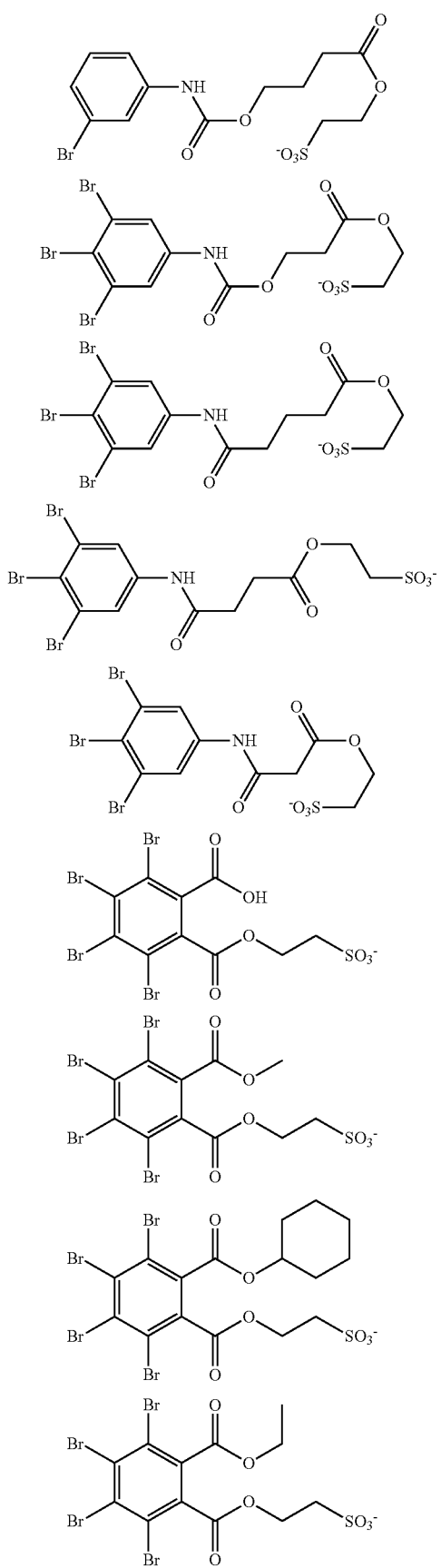
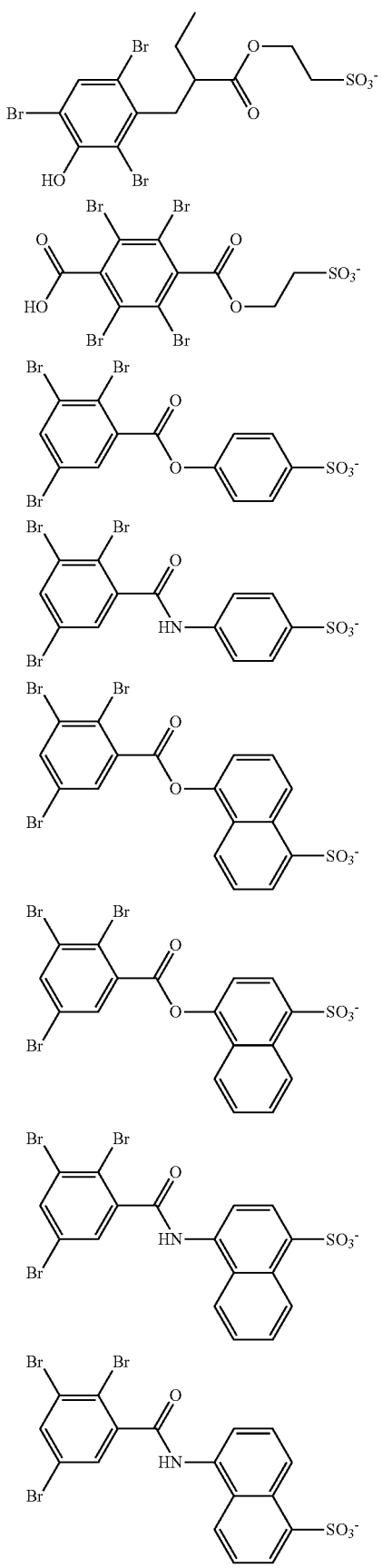

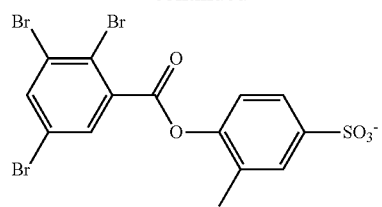
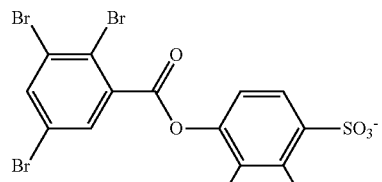
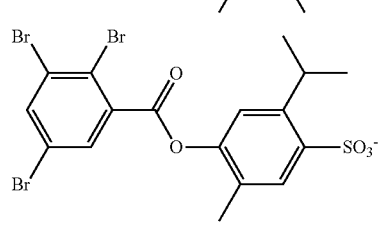
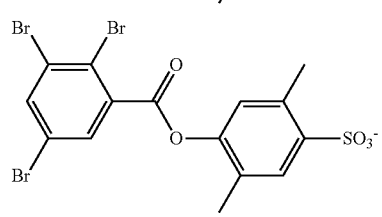
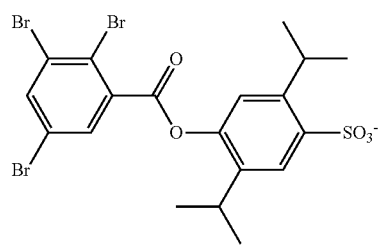
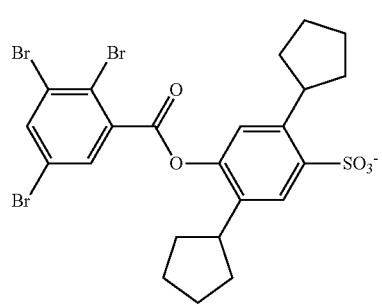
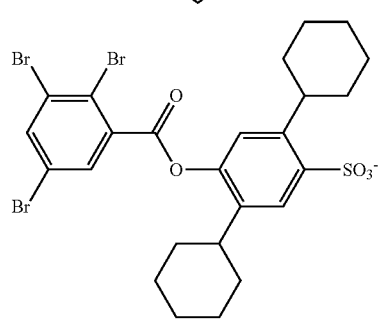
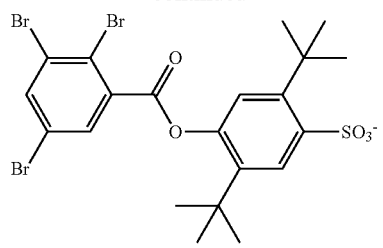
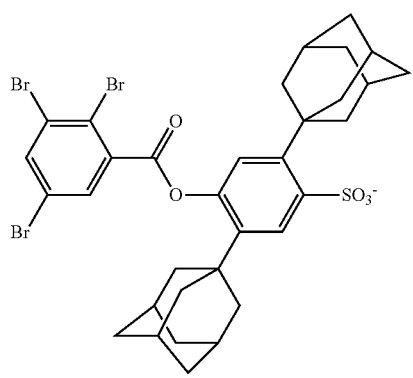
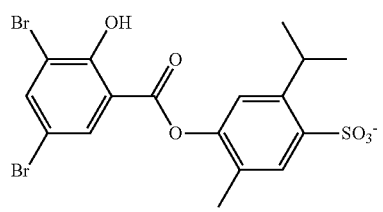
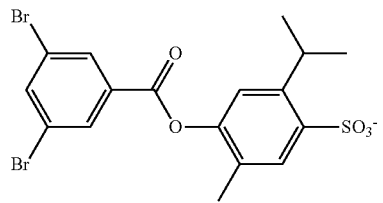
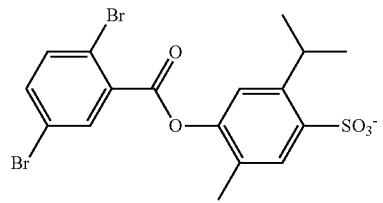
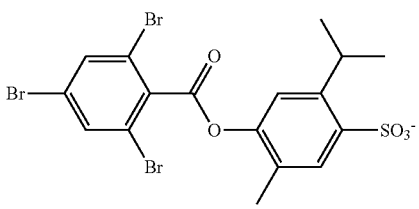
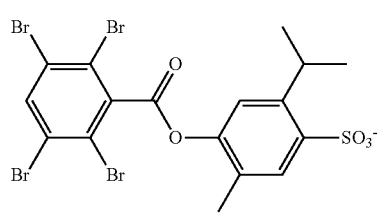

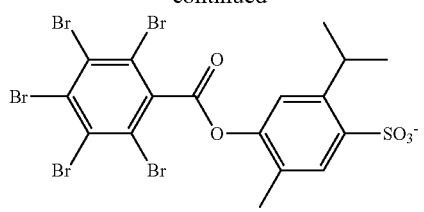
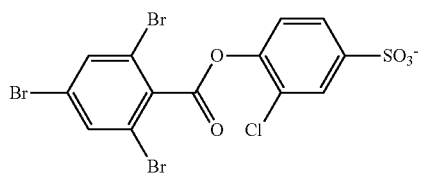
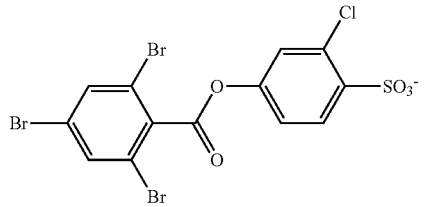
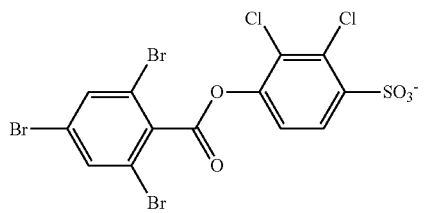
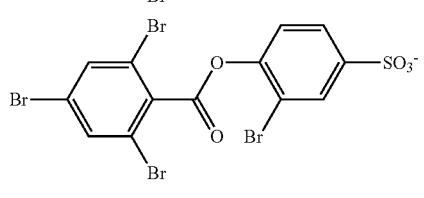
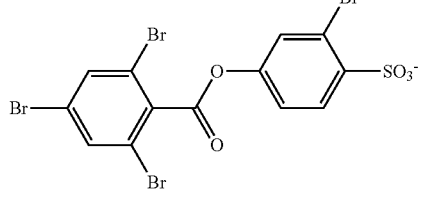
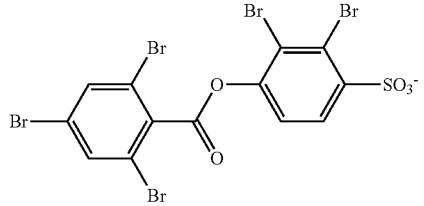
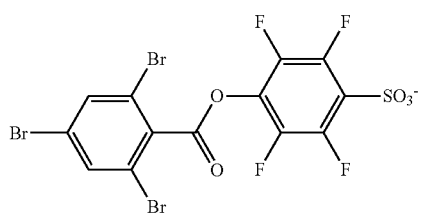

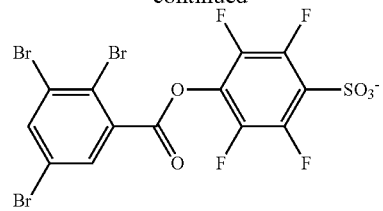
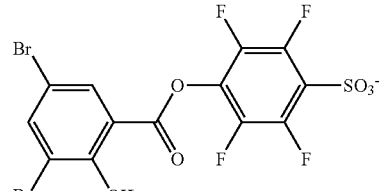
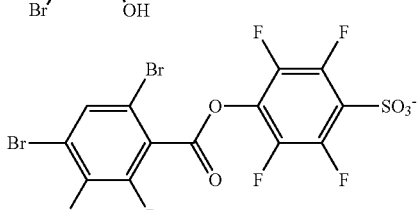
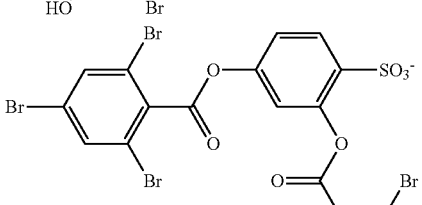
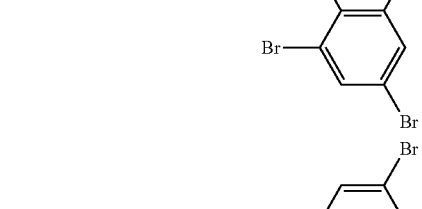
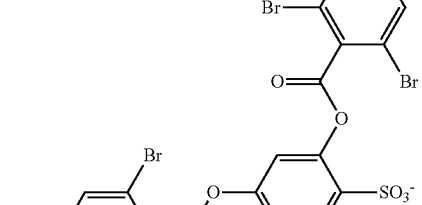
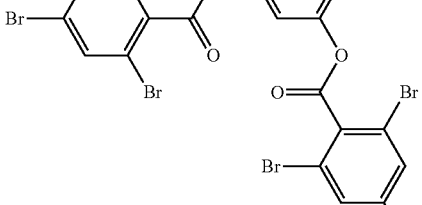
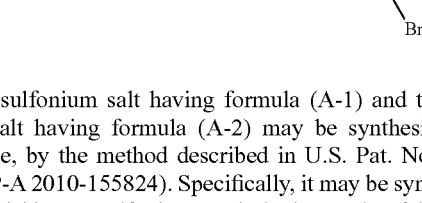

The sulfonium salt having formula (A-1) and the iodonium salt having formula (A-2) may be synthesized, for example, by the method described in U.S. Pat. No. 8,394,570 (JP-A 2010-155824). Specifically, it may be synthesized by furnishing a sulfonium or iodonium salt of hydroxy-containing sulfonic acid such as 2-hydroxyethane-1-sulfonic acid (or isethionic acid), esterifying the hydroxyl group of the salt with a brominated benzoic acid, and effecting ion exchange between the resulting brominated benzene-containing sulfonic acid and a sulfonium chloride or iodonium chloride.

In the resist composition, the sulfonium salt having formula (A-1) or iodonium salt having formula (A-2) is preferably used in an amount of 0.001 to 50 parts, more preferably 0.01 to 40 parts by weight per 100 parts by weight of the base polymer, as viewed from sensitivity and acid diffusion suppressing effect.

Base Polymer

Where the resist composition is of positive tone, the base polymer comprises recurring units containing an acid labile group, preferably recurring units having the formula (a1) or recurring units having the formula (a2). These units are simply referred to as recurring units (a1) and (a2).

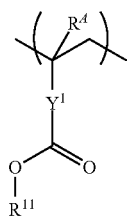

(a1)

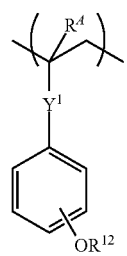

(a2)

Herein $R^4$ is each independently hydrogen or methyl. $Y^1$ is a single bond, phenylene group, naphthylene group, or a $C_1$-$C_{12}$ linking group containing an ester bond and/or lactone ring. $Y^2$ is a single bond or ester bond. $R^{11}$ and $R^{12}$ each are an acid labile group. When the base polymer contains both recurring units (a1) and (a2), $R^{11}$ and $R^{12}$ may be identical or different.

Examples of the monomer from which recurring units (a1) are derived are shown below, but not limited thereto. $R^4$ and $R^{11}$ are as defined above.

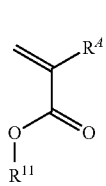
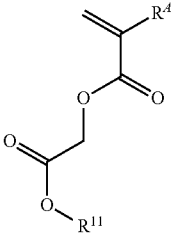
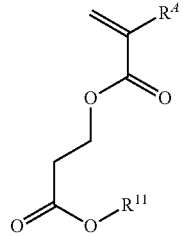

-continued

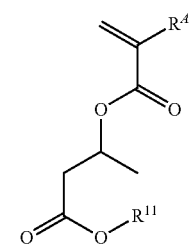
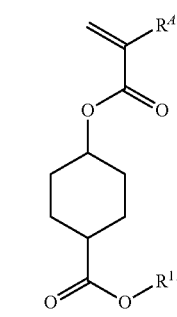
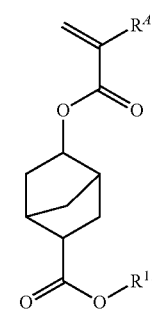
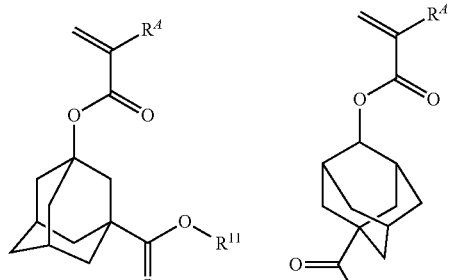
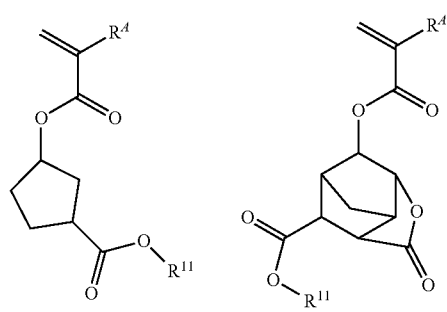
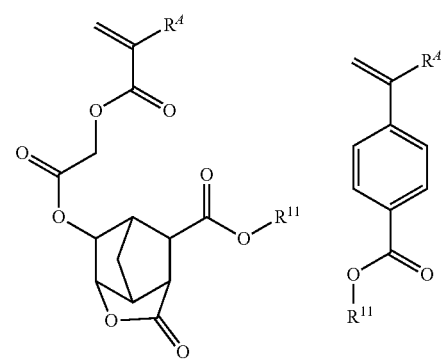

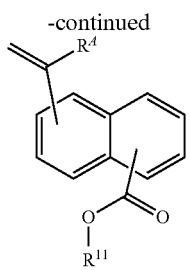

Examples of the monomer from which recurring units (a2) are derived are shown below, but not limited thereto. $R^A$ and $R^{12}$ are as defined above.

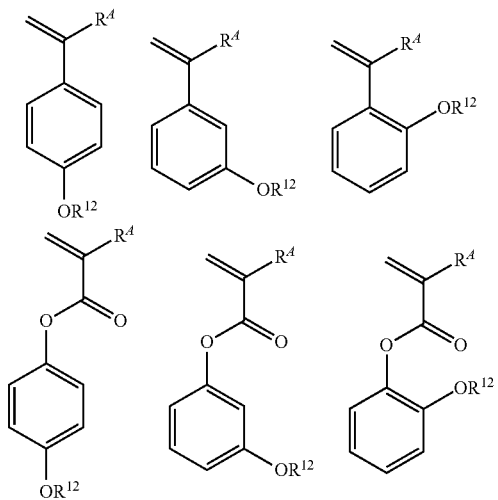

The acid labile groups represented by $R^{11}$ and $R^{12}$ in the recurring units (a1) and (a2) may be selected from a variety of such groups, for example, those groups described in JP-A 2013-080033 (U.S. Pat. No. 8,574,817) and JP-A 2013-083821 (U.S. Pat. No. 8,846,303).

Typical of the acid labile group are groups of the following formulae (AL-1) to (AL-3).

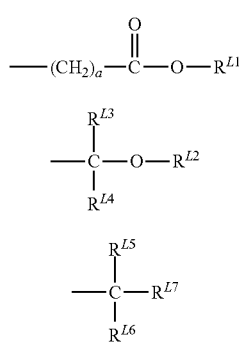

In formulae (AL-1) and (AL-2), $R^{L1}$ and $R^{L2}$ are each independently a $C_1$-$C_{40}$ monovalent hydrocarbon group which may contain a heteroatom such as oxygen, sulfur, nitrogen or fluorine. The monovalent hydrocarbon groups may be straight, branched or cyclic, with alkyl groups of 1 to 40 carbon atoms, especially 1 to 20 carbon atoms being preferred. In formula (AL-1), "a" is an integer of 0 to 10, especially 1 to 5.

In formula (AL-2), $R^{L3}$ and $R^{L4}$ are each independently hydrogen or a $C_1$-$C_{20}$ monovalent hydrocarbon group which may contain a heteroatom such as oxygen, sulfur, nitrogen or fluorine. The monovalent hydrocarbon groups may be straight, branched or cyclic, with $C_1$-$C_{20}$ alkyl groups being preferred. Any two of $R^{L2}$, $R^{L3}$ and $R^{L4}$ may bond together to form a ring with the carbon atom or carbon and oxygen atoms to which they are attached. The ring contains 3 to 20 carbon atoms, preferably 4 to 16 carbon atoms, and is typically alicyclic.

In formula (AL-3), $R^{L5}$, $R^{L6}$ and $R^{L7}$ are each independently a $C_1$-$C_{20}$ monovalent hydrocarbon group which may contain a heteroatom such as oxygen, sulfur, nitrogen or fluorine. The monovalent hydrocarbon groups may be straight, branched or cyclic, with $C_1$-$C_{20}$ alkyl groups being preferred. Any two of $R^{L5}$, $R^{L6}$ and $R^{L7}$ may bond together to form a ring with the carbon atom to which they are attached. The ring contains 3 to 20 carbon atoms, preferably 4 to 16 carbon atoms and is typically alicyclic.

The base polymer may further comprise recurring units (b) having a phenolic hydroxyl group as an adhesive group. Examples of suitable monomers from which recurring units (b) are derived are given below, but not limited thereto. Herein $R^A$ is as defined above.

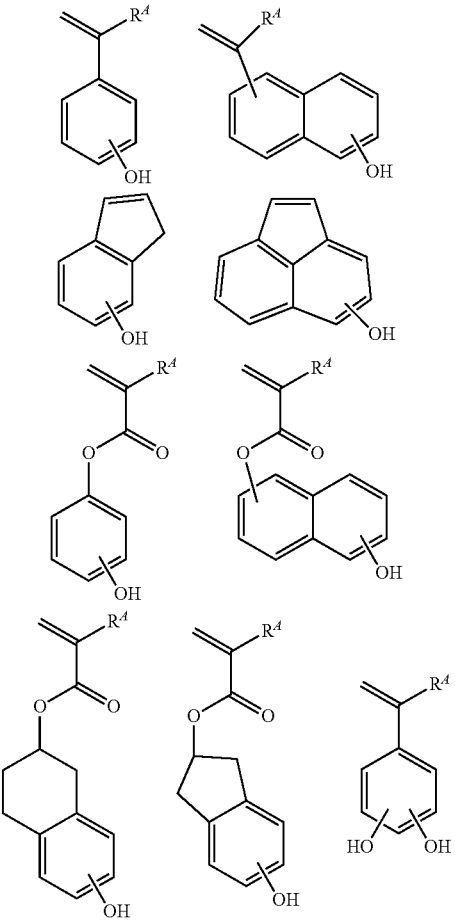

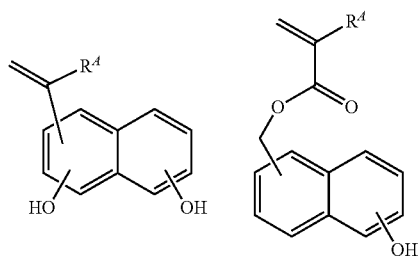
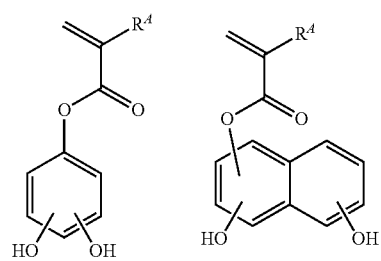
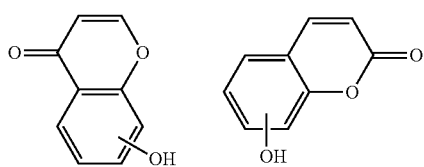
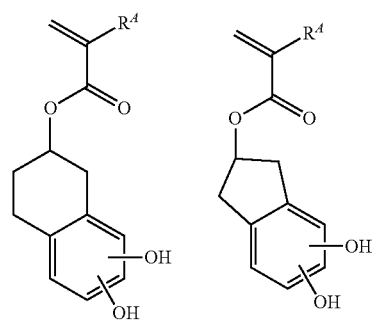

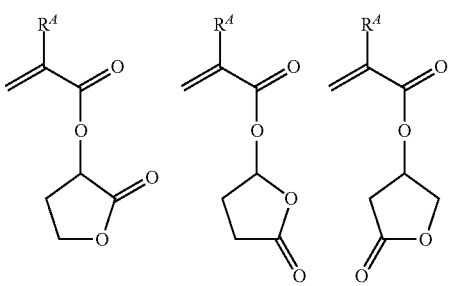
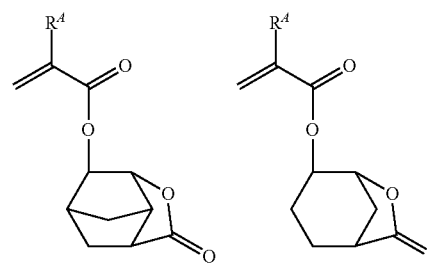
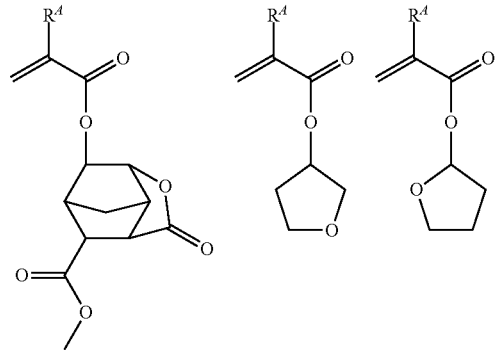
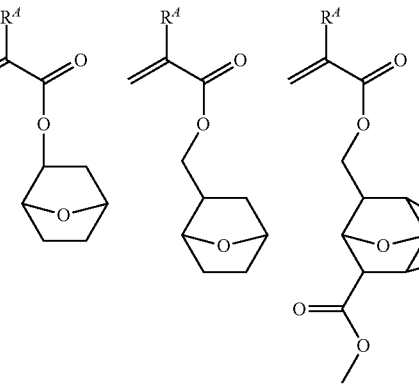

Further, recurring units (c) having another adhesive group selected from hydroxyl (other than the foregoing phenolic hydroxyl), carboxyl, lactone ring, ether bond, ester bond, carbonyl and cyano groups may also be incorporated in the base polymer. Examples of suitable monomers from which recurring units (c) are derived are given below, but not limited thereto. Herein $R^A$ is as defined above.

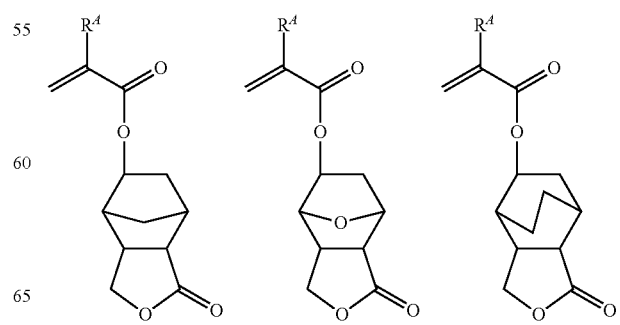

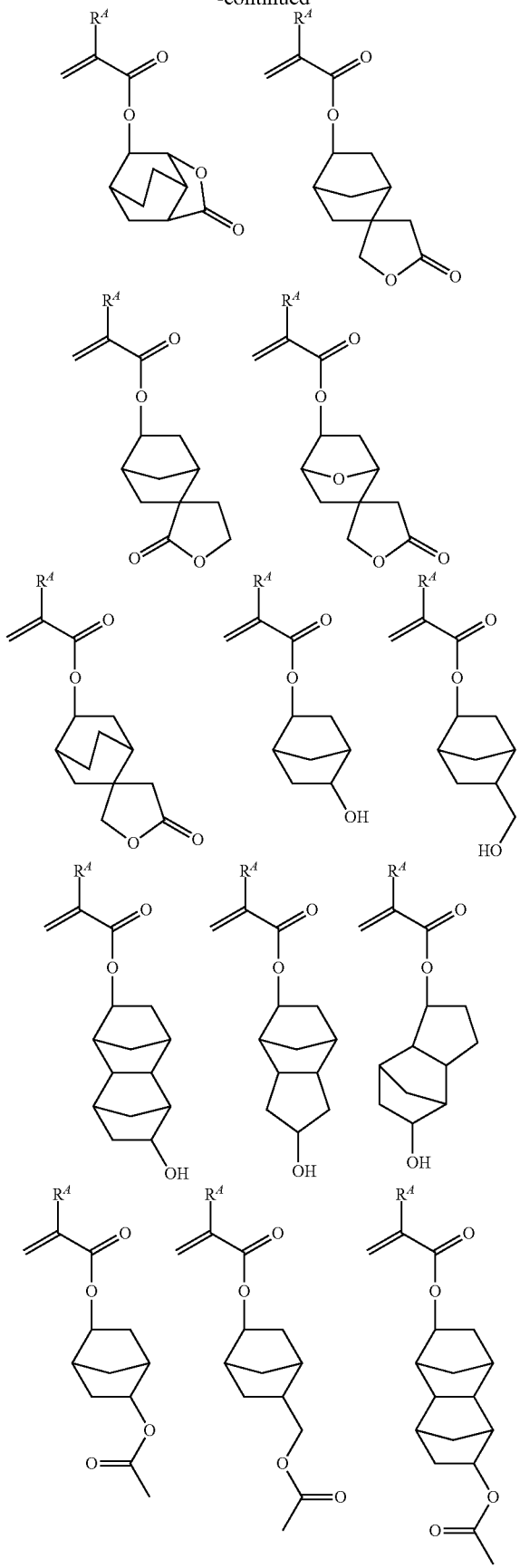
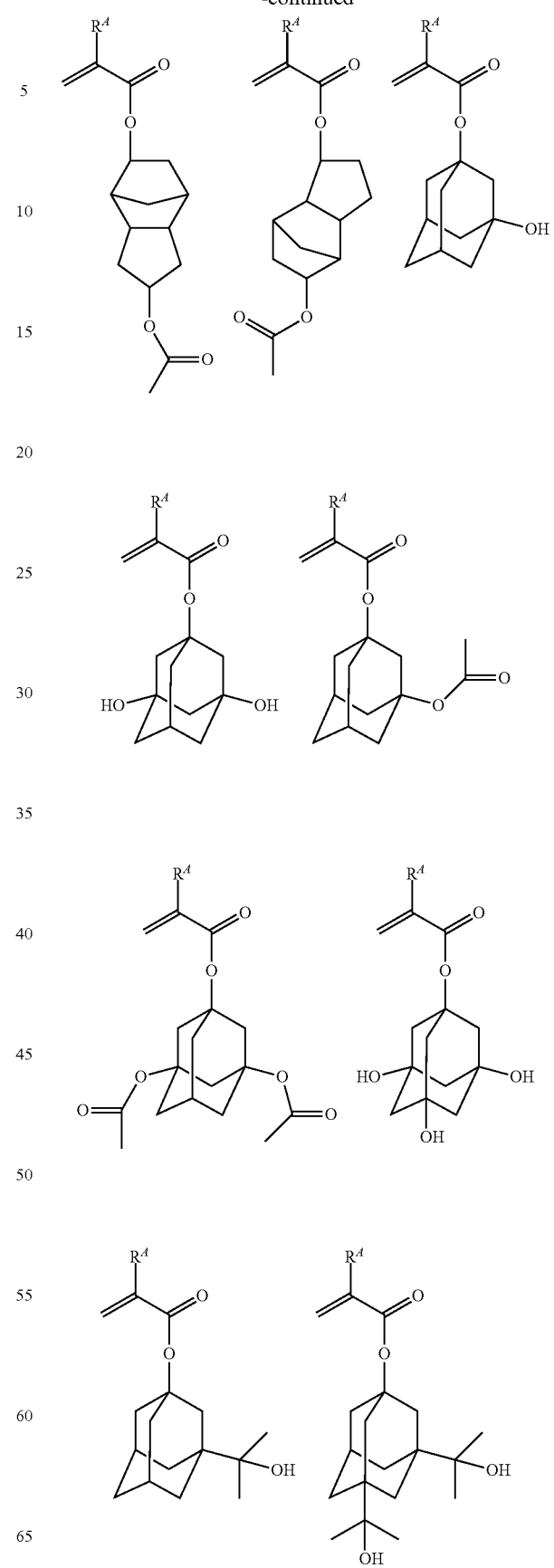

-continued
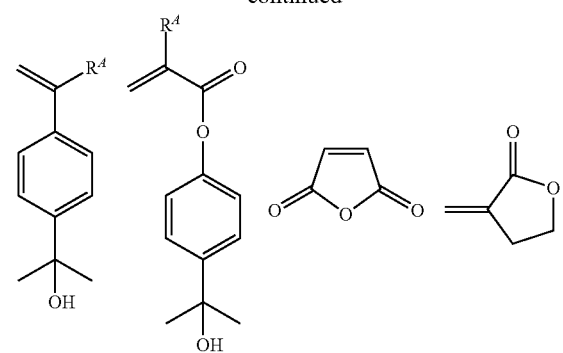
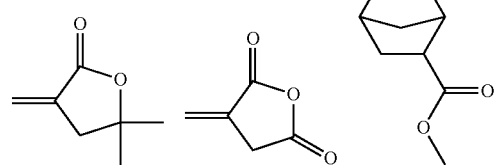
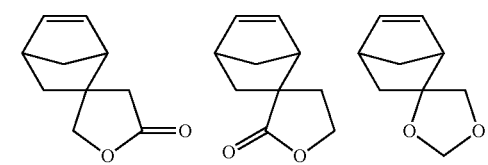
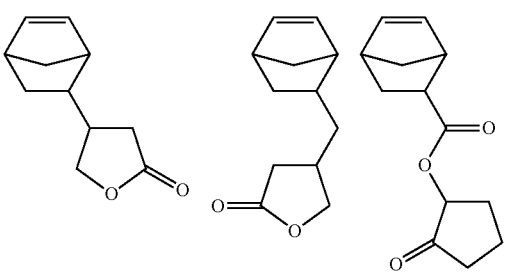
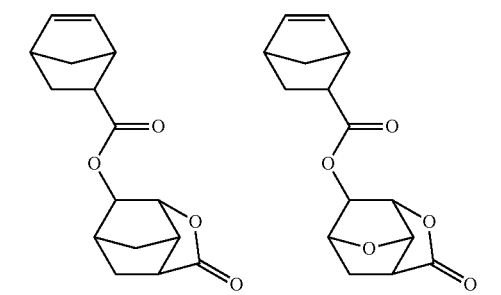
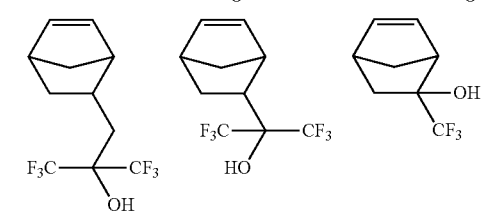
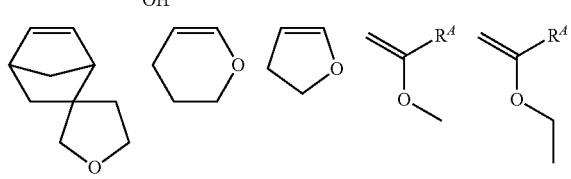
-continued
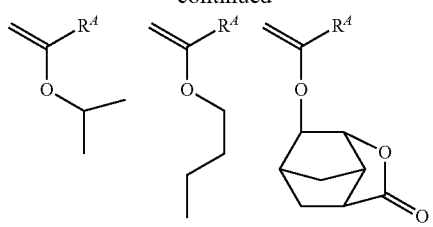
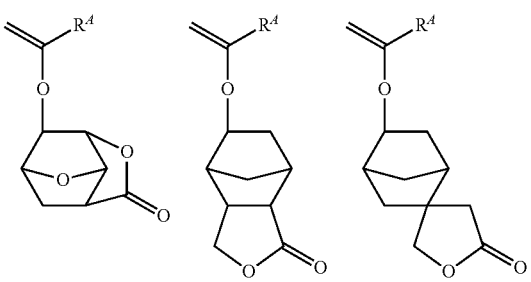
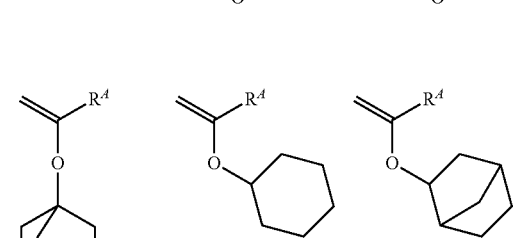
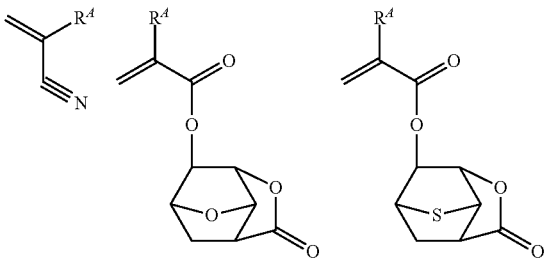
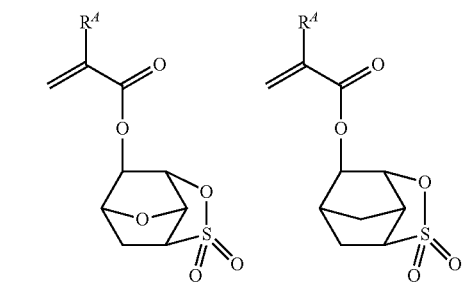
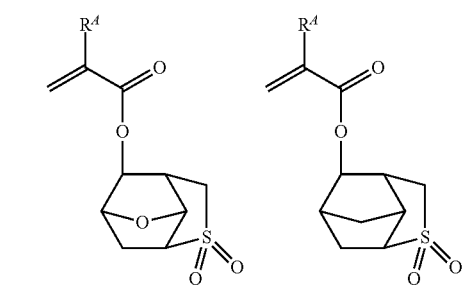

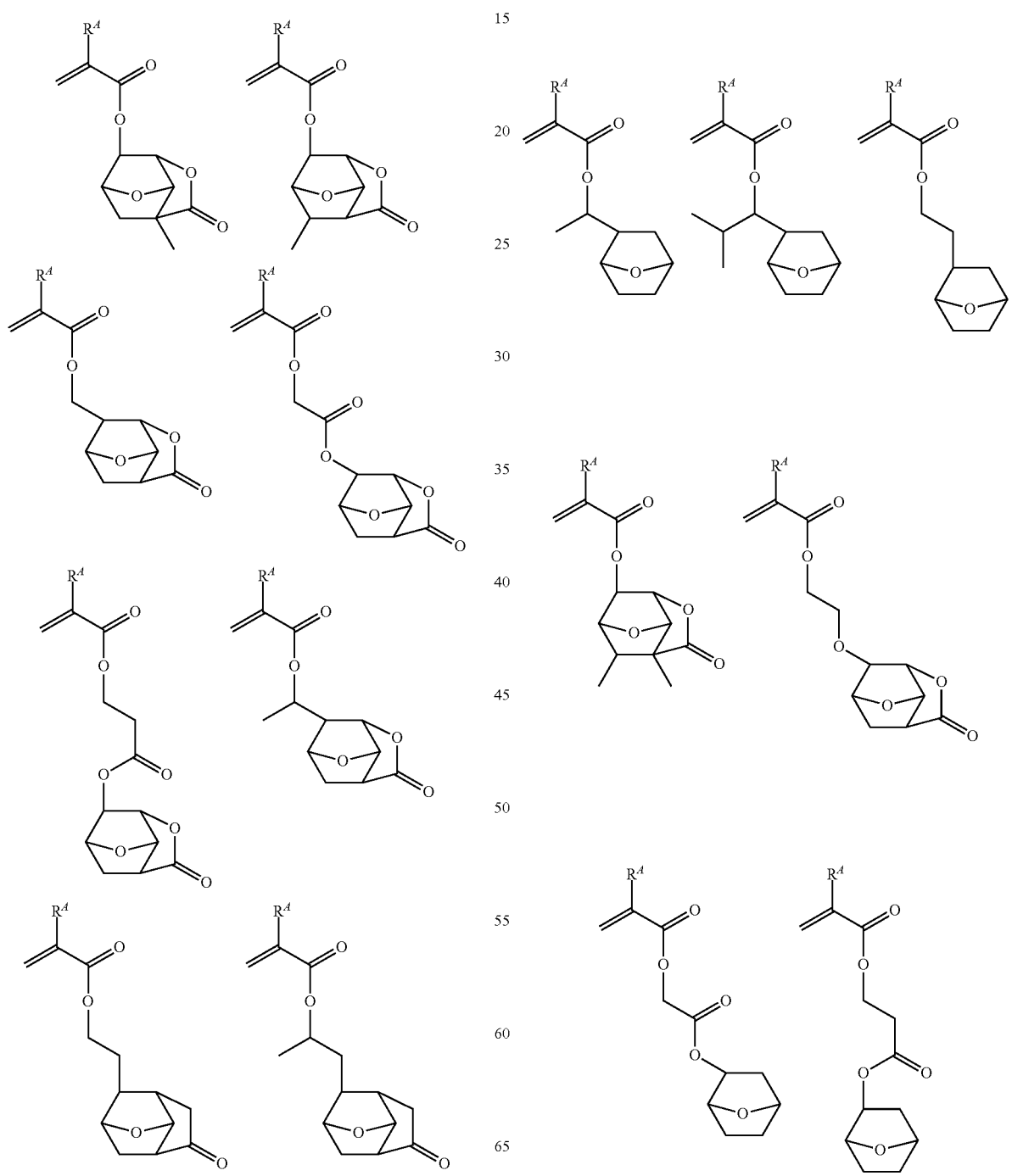

-continued
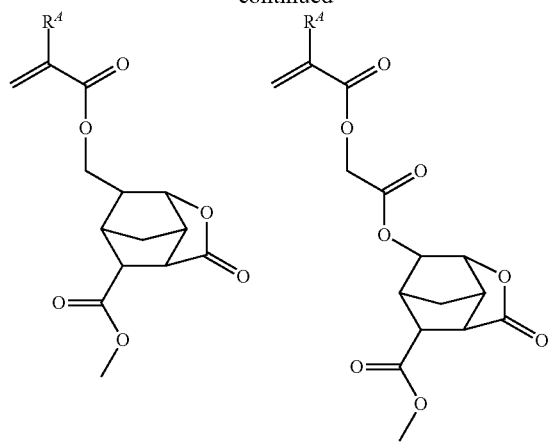
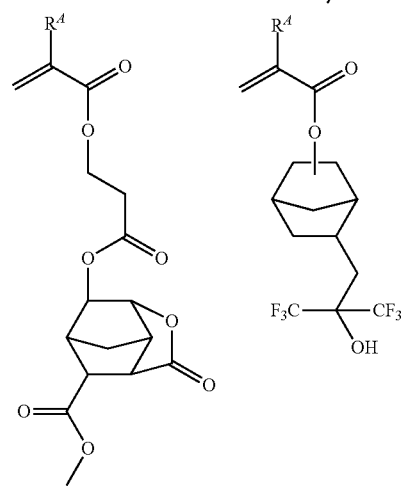
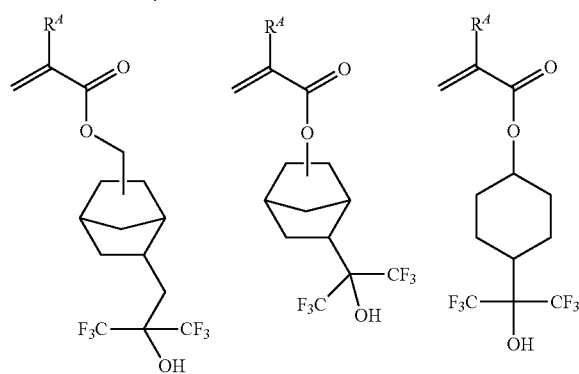
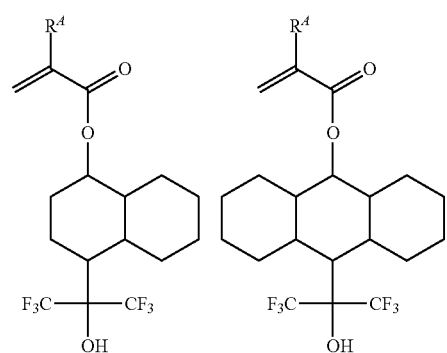
-continued
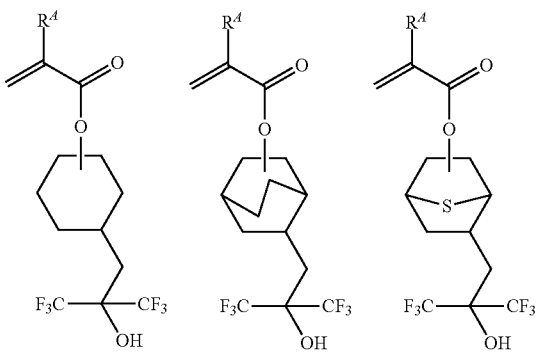
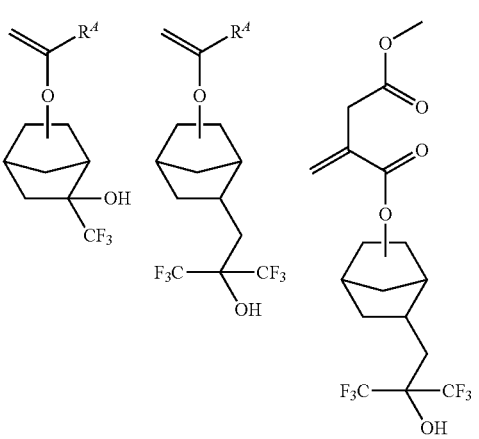
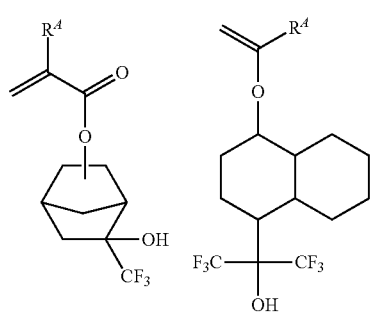

-continued
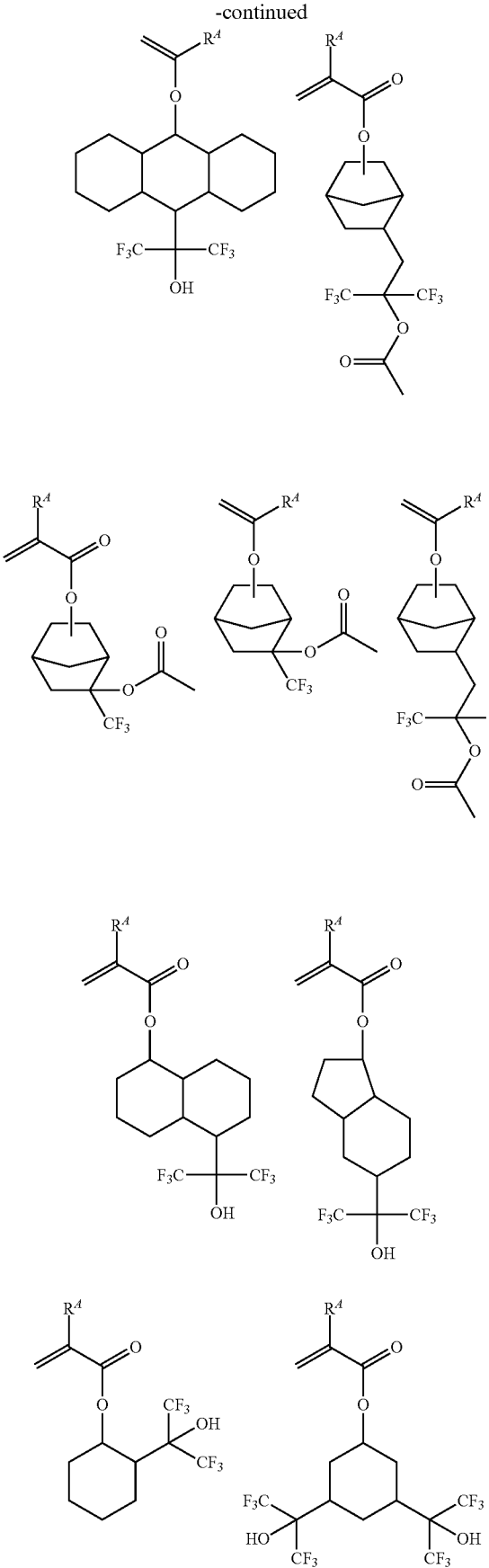
-continued
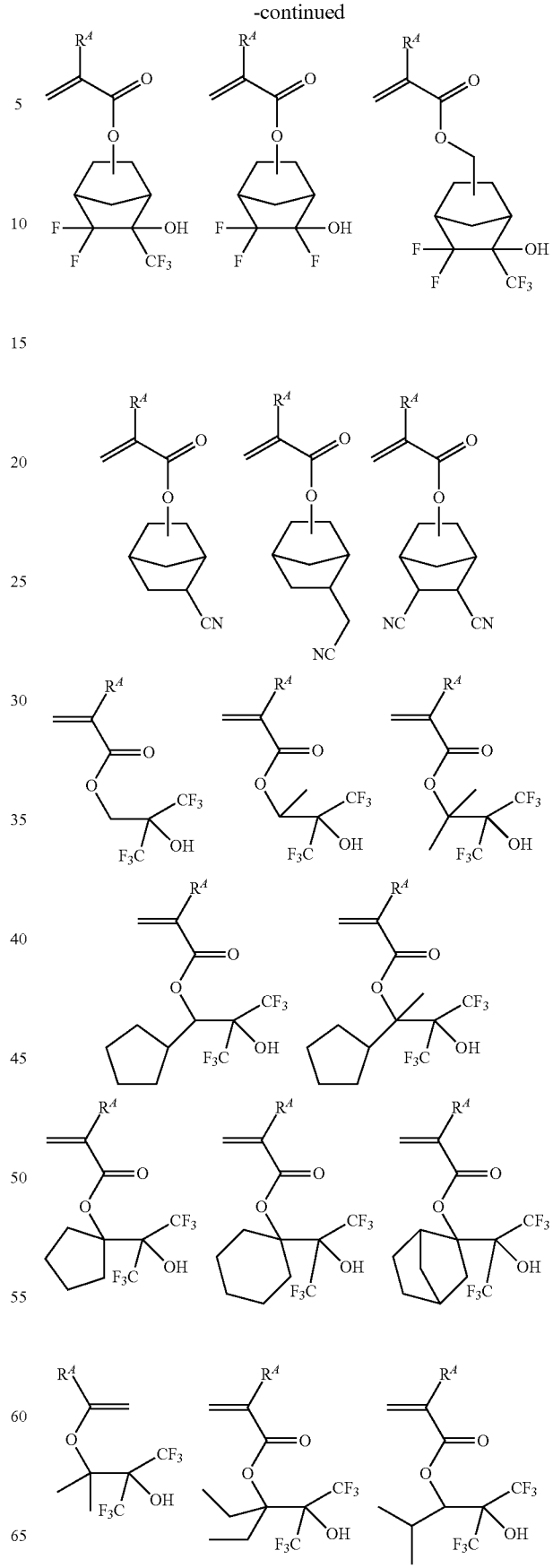

-continued
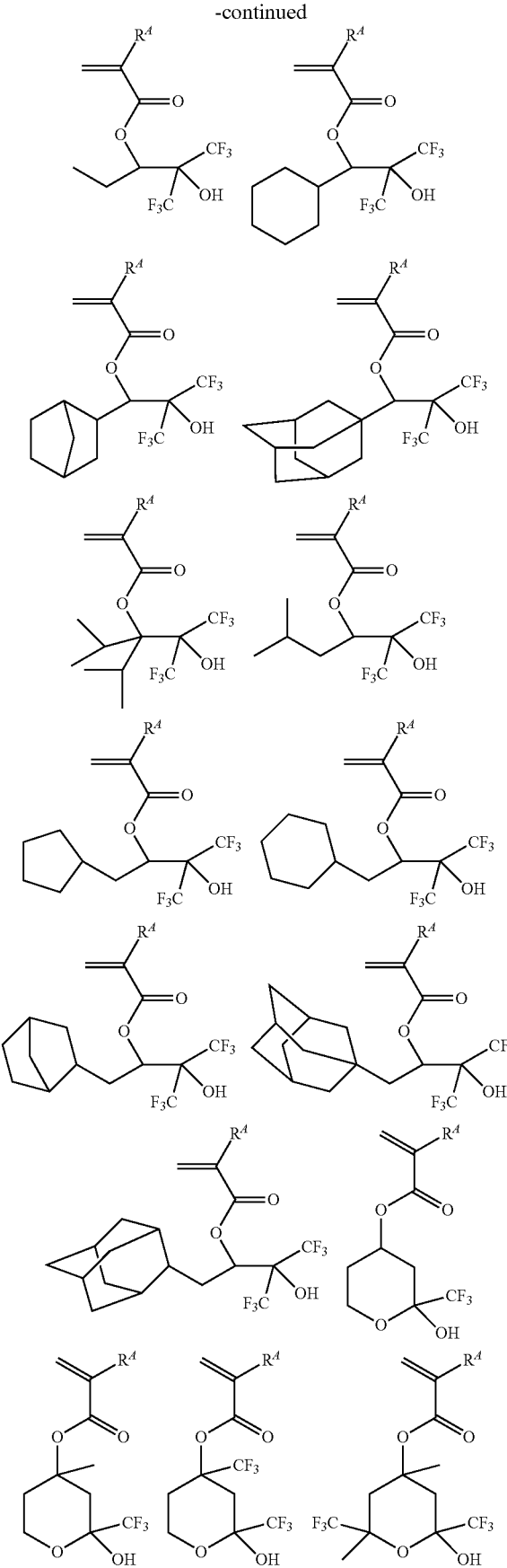
-continued
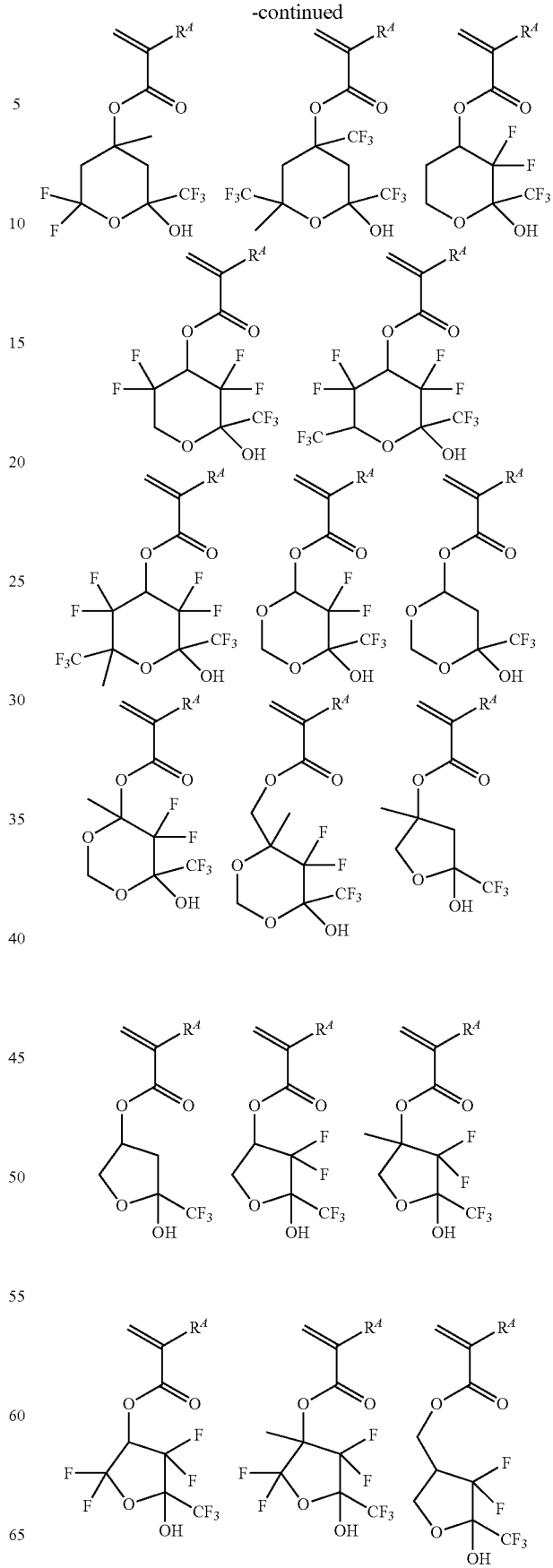

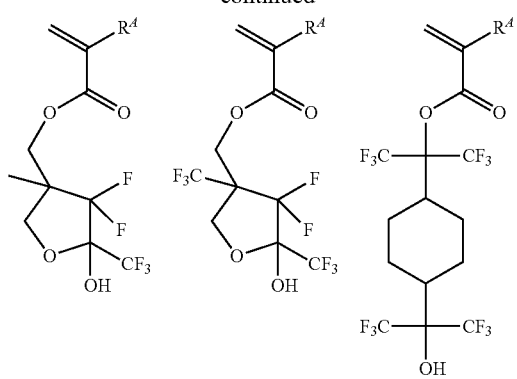
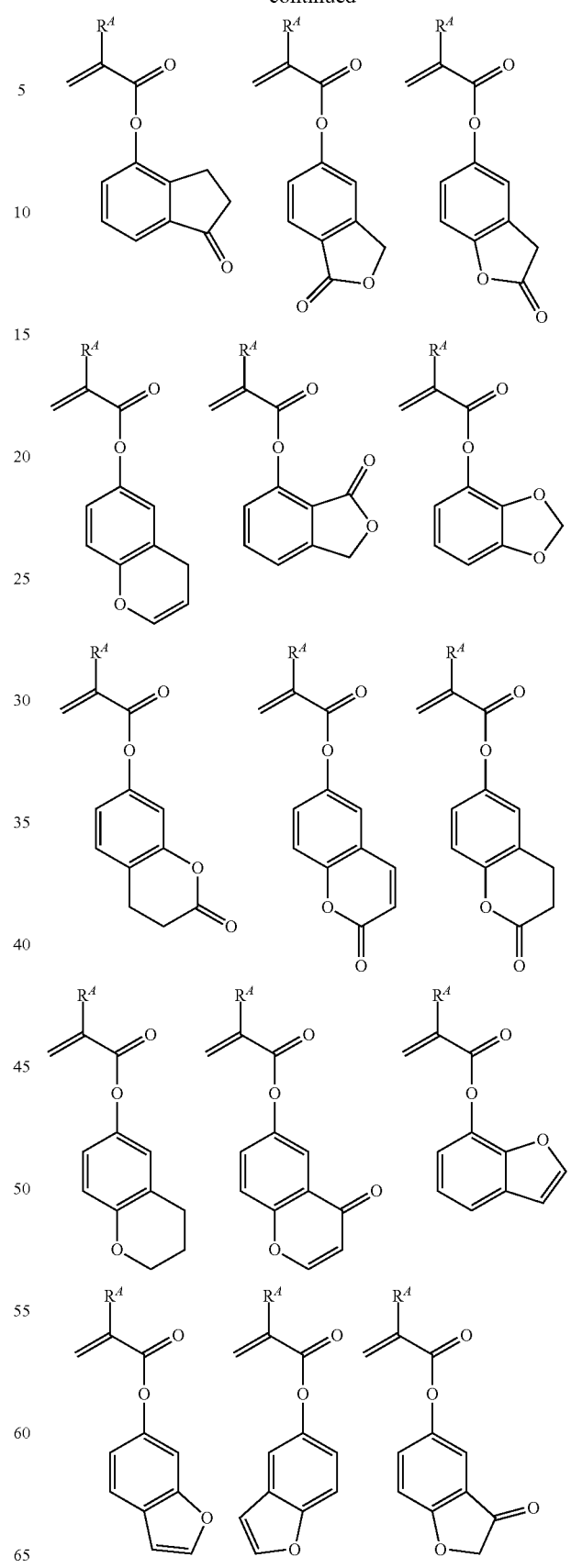

77
-continued
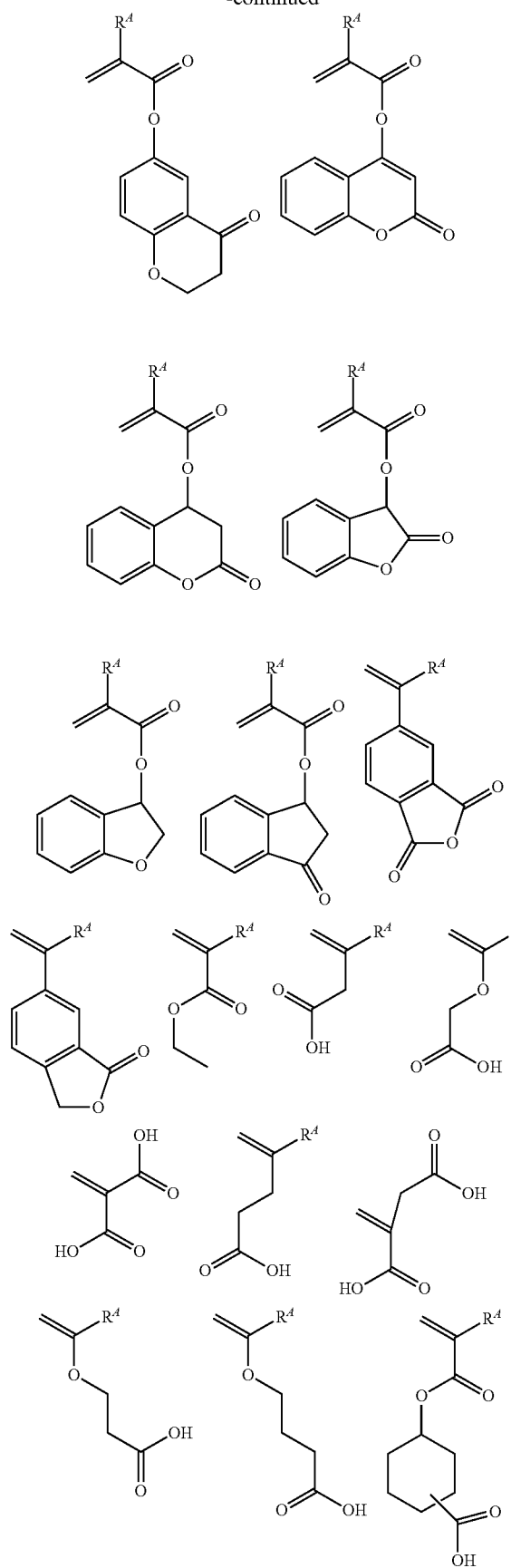
78
-continued
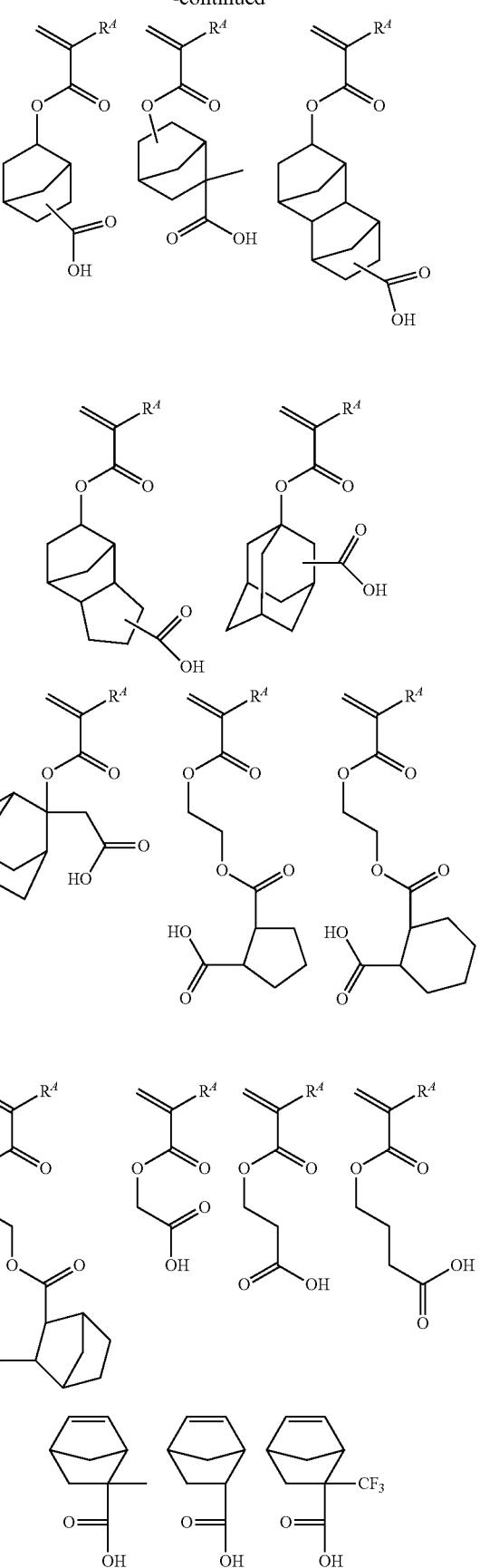

-continued

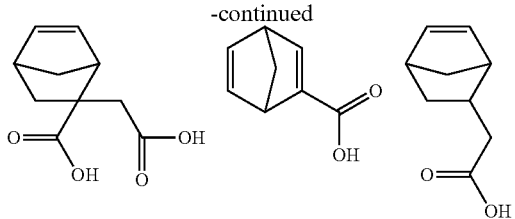

In another preferred embodiment, the base polymer may further comprise recurring units (d) selected from units of indene, benzofuran, benzothiophene, acenaphthylene, chromone, coumarin, and norbornadiene, or derivatives thereof. Suitable monomers are exemplified below.

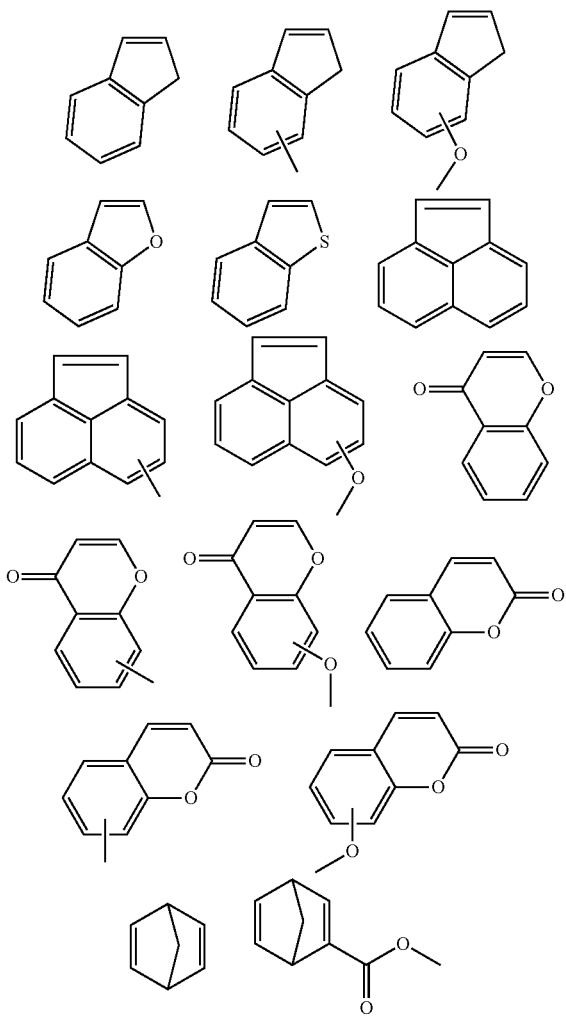

Besides the recurring units described above, further recurring units (e) may be incorporated in the base polymer, examples of which include styrene, vinylnaphthalene, vinylanthracene, vinylpyrene, methyleneindene, vinylpyridine, and vinylcarbazole.

In a further embodiment, recurring units (f) derived from an onium salt having a polymerizable unsaturated bond may be incorporated in the base polymer. The preferred recurring units (f) are recurring units having the following formulae (f1), (f2) and (f3). These units are simply referred to as recurring units (f1), (f2) and (f3), which may be used alone or in combination of two or more types.

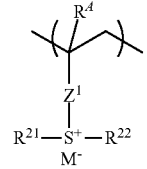 (f1)

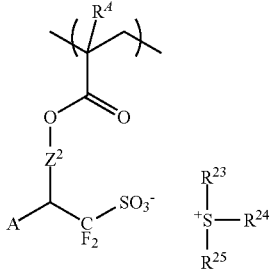 (f2)

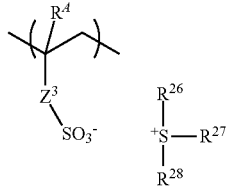 (f3)

Herein $R^A$ is each independently hydrogen or methyl. $Z^1$ is a single bond, phenylene group, —O—$Z^{12}$—, or —C(=O)—$Z^{11}$—$Z^{12}$—, wherein $Z^{11}$ is —O— or —NH—, and $Z^{12}$ is a $C_1$-$C_6$ alkylene, $C_2$-$C_6$ alkenylene or phenylene group, which may contain a carbonyl, ester bond, ether bond or hydroxyl moiety. $Z^2$ is a single bond, —$Z^{21}$—C(=O)—O—, —$Z^{21}$—O— or —$Z^{21}$—O—C(=O)—, wherein $Z^{21}$ is a $C_1$-$C_{12}$ alkylene group which may contain a carbonyl moiety, ester bond or ether bond. $Z^3$ is a single bond, methylene, ethylene, phenylene or fluorinated phenylene group, —O—$Z^{32}$—, or —C(=O)—$Z^{31}$-$Z^{32}$—, wherein $Z^{31}$ is —O— or —NH—, and $Z^{32}$ is a $C_1$-$C_6$ alkylene, phenylene, fluorinated phenylene, trifluoromethyl-substituted phenylene, or $C_2$-$C_6$ alkenylene group, which may contain a carbonyl, ester bond, ether bond or hydroxyl moiety. "A" is hydrogen or trifluoromethyl.

$R^{21}$ to $R^{28}$ are each independently a $C_1$-$C_{20}$ monovalent hydrocarbon group which may contain a heteroatom. Any two of $R^{23}$, $R^{24}$ and $R^{25}$ or any two of $R^{26}$, $R^{27}$ and $R^{28}$ may bond together to form a ring with the sulfur atom to which they are attached. The monovalent hydrocarbon group may be straight, branched or cyclic and examples thereof are as exemplified above for $R^3$ to $R^5$ in formulae (A-1) and (A-2). The sulfonium cation in formulae (f2) and (0) is preferably selected from the above-exemplified cations in the sulfonium salt having formula (A-1) or (A-2).

In formula (f1), $M^-$ is a non-nucleophilic counter ion. Examples of the non-nucleophilic counter ion include halide ions such as chloride and bromide ions; fluoroalkylsulfonate ions such as triflate, 1,1,1-trifluoroethanesulfonate, and nonafluorobutanesulfonate; arylsulfonate ions such as tosylate, benzenesulfonate, 4-fluorobenzenesulfonate, and 1,2,3,4,5-pentafluorobenzenesulfonate; alkylsulfonate ions such as mesylate and butanesulfonate; imide ions such as bis(trifluoromethylsulfonyl)imide, bis(perfluoroethylsulfonyl)

imide and bis(perfluorobutylsulfonyl)imide; methide ions such as tris(trifluoromethylsulfonyl)methide and tris(perfluoroethylsulfonyl)methide.

Also included are sulfonate ions having fluorine substituted at α-position as represented by the formula (K-1) and sulfonate ions having fluorine substituted at α- and β-positions as represented by the formula (K-2).

$$R^{51}-CF_2-SO_3^- \quad (K\text{-}1)$$

$$\begin{array}{c} R^{52}-O \\ \phantom{R^{52}-O}\diagdown \\ \phantom{R^{52}-O}\phantom{-}CF_2-SO_3^- \\ F_3C \end{array} \quad (K\text{-}2)$$

In formula (K-1), $R^{51}$ is hydrogen, or a $C_1$-$C_{20}$ alkyl group, $C_2$-$C_{20}$ alkenyl group, or $C_6$-$C_{20}$ aryl group, which may contain an ether bond, ester bond, carbonyl moiety, lactone ring, or fluorine atom. The alkyl and alkenyl groups may be straight, branched or cyclic.

In formula (K-2), $R^{52}$ is hydrogen, or a $C_1$-$C_{30}$ alkyl group, $C_2$-$C_{30}$ acyl group, $C_2$-$C_{20}$ alkenyl group, $C_6$-$C_{20}$ aryl group or $C_6$-$C_{20}$ aryloxy group, which may contain an ether bond, ester bond, carbonyl moiety or lactone ring. The alkyl and alkenyl groups may be straight, branched or cyclic.

Examples of the monomer from which recurring unit (f1) is derived are shown below, but not limited thereto. $R^A$ and $M^-$ are as defined above.

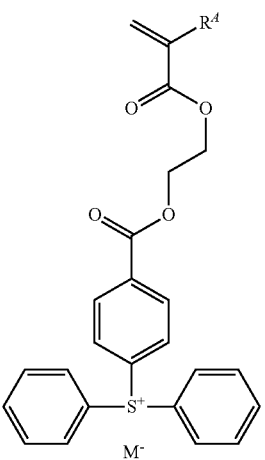

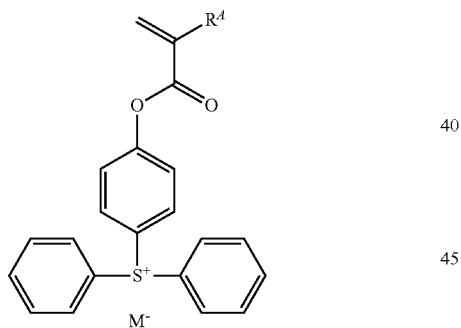

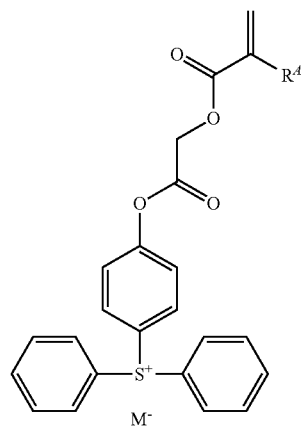

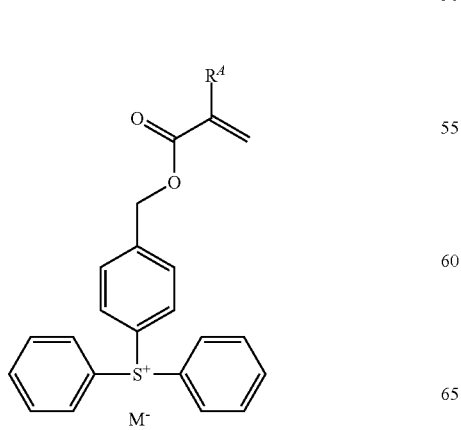

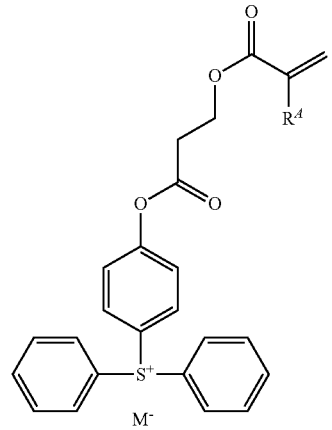

83
-continued
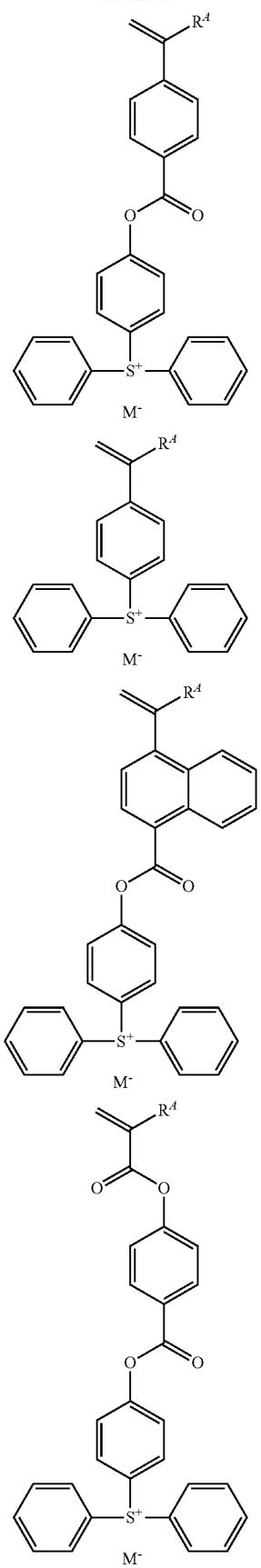
84
-continued
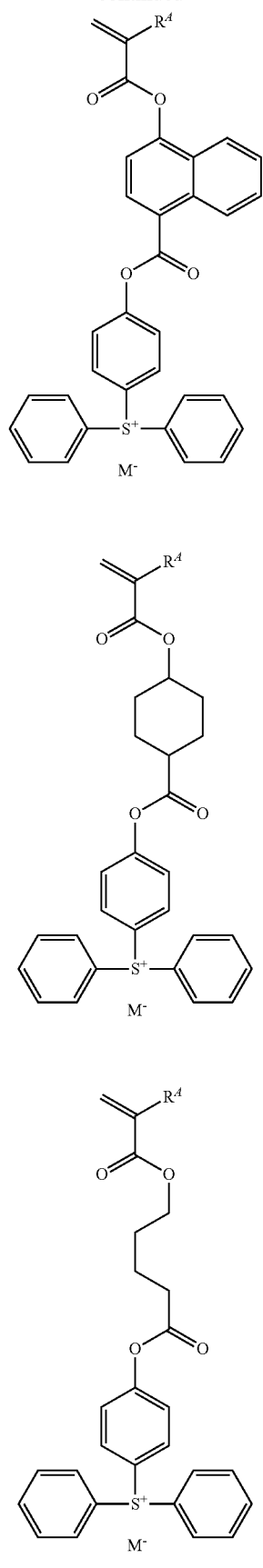

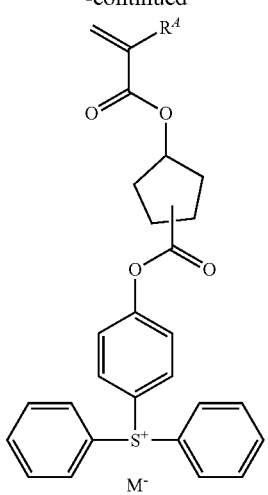
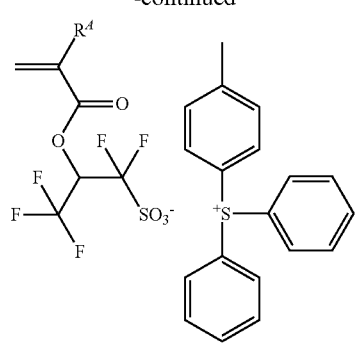
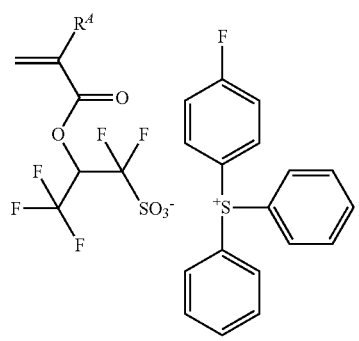
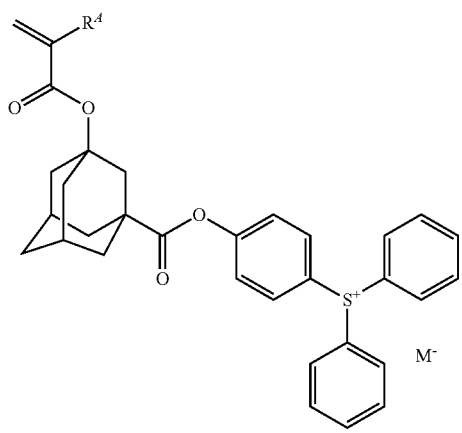
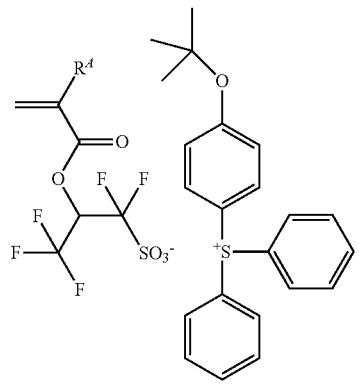
Examples of the monomer from which recurring unit (f2) is derived are shown below, but not limited thereto. $R^A$ is as defined above.
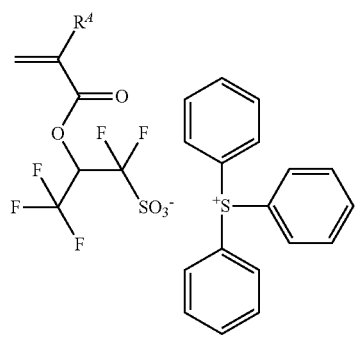
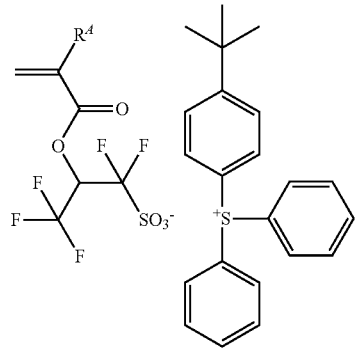
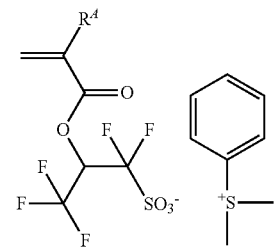

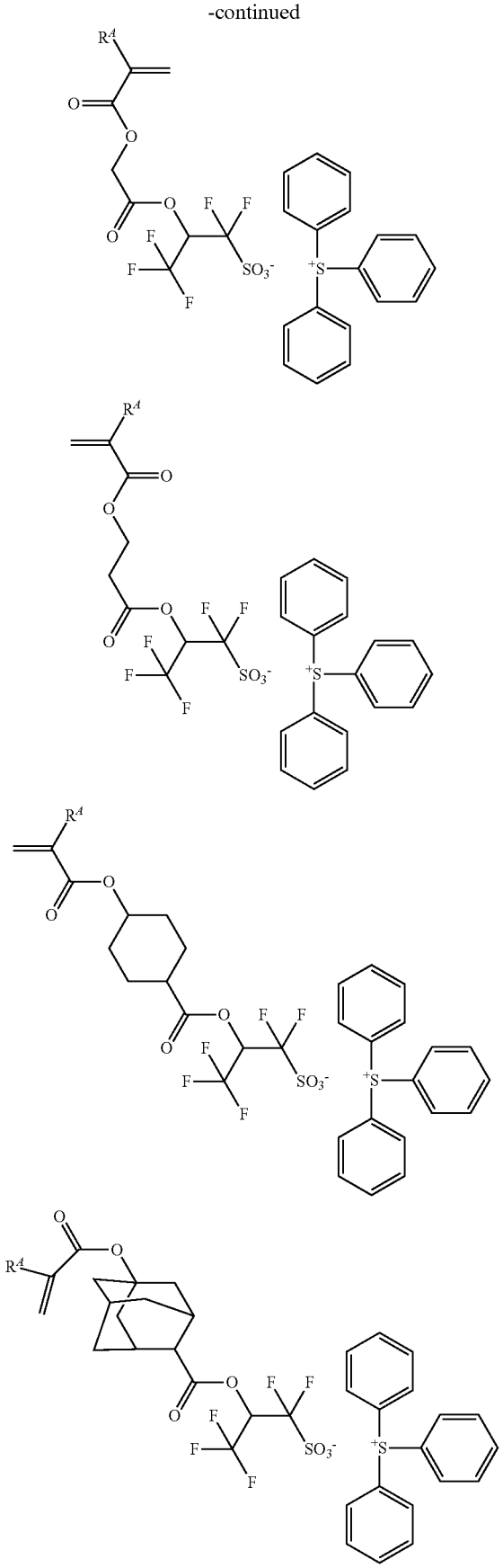

89
-continued
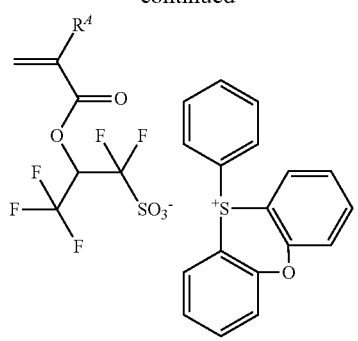
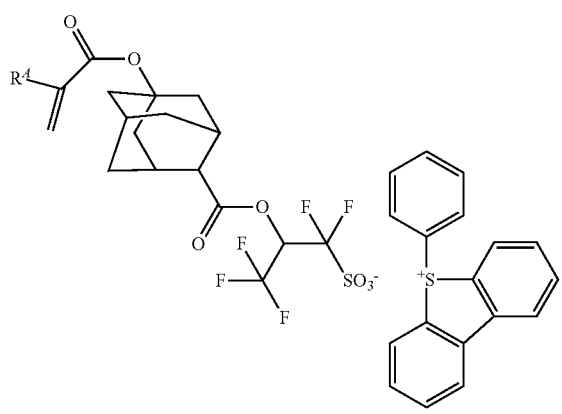
90
-continued
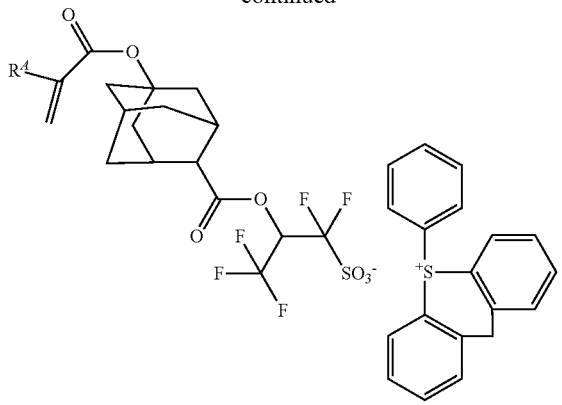
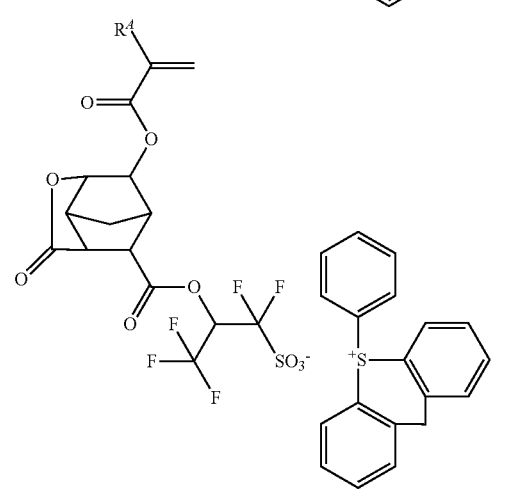
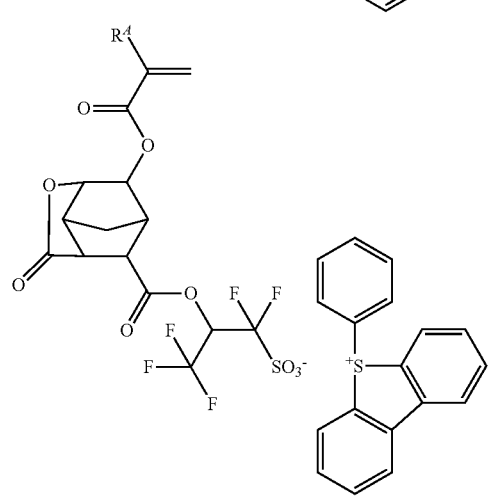
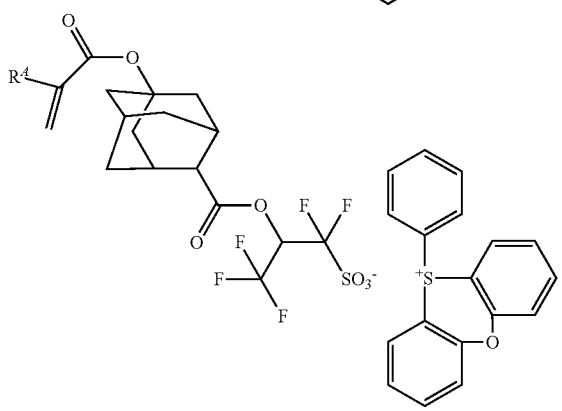

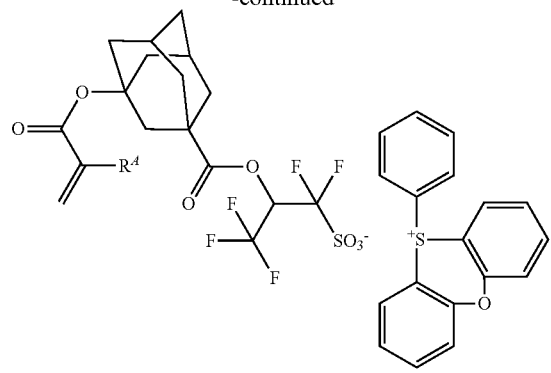
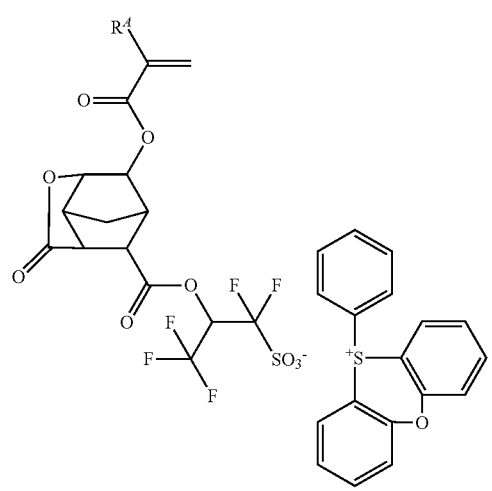
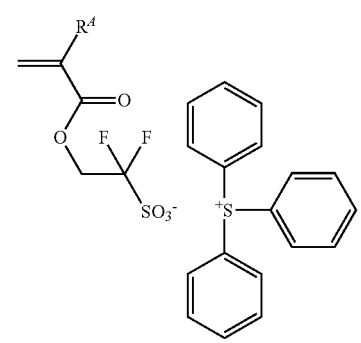
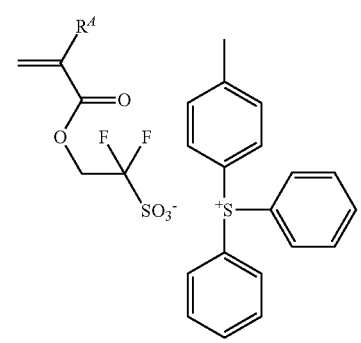
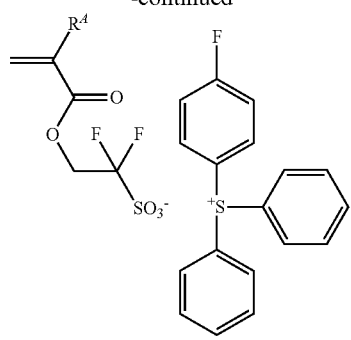
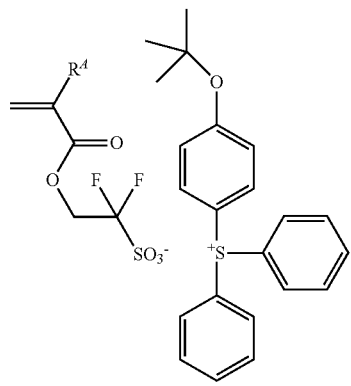
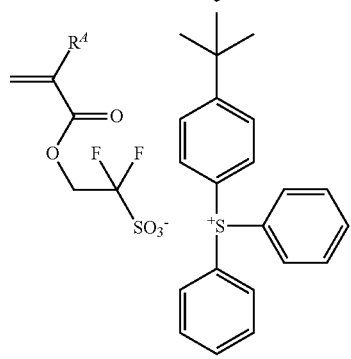
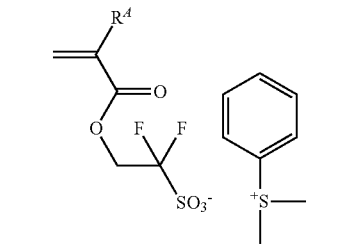
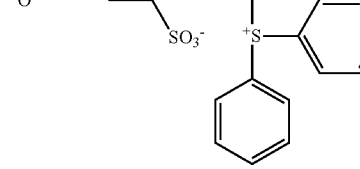

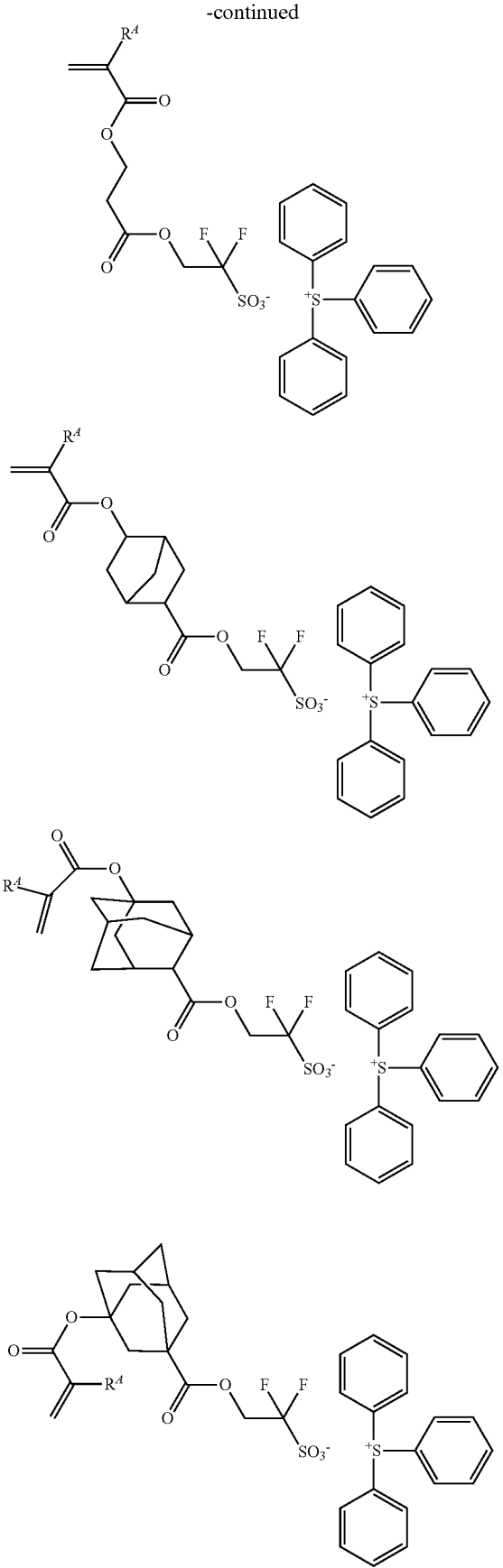
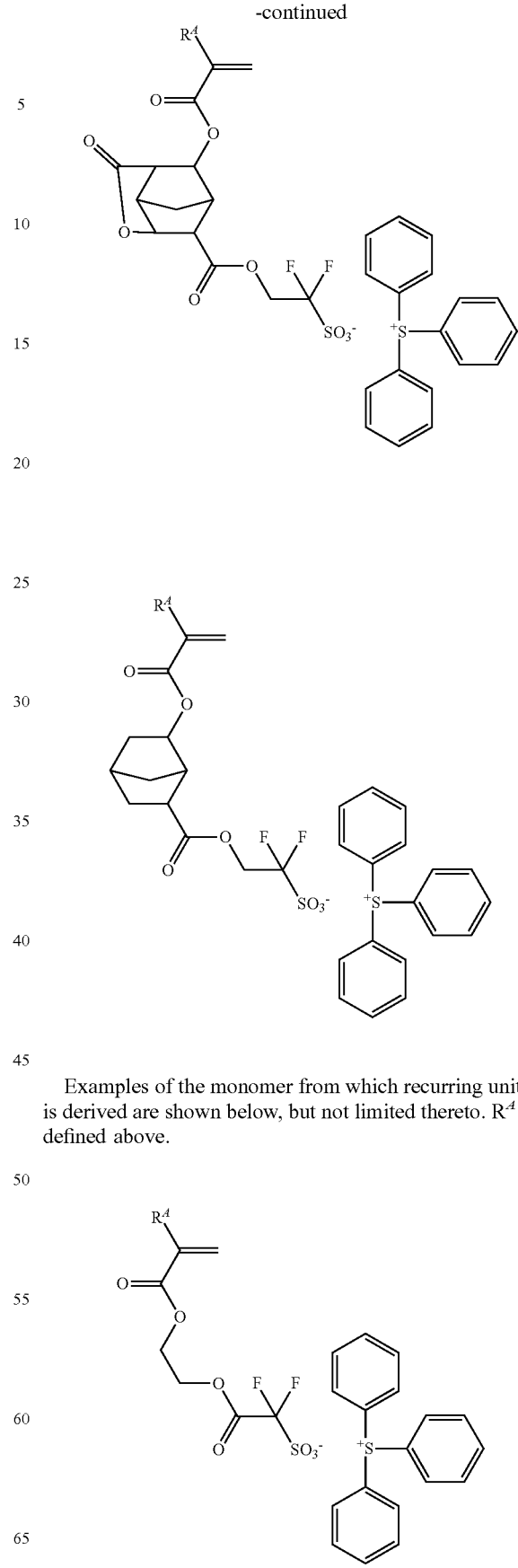
Examples of the monomer from which recurring unit (f3) is derived are shown below, but not limited thereto. $R^A$ is as defined above.

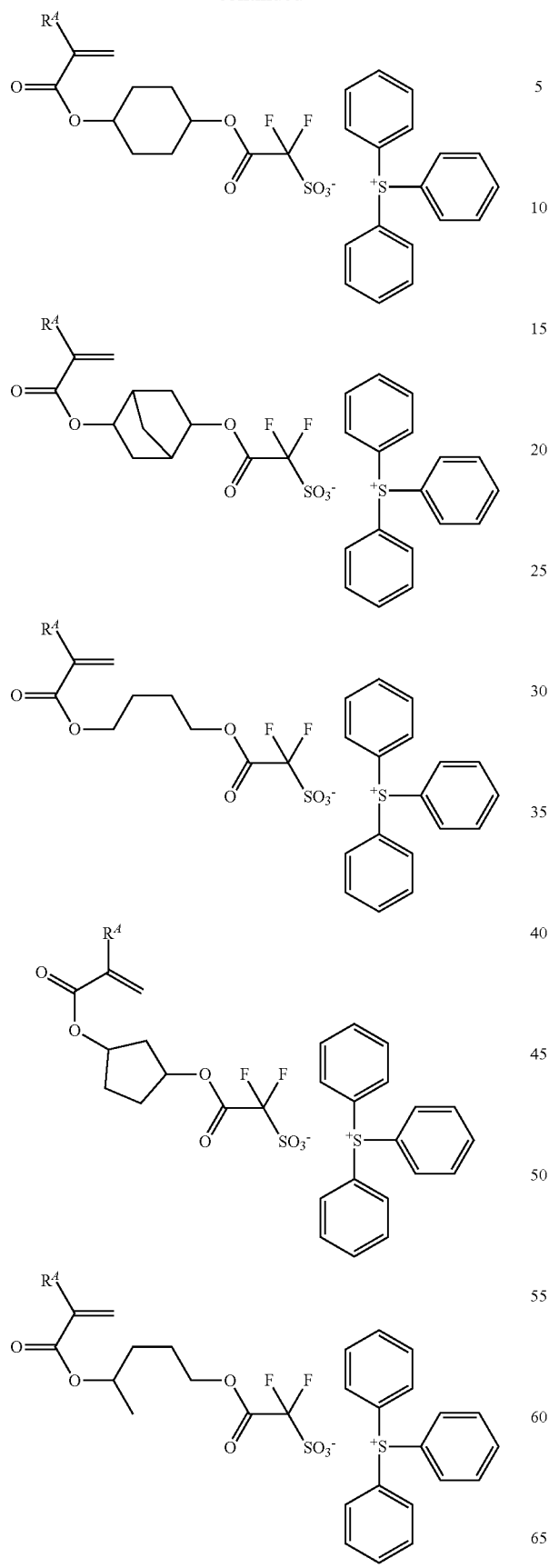
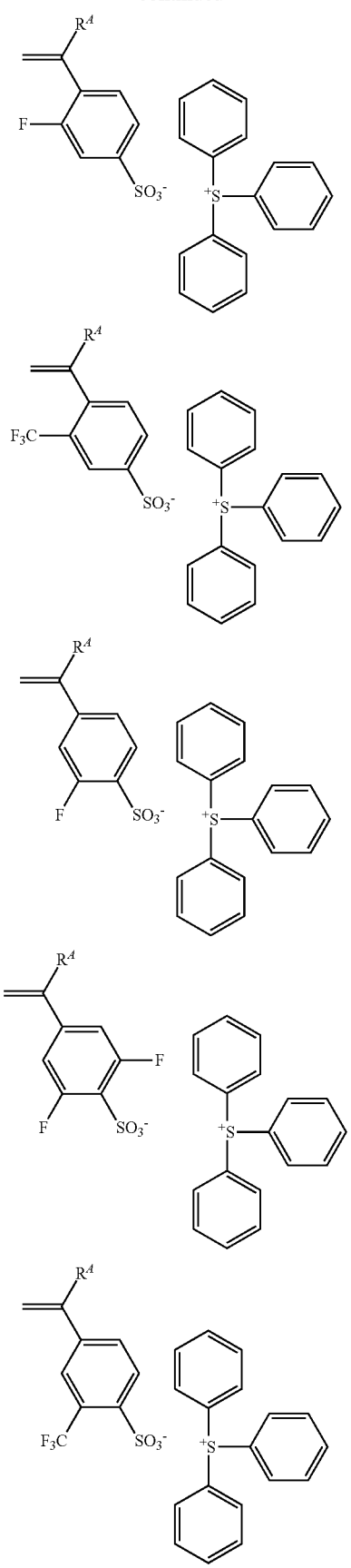

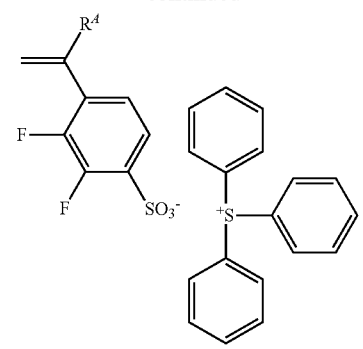
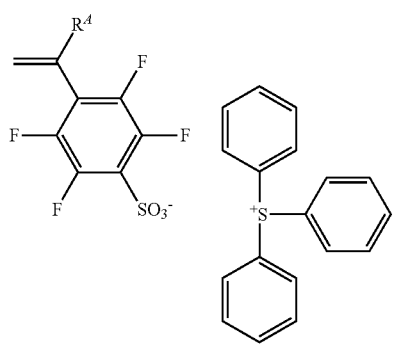
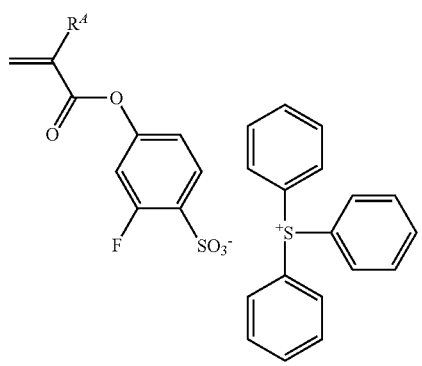
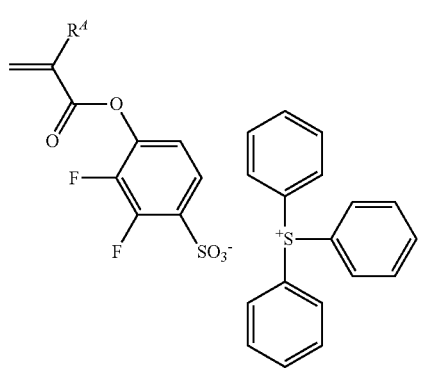
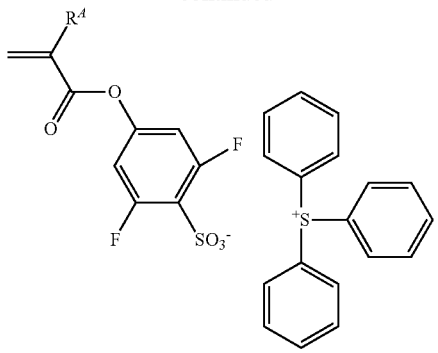
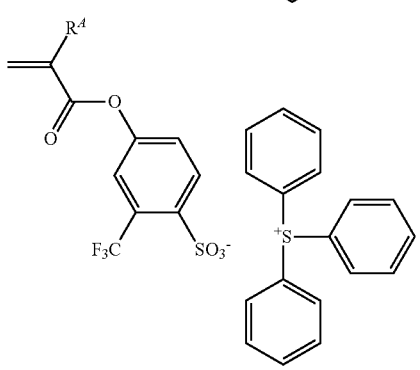
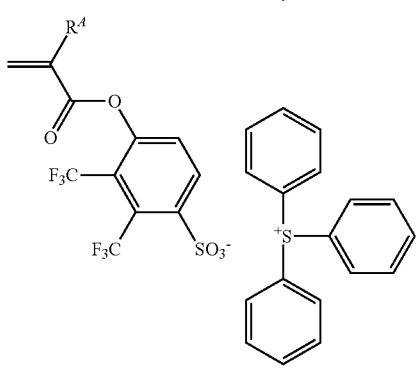
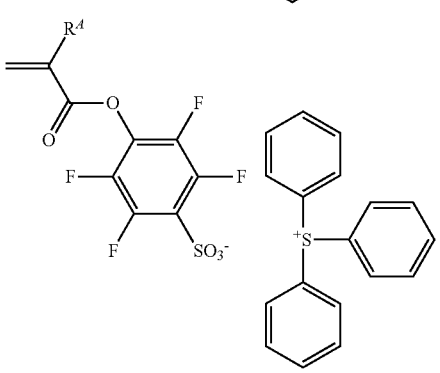
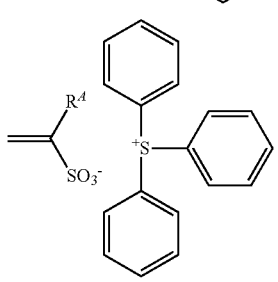

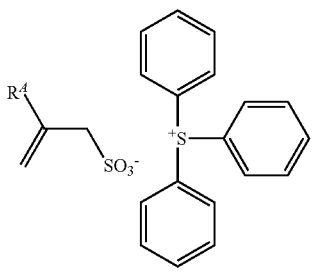

The attachment of an acid generator to the polymer main chain is effective in restraining acid diffusion, thereby preventing a reduction of resolution due to blur by acid diffusion. Also edge roughness is improved since the acid generator is uniformly distributed. Where a base polymer containing recurring units (f) is used, the addition of a separate PAG (to be described later) may be omitted.

The base polymer for formulating the positive resist composition comprises recurring units (a1) or (a2) having an acid labile group as essential component and additional recurring units (b), (c), (d), (e), and (f) as optional components. A fraction of units (a1), (a2), (b), (c), (d), (e), and (0 is: preferably $0≤a1<1.0$, $0≤a2<1.0$, $0<a1+a2<1.0$, $0≤b≤0.9$, $0≤c≤0.9$, $0≤d≤0.8$, $0≤e≤0.8$, and $0≤f≤0.5$; more preferably $0≤a1≤0.9$, $0≤a2≤0.9$, $0.1≤a1+a2≤0.9$, $0≤b≤0.8$, $0≤c≤0.8$, $0≤d≤0.7$, $0≤e≤0.7$, and $0≤f≤0.4$; and even more preferably $0≤a1≤0.8$, $0≤a2≤0.8$, $0.1≤a1+a2≤0.8$, $0≤b≤0.75$, $0≤c≤0.75$, $0≤d≤0.6$, $0≤e≤0.6$, and $0≤f≤0.3$. Notably, $f=f1+f2+f3$, meaning that unit (f) is at least one of units (f1) to (f3), and $a1+a2+b+c+d+e+f=1.0$.

For the base polymer for formulating the negative resist composition, an acid labile group is not necessarily essential. The base polymer comprises recurring units (b), and optionally recurring units (c), (d), (e), and/or (0. A fraction of these units is: preferably $0<b≤1.0$, $0≤c≤0.9$, $0≤d≤0.8$, $0≤e≤0.8$, and $0≤f≤0.5$; more preferably $0.2≤b≤1.0$, $0≤c≤0.8$, $0≤d≤0.7$, $0≤e≤0.7$, and $0≤f≤0.4$; and even more preferably $0.3≤b≤1.0$, $0≤c≤0.75$, $0≤d≤0.6$, $0≤e≤0.6$, and $0≤f≤0.3$. Notably, $f=f1+f2+f3$, meaning that unit (f) is at least one of units (f1) to (f3), and $b+c+d+e+f=1.0$.

The base polymer may be synthesized by any desired methods, for example, by dissolving one or more monomers selected from the monomers corresponding to the foregoing recurring units in an organic solvent, adding a radical polymerization initiator thereto, and heating for polymerization. Examples of the organic solvent which can be used for polymerization include toluene, benzene, tetrahydrofuran, diethyl ether, and dioxane. Examples of the polymerization initiator used herein include 2,2'-azobisisobutyronitrile (AIBN), 2,2'-azobis(2,4-dimethylvaleronitrile), dimethyl 2,2-azobis(2-methylpropionate), benzoyl peroxide, and lauroyl peroxide. Preferably the reaction temperature is 50 to 80° C., and the reaction time is 2 to 100 hours, more preferably 5 to 20 hours.

In the case of a monomer having a hydroxyl group, the hydroxyl group may be replaced by an acetal group susceptible to deprotection with acid, typically ethoxyethoxy, prior to polymerization, and the polymerization be followed by deprotection with weak acid and water. Alternatively, the hydroxyl group may be replaced by an acetyl, formyl, pivaloyl or similar group prior to polymerization, and the polymerization be followed by alkaline hydrolysis.

When hydroxystyrene or hydroxyvinylnaphthalene is copolymerized, an alternative method is possible. Specifically, acetoxystyrene or acetoxyvinylnaphthalene is used instead of hydroxystyrene or hydroxyvinylnaphthalene, and after polymerization, the acetoxy group is deprotected by alkaline hydrolysis, for thereby converting the polymer product to hydroxystyrene or hydroxyvinylnaphthalene. For alkaline hydrolysis, a base such as aqueous ammonia or triethylamine may be used. Preferably the reaction temperature is −20° C. to 100° C., more preferably 0° C. to 60° C., and the reaction time is 0.2 to 100 hours, more preferably 0.5 to 20 hours.

The base polymer should preferably have a weight average molecular weight (Mw) in the range of 1,000 to 500,000, and more preferably 2,000 to 30,000, as measured by GPC versus polystyrene standards using tetrahydrofuran (THF) solvent. With too low a Mw, the resist composition may become less heat resistant. A polymer with too high a Mw may lose alkaline solubility and give rise to a footing phenomenon after pattern formation.

If a base polymer has a wide molecular weight distribution or dispersity (Mw/Mn), which indicates the presence of lower and higher molecular weight polymer fractions, there is a possibility that foreign matter is left on the pattern or the pattern profile is degraded. The influences of molecular weight and dispersity become stronger as the pattern rule becomes finer. Therefore, the base polymer should preferably have a narrow dispersity (Mw/Mn) of 1.0 to 2.0, especially 1.0 to 1.5, in order to provide a resist composition suitable for micropatterning to a small feature size.

The base polymer may be a blend of two or more polymers (defined herein) which differ in compositional ratio, Mw or Mw/Mn. Also the base polymer may or may not contain a polymer different from the polymer defined herein, although it is preferred that the base polymer be free of a different polymer.

Acid Generator

The resist composition may include an acid generator (also referred to as acid generator of addition type) capable of generating a stronger acid than the brominated benzene-containing sulfonic acid. Now that the resist composition contains an acid generator of addition type, the onium salt functions as a quencher and the resist composition functions as a chemically amplified positive or negative resist composition. As a result of adding an acid generator, the resist composition becomes quite useful because its sensitivity becomes higher and other properties become better. It is noted that no acid generator of addition type need be added when the base polymer contains recurring units (f), that is, an acid generator has been bound in the base polymer.

The acid generator of addition type is typically a compound (PAG) capable of generating an acid upon exposure to actinic ray or radiation. Although the PAG used herein may be any compound capable of generating an acid upon exposure to high-energy radiation, those compounds capable of generating fluorinated sulfonic acid, imide acid (imidic acid) or methide acid are preferred. Suitable PAGs include sulfonium salts, iodonium salts, sulfonyldiazomethane, N-sulfonyloxyimide, and oxime-O-sulfonate acid generators. Exemplary PAGs are described in JP-A 2008-111103, paragraphs [0122]-[0142] (U.S. Pat. No. 7,537,880).

As the PAG used herein, those having the formula (1) are preferred.

(1)

In formula (1), $R^{101}$, $R^{102}$ and $R^{103}$ are each independently a $C_1$-$C_{20}$ monovalent hydrocarbon group which may contain a heteroatom. Any two of $R^{101}$, $R^{102}$ and $R^{103}$ may bond together to form a ring with the sulfur atom to which they are attached. The monovalent hydrocarbon group may be straight, branched or cyclic, and examples thereof are as described above in conjunction with $R^3$ to $R^5$ in formulae (A-1) and (A-2).

Examples of the cation of the sulfonium salt having formula (1) are as exemplified above for the cation of the sulfonium salt having formula (A-1) or (A-2).

In formula (1), $X^-$ is an anion of the following formula (1A), (1B), (1C) or (1D).

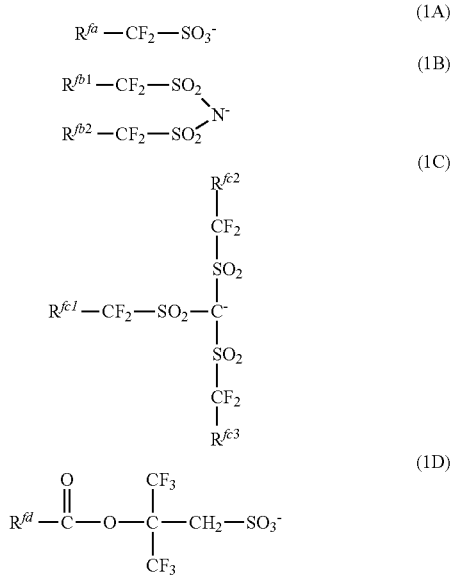

In formula (1A), $R^{fa}$ is fluorine or a $C_1$-$C_{40}$ monovalent hydrocarbon group which may contain a heteroatom. The monovalent hydrocarbon group may be straight, branched or cyclic, and examples thereof are as will be exemplified for $R^{105}$ later.

Of the anions of formula (1A), an anion having the formula (1A') is preferred.

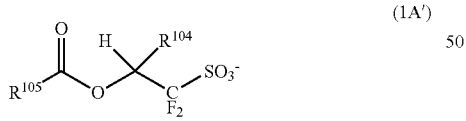

In formula (1A'), $R^{104}$ is hydrogen or trifluoromethyl, preferably trifluoromethyl. $R^{105}$ is a $C_1$-$C_{38}$ monovalent hydrocarbon group which may contain a heteroatom. Suitable heteroatoms include oxygen, nitrogen, sulfur and halogen, with oxygen being preferred. Those monovalent hydrocarbon groups of 6 to 30 carbon atoms are preferred because a high resolution is available in fine pattern formation. The monovalent hydrocarbon groups may be straight, branched or cyclic. Suitable monovalent hydrocarbon groups include straight or branched alkyl groups such as methyl, ethyl, propyl, isopropyl, butyl, isobutyl, s-butyl, t-butyl, pentyl, neopentyl, hexyl, heptyl, 2-ethylhexyl, nonyl, undecyl, tridecyl, pentadecyl, heptadecyl, and icosanyl; monovalent saturated cycloaliphatic hydrocarbon groups such as cyclopentyl, cyclohexyl, 1-adamantyl, 2-adamantyl, 1-adamantylmethyl, norbornyl, norbornylmethyl, tricyclodecanyl, tetracyclododecanyl, tetracyclododecanylmethyl, and dicyclohexylmethyl; monovalent unsaturated aliphatic hydrocarbon groups such as allyl and 3-cyclohexenyl; and aralkyl groups such as benzyl and diphenylmethyl. Suitable heteroatom-containing monovalent hydrocarbon groups include tetrahydrofuryl, methoxymethyl, ethoxymethyl, methylthiomethyl, acetamidomethyl, trifluoroethyl, (2-methoxyethoxy)methyl, acetoxymethyl, 2-carboxy-1-cyclohexyl, 2-oxopropyl, 4-oxo-1-adamantyl, and 3-oxocyclohexyl. Also included are the foregoing groups in which at least one hydrogen is substituted by a moiety containing a heteroatom such as oxygen, sulfur, nitrogen or halogen, or in which at least one carbon is substituted by a moiety containing a heteroatom such as oxygen, sulfur or nitrogen, so that the group may contain a hydroxyl, cyano, carbonyl, ether bond, ester bond, sulfonic acid ester bond, carbonate, lactone ring, sultone ring, carboxylic acid anhydride or haloalkyl moiety.

With respect to the synthesis of the sulfonium salt having an anion of formula (1A'), reference may be made to JP-A 2007-145797, JP-A 2008-106045, JP-A 2009-007327, and JP-A 2009-258695. Also useful are the sulfonium salts described in JP-A 2010-215608, JP-A 2012-041320, JP-A 2012-106986, and JP-A 2012-153644.

Examples of the anion having formula (1A) are shown below, but not limited thereto.

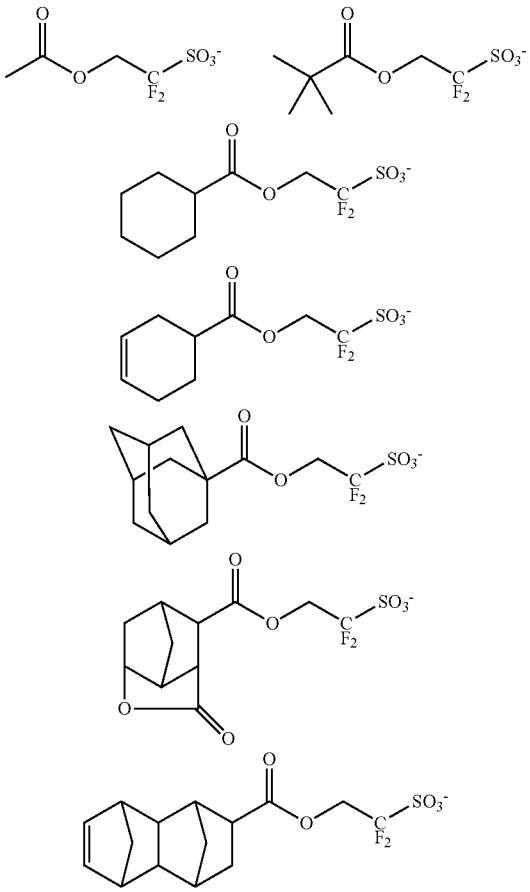

103
-continued
104
-continued
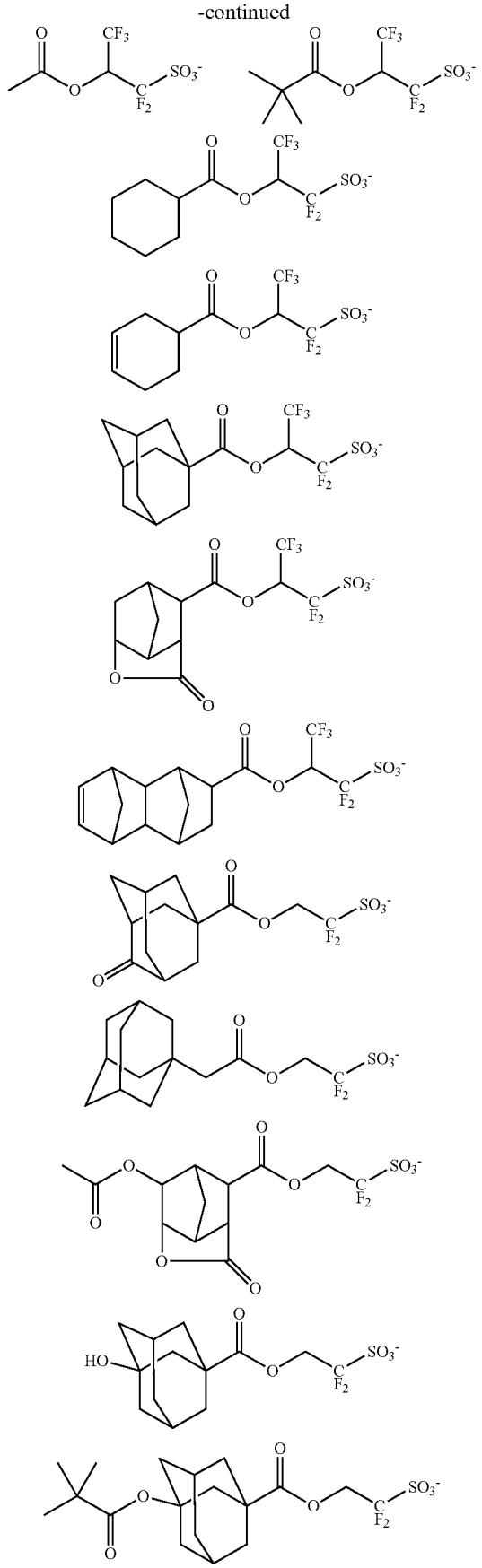
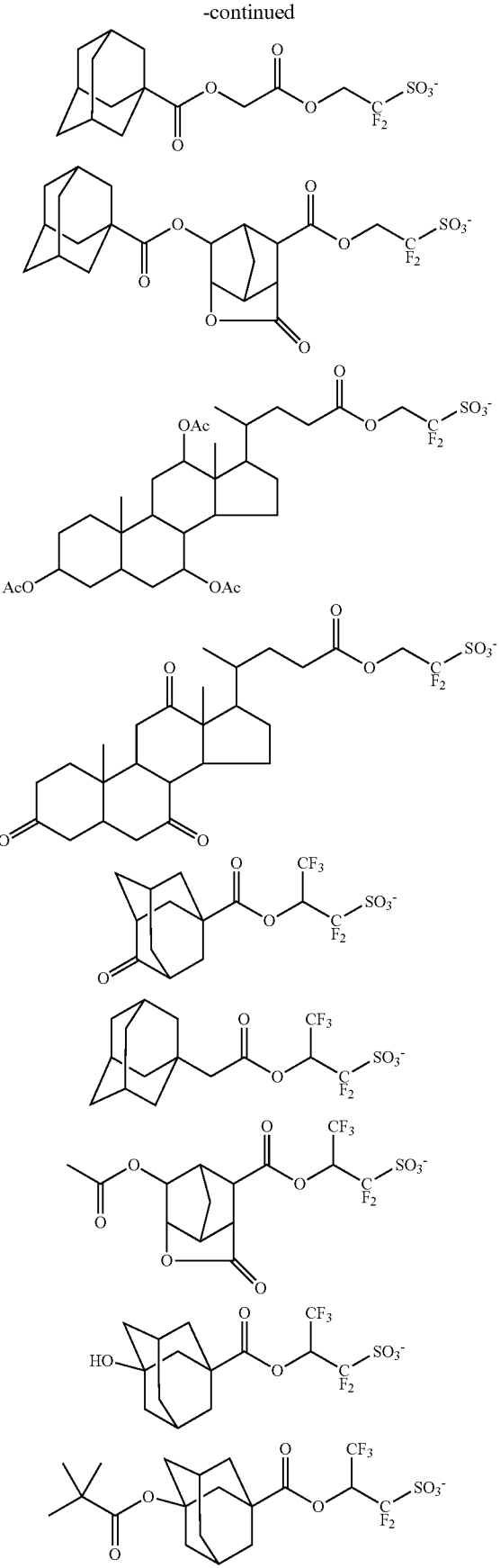

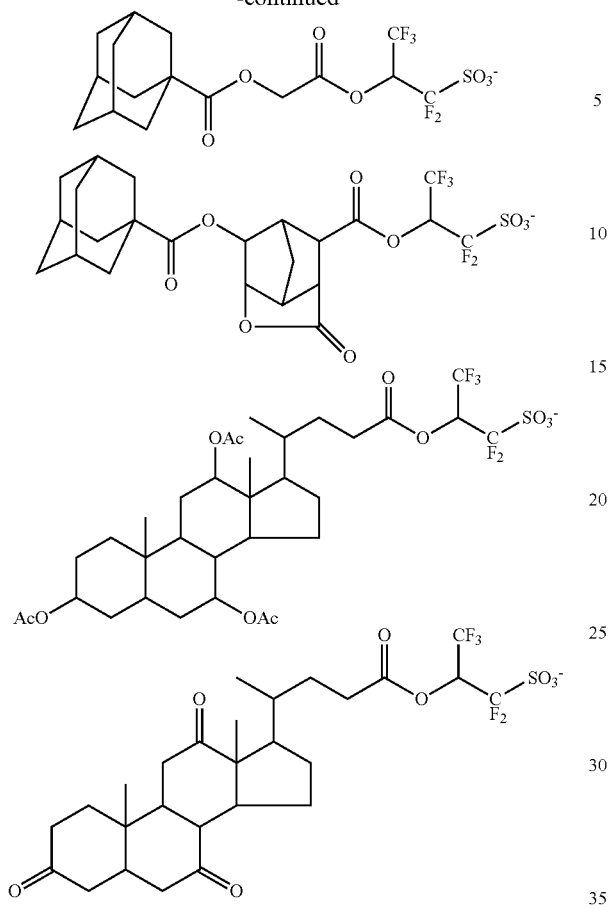

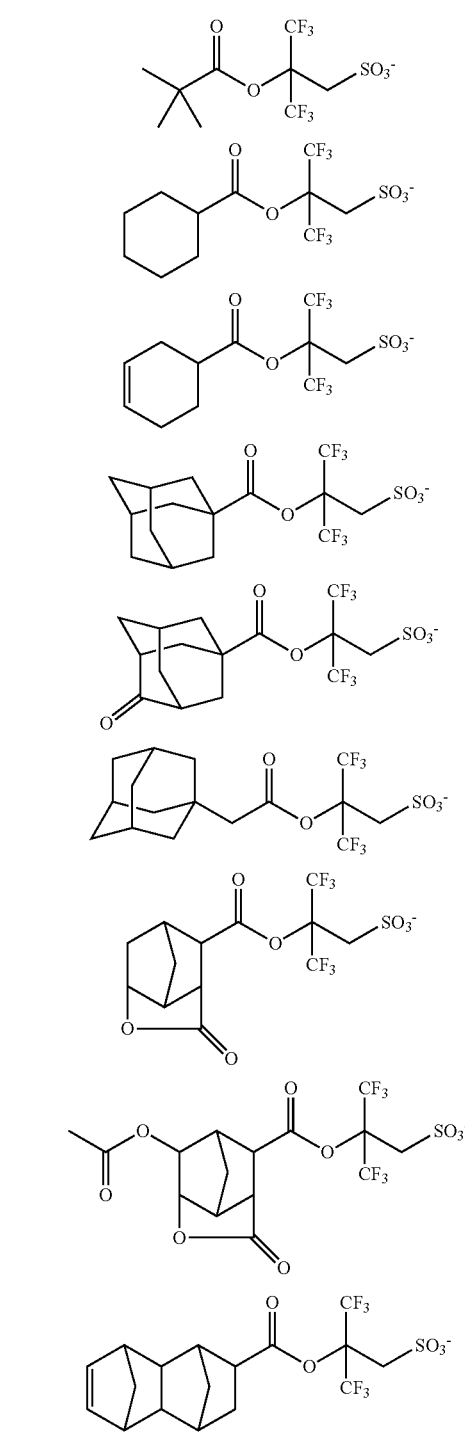

In formula (1B), $R^{fb1}$ and $R^{fb2}$ are each independently fluorine or a $C_1$-$C_{40}$ monovalent hydrocarbon group which may contain a heteroatom. The monovalent hydrocarbon groups may be straight, branched or cyclic, and examples thereof are as exemplified above for $R^{105}$. Preferably $R^{fb1}$ and $R^{fb2}$ each are fluorine or a straight $C_1$-$C_4$ fluorinated alkyl group. A pair of $R^{fb1}$ and $R^{fb2}$ may bond together to form a ring with the linkage (—$CF_2$—$SO_2$—$N^-$—$SO_2$—$CF_2$—) to which they are attached, and preferably the pair is a fluorinated ethylene or fluorinated propylene group.

In formula (1C), $R^{fb1}$, $R^{fc2}$ and $R^{fc3}$ are each independently fluorine or a $C_1$-$C_{40}$ monovalent hydrocarbon group which may contain a heteroatom. The monovalent hydrocarbon groups may be straight, branched or cyclic, and examples thereof are as exemplified above for $R^{105}$. Preferably $R^{fb1}$, $R^{fc2}$ and $R^{fc3}$ each are fluorine or a straight $C_1$-$C_4$ fluorinated alkyl group. A pair of $R^{fc1}$ and $R^{fc2}$ may bond together to form a ring with the linkage (—$CF_2$—$SO_2$—$C^-$—$SO_2$—$CF_2$—) to which they are attached, and preferably the pair is a fluorinated ethylene or fluorinated propylene group.

In formula (1D), $R^{fd}$ is a $C_1$-$C_{40}$ monovalent hydrocarbon group which may contain a heteroatom. The monovalent hydrocarbon groups may be straight, branched or cyclic, and examples thereof are as exemplified above for $R^{105}$.

With respect to the synthesis of the sulfonium salt having an anion of formula (1D), reference is made to JP-A 2010-215608 and JP-A 2014-133723.

Examples of the anion having formula (1D) are shown below, but not limited thereto.

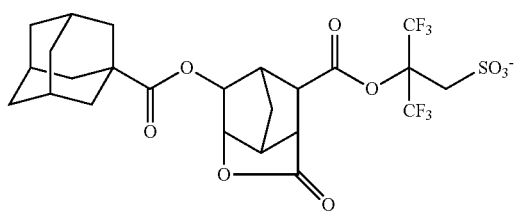

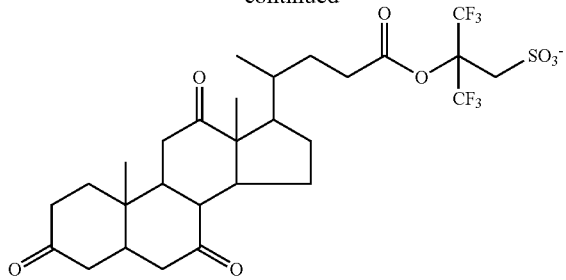

The compound having the anion of formula (1D) has a sufficient acid strength to cleave acid labile groups in the base polymer because it is free of fluorine at α-position of sulfo group, but has two trifluoromethyl groups at β-position. Thus the compound is a useful PAG.

Further, compounds having the formula (2) are useful as the PAG.

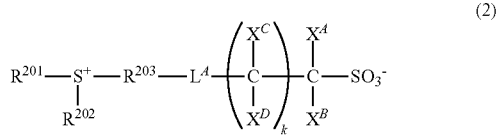

In formula (2), $R^{201}$ and $R^{202}$ are each independently a $C_1$-$C_{30}$ monovalent hydrocarbon group which may contain a heteroatom. $R^{203}$ is a $C_1$-$C_{30}$ divalent hydrocarbon group which may contain a heteroatom. Any two of $R^{201}$, $R^{202}$ and $R^{203}$ may bond together to form a ring with the sulfur atom to which they are attached. $L^A$ is a single bond or ether bond, or a $C_1$-$C_{20}$ divalent hydrocarbon group which may contain a heteroatom. $X^A$, $X^B$, $X^C$ and $X^D$ are each independently hydrogen, fluorine or trifluoromethyl, with the proviso that at least one of $X^A$, $X^B$, $X^C$ and $X^D$ is fluorine or trifluoromethyl, and k is an integer of 0 to 3.

The monovalent hydrocarbon groups may be straight, branched or cyclic and include straight or branched alkyl groups such as methyl, ethyl, propyl, isopropyl, n-butyl, s-butyl, t-butyl, n-pentyl, t-pentyl, n-hexyl, n-octyl, n-nonyl, n-decyl, and 2-ethylhexyl; monovalent saturated cyclic hydrocarbon groups such as cyclopentyl, cyclohexyl, cyclopentylmethyl, cyclopentylethyl, cyclopentylbutyl, cyclohexylmethyl, cyclohexylethyl, cyclohexylbutyl, norbornyl, oxanorbornyl, tricyclo[5.2.1.0$^{2,6}$]decanyl, and adamantyl; and aryl groups such as phenyl, naphthyl and anthracenyl. Also included are the foregoing groups in which at least one hydrogen is substituted by a heteroatom such as oxygen, sulfur, nitrogen or halogen, or in which at least one carbon is substituted by a moiety containing a heteroatom such as oxygen, sulfur or nitrogen, so that the group may contain a hydroxyl, cyano, carbonyl, ether bond, ester bond, sulfonic acid ester bond, carbonate, lactone ring, sultone ring, carboxylic acid anhydride or haloalkyl moiety.

The divalent hydrocarbon groups may be straight, branched or cyclic, and examples thereof include linear or branched alkane diyl groups such as methylene, ethylene, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, tridecane-1,13-diyl, tetradecane-1,14-diyl, pentadecane-1,15-diyl, hexadecane-1,16-diyl, heptadecane-1,17-diyl; saturated cyclic divalent hydrocarbon groups such as cyclopentanediyl, cyclohexanediyl, norbornanediyl, and adamantanediyl; and unsaturated cyclic divalent hydrocarbon groups such as phenylene and naphthylene. Also included are the foregoing groups in which at least one hydrogen atom is substituted by an alkyl group such as methyl, ethyl, propyl, n-butyl or t-butyl, or in which at least one hydrogen atom is substituted by a moiety containing a heteroatom such as oxygen, sulfur, nitrogen or halogen, or in which at least one carbon atom is substituted by a moiety containing a heteroatom such as oxygen, sulfur or nitrogen, so that the group may contain a hydroxyl, cyano, carbonyl, ether bond, ester bond, sulfonic acid ester bond, carbonate, lactone ring, sultone ring, carboxylic acid anhydride or haloalkyl moiety. Suitable heteroatoms include oxygen, nitrogen, sulfur and halogen, with oxygen being preferred.

Of the PAGs having formula (2), those having formula (2') are preferred.

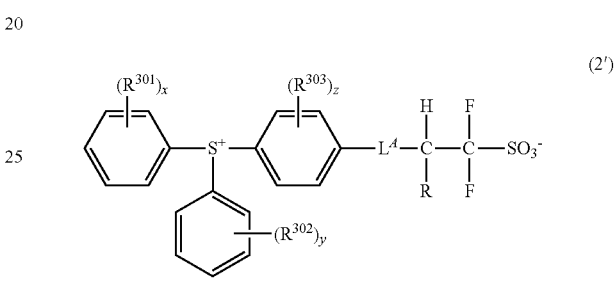

In formula (2'), $L^A$ is as defined above. R is hydrogen or trifluoromethyl, preferably trifluoromethyl. $R^{301}$, $R^{302}$ and $R^{303}$ are each independently hydrogen or a $C_1$-$C_{20}$ monovalent hydrocarbon group which may contain a heteroatom. The monovalent hydrocarbon groups may be straight, branched or cyclic, and examples thereof are as exemplified above for $R^{105}$. The subscripts x and y each are an integer of 0 to 5, and z is an integer of 0 to 4.

Examples of the PAG having formula (2) are shown below, but not limited thereto. Herein R is as defined above.

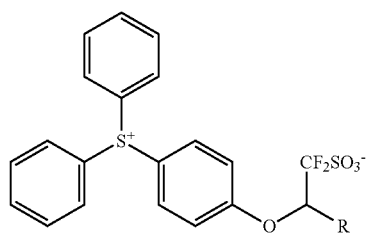

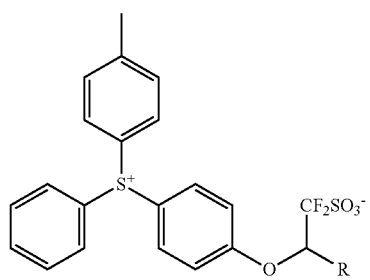

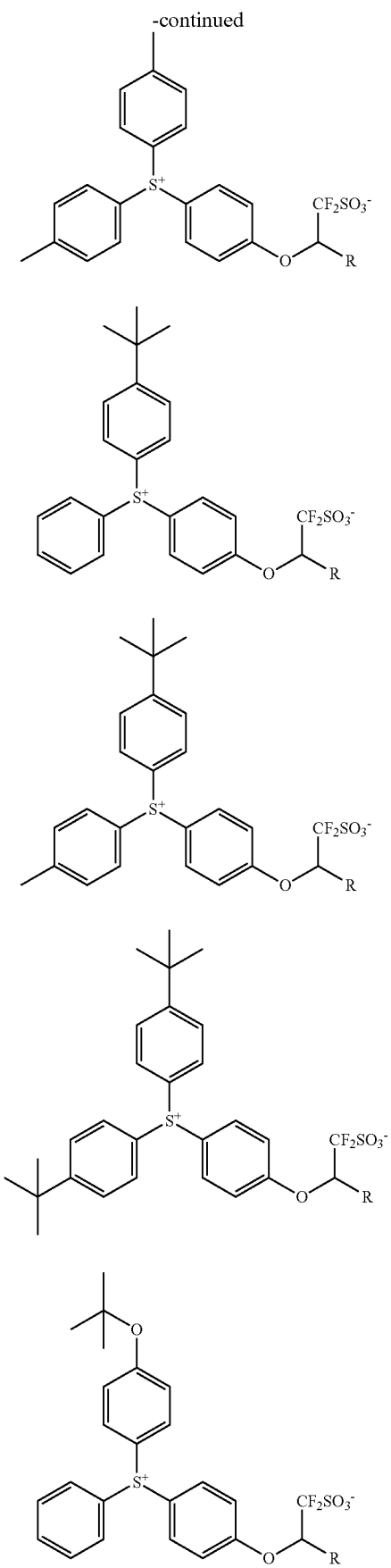
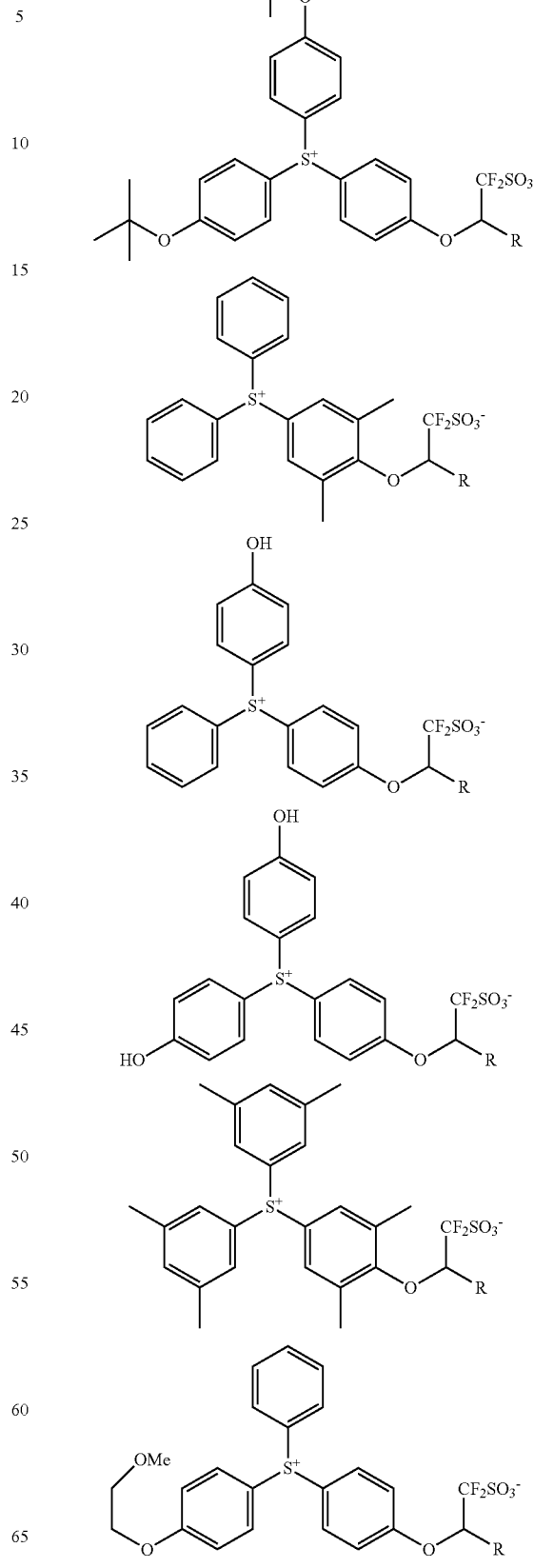

111
-continued
112
-continued
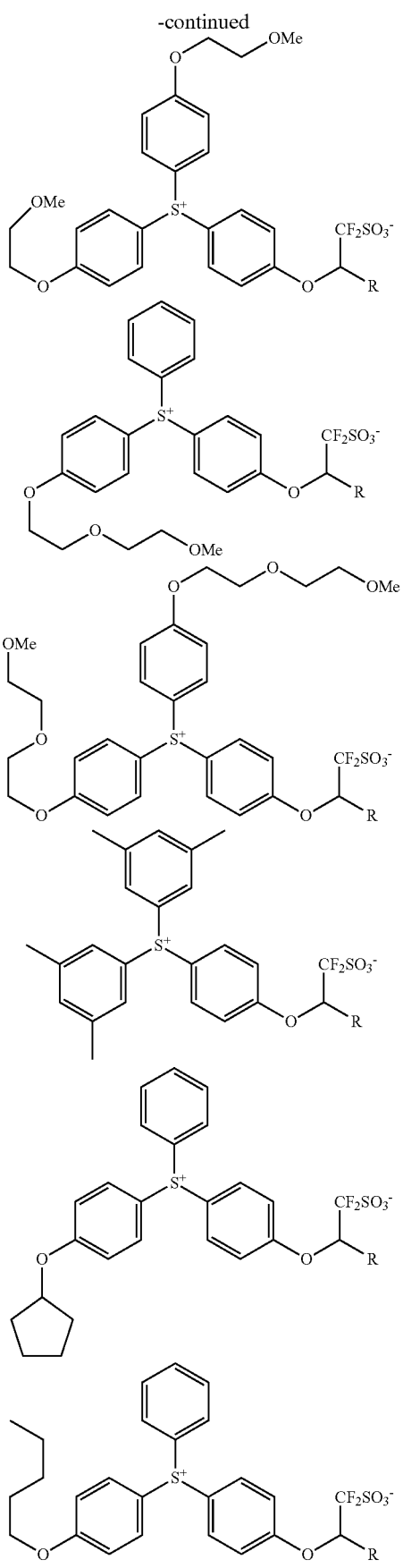
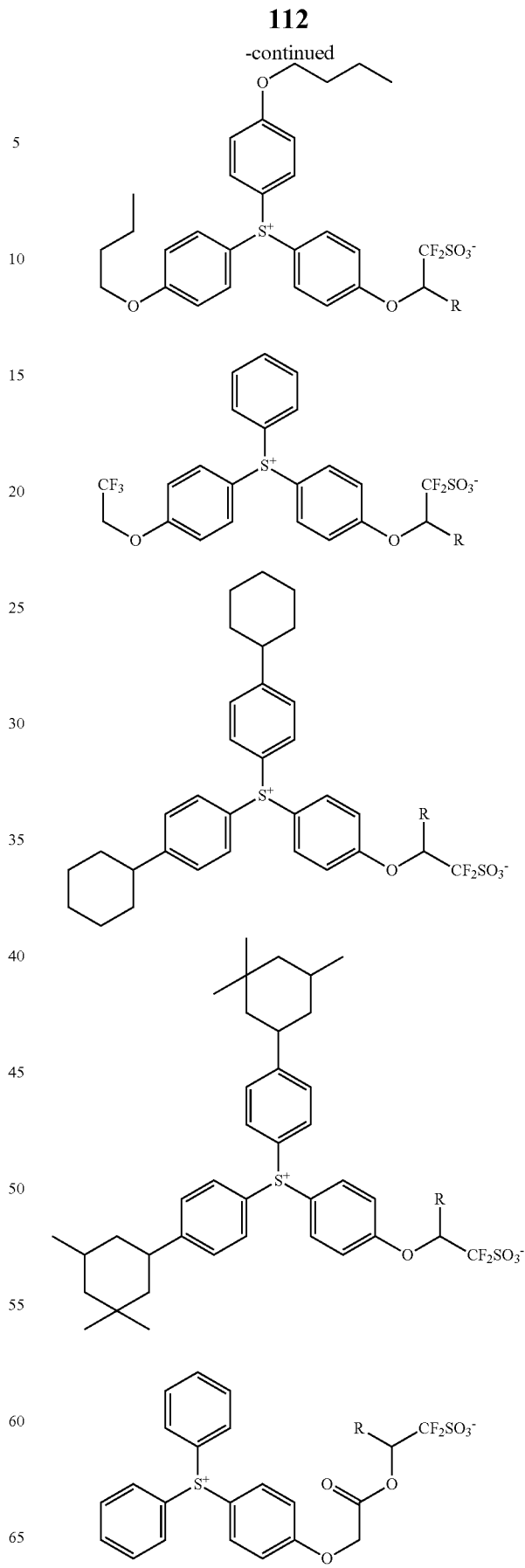

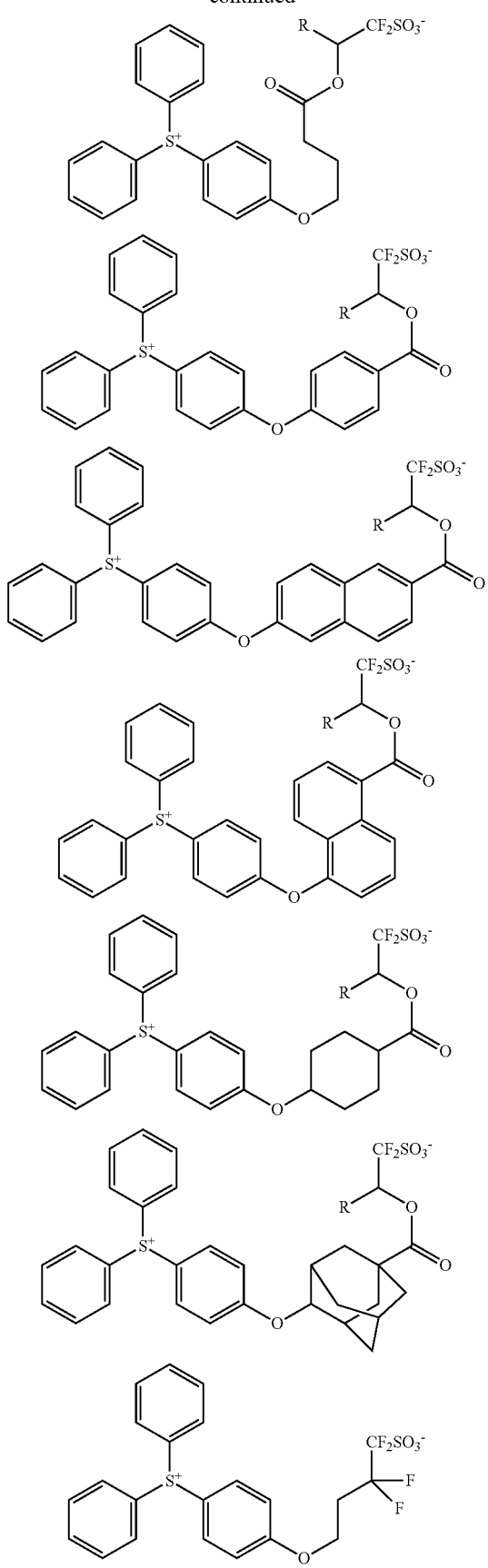
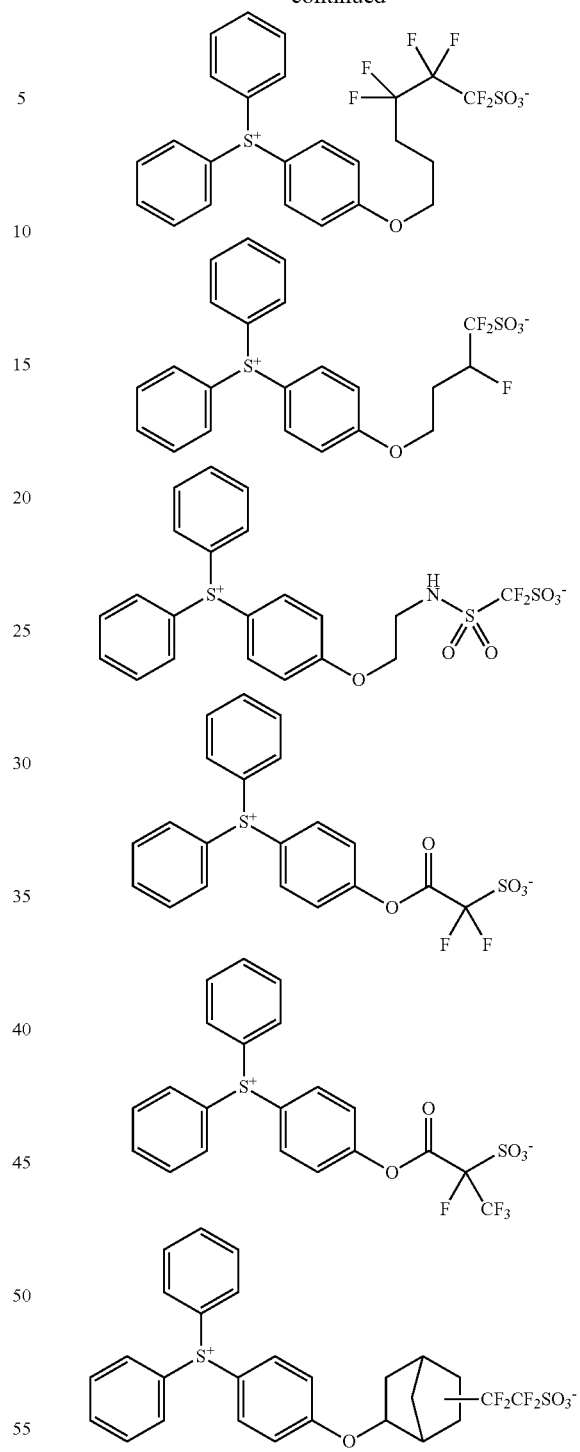

Of the foregoing PAGs, those compounds having an anion of formula (1A') or (1D) are especially preferred because of reduced acid diffusion and high solubility in resist solvent, and those compounds having an anion of formula (2') are especially preferred because of minimized acid diffusion.

Sulfonium and iodonium salts of iodized anions are also useful as the PAG. Preferred are sulfonium and iodonium salts of iodized benzoyloxy-containing fluorinated sulfonic acid having the formulae (3-1) and (3-2).

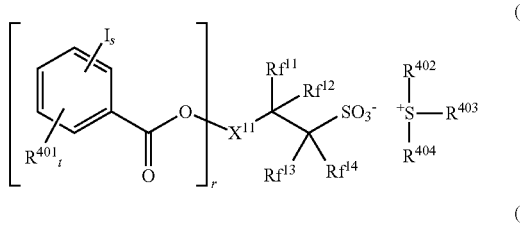

(3-1)

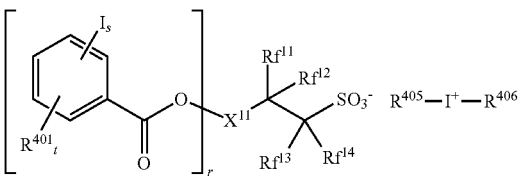

(3-2)

In formulae (3-1) and (3-2), $R^{401}$ is hydrogen, hydroxyl, carboxyl, nitro, cyano, fluorine, chlorine, bromine, amino group, or a $C_1$-$C_{20}$ alkyl, $C_1$-$C_{20}$ alkoxy, $C_2$-$C_{20}$ alkoxycarbonyl, $C_2$-$C_{20}$ acyloxy or $C_1$-$C_4$ alkylsulfonyloxy group, which may contain fluorine, chlorine, bromine, hydroxy, amino or alkoxy moiety, or —$NR^{407}$—$C(=O)$—$R^{408}$ or —$NR^{407}$—$C(=O)$—$O$—$R^{408}$, wherein $R^{407}$ is hydrogen, or a $C_1$-$C_6$ alkyl group which may contain halogen, hydroxy, alkoxy, acyl or acyloxy moiety, $R^{408}$ is a $C_1$-$C_{16}$ alkyl, $C_2$-$C_{16}$ alkenyl, or $C_6$-$C_{12}$ aryl group, which may contain halogen, hydroxy, alkoxy, acyl or acyloxy moiety.

$X^{11}$ is a single bond or a $C_1$-$C_{20}$ divalent linking group when r=1, or a $C_1$-$C_{20}$ tri- or tetravalent linking group when r=2 or 3, the linking group optionally containing an oxygen, sulfur or nitrogen atom. $Rf^{11}$ to $Rf^{14}$ are each independently hydrogen, fluorine or trifluoromethyl, at least one of $Rf^{11}$ to $Rf^{14}$ being fluorine or trifluoromethyl. $Rf^{11}$ and $Rf^{12}$, taken together, may form a carbonyl group.

$R^{402}$, $R^{403}$, $R^{404}$, $R^{405}$ and $R^{406}$ are each independently a $C_1$-$C_{20}$ monovalent hydrocarbon group which may contain a heteroatom. Any two of $R^{402}$, $R^{403}$ and $R^{404}$ may bond together to form a ring with the sulfur atom to which they are attached. The monovalent hydrocarbon group may be straight, branched or cyclic, and examples thereof are as exemplified above for $R^3$ to $R^5$ in formulae (A-1) and (A-2). The subscript r is an integer of 1 to 3, s is an integer of 1 to 5, and t is an integer of 0 to 3.

The foregoing alkyl, alkoxy, alkoxycarbonyl, acyloxy, alkylsulfonyloxy, alkenyl and alkynyl groups may be straight, branched or cyclic.

Of the sulfonium and iodonium salts having iodized anions, sulfonium and iodonium salts of iodized benzene-containing fluorinated sulfonic acid having the formulae (3-3) and (3-4) are also preferred.

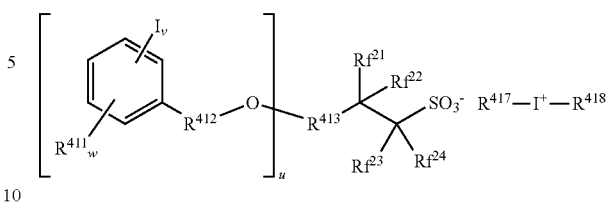

(3-3)

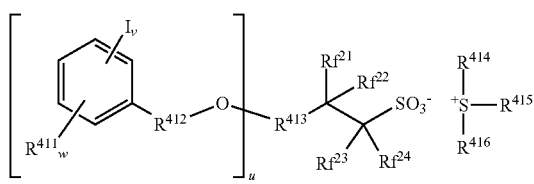

(3-4)

In formulae (3-3) and (3-4), $R^{411}$ is each independently a hydroxyl, $C_1$-$C_{20}$ alkyl or alkoxy group, $C_2$-$C_{20}$ acyl or acyloxy group, fluorine, chlorine, bromine, amino, or alkoxycarbonyl-substituted amino group. $R^{412}$ is each independently a single bond or $C_1$-$C_4$ alkylene group. $R^{413}$ is a single bond or $C_1$-$C_{20}$ divalent linking group when u=1, or a $C_1$-$C_{20}$ tri- or tetravalent linking group when u=2 or 3, the linking group optionally containing an oxygen, sulfur or nitrogen atom.

$Rf^{21}$ to $Rf^{24}$ are each independently hydrogen, fluorine or trifluoromethyl, at least one of $Rf^{21}$ to $Rf^{24}$ being fluorine or trifluoromethyl. $Rf^{21}$ and $Rf^{22}$, taken together, may form a carbonyl group.

$R^{414}$, $R^{415}$, $R^{416}$, $R^{417}$ and $R^{418}$ are each independently a $C_1$-$C_{20}$ monovalent hydrocarbon group which may contain a heteroatom. Any two of $R^{414}$, $R^{415}$ and $R^{416}$ may bond together to form a ring with the sulfur atom to which they are attached. The monovalent hydrocarbon group may be straight, branched or cyclic, and examples thereof are as exemplified above for $R^3$ to $R^5$ in formulae (A-1) and (A-2). The subscript u is an integer of 1 to 3, v is an integer of 1 to 5, and w is an integer of 0 to 3.

The foregoing alkyl, alkoxy, acyl, acyloxy and alkenyl groups may be straight, branched or cyclic.

The cation in the sulfonium salt having formula (3-1) or (3-3) is as exemplified above for the cation in the sulfonium salt of formula (A-1). The cation in the iodonium salt having formula (3-2) or (3-4) is as exemplified above for the cation in the iodonium salt of formula (A-2).

Examples of the anion moiety in the onium salts having formulae (3-1) to (3-4) are given below, but not limited thereto.

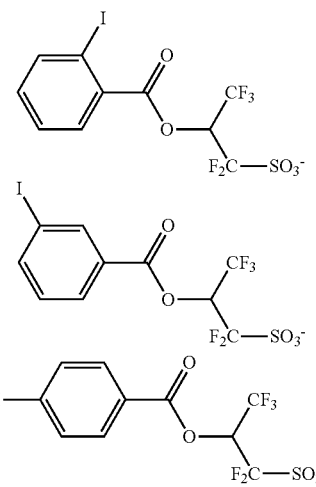

117
-continued
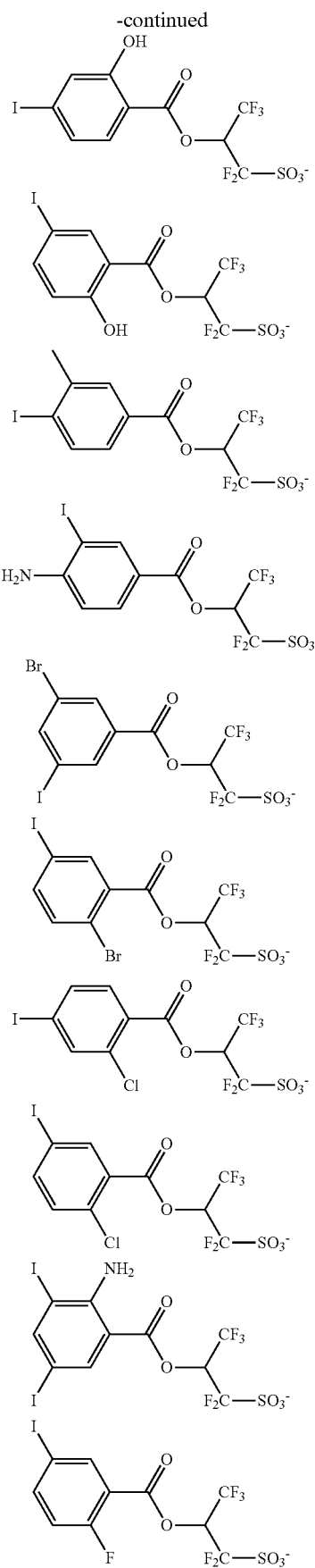
118
-continued
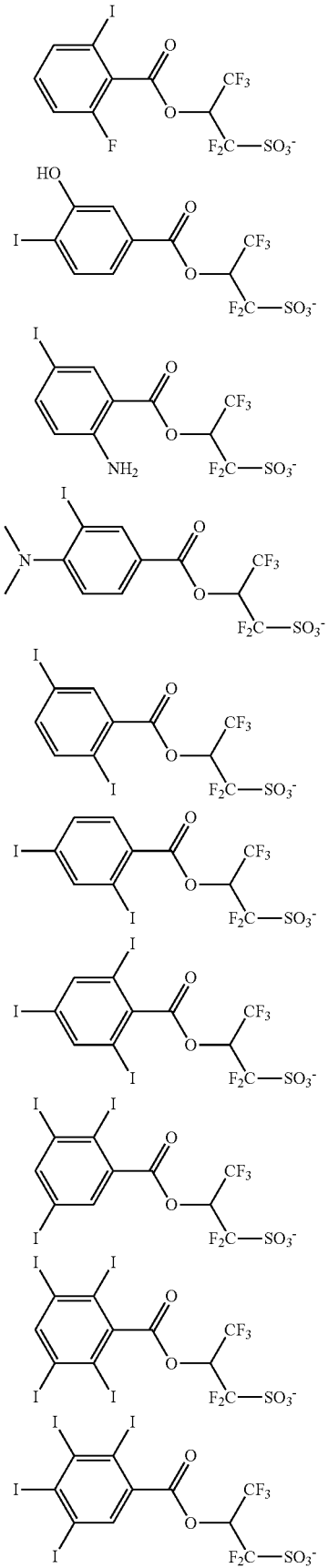

119
-continued
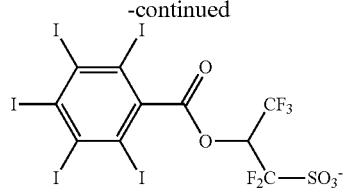
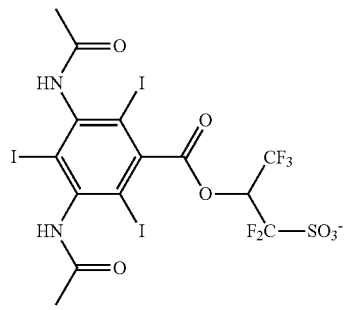
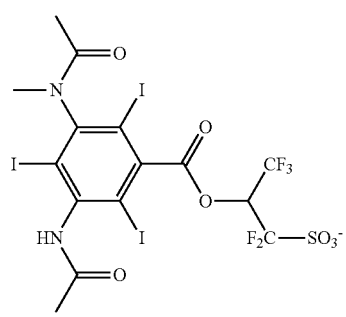
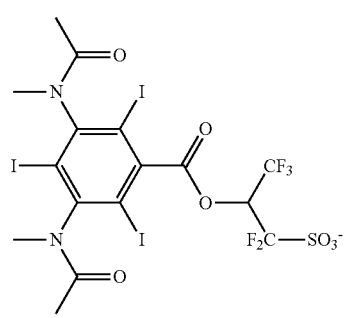
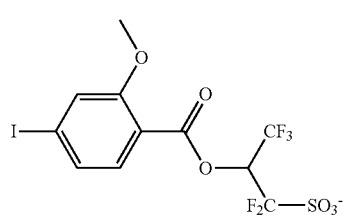
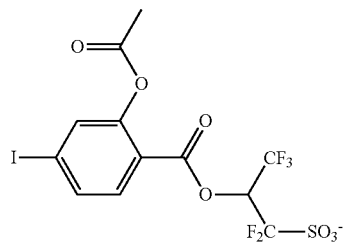
120
-continued
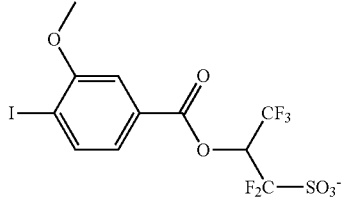
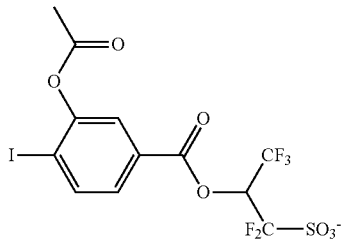
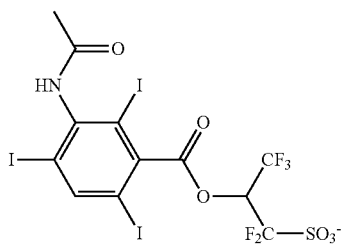
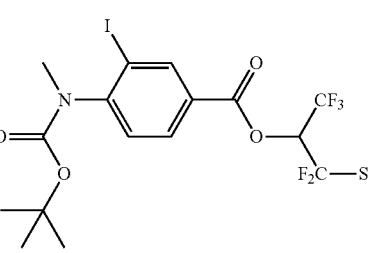
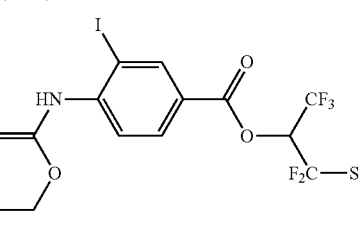
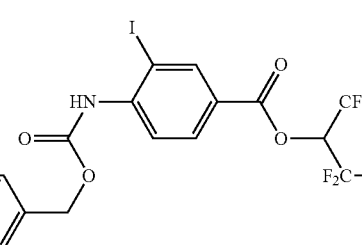
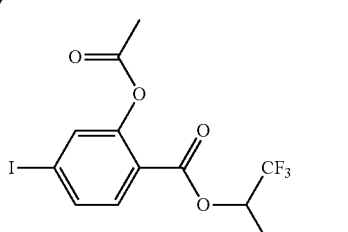

121
-continued
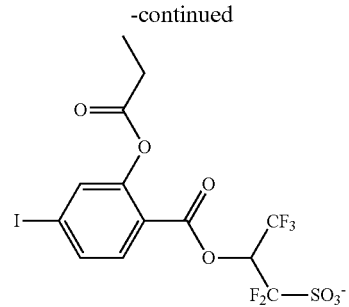
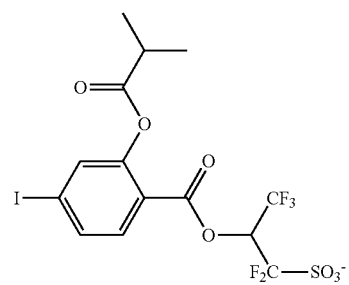
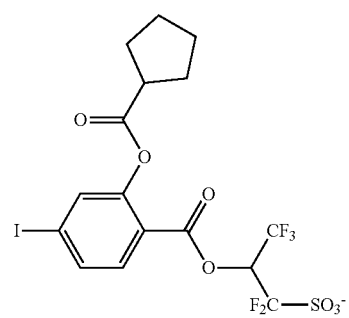
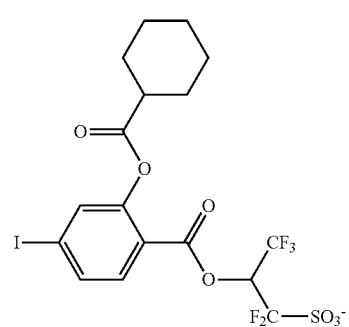
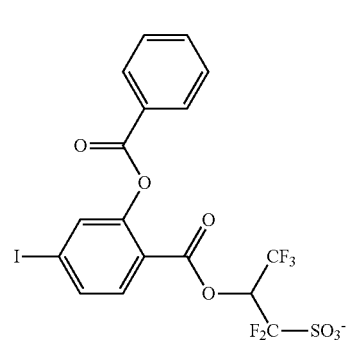
122
-continued
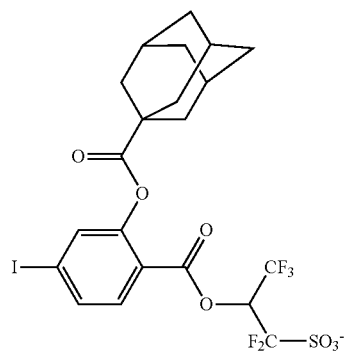
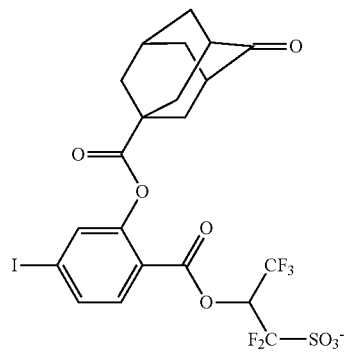
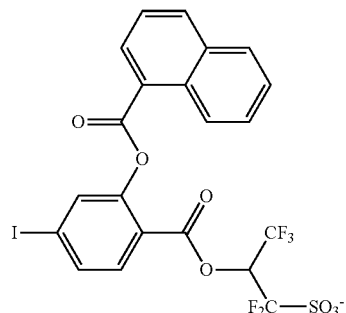
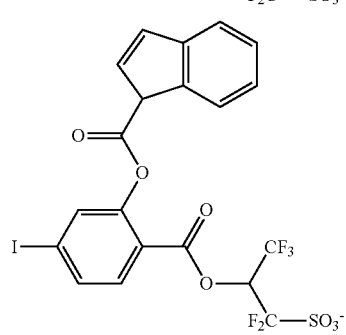
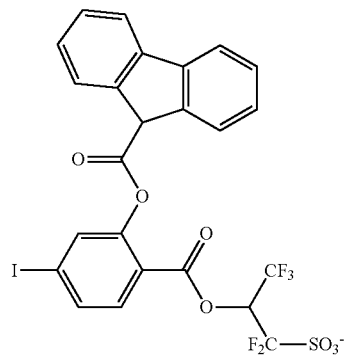

123
-continued
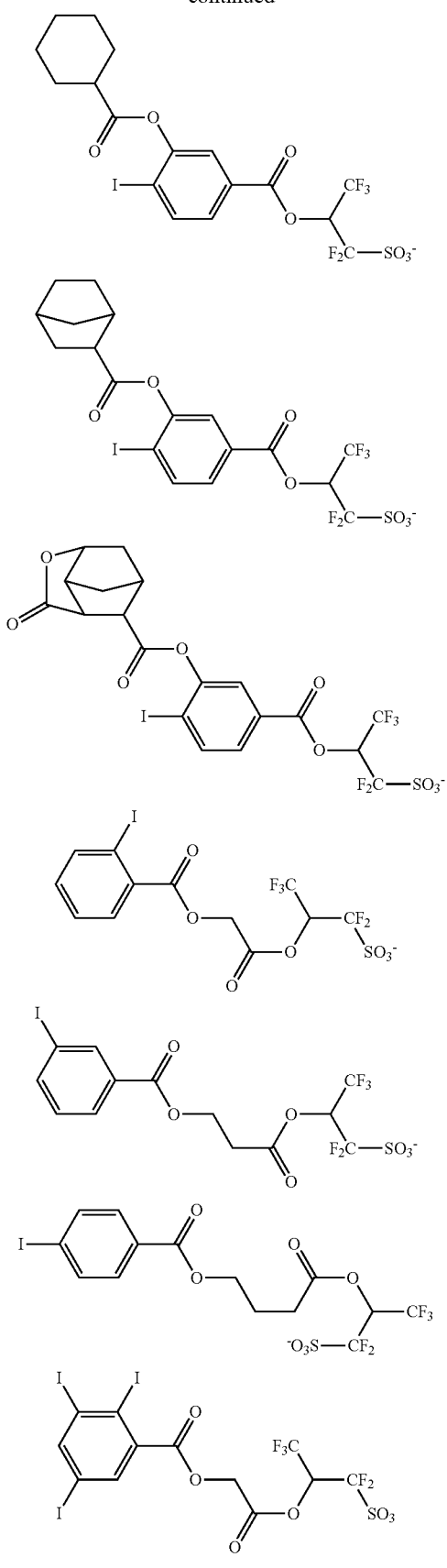
124
-continued
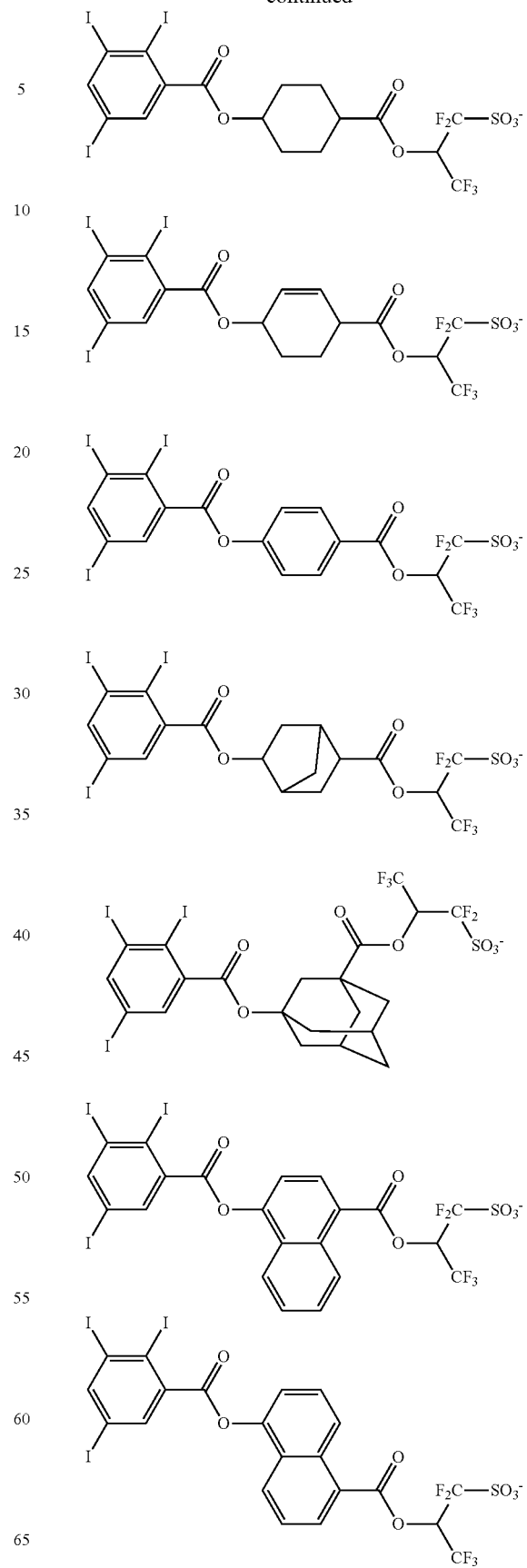

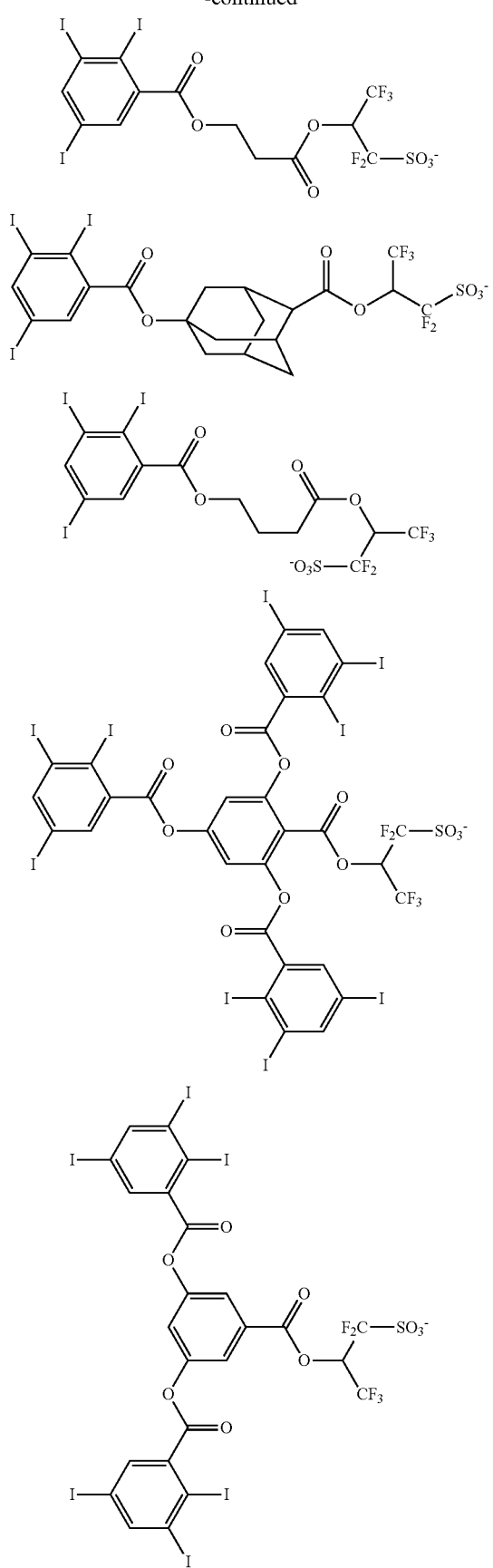
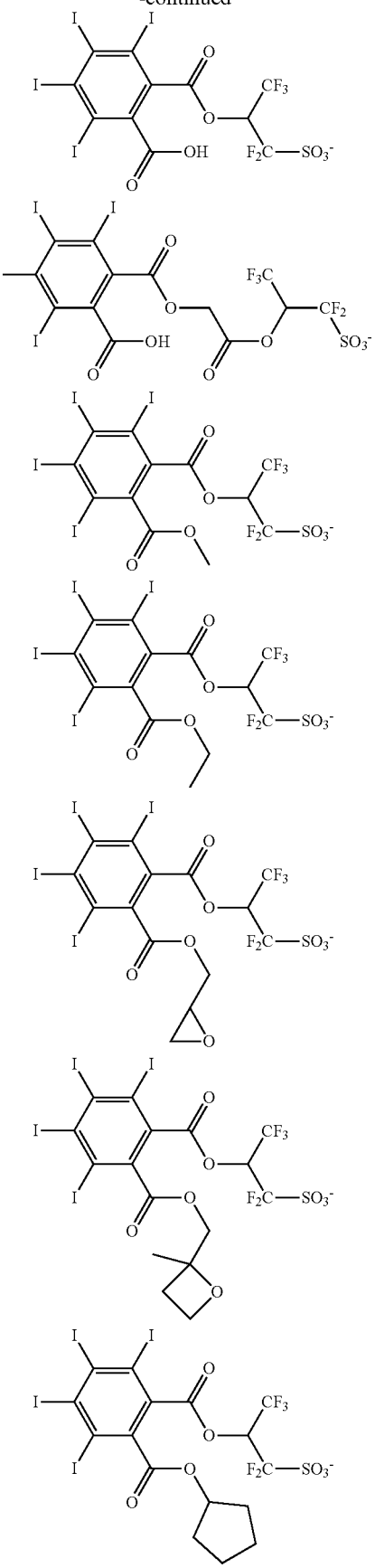

127
-continued
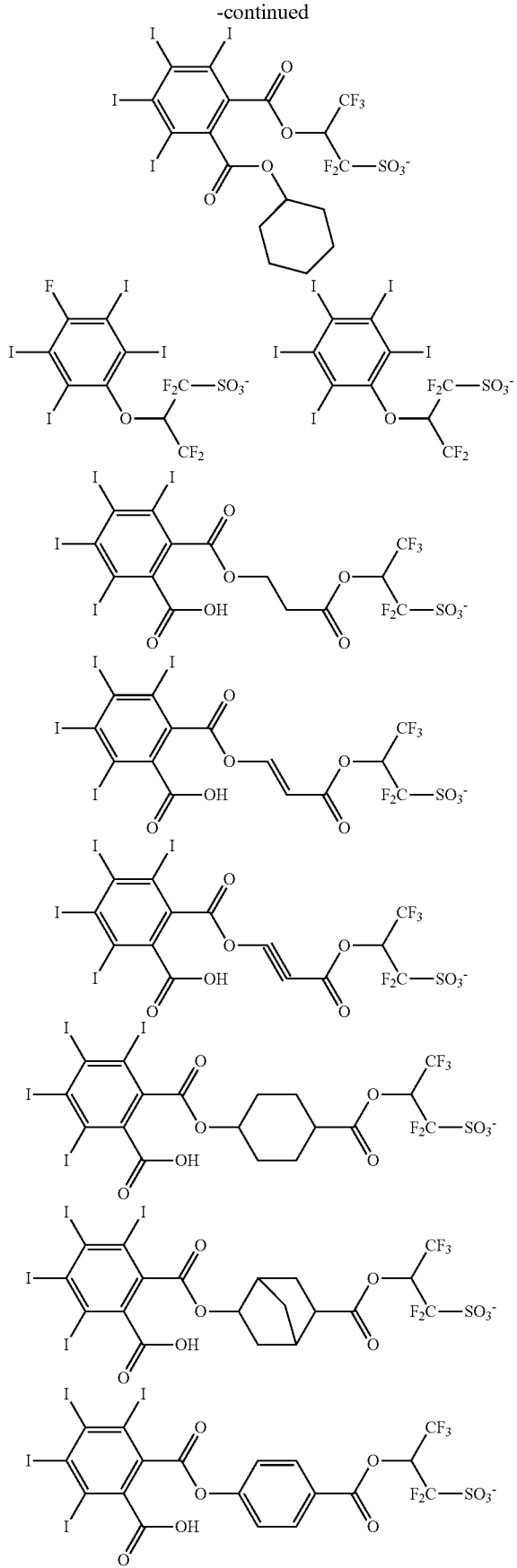
128
-continued
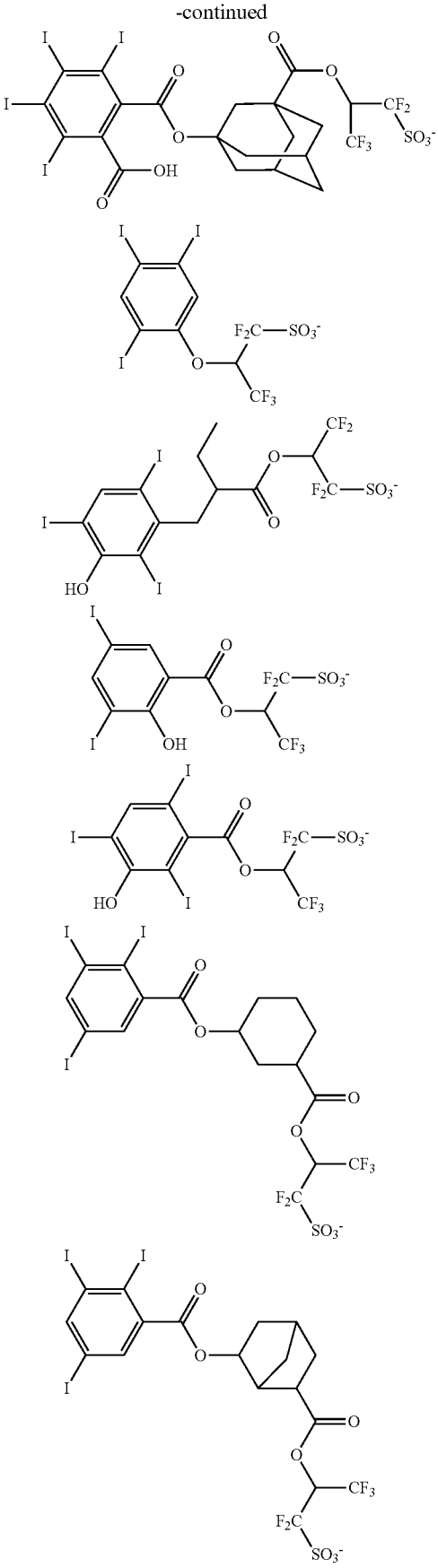

129
-continued
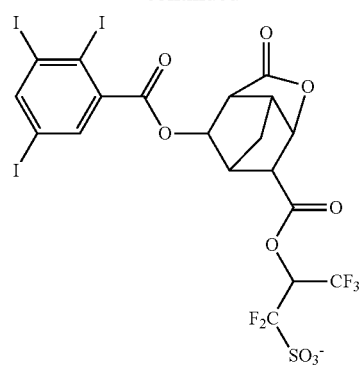
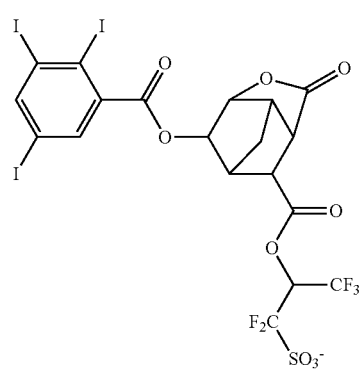
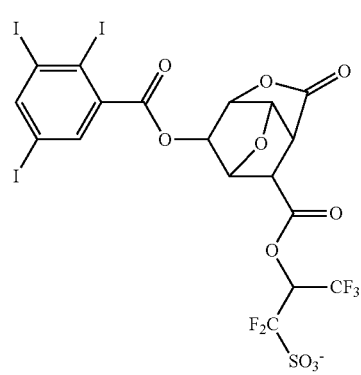
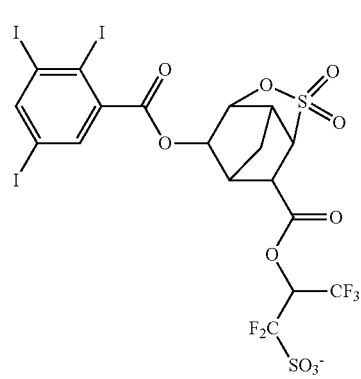
130
-continued
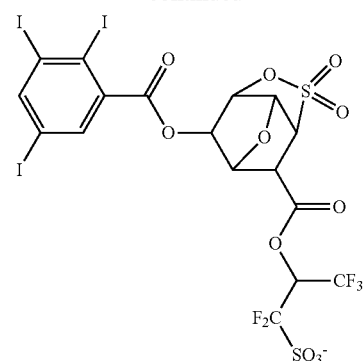
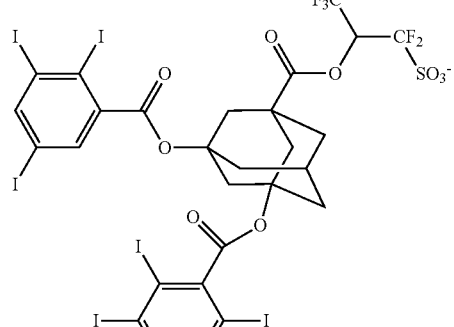
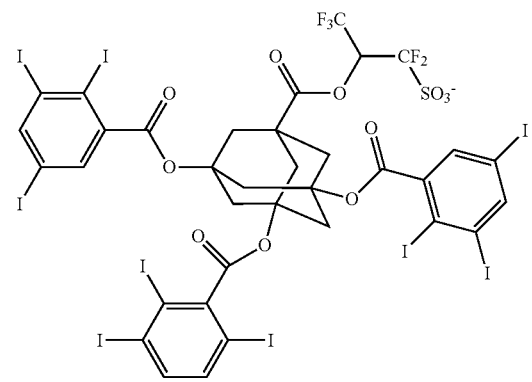
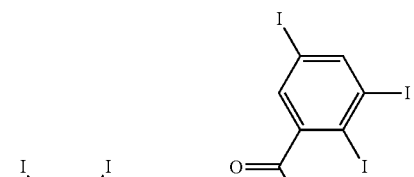
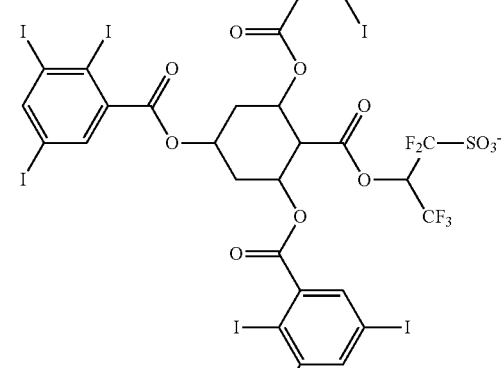

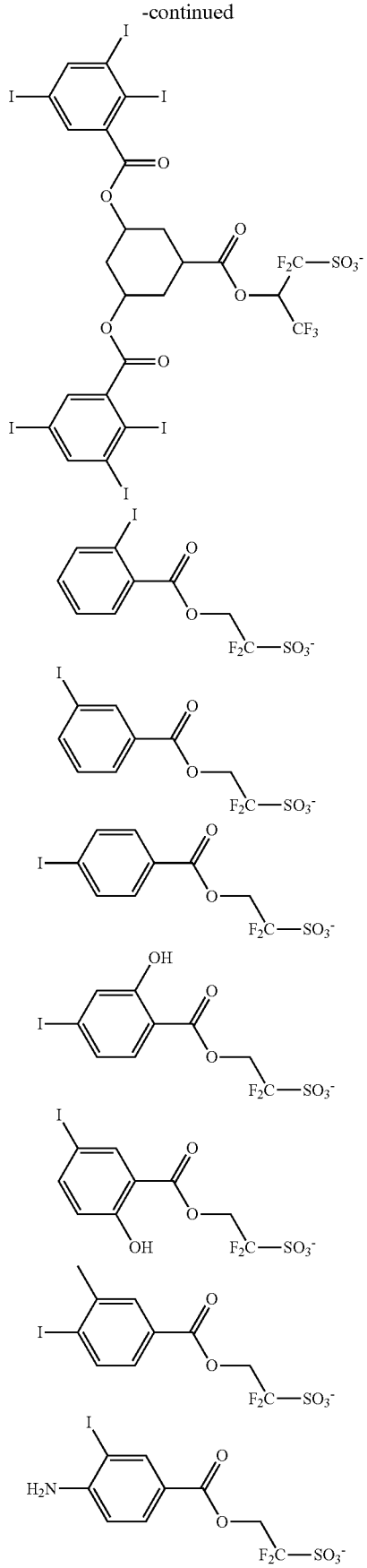
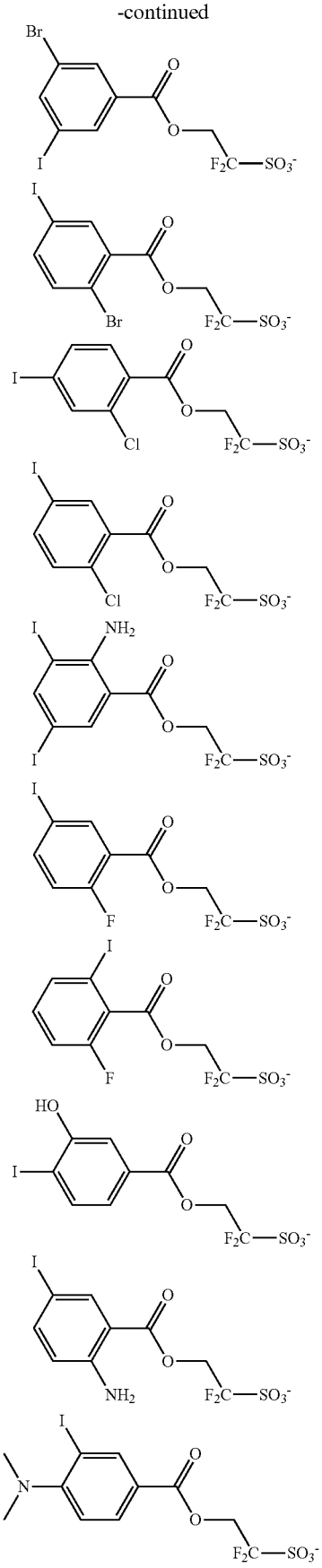

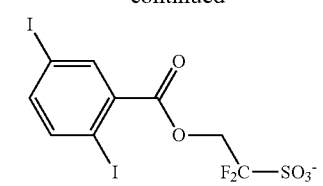
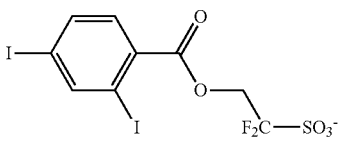
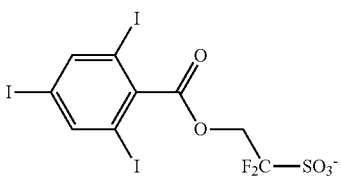
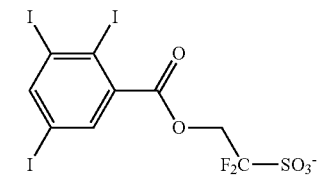
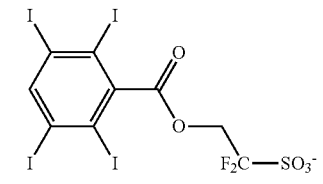
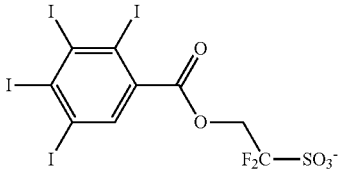
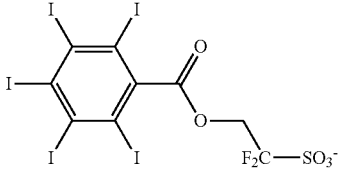
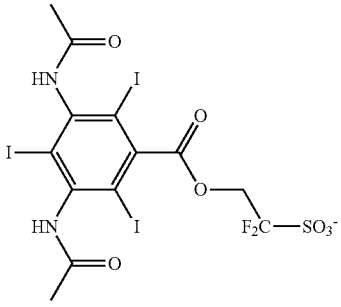
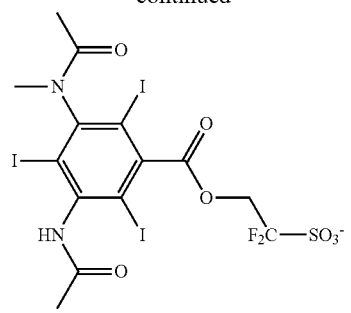
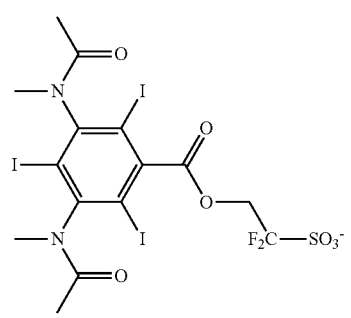
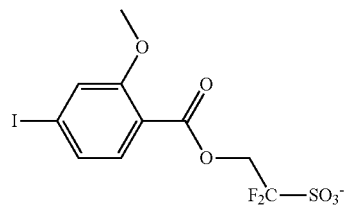
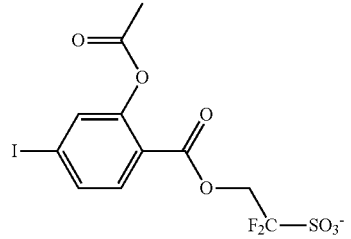
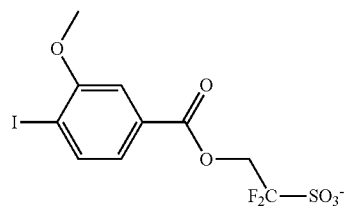
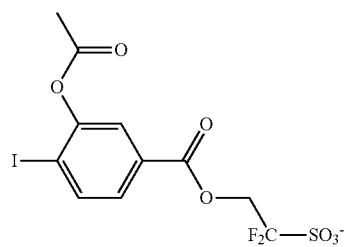

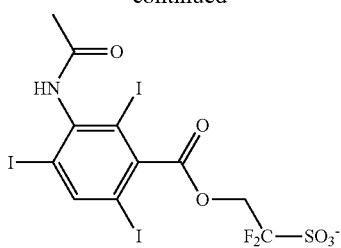
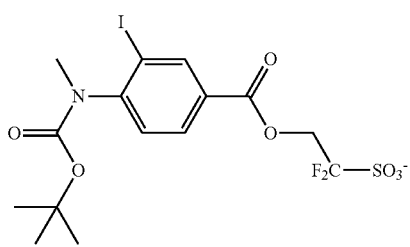
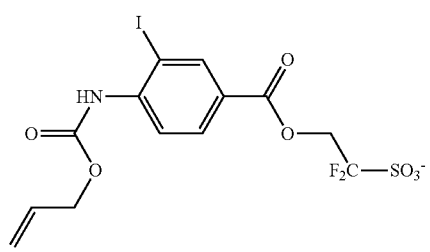
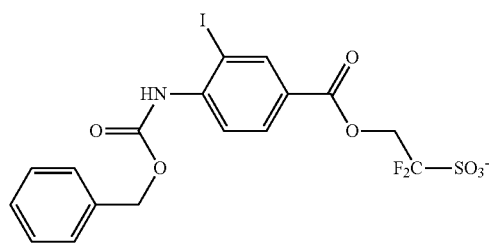
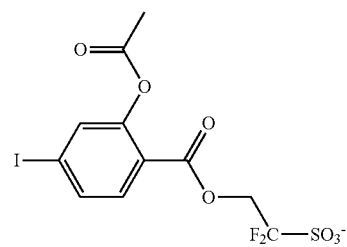
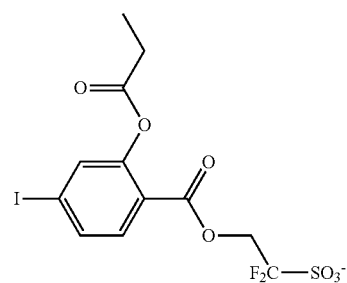
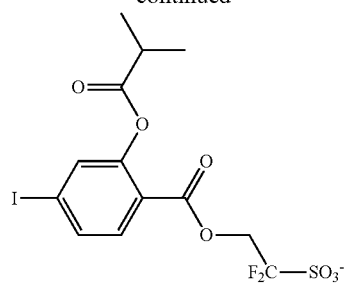
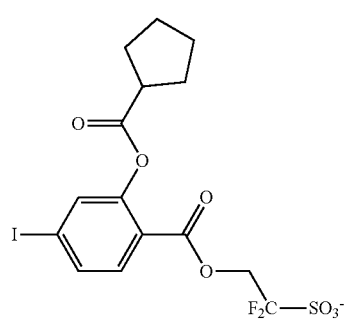
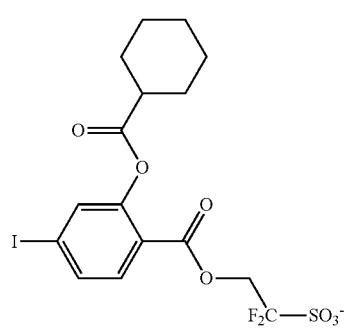
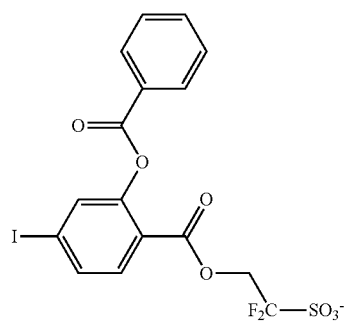
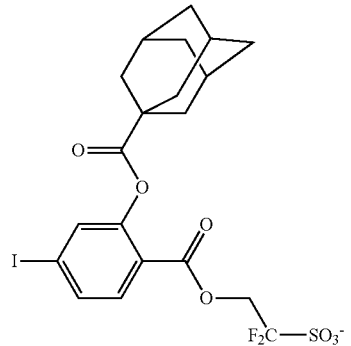

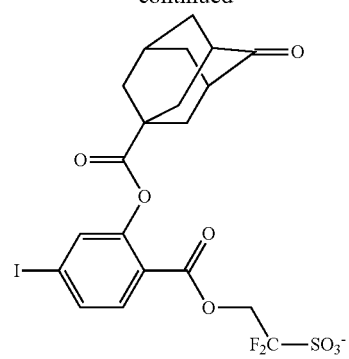
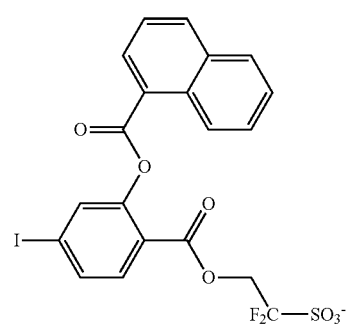
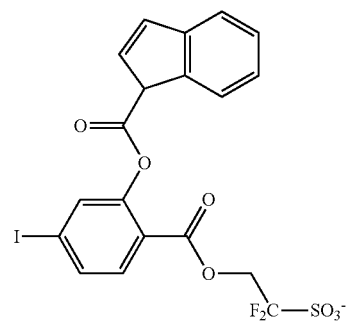
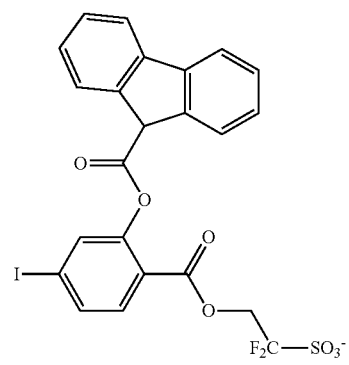
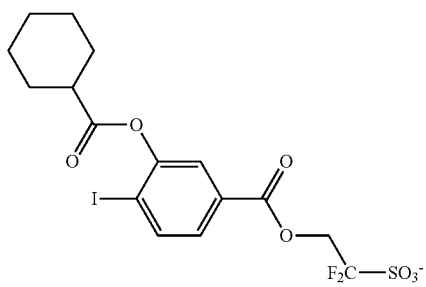
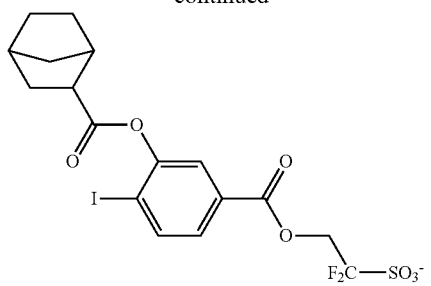
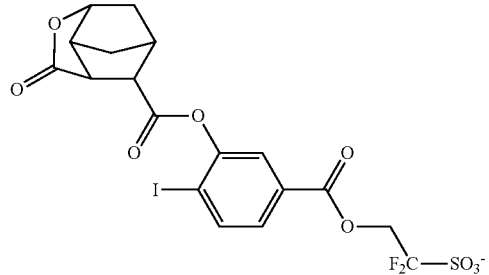
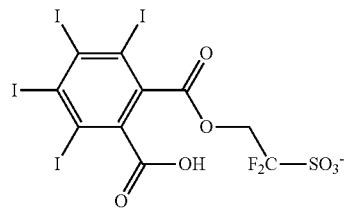
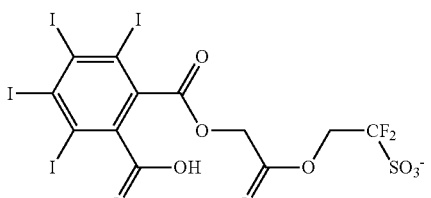
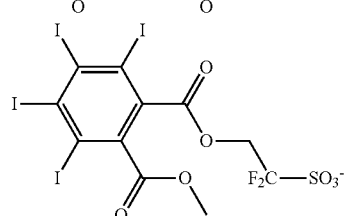
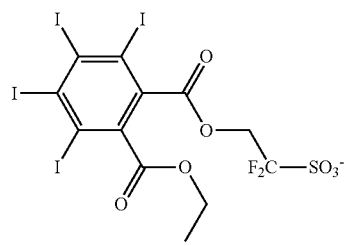
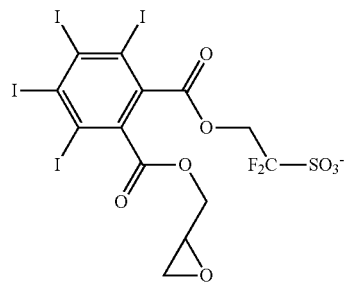

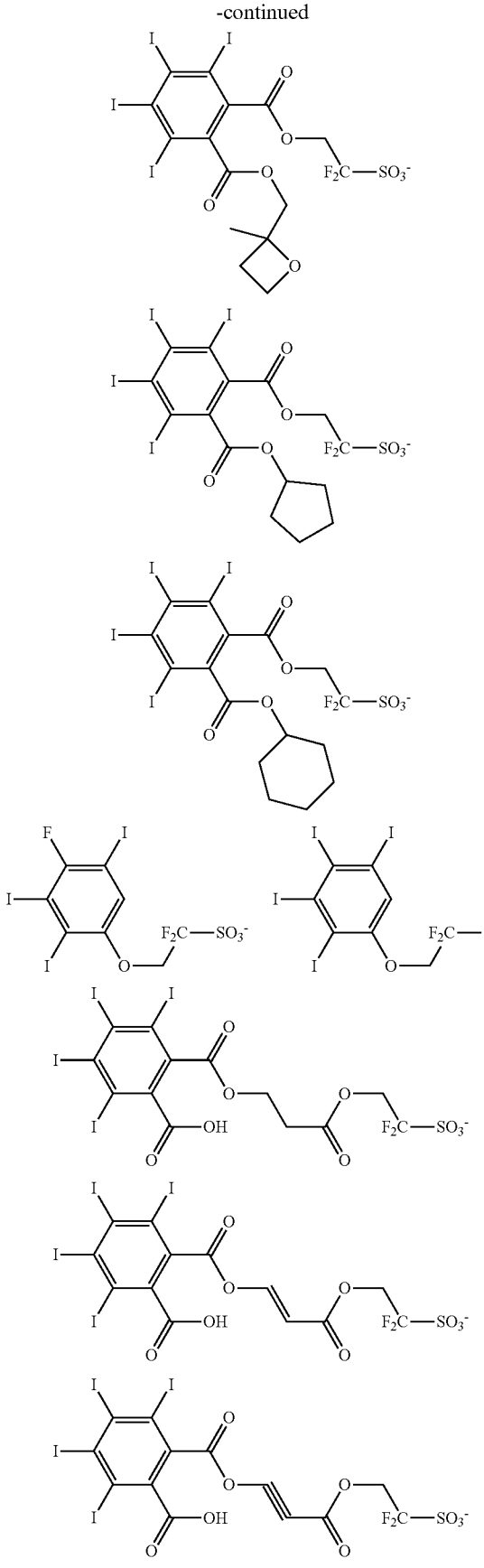
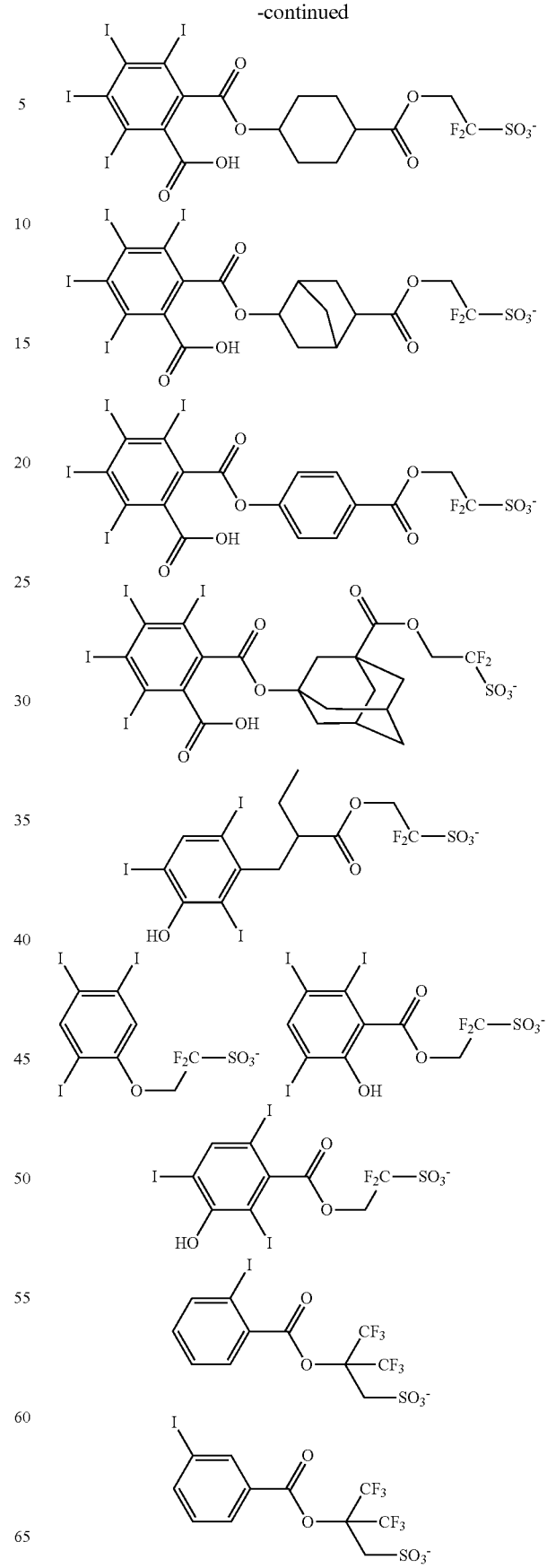

-continued
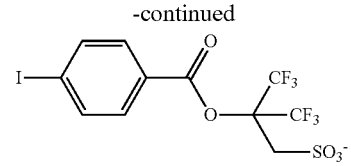
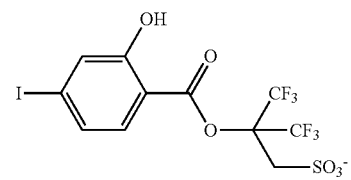
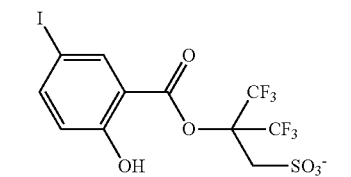
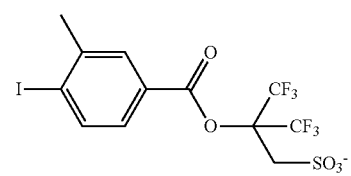
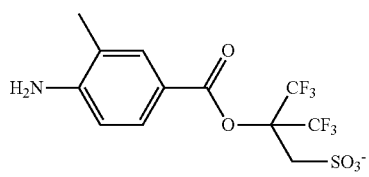
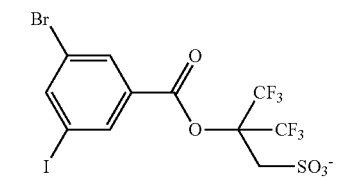
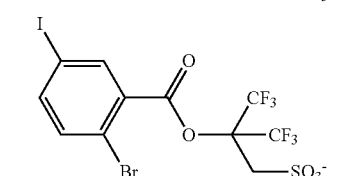
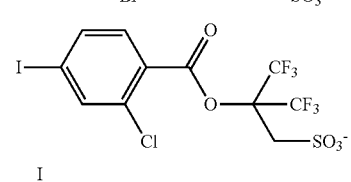
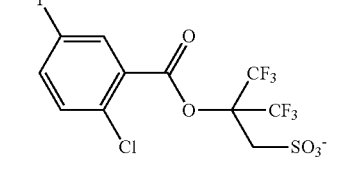
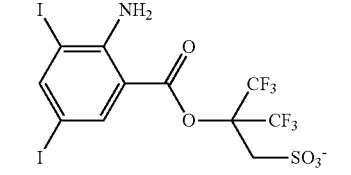
-continued
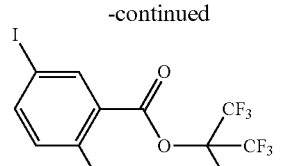
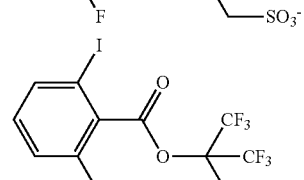
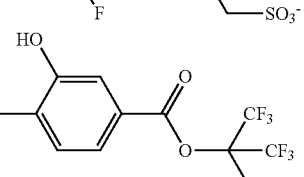
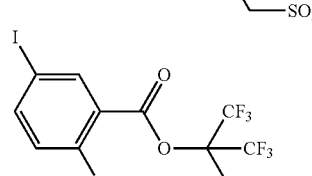
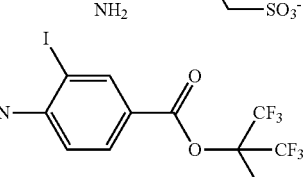
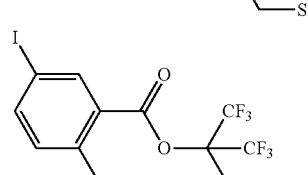
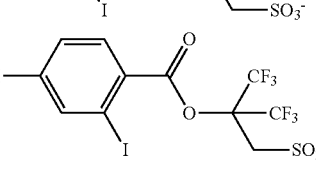
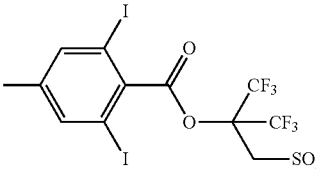
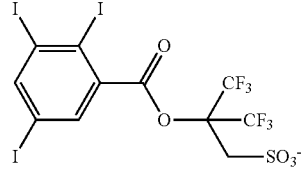
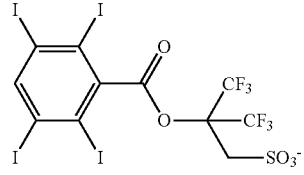

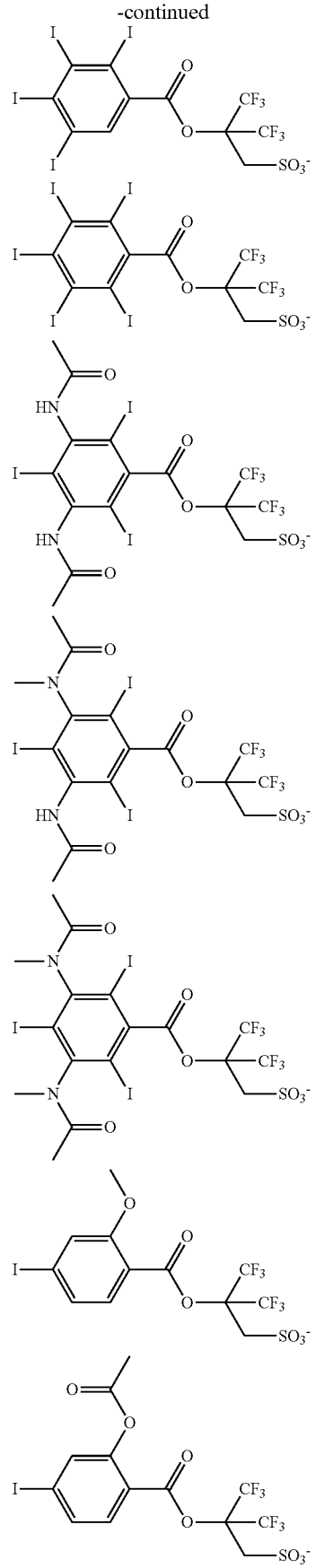
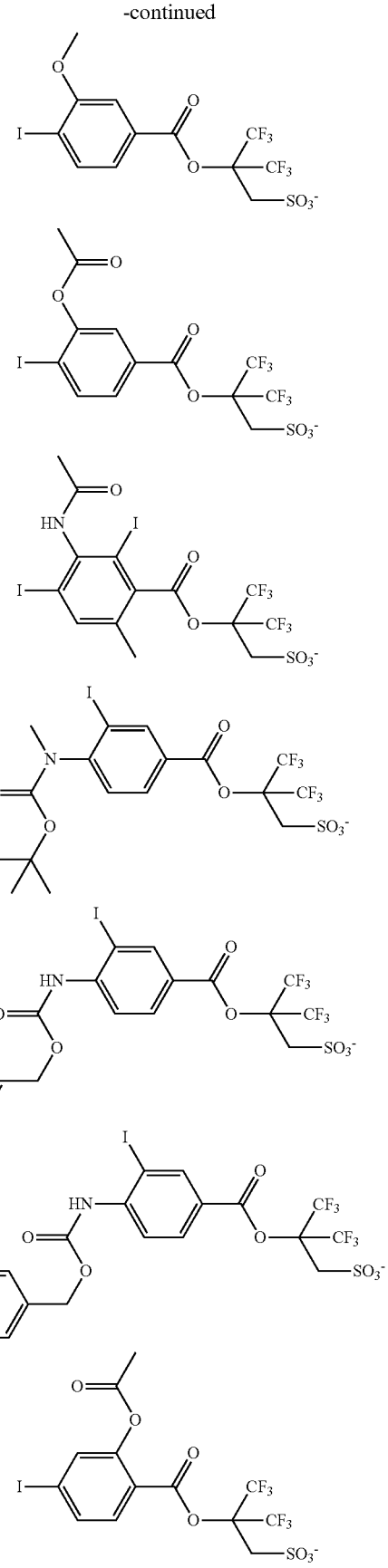

145
-continued
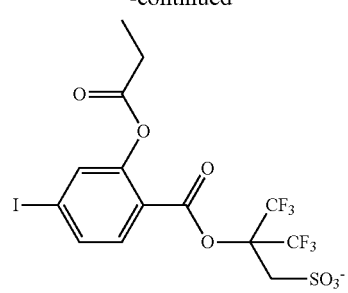
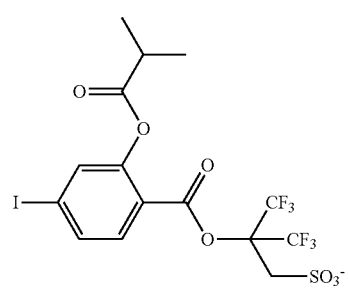
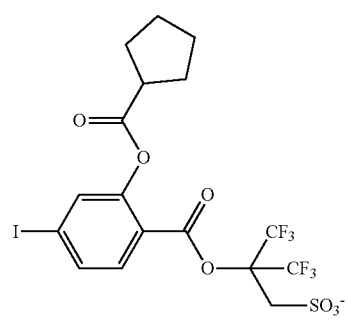
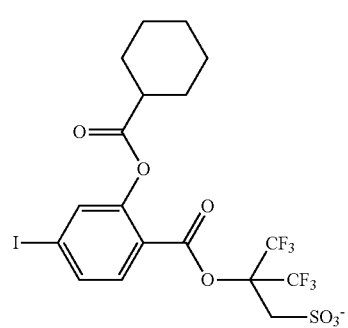
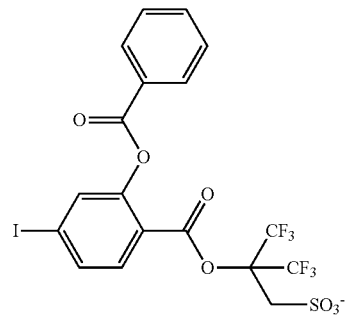
146
-continued
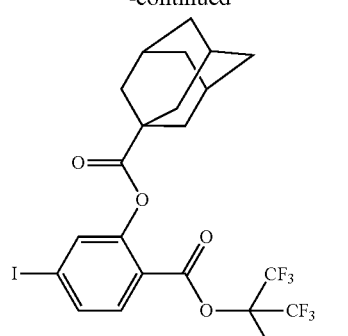
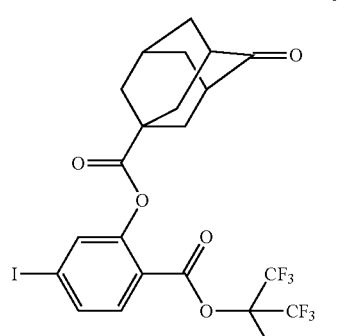
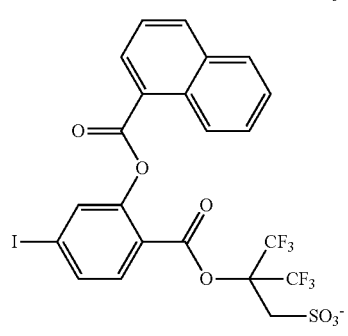
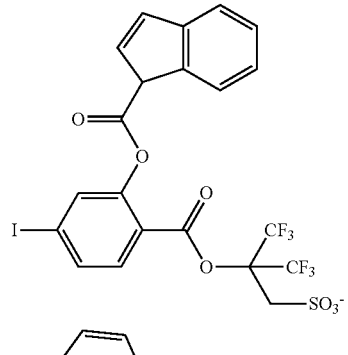
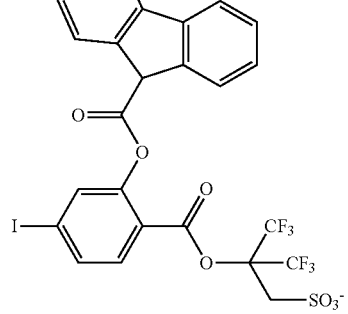

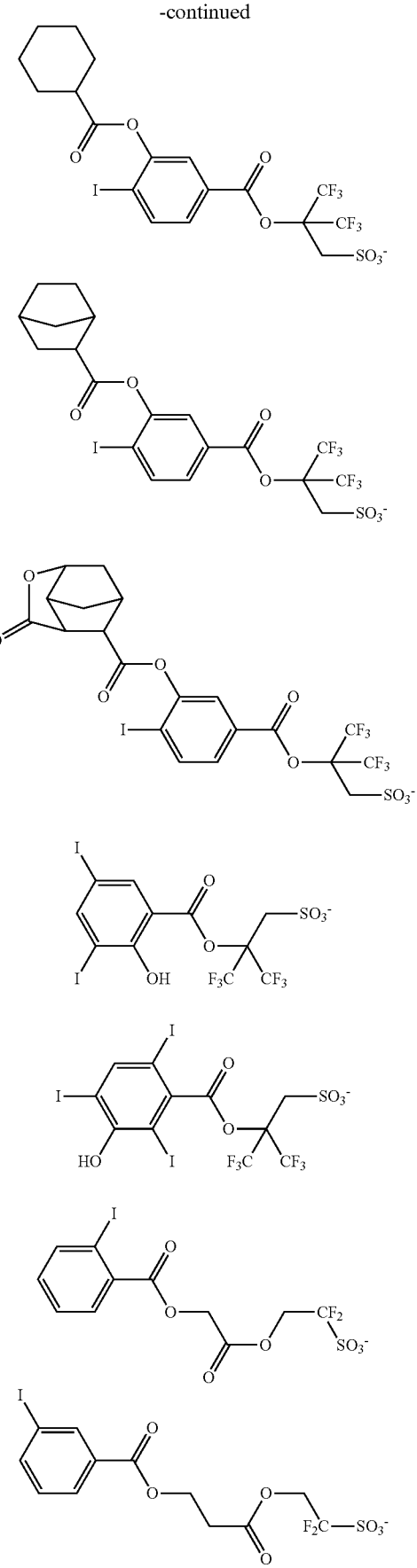
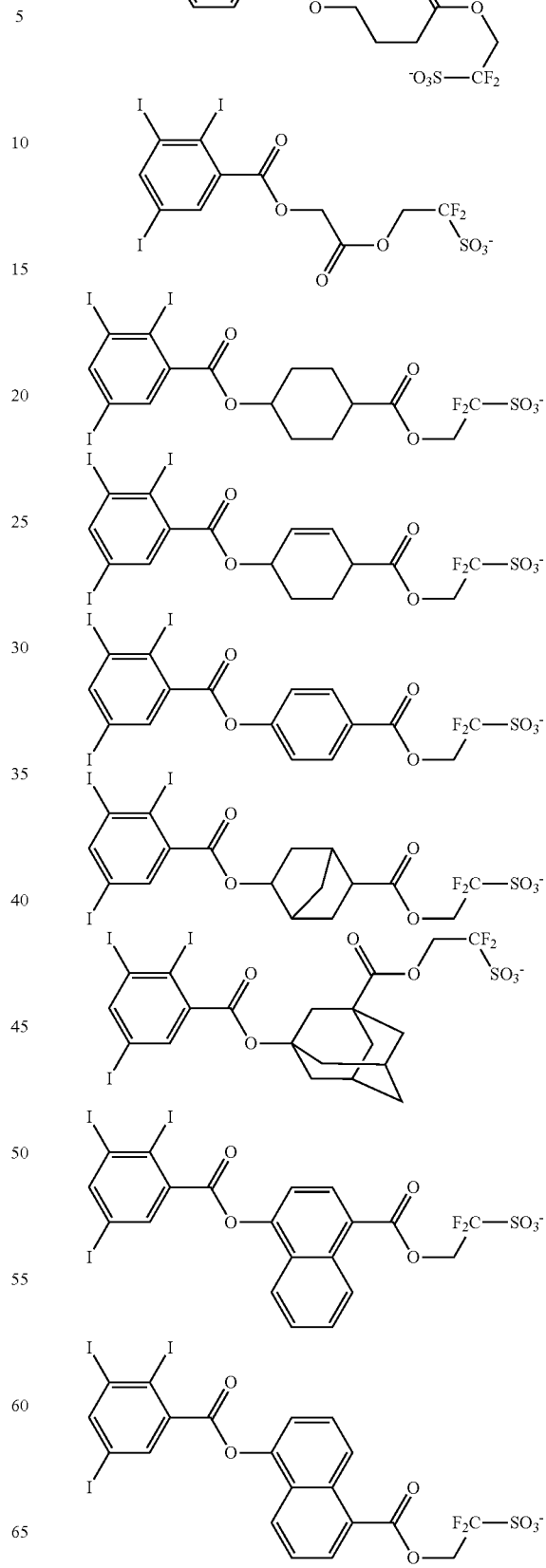

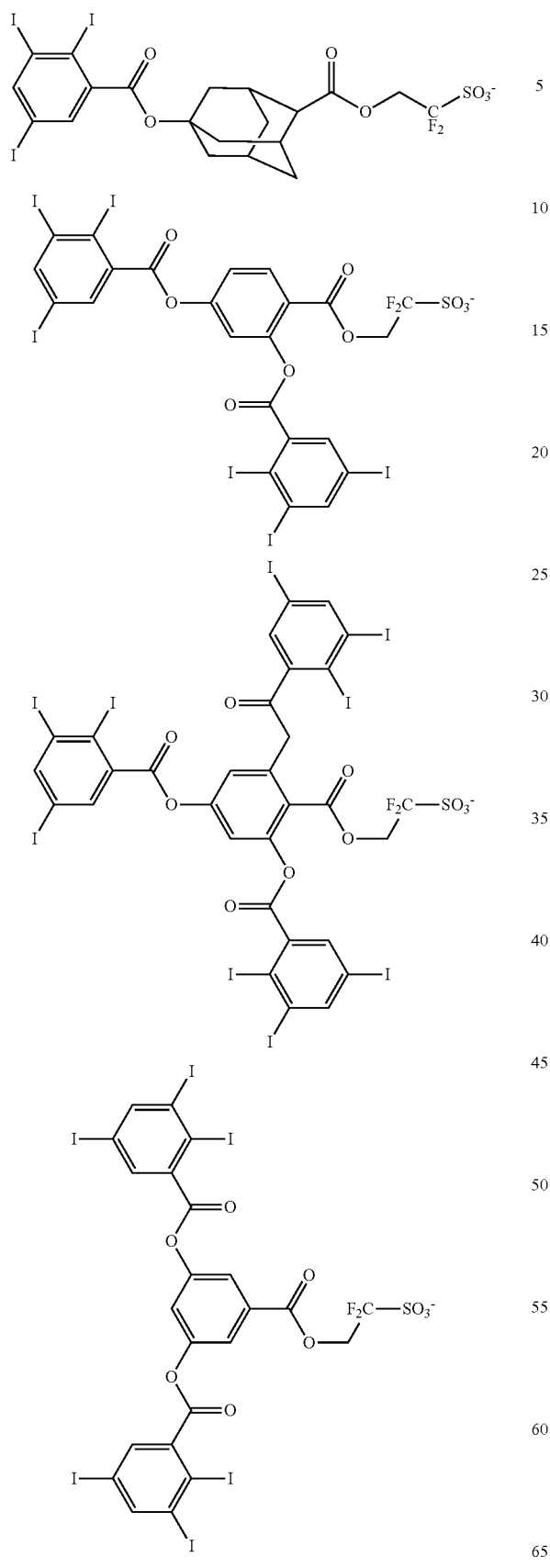

151
-continued
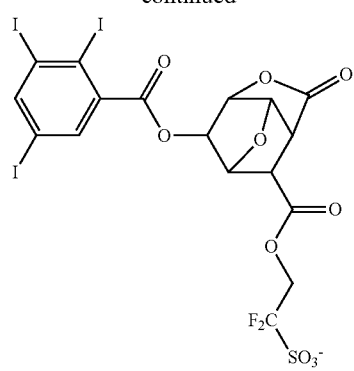
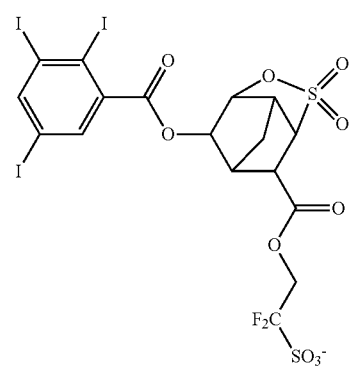
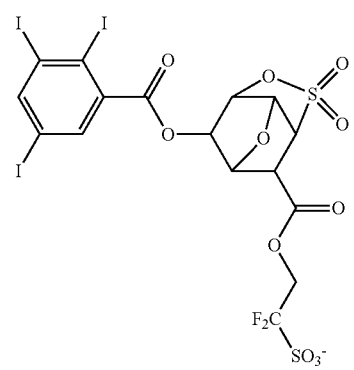
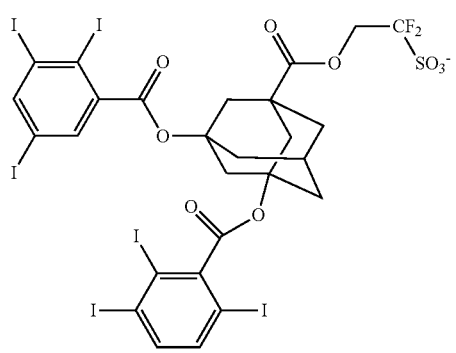
152
-continued
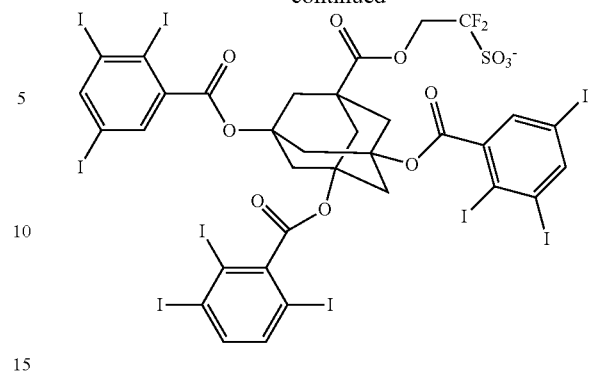
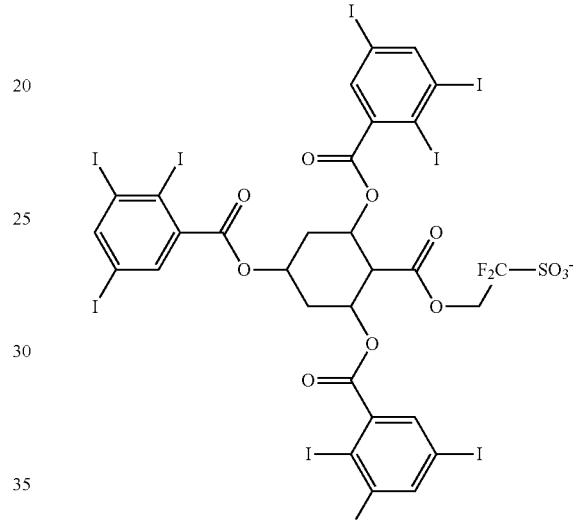
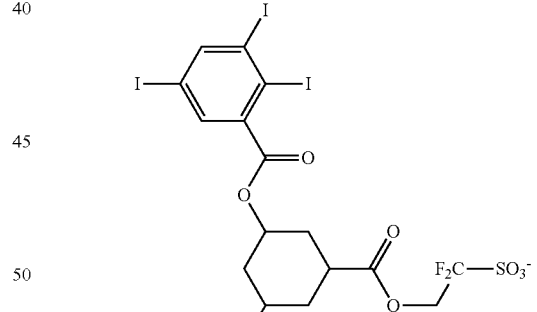
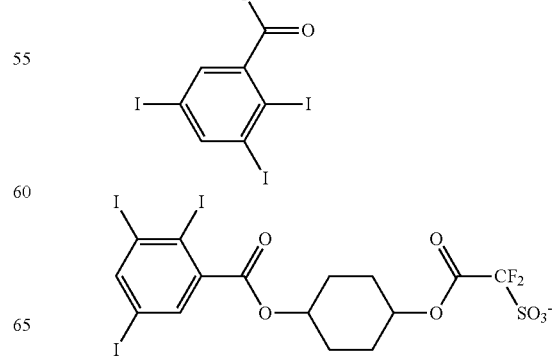

153
-continued
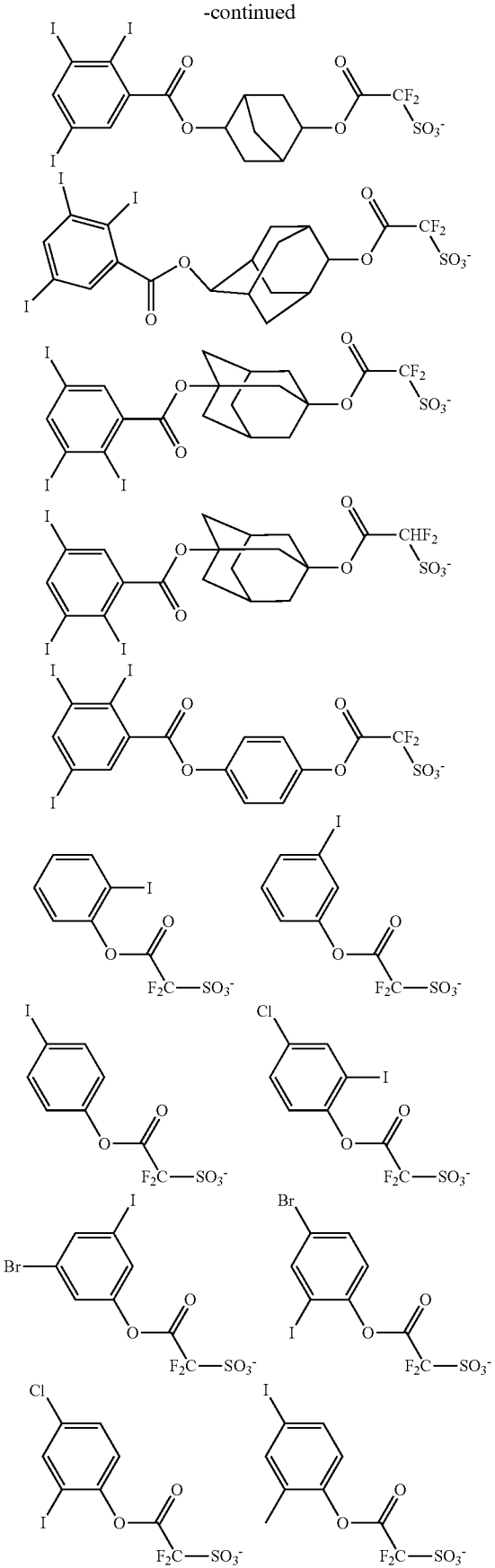
154
-continued
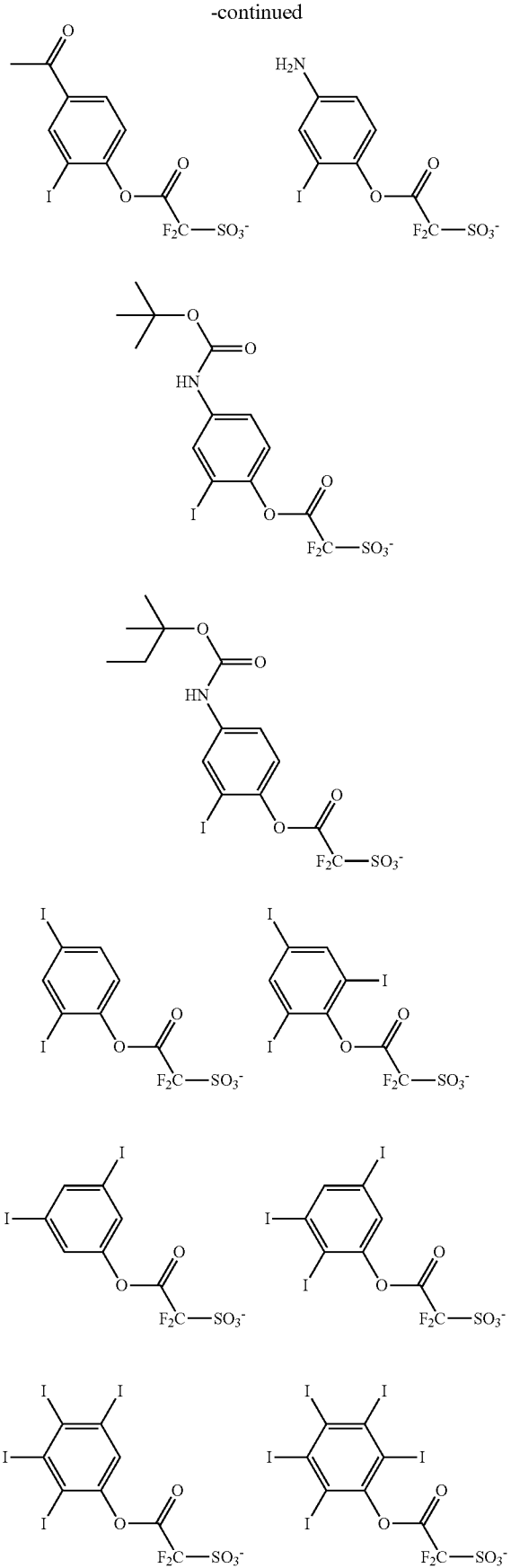

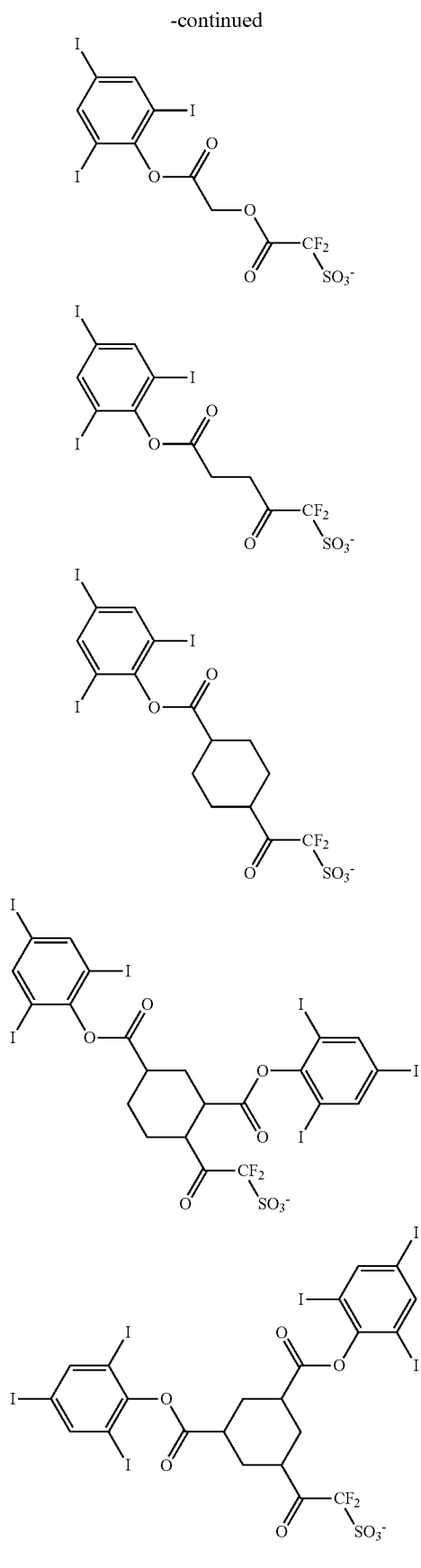
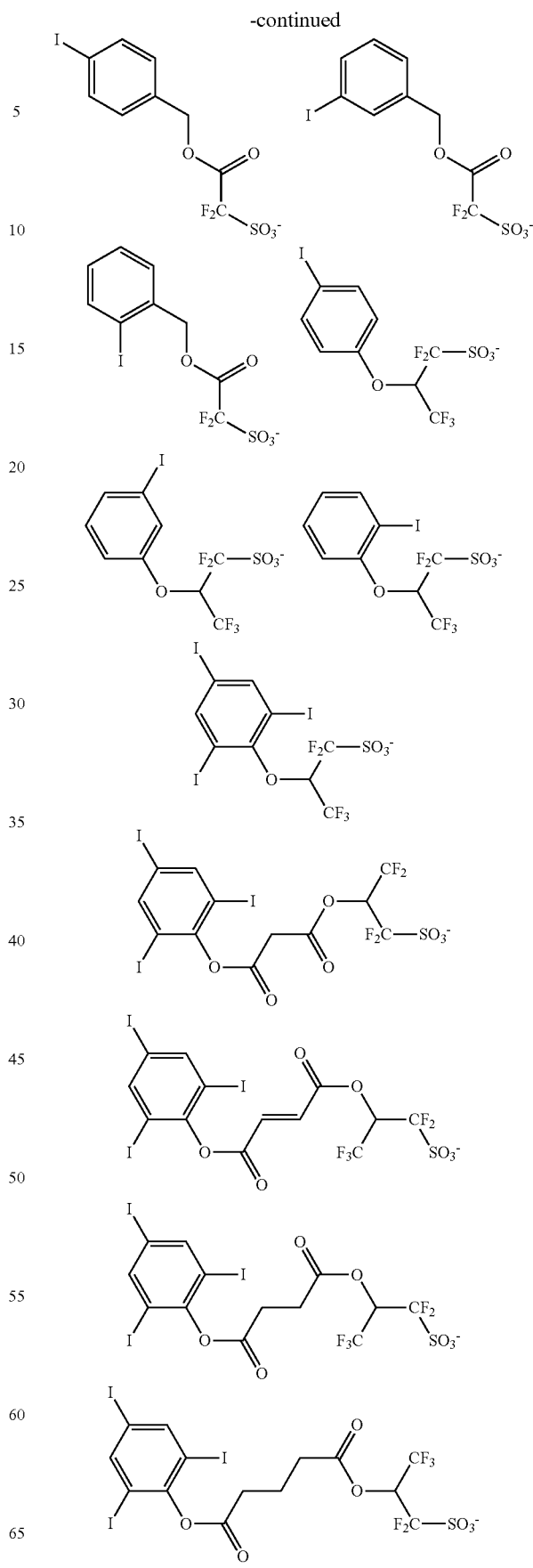

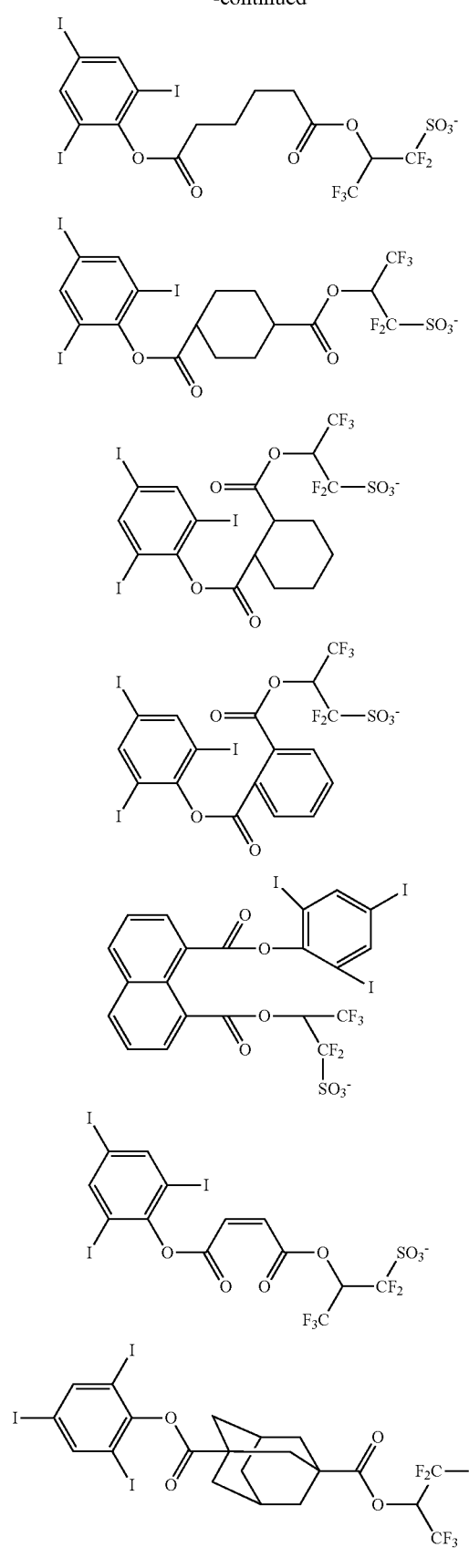
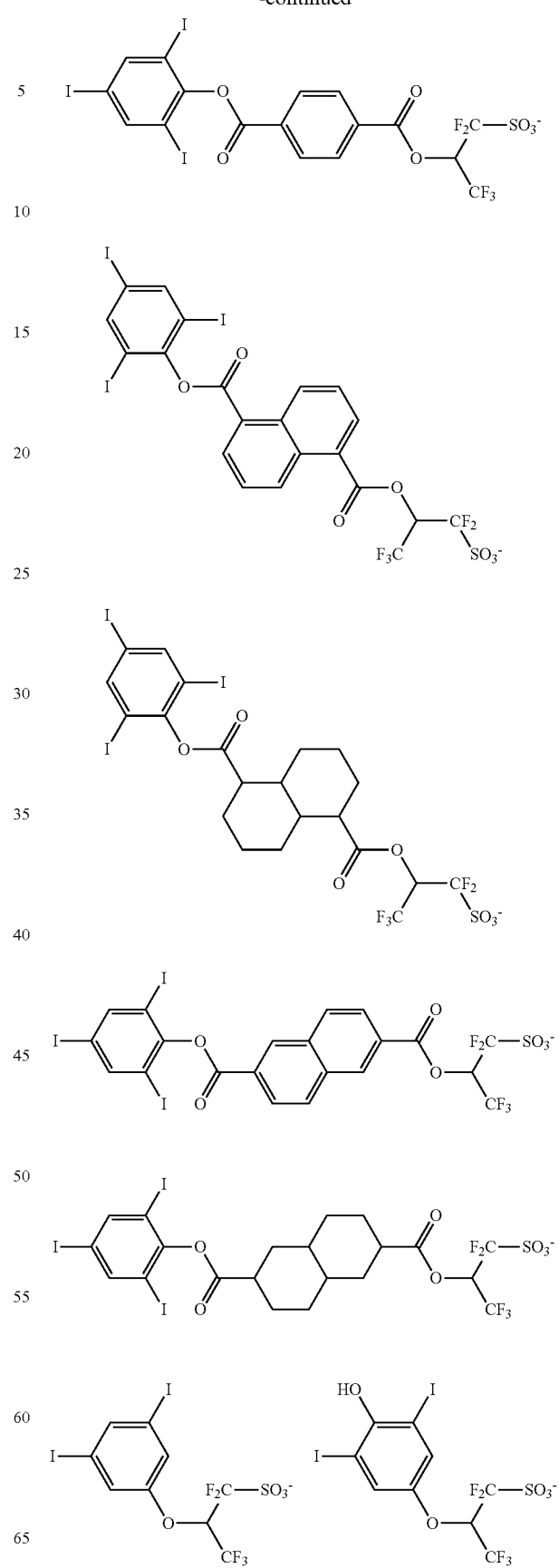

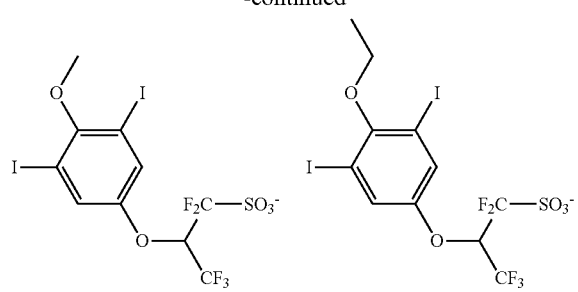
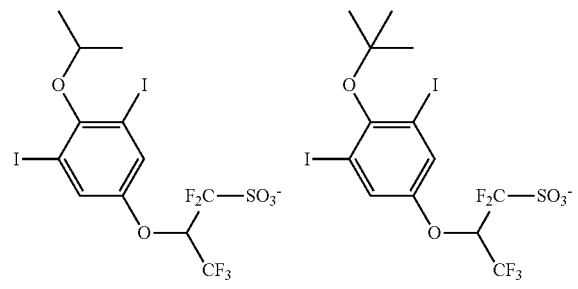
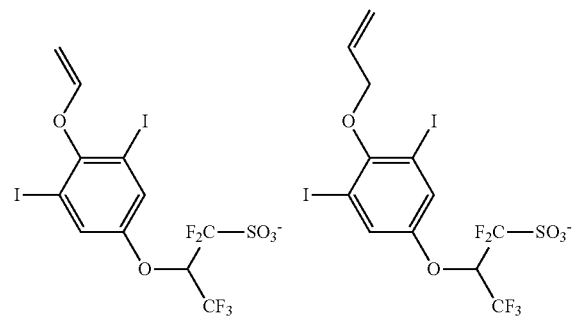
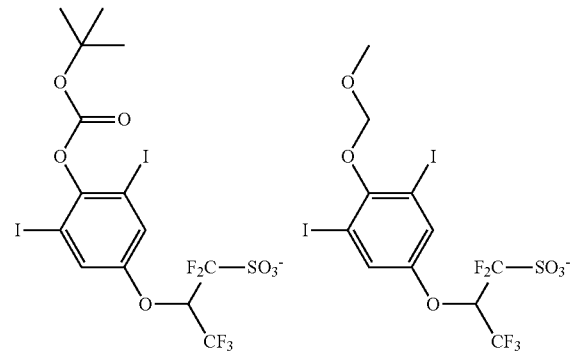
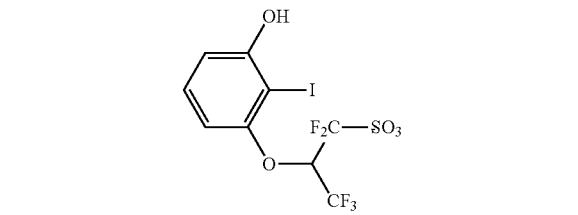
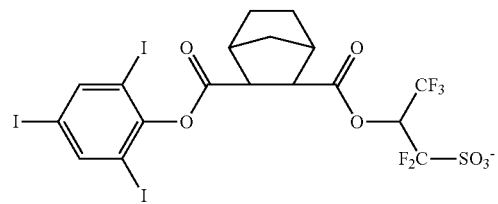
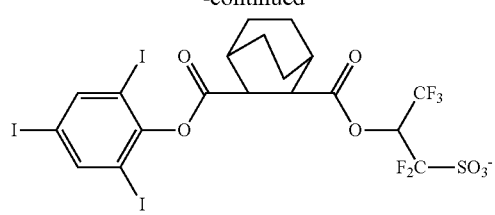
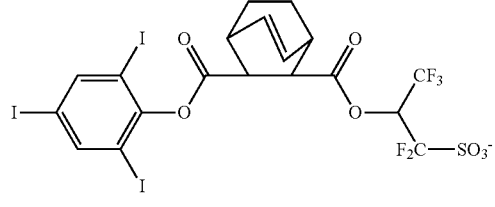
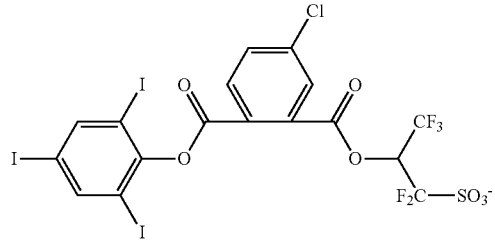
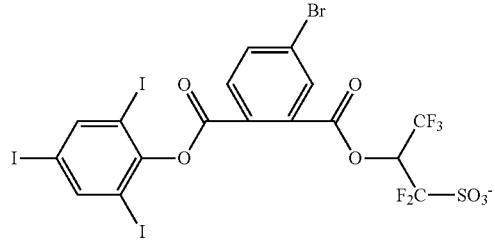
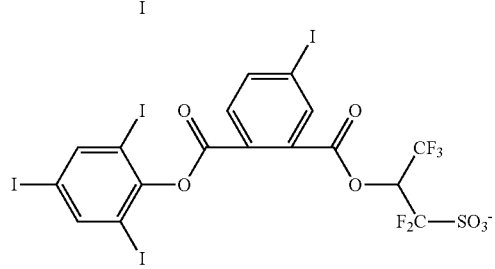
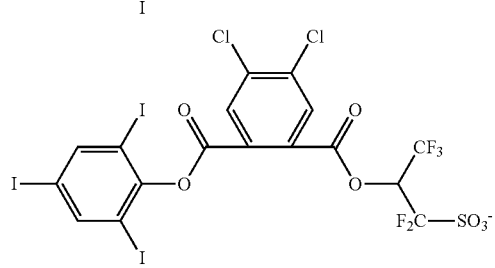
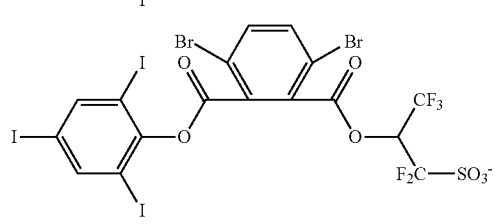

-continued
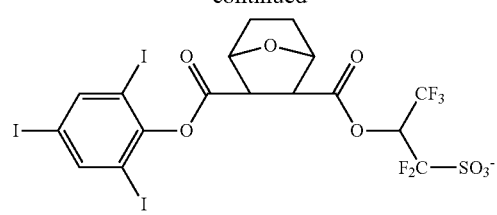
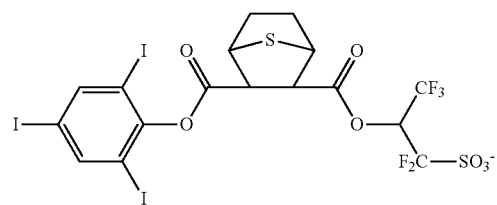
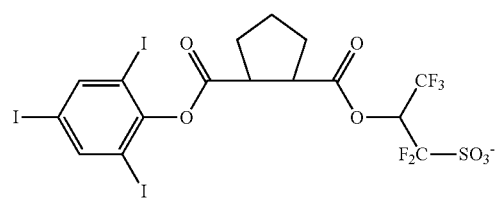
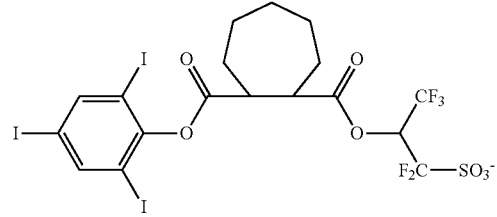
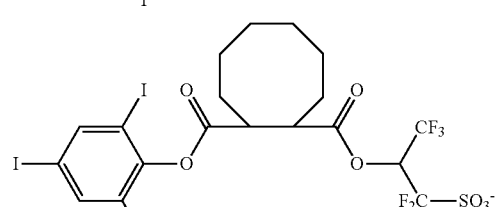
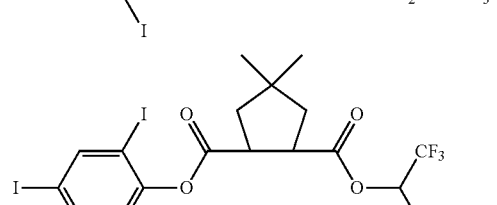
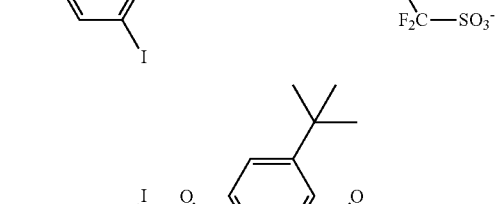
-continued
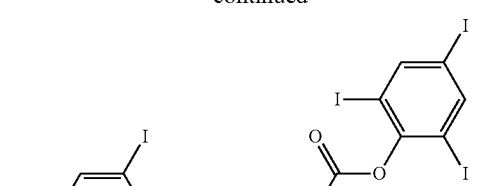
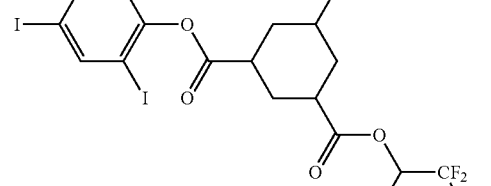
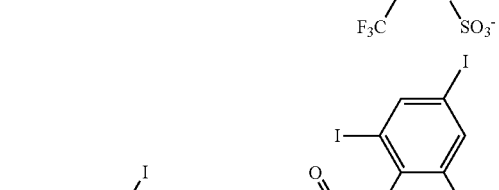
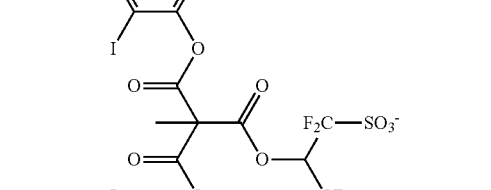

163
-continued
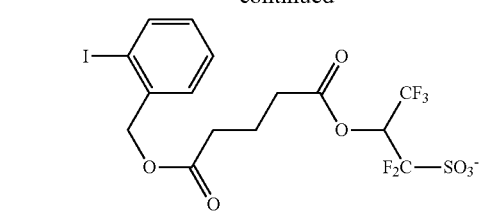
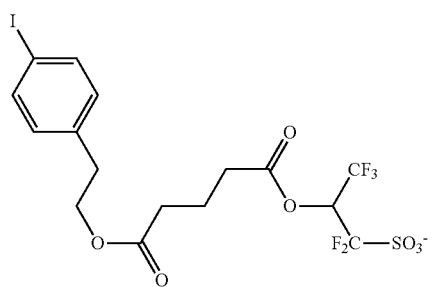
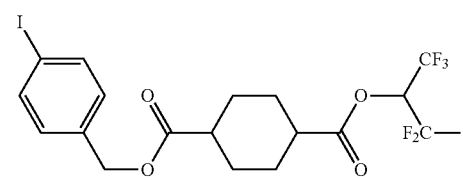
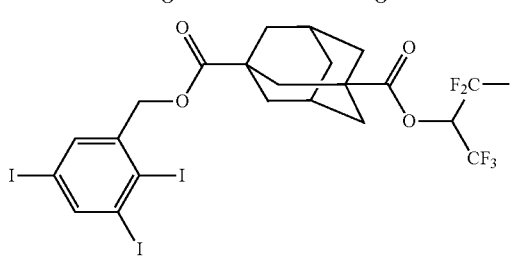
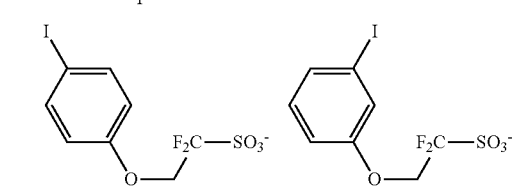
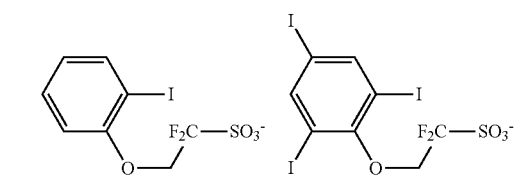
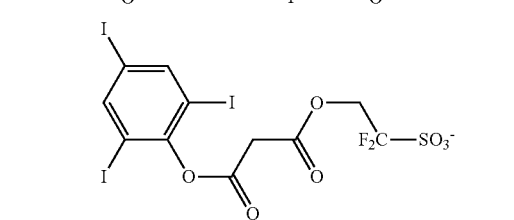
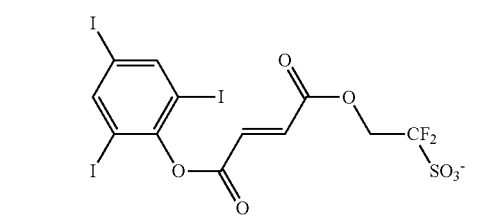
164
-continued
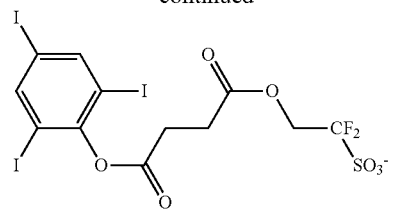
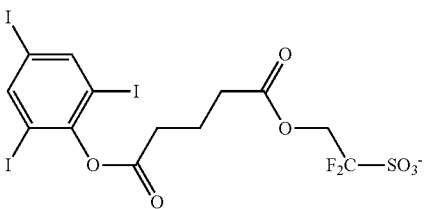
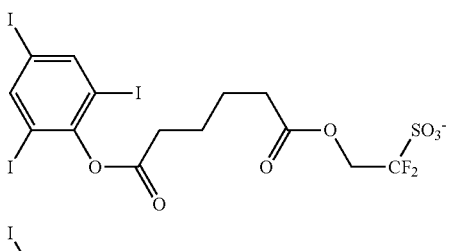
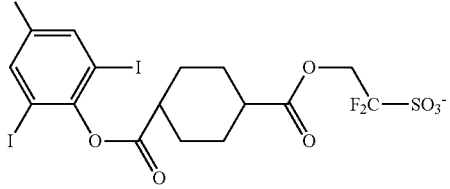
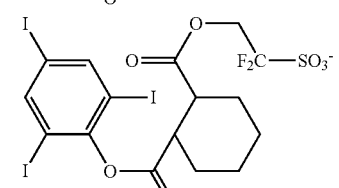
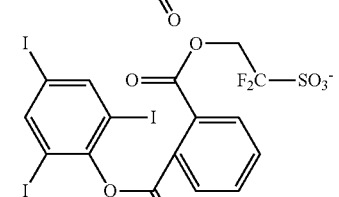
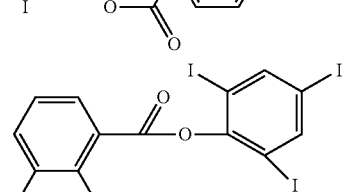
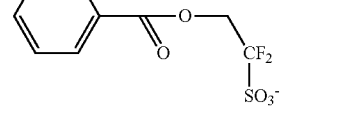
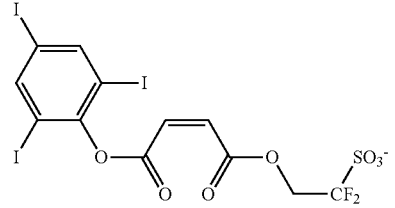

165
-continued
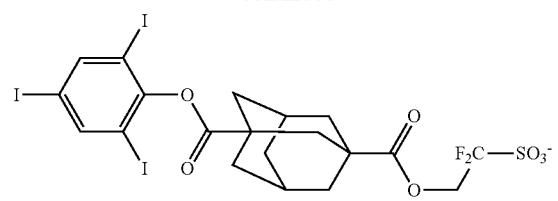
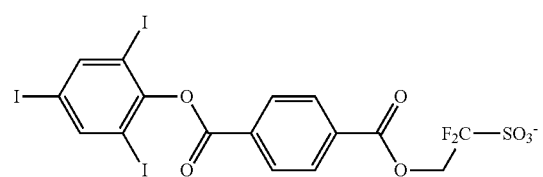
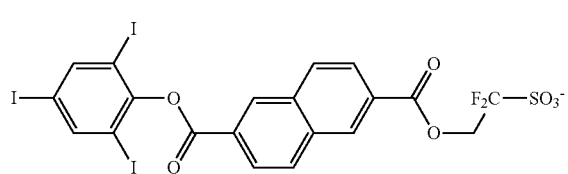
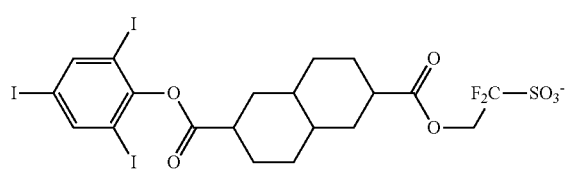
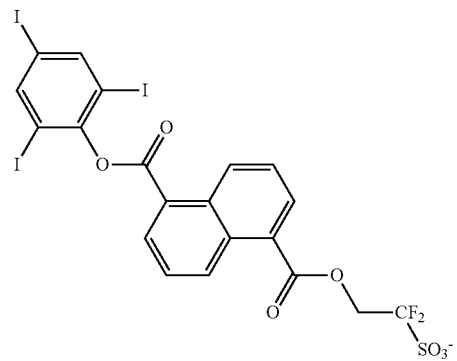
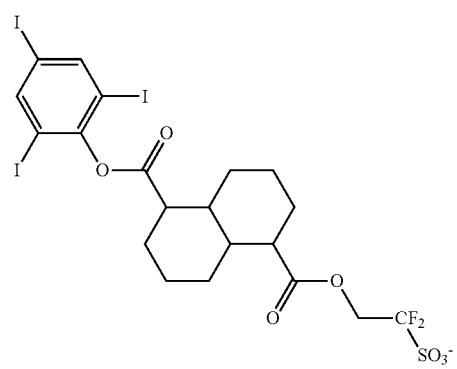
166
-continued
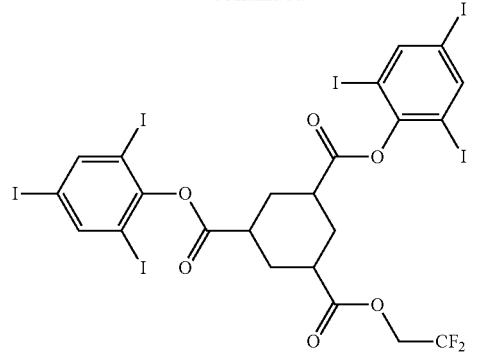
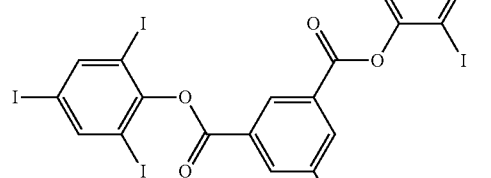
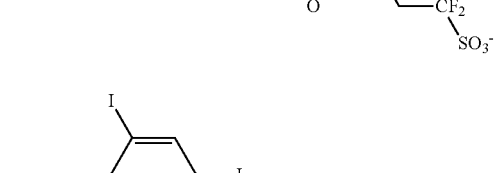
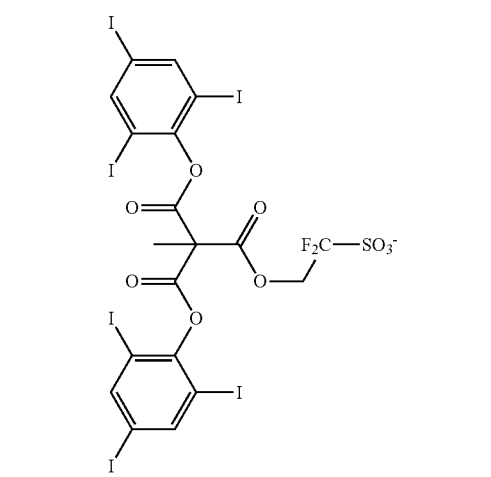
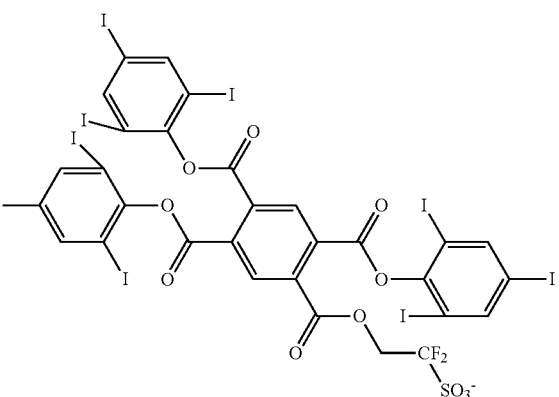

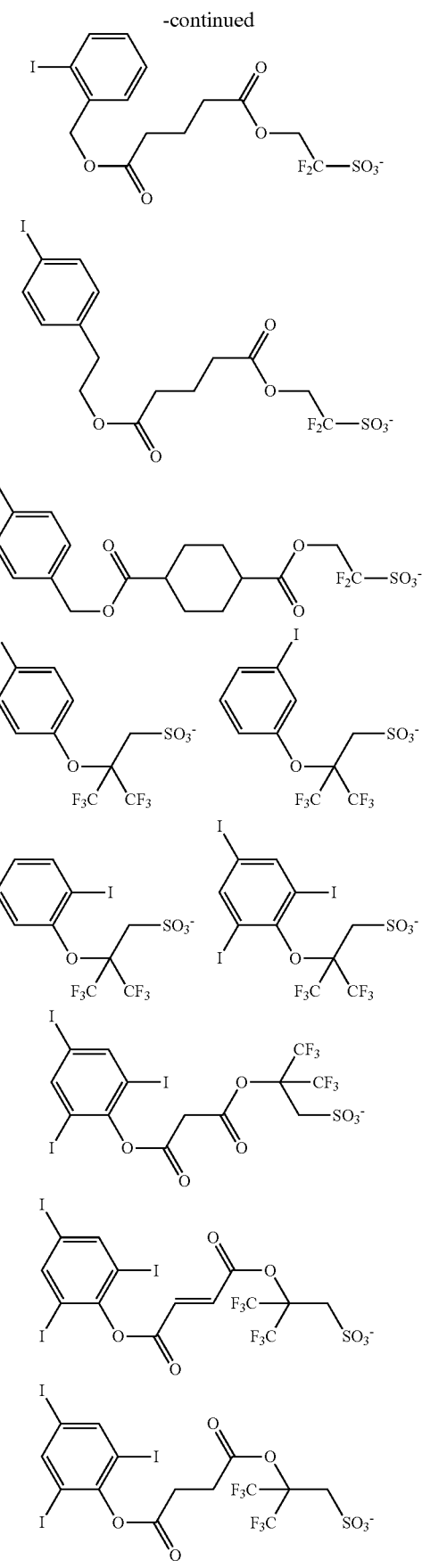
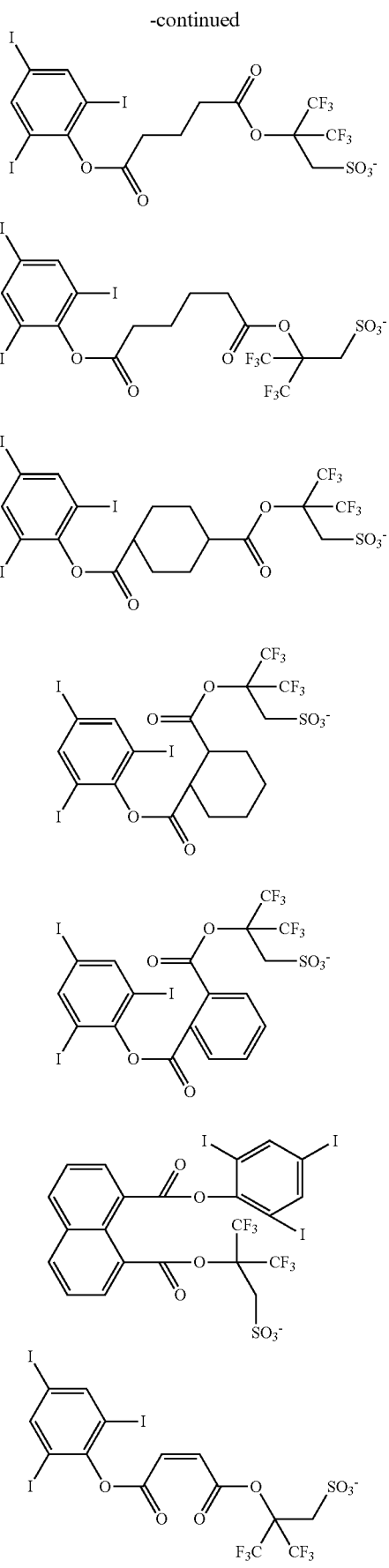

169
-continued
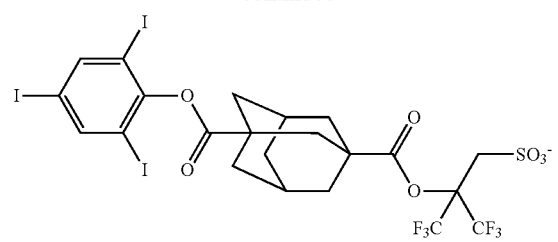
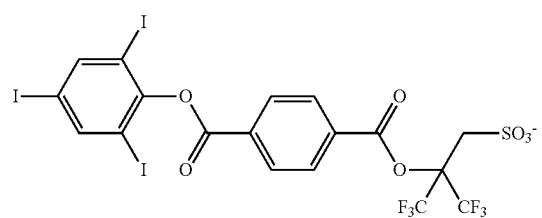
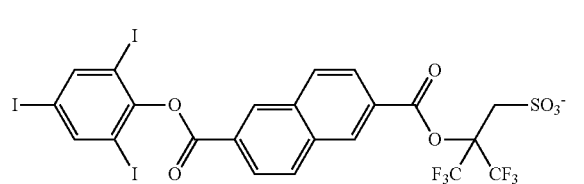
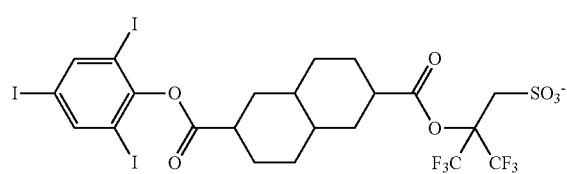
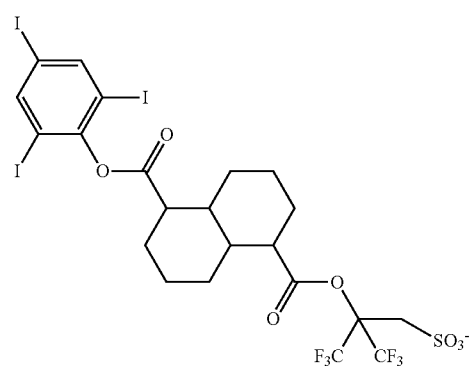
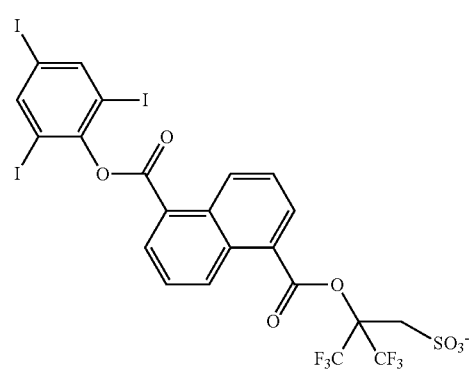
170
-continued
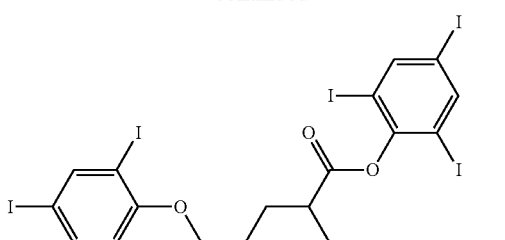
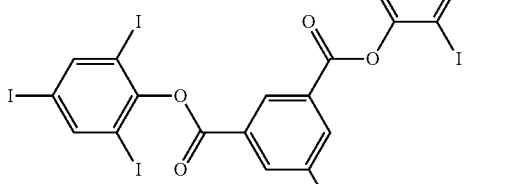
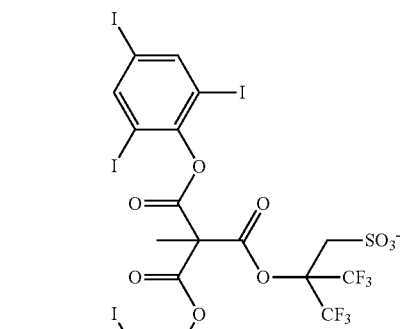
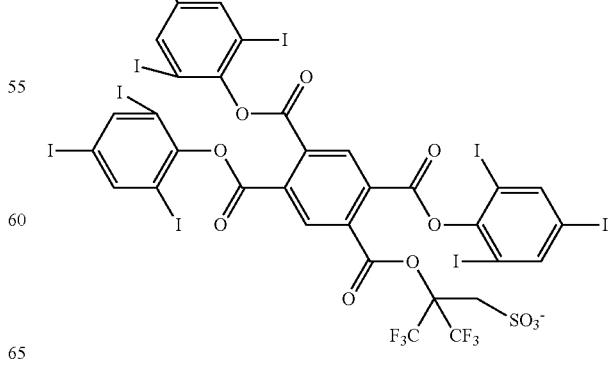

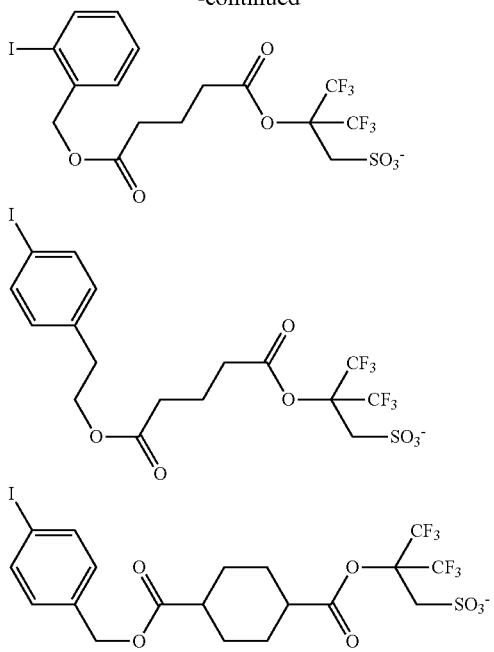

Further, a sulfonium or iodonium salt having a brominated anion may be used as the PAG. Examples of the brominated anion are those having formulae (3-1) to (3-4) wherein iodine is replaced by bromine. Examples of the brominated anion are the same as examples of the iodized anion except that iodine is replaced by bromine.

When the resist composition contains the acid generator of addition type, an appropriate amount of the generator added is 0.1 to 50 parts, more preferably 1 to 40 parts by weight per 100 parts by weight of the base polymer.

Quencher

Where the onium salt functions as a quencher or functions as an acid generator, the resist composition of the invention may contain a quencher other than the onium salt. The other quencher is typically selected from conventional basic compounds. Conventional basic compounds include primary, secondary, and tertiary aliphatic amines, mixed amines, aromatic amines, heterocyclic amines, nitrogen-containing compounds with carboxyl group, nitrogen-containing compounds with sulfonyl group, nitrogen-containing compounds with hydroxyl group, nitrogen-containing compounds with hydroxyphenyl group, alcoholic nitrogen-containing compounds, amide derivatives, imide derivatives, and carbamate derivatives. Also included are primary, secondary, and tertiary amine compounds, specifically amine compounds having a hydroxyl, ether, ester, lactone ring, cyano, or sulfonic acid ester group as described in JP-A 2008-111103, paragraphs [0146]-[0164], and compounds having a carbamate group as described in JP 3790649. Addition of a basic compound may be effective for further suppressing the diffusion rate of acid in the resist film or correcting the pattern profile.

Onium salts such as sulfonium salts, iodonium salts and ammonium salts of sulfonic acids which are not fluorinated at α-position as described in U.S. Pat. No. 8,795,942 (JP-A 2008-158339) and similar onium salts of carboxylic acid may also be used as the other quencher. While an α-fluorinated sulfonic acid, imide acid, and methide acid are necessary to deprotect the acid labile group of carboxylic acid ester, an α-non-fluorinated sulfonic acid or carboxylic acid is released by salt exchange with an α-non-fluorinated onium salt. An α-non-fluorinated sulfonic acid and a carboxylic acid function as a quencher because they do not induce deprotection reaction.

Also useful are quenchers of polymer type as described in U.S. Pat. No. 7,598,016 (JP-A 2008-239918). The polymeric quencher segregates at the resist surface after coating and thus enhances the rectangularity of resist pattern. When a protective film is applied as is often the case in the immersion lithography, the polymeric quencher is also effective for preventing a film thickness loss of resist pattern or rounding of pattern top.

The other quencher is preferably added in an amount of 0 to 5 parts, more preferably 0 to 4 parts by weight per 100 parts by weight of the base polymer.

Other Components

With the base polymer and onium salt as described above, other components such as an organic solvent, surfactant, dissolution inhibitor, and crosslinker may be blended in any desired combination to formulate a positive or negative resist composition. This positive or negative resist composition has a very high sensitivity in that the dissolution rate in developer of the base polymer in exposed areas is accelerated by catalytic reaction. In addition, the resist film has a high dissolution contrast, resolution, exposure latitude, and process adaptability, and provides a good pattern profile after exposure, and minimal proximity bias because of restrained acid diffusion. By virtue of these advantages, the composition is fully useful in commercial application and suited as a pattern-forming material for the fabrication of VLSIs. Particularly when an acid generator is added to formulate a chemically amplified positive resist composition capable of utilizing acid catalyzed reaction, the resist composition is quite useful by virtue of a higher sensitivity and better properties.

Examples of the organic solvent used herein are described in JP-A 2008-111103, paragraphs [0144]-[0145] (U.S. Pat. No. 7,537,880). Exemplary solvents include ketones such as cyclohexanone, cyclopentanone and methyl-2-n-pentyl ketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, t-butyl acetate, t-butyl propionate, and propylene glycol mono-t-butyl ether acetate; and lactones such as γ-butyrolactone, which may be used alone or in admixture.

The organic solvent is preferably added in an amount of 100 to 10,000 parts, and more preferably 200 to 8,000 parts by weight per 100 parts by weight of the base polymer.

Exemplary surfactants are described in JP-A 2008-111103, paragraphs [0165]-[0166]. Inclusion of a surfactant may improve or control the coating characteristics of the resist composition. The surfactant may be used alone or in admixture. The surfactant is preferably added in an amount of 0.0001 to 10 parts by weight per 100 parts by weight of the base polymer.

In the case of positive resist compositions, inclusion of a dissolution inhibitor may lead to an increased difference in dissolution rate between exposed and unexposed areas and a further improvement in resolution. In the case of negative resist compositions, a negative pattern may be formed by adding a crosslinker to reduce the dissolution rate of exposed area.

The dissolution inhibitor which can be used herein is a compound having at least two phenolic hydroxyl groups on the molecule, in which an average of from 0 to 100 mol % of all the hydrogen atoms on the phenolic hydroxyl groups are replaced by acid labile groups or a compound having at least one carboxyl group on the molecule, in which an average of 50 to 100 mol % of all the hydrogen atoms on the carboxyl groups are replaced by acid labile groups, both the compounds having a molecular weight of 100 to 1,000, and preferably 150 to 800. Typical are bisphenol A, trisphenol, phenolphthalein, cresol novolac, naphthalenecarboxylic acid, adamantanecarboxylic acid, and cholic acid derivatives in which the hydrogen atom on the hydroxyl or carboxyl group is replaced by an acid labile group, as described in U.S. Pat. No. 7,771,914 (JP-A 2008-122932, paragraphs [0155]-[0178]).

In the positive resist composition, the dissolution inhibitor is preferably added in an amount of 0 to 50 parts, more preferably 5 to 40 parts by weight per 100 parts by weight of the base polymer.

Suitable crosslinkers which can be used herein include epoxy compounds, melamine compounds, guanamine compounds, glycoluril compounds and urea compounds having substituted thereon at least one group selected from among methylol, alkoxymethyl and acyloxymethyl groups, isocyanate compounds, azide compounds, and compounds having a double bond such as an alkenyl ether group. These compounds may be used as an additive or introduced into a polymer side chain as a pendant. Hydroxy-containing compounds may also be used as the crosslinker. The crosslinker may be used alone or in admixture.

Of the foregoing crosslinkers, examples of suitable epoxy compounds include tris(2,3-epoxypropyl) isocyanurate, trimethylolmethane triglycidyl ether, trimethylolpropane triglycidyl ether, and triethylolethane triglycidyl ether. Examples of the melamine compound include hexamethylol melamine, hexamethoxymethyl melamine, hexamethylol melamine compounds having 1 to 6 methylol groups methoxymethylated and mixtures thereof, hexamethoxyethyl melamine, hexaacyloxymethyl melamine, hexamethylol melamine compounds having 1 to 6 methylol groups acyloxymethylated and mixtures thereof. Examples of the guanamine compound include tetramethylol guanamine, tetramethoxymethyl guanamine, tetramethylol guanamine compounds having 1 to 4 methylol groups methoxymethylated and mixtures thereof, tetramethoxyethyl guanamine, tetraacyloxyguanamine, tetramethylol guanamine compounds having 1 to 4 methylol groups acyloxymethylated and mixtures thereof. Examples of the glycoluril compound include tetramethylol glycoluril, tetramethoxyglycoluril, tetramethoxymethyl glycoluril, tetramethylol glycoluril compounds having 1 to 4 methylol groups methoxymethylated and mixtures thereof, tetramethylol glycoluril compounds having 1 to 4 methylol groups acyloxymethylated and mixtures thereof. Examples of the urea compound include tetramethylol urea, tetramethoxymethyl urea, tetramethylol urea compounds having 1 to 4 methylol groups methoxymethylated and mixtures thereof, and tetramethoxyethyl urea.

Suitable isocyanate compounds include tolylene diisocyanate, diphenylmethane diisocyanate, hexamethylene diisocyanate and cyclohexane diisocyanate. Suitable azide compounds include 1,1'-biphenyl-4,4'-bisazide, 4,4'-methylidenebisazide, and 4,4'-oxybisazide. Examples of the alkenyl ether group-containing compound include ethylene glycol divinyl ether, triethylene glycol divinyl ether, 1,2-propanediol divinyl ether, 1,4-butanediol divinyl ether, tetramethylene glycol divinyl ether, neopentyl glycol divinyl ether, trimethylol propane trivinyl ether, hexanediol divinyl ether, 1,4-cyclohexanediol divinyl ether, pentaerythritol trivinyl ether, pentaerythritol tetravinyl ether, sorbitol tetravinyl ether, sorbitol pentavinyl ether, and trimethylol propane trivinyl ether.

In the negative resist composition, the crosslinker is preferably added in an amount of 0.1 to 50 parts, more preferably 1 to 40 parts by weight per 100 parts by weight of the base polymer.

To the resist composition, a polymeric additive (or water repellency improver) may also be added for improving the water repellency on surface of a resist film as spin coated. The water repellency improver may be used in the topcoat-less immersion lithography. Suitable water repellency improvers include polymers having a fluoroalkyl group and polymers having a specific structure with a 1,1,1,3,3,3-hexafluoro-2-propanol residue and are described in JP-A 2007-297590 and JP-A 2008-111103, for example. The water repellency improver to be added to the resist composition should be soluble in the organic solvent as the developer. The water repellency improver of specific structure with a 1,1,1,3,3,3-hexafluoro-2-propanol residue is well soluble in the developer. A polymer having an amino group or amine salt copolymerized as recurring units may serve as the water repellent additive and is effective for preventing evaporation of acid during PEB, thus preventing any hole pattern opening failure after development. An appropriate amount of the water repellency improver is 0 to 20 parts, preferably 0.5 to 10 parts by weight per 100 parts by weight of the base polymer.

Also, an acetylene alcohol may be blended in the resist composition. Suitable acetylene alcohols are described in JP-A 2008-122932, paragraphs [0179]-[0182]. An appropriate amount of the acetylene alcohol blended is 0 to 5 parts by weight per 100 parts by weight of the base polymer.

Process

The resist composition is used in the fabrication of various integrated circuits. Pattern formation using the resist composition may be performed by well-known lithography processes. The process generally involves coating, prebaking, exposure, post-exposure baking (PEB), and development. If necessary, any additional steps may be added.

For example, the positive resist composition is first applied onto a substrate on which an integrated circuit is to be formed (e.g., Si, $SiO_2$, SiN, SiON, TiN, WSi, BPSG, SOG, or organic antireflective coating) or a substrate on which a mask circuit is to be formed (e.g., Cr, CrO, CrON, $MoSi_2$, or $SiO_2$) by a suitable coating technique such as spin coating, roll coating, flow coating, dipping, spraying or doctor coating. The coating is prebaked on a hotplate at a temperature of 60 to 150° C. for 10 seconds to 30 minutes, preferably at 80 to 120° C. for 30 seconds to 20 minutes. The resulting resist film is generally 0.01 to 2.0 µm thick.

The resist film is then exposed to a desired pattern of high-energy radiation such as UV, deep-UV, EB, EUV, x-ray, soft x-ray, excimer laser light, γ-ray or synchrotron radiation, directly or through a mask. The exposure dose is preferably about 1 to 200 $mJ/cm^2$, more preferably about 10 to 100 $mJ/cm^2$, or about 0.1 to 100 $\mu C/cm^2$, more preferably about 0.5 to 50 $\mu C/cm^2$. The resist film is further baked (PEB) on a hotplate at 60 to 150° C. for 10 seconds to 30 minutes, preferably at 80 to 120° C. for 30 seconds to 20 minutes.

Thereafter the resist film is developed with a developer in the form of an aqueous base solution for 3 seconds to 3 minutes, preferably 5 seconds to 2 minutes by conventional techniques such as dip, puddle and spray techniques. A typical developer is a 0.1 to 10 wt %, preferably 2 to 5 wt % aqueous solution of tetramethylammonium hydroxide (TMAH), tetraethylammonium hydroxide (TEAH), tetrapropylammonium hydroxide (TPAH), or tetrabutylammonium hydroxide (TBAH). The resist film in the exposed area is dissolved in the developer whereas the resist film in the unexposed area is not dissolved. In this way, the desired positive pattern is formed on the substrate. Inversely in the case of negative resist, the exposed area of resist film is insolubilized and the unexposed area is dissolved in the developer. It is appreciated that the resist composition of the invention is best suited for micro-patterning using such high-energy radiation as KrF and ArF excimer laser, EB, EUV, x-ray, soft x-ray, γ-ray and synchrotron radiation.

In an alternative embodiment, a negative pattern may be formed via organic solvent development using a positive resist composition comprising a base polymer having an acid labile group. The developer used herein is preferably selected from among 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, pentyl acetate, butenyl acetate, isopentyl acetate, propyl formate, butyl formate, isobutyl formate, pentyl formate, isopentyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, pentyl lactate, isopentyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate, and mixtures thereof.

At the end of development, the resist film is rinsed. As the rinsing liquid, a solvent which is miscible with the developer and does not dissolve the resist film is preferred. Suitable solvents include alcohols of 3 to 10 carbon atoms, ether compounds of 8 to 12 carbon atoms, alkanes, alkenes, and alkynes of 6 to 12 carbon atoms, and aromatic solvents. Specifically, suitable alcohols of 3 to 10 carbon atoms include n-propyl alcohol, isopropyl alcohol, 1-butyl alcohol, 2-butyl alcohol, isobutyl alcohol, t-butyl alcohol, 1-pentanol, 2-pentanol, 3-pentanol, t-pentyl alcohol, neopentyl alcohol, 2-methyl-1-butanol, 3-methyl-1-butanol, 3-methyl-3-pentanol, cyclopentanol, 1-hexanol, 2-hexanol, 3-hexanol, 2,3-dimethyl-2-butanol, 3,3-dimethyl-1-butanol, 3,3-dimethyl-2-butanol, 2-ethyl-1-butanol, 2-methyl-1-pentanol, 2-methyl-2-pentanol, 2-methyl-3-pentanol, 3-methyl-1-pentanol, 3-methyl-2-pentanol, 3-methyl-3-pentanol, 4-methyl-1-pentanol, 4-methyl-2-pentanol, 4-methyl-3-pentanol, cyclohexanol, and 1-octanol. Suitable ether compounds of 8 to 12 carbon atoms include di-n-butyl ether, diisobutyl ether, di-s-butyl ether, di-n-pentyl ether, diisopentyl ether, di-s-pentyl ether, di-t-pentyl ether, and di-n-hexyl ether. Suitable alkanes of 6 to 12 carbon atoms include hexane, heptane, octane, nonane, decane, undecane, dodecane, methylcyclopentane, dimethylcyclopentane, cyclohexane, methylcyclohexane, dimethylcyclohexane, cycloheptane, cyclooctane, and cyclononane. Suitable alkenes of 6 to 12 carbon atoms include hexene, heptene, octene, cyclohexene, methylcyclohexene, dimethylcyclohexene, cycloheptene, and cyclooctene. Suitable alkynes of 6 to 12 carbon atoms include hexyne, heptyne, and octyne. Suitable aromatic solvents include toluene, xylene, ethylbenzene, isopropylbenzene, t-butylbenzene and mesitylene. The solvents may be used alone or in admixture.

Rinsing is effective for minimizing the risks of resist pattern collapse and defect formation. However, rinsing is not essential. If rinsing is omitted, the amount of solvent used may be reduced.

A hole or trench pattern after development may be shrunk by the thermal flow, RELACS® or DSA process. A hole pattern is shrunk by coating a shrink agent thereto, and baking such that the shrink agent may undergo crosslinking at the resist surface as a result of the acid catalyst diffusing from the resist layer during bake, and the shrink agent may attach to the sidewall of the hole pattern. The bake is preferably at a temperature of 70 to 180° C., more preferably 80 to 170° C., for a time of 10 to 300 seconds. The extra shrink agent is stripped and the hole pattern is shrunk.

EXAMPLE

Examples of the invention are given below by way of illustration and not by way of limitation. The abbreviation "pbw" is parts by weight.

Sulfonium salts 1 to 17 and iodonium salts 1 to 6 of brominated benzene-containing sulfonic acid used in resist compositions are identified below. Sulfonium salts 1 to 17 or iodonium salts 1 to 6 were synthesized by ion exchange between a brominated benzene-containing sulfonic acid providing the anion shown below and a sulfonium or iodonium chloride providing the cation shown below.

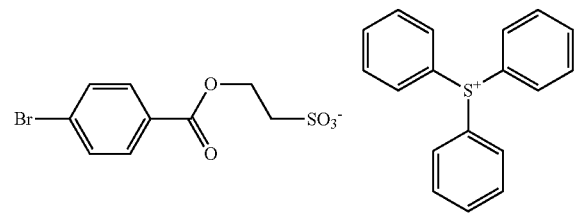

Sulfonium salt 1

Sulfonium salt 2

Sulfonium salt 3

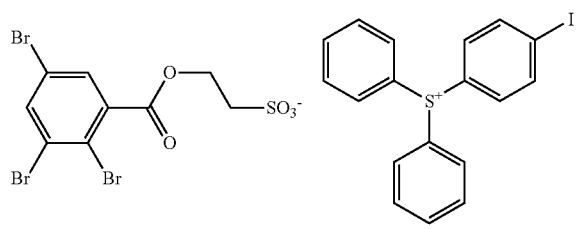
Sulfonium salt 4
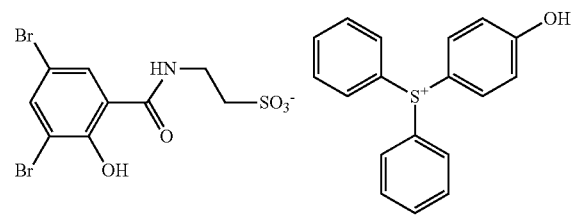
Sulfonium salt 5
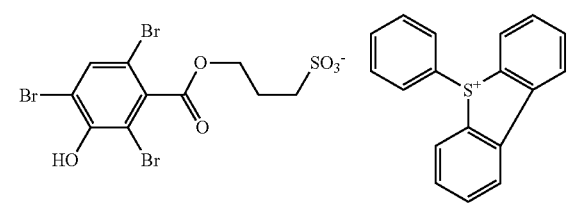
Sulfonium salt 6
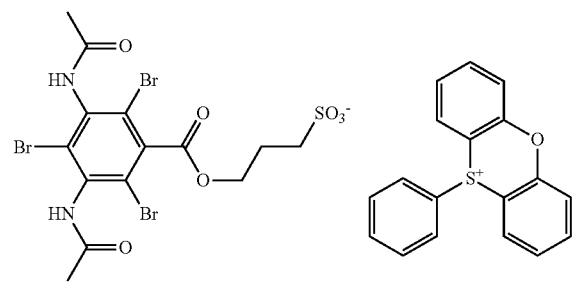
Sulfonium salt 7
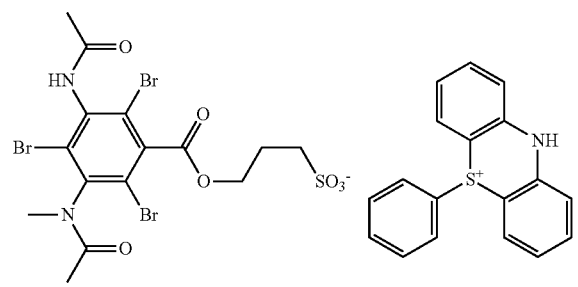
Sulfonium salt 8
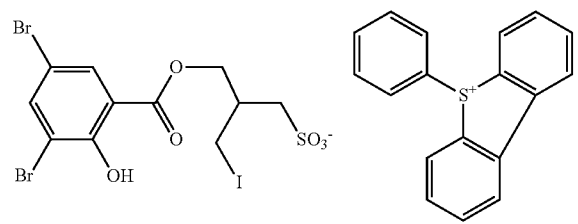
Sulfonium salt 9
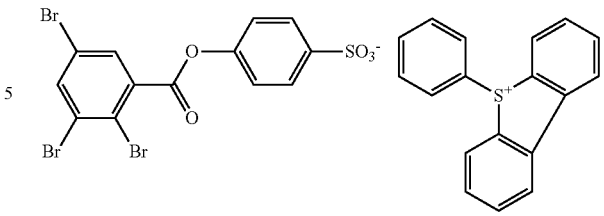
Sulfonium salt 10
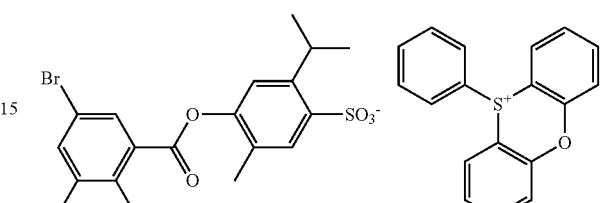
Sulfonium salt 11
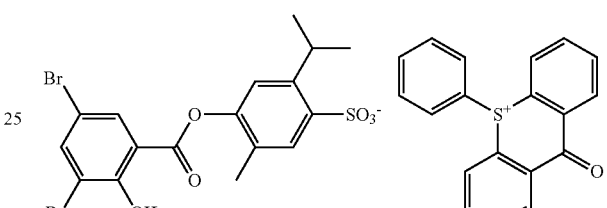
Sulfonium salt 12
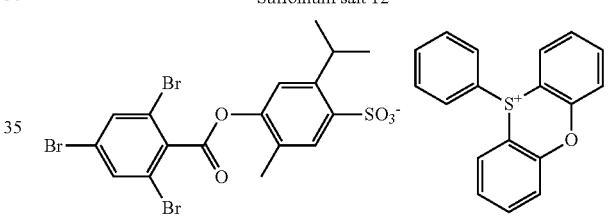
Sulfonium salt 13
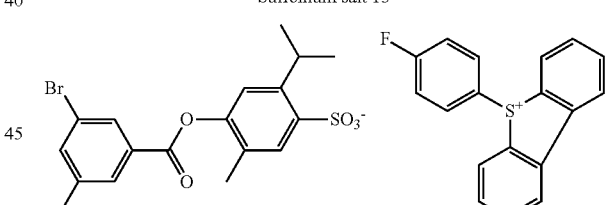
Sulfonium salt 14
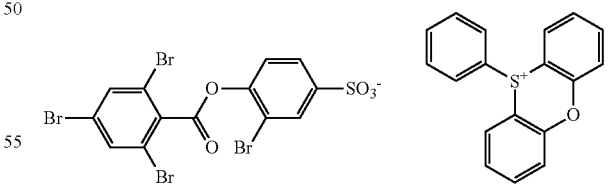
Sulfonium salt 15
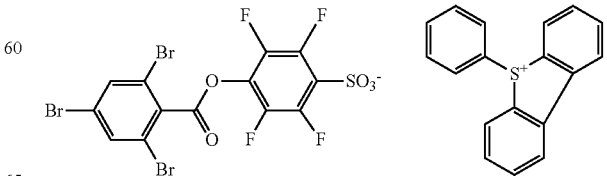
Sulfonium salt 16

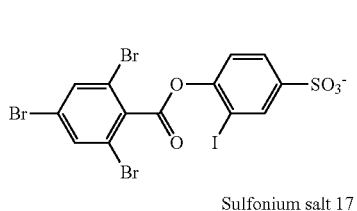

Sulfonium salt 17

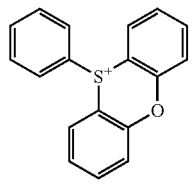

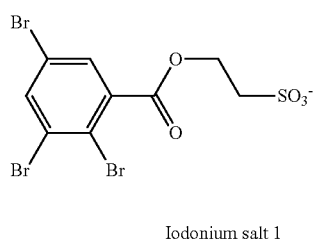

Iodonium salt 1

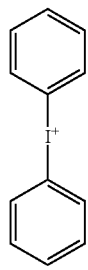

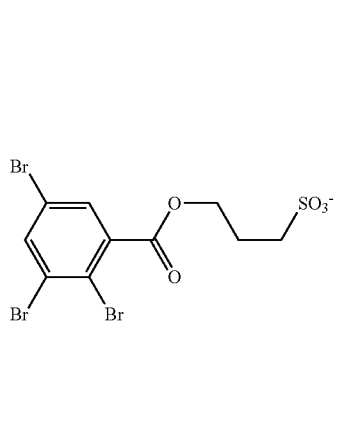

Iodonium salt 2

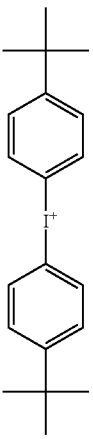

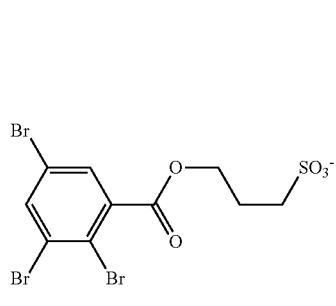

Iodonium salt 3

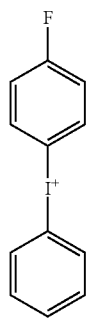

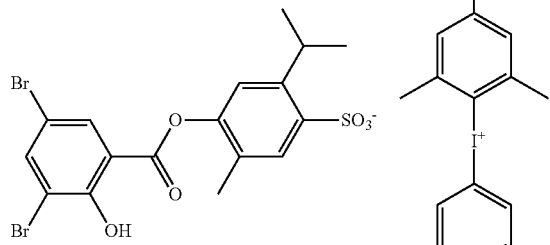

Iodonium salt 4

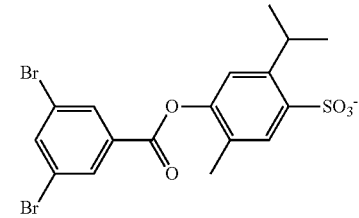

Iodonium salt 5

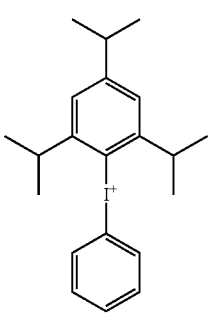

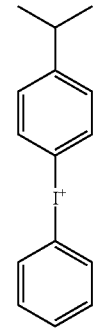

Iodonium salt 6

Synthesis Example

Synthesis of Base Polymers (Polymers 1 to 6)

Base polymers were prepared by combining suitable monomers, effecting copolymerization reaction thereof in tetrahydrofuran (THF) solvent, pouring the reaction solution into methanol for crystallization, repeatedly washing with hexane, isolation, and drying. The resulting polymers, designated Polymers 1 to 6, were analyzed for composition by $^1$H-NMR spectroscopy, and for Mw and Mw/Mn by GPC versus polystyrene standards using THF solvent.

Polymer 1

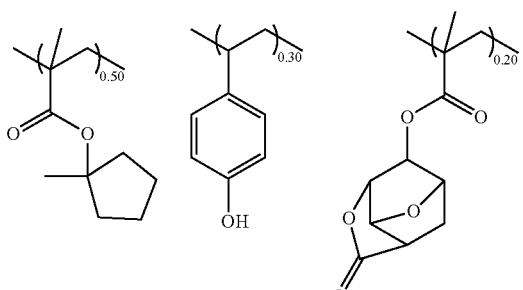

Mw = 8,600
Mw/Mn = 1.73

Polymer 2
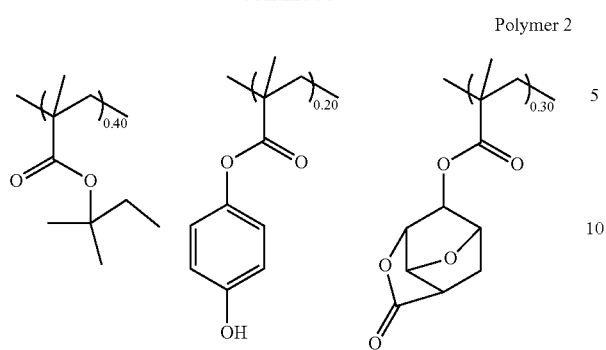
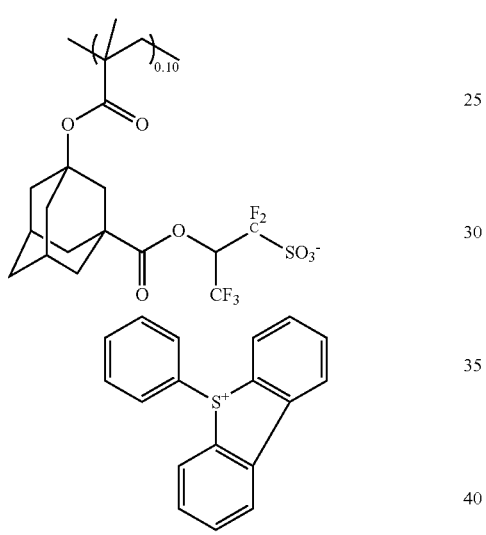
Mw = 8,900
Mw/Mn = 1.89
Polymer 3
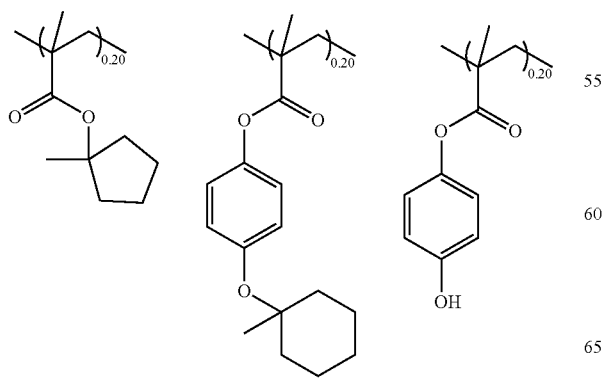
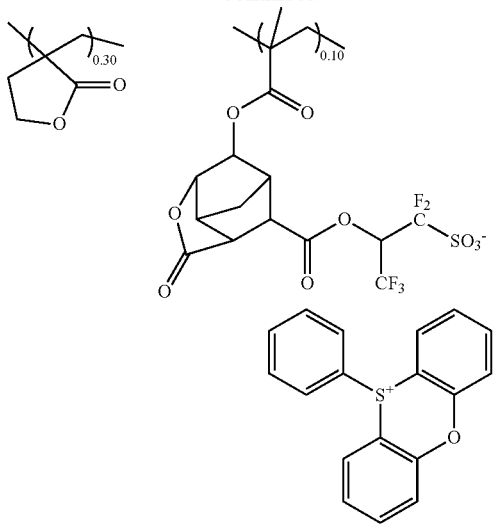
Mw = 7,600
Mw/Mn = 1.73
Polymer 4
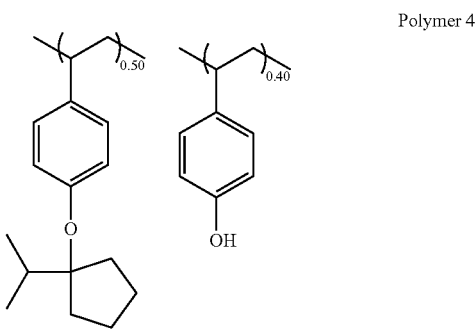
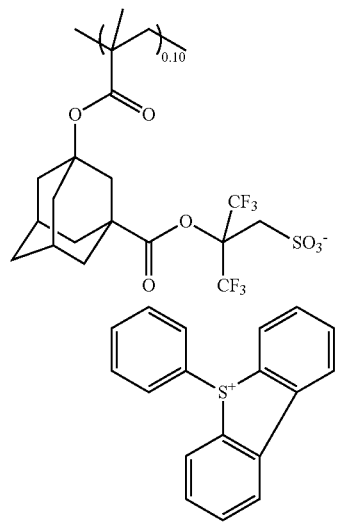
Mw = 8,800
Mw/Mn = 1.77

Polymer 5

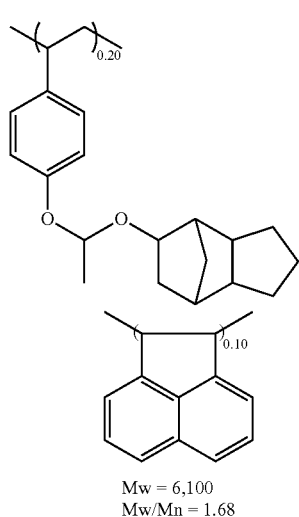

Mw = 6,100
Mw/Mn = 1.68

Polymer 6

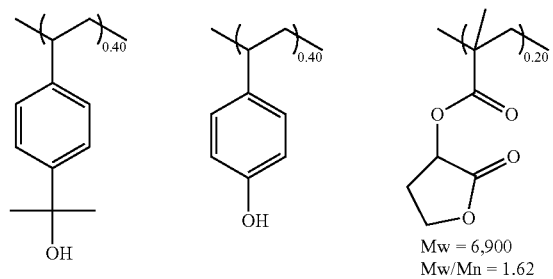

Mw = 6,900
Mw/Mn = 1.62

Examples and Comparative Examples

Resist compositions were prepared by dissolving the polymer and selected components in a solvent in accordance with the recipe shown in Tables 1 and 2, and filtering through a filter having a pore size of 0.2 μm. The solvent contained 100 ppm of surfactant FC-4430 (3M). The components in Tables 1 and 2 are as identified below.

Organic Solvents:
  PGMEA (propylene glycol monomethyl ether acetate)
  GBL (γ-butyrolactone)
  CyH (cyclohexanone)
  PGME (propylene glycol monomethyl ether)

Acid Generators: PAG 1 to PAG 6 of the Following Structural Formulae

PAG 1

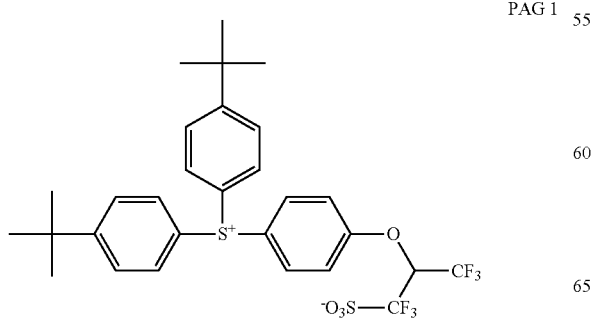

PAG 2

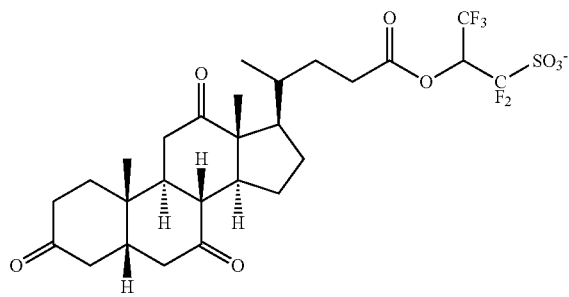

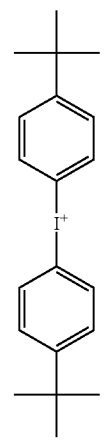

PAG 3

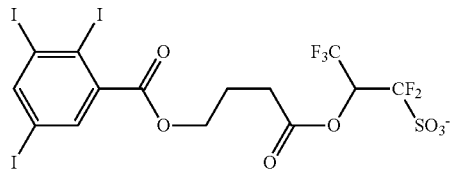

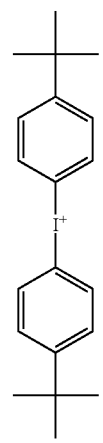

PAG 4

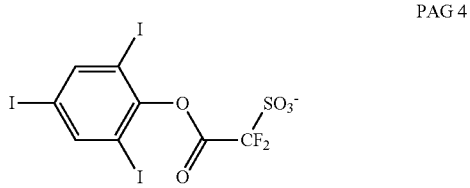

-continued
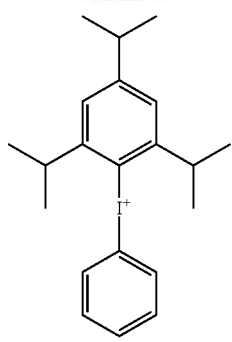
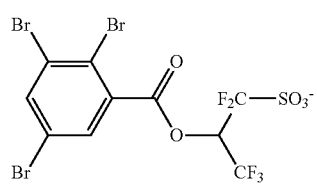
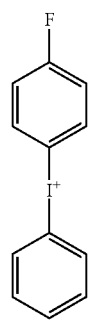
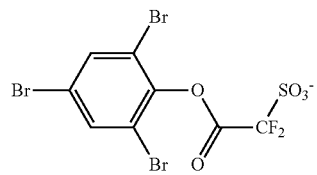
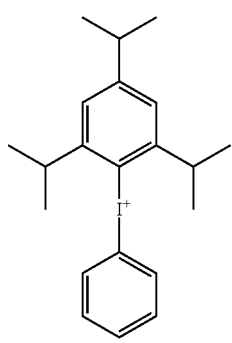
Comparative Sulfonium Salts 1 to 4 and Comparative Iodonium Salt 1 of the Following Structural Formulae
PAG 5
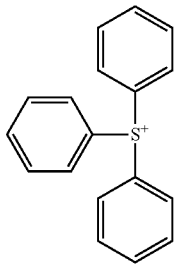 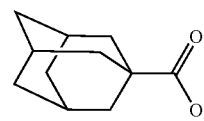
Comparative sulfonium salt 1
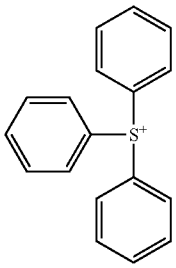 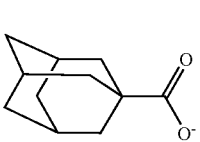
Comparative sulfonium salt 2
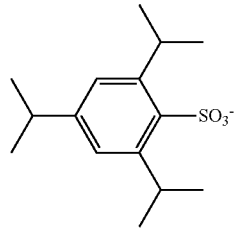 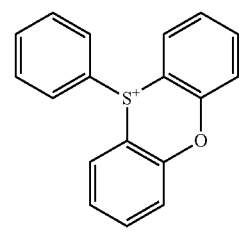
Comparative sulfonium salt 3
PAG 6
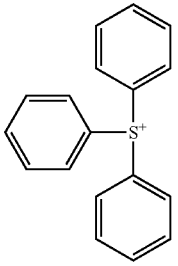 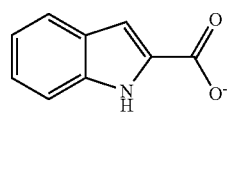
Comparative sulfonium salt 4
Comparative iodonium salt 1

EB Lithography Test

Examples 1 to 27 and Comparative Examples 1 to 6

A silicon substrate was coated with an antireflective coating of 60 nm thick (DUV-4, Nissan Chemical Corp.). Each of the resist compositions in Tables 1 and 2 was spin coated on the substrate and prebaked on a hotplate at 105° C. for 60 seconds to form a resist film of 50 nm thick. The resist film was exposed to electron beam using an EB lithography system ELS-F125 (Elionix Co., Ltd., accelerating voltage 125 kV), then baked (PEB) on a hotplate at the temperature shown in Tables 1 and 2 for 60 seconds, and developed with a 2.38 wt % TMAH aqueous solution for 30 seconds to form a pattern. In Examples 1 to 26 and Comparative Examples 1 to 5, a positive resist pattern, i.e., hole pattern having a size of 24 nm was formed. In Example 27 and Comparative Example 6, a negative resist pattern, i.e., dot pattern having a size of 24 nm was formed.

The resist pattern was observed under CD-SEM (CG-5000, Hitachi High-Technologies Corp.). The exposure dose that provides a hole or dot pattern having a size of 24 nm is reported as sensitivity. The size of 50 holes or dots was measured, from which a size variation (3σ) was computed and reported as CDU.

The resist composition is shown in Tables 1 and 2 together with the sensitivity and CDU of EB lithography.

TABLE 1

| | | Polymer (pbw) | Acid generator (pbw) | Quencher (pbw) | Organic solvent (pbw) | PEB temp. (° C.) | Sensitivity (μC/cm$^2$) | CDU (nm) |
|---|---|---|---|---|---|---|---|---|
| Example | 1 | Polymer 1 (100) | PAG 1 (30) | Sulfonium salt 1 (3.40) | PGMEA (400) CyH (2,000) PGME (100) | 90 | 360 | 2.9 |
| | 2 | Polymer 1 (100) | PAG 2 (30) | Sulfonium salt 2 (3.86) | PGMEA (400) CyH (2,000) PGME (100) | 90 | 350 | 2.8 |
| | 3 | Polymer 1 (100) | PAG 2 (30) | Sulfonium salt 3 (4.58) | PGMEA (400) CyH (2,000) PGME (100) | 90 | 340 | 2.9 |
| | 4 | Polymer 1 (100) | PAG 2 (30) | Sulfonium salt 4 (4.70) | PGMEA (400) CyH (2,000) PGME (100) | 90 | 300 | 2.5 |
| | 5 | Polymer 1 (100) | PAG 2 (30) | Sulfonium salt 5 (4.10) | PGMEA (400) CyH (2,000) PGME (100) | 90 | 360 | 2.6 |
| | 6 | Polymer 1 (100) | PAG 2 (30) | Sulfonium salt 6 (4.50) | PGMEA (400) CyH (2,000) PGME (100) | 90 | 290 | 2.4 |
| | 7 | Polymer 1 (100) | PAG 2 (30) | Sulfonium salt 7 (5.20) | PGMEA (400) CyH (2,000) PGME (100) | 90 | 360 | 2.5 |
| | 8 | Polymer 1 (100) | PAG 2 (30) | Sulfonium salt 8 (5.30) | PGMEA (400) CyH (2,000) PGME (100) | 90 | 370 | 2.4 |
| | 9 | Polymer 2 (100) | — | Sulfonium salt 9 (4.90) | PGMEA (2,200) GBL (400) | 100 | 340 | 2.0 |
| | 10 | Polymer 3 (100) | — | Sulfonium salt 10 (4.60) | PGMEA (400) CyH (2,000) PGME (100) | 90 | 350 | 1.8 |
| | 11 | Polymer 3 (100) | PAG 3 (15) | Sulfonium salt 9 (4.20) | PGMEA (400) CyH (2,000) PGME (100) | 90 | 250 | 2.6 |
| | 12 | Polymer 3 (100) | PAG 4 (15) | Iodonium salt 1 (4.50) | PGMEA (400) CyH (2,000) PGME (100) | 90 | 230 | 2.2 |
| | 13 | Polymer 3 (100) | PAG 5 (15) | Iodonium salt 2 (4.60) | PGMEA (400) CyH (2,000) PGME (100) | 90 | 220 | 2.2 |
| | 14 | Polymer 3 (100) | PAG 6 (15) | Iodonium salt 3 (4.70) | PGMEA (400) CyH (2,000) PGME (100) | 90 | 210 | 2.2 |
| | 15 | Polymer 3 (100) | Sulfonium salt 16 (15) | Sulfonium salt 10 (5.60) | PGMEA (400) CyH (2,000) PGME (100) | 90 | 240 | 2.4 |
| | 16 | Polymer 4 (100) | — | Sulfonium salt 7 (5.20) | PGMEA (400) CyH (2,000) PGME (100) | 110 | 340 | 2.0 |
| | 17 | Polymer 5 (100) | Sulfonium salt 10 (15) | Comparative sulfonium salt 2 (2.65) | PGMEA (400) CyH (2,000) PGME (100) | 110 | 320 | 2.9 |
| | 18 | Polymer 5 (100) | Sulfonium salt 11 (15) | Comparative sulfonium salt 2 (2.65) | PGMEA (400) CyH (2,000) PGME (100) | 110 | 320 | 2.9 |
| | 19 | Polymer 5 (100) | Sulfonium salt 12 (15) | Comparative sulfonium salt 2 (2.65) | PGMEA (400) CyH (2,000) PGME (100) | 110 | 380 | 3.0 |
| | 20 | Polymer 5 (100) | Sulfonium salt 13 (15) | Comparative sulfonium salt 2 (2.65) | PGMEA (400) CyH (2,000) PGME (100) | 110 | 370 | 3.2 |

TABLE 2

| | | Polymer (pbw) | Acid generator (pbw) | Quencher (pbw) | Organic solvent (pbw) | PEB temp. (°C.) | Sensitivity (μC/cm²) | CDU (nm) |
|---|---|---|---|---|---|---|---|---|
| Example | 21 | Polymer 5 (100) | Sulfonium salt 14 (15) | Comparative sulfonium salt 2 (2.60) | PGMEA (400) CyH (2,000) PGME (100) | 110 | 340 | 2.8 |
| | 22 | Polymer 5 (100) | Sulfonium salt 15 (15) | Comparative sulfonium salt 2 (2.60) | PGMEA (400) CyH (2,000) PGME (100) | 110 | 350 | 2.9 |
| | 23 | Polymer 5 (100) | Iodonium salt 4 (15) | Comparative sulfonium salt 2 (2.60) | PGMEA (400) CyH (2,000) PGME (100) | 110 | 350 | 2.6 |
| | 24 | Polymer 5 (100) | Iodonium salt 5 (15) | Comparative sulfonium salt 2 (2.60) | PGMEA (400) CyH (2,000) PGME (100) | 110 | 330 | 2.6 |
| | 25 | Polymer 5 (100) | Iodonium salt 6 (15) | Comparative sulfonium salt 2 (2.60) | PGMEA (400) CyH (2,000) PGME (100) | 110 | 320 | 2.6 |
| | 26 | Polymer 5 (100) | Sulfonium salt 17 (15) | Comparative sulfonium salt 4 (2.60) | PGMEA (400) CyH (2,000) PGME (100) | 110 | 310 | 2.7 |
| | 27 | Polymer 6 (100) | PAG 1 (15) | Sulfonium salt 2 (3.86) | PGMEA (400) CyH (2,000) PGME (100) | 110 | 360 | 3.2 |
| Comparative Example | 1 | Polymer 1 (100) | PAG 2 (30) | Comparative sulfonium salt 1 (3.30) | PGMEA (400) CyH (2,000) PGME (100) | 90 | 410 | 3.5 |
| | 2 | Polymer 1 (100) | PAG 2 (30) | Comparative sulfonium salt 2 (2.60) | PGMEA (400) CyH (2,000) PGME (100) | 90 | 420 | 3.8 |
| | 3 | Polymer 1 (100) | PAG 2 (30) | Comparative sulfonium salt 3 (3.20) | PGMEA (400) CyH (2,000) PGME (100) | 90 | 430 | 3.9 |
| | 4 | Polymer 1 (100) | PAG 2 (30) | Comparative iodonium salt 1 (3.70) | PGMEA (400) CyH (2,000) PGME (100) | 90 | 400 | 3.8 |
| | 5 | Polymer 5 (100) | Comparative sulfonium salt 3 (15) | Comparative sulfonium salt 2 (2.60) | PGMEA (400) CyH (2,000) PGME (100) | 110 | 400 | 4.0 |
| | 6 | Polymer 6 (100) | PAG 1 (15) | Comparative sulfonium salt 1 (3.30) | PGMEA (400) CyH (2,000) PGME (100) | 110 | 450 | 4.8 |

It is demonstrated in Tables 1 and 2 that resist compositions comprising a sulfonium salt of formula (A-1) or iodonium salt of formula (A-2) offer a high sensitivity and improved CDU.

Japanese Patent Application No. 2017-200092 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A resist composition comprising a base polymer and a sulfonium salt having the formula (A-1) and/or an iodonium salt having the formula (A-2):

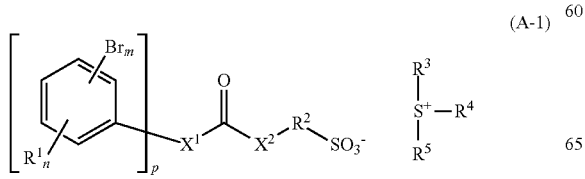

(A-1)

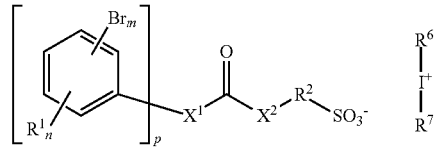

(A-2)

wherein $R^1$ is hydroxyl, carboxyl, $C_1$-$C_6$ alkyl, $C_1$-$C_6$ alkoxy, $C_2$-$C_6$ acyloxy, fluorine, chlorine, amino, —$NR^8$—C(=O)—$R^9$, or —$NR^8$—C(=O)—O—$R^9$, $R^8$ is hydrogen or a $C_1$-$C_6$ alkyl group, $R^9$ is a $C_1$-$C_6$ alkyl, $C_2$-$C_8$ alkenyl or $C_7$-$C_{20}$ aralkyl group, $R^2$ is a $C_2$-$C_{12}$ alkylene group in which at least one hydrogen may be substituted by a halogen other than fluorine, or a $C_6$-$C_{10}$ arylene group in which at least one hydrogen may be substituted by a $C_1$-$C_{10}$ alkyl, $C_1$-$C_{10}$ alkoxy, halogen or hydroxyl moiety, $R^3$, $R^4$ and $R^5$ are each independently fluorine, chlorine, bromine, iodine or a $C_1$-$C_{20}$ monovalent hydrocarbon group which may contain a heteroatom, any two of $R^3$, $R^4$ and $R^5$ may bond together to form a ring with the sulfur atom to which they are attached, $R^6$ and $R^7$ are each independently trifluoromethyl or a $C_1$-$C_{20}$ monovalent hydrocarbon group which may contain a heteroatom, $X^1$ is a single bond or a (p+1)-valent $C_1$-$C_{20}$ linking group which may contain an ether bond, carbonyl, ester bond, amide bond, sultone, lactam, carbonate, halogen, hydroxyl or carboxyl moiety, $X^2$ is an ether bond, m is an integer of 1 to 5, n is an integer of 0 to 3, m+n is 1 to 5, and p is an integer of 1 to 3.

2. The resist composition of claim 1 wherein m is equal to 2 or 3.

3. The resist composition of claim 1 wherein the sulfonium salt and/or iodonium salt functions is a quencher.

4. The resist composition of claim 3, further comprising an acid generator capable of generating sulfonic acid, imide acid or methide acid.

5. The resist composition of claim 1 wherein the sulfonium salt and/or iodonium salt functions is an acid generator.

6. The resist composition of claim 5, further comprising a quencher.

7. The resist composition of claim 1, further comprising an organic solvent.

8. The resist composition of claim 1 wherein the base polymer comprises recurring units having the formula (a1) or recurring units having the formula (a2):

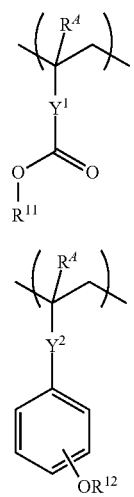

wherein $R^A$ is each independently hydrogen or methyl, $Y^1$ is a single bond, phenylene group, naphthylene group, or $C_1$-$C_{12}$ linking group containing an ester bond and/or lactone ring, $Y^2$ is a single bond or ester bond, $R^{11}$ and $R^{12}$ each are an acid labile group.

9. The resist composition of claim 8, further comprising a dissolution inhibitor.

10. The resist composition of claim 8 which is a chemically amplified positive resist composition.

11. The resist composition of claim 1 wherein the base polymer is free of an acid labile group.

12. The resist composition of claim 11, further comprising a crosslinker.

13. The resist composition of claim 11 which is a chemically amplified negative resist composition.

14. The resist composition of claim 1, further comprising a surfactant.

15. A resist composition comprising a base polymer and a sulfonium salt having the formula (A-1) and/or an iodonium salt having the formula (A-2):

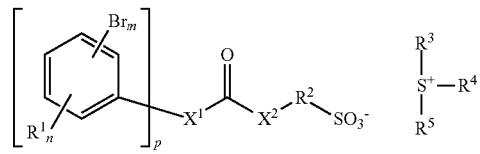

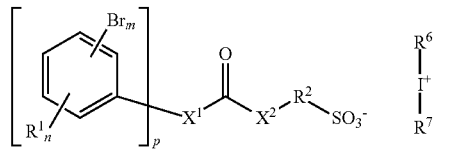

wherein $R^1$ is hydroxyl, carboxyl, $C_1$-$C_6$ alkyl, $C_1$-$C_6$ alkoxy, $C_2$-$C_6$ acyloxy, fluorine, chlorine, amino, —$NR^8$—$C(=O)$—$R^9$, or —$NR^8$—$C(=O)$—$O$—$R^9$, $R^8$ is hydrogen or a $C_1$-$C_6$ alkyl group, $R^9$ is a $C_1$-$C_6$ alkyl, $C_2$-$C_8$ alkenyl or $C_7$-$C_{20}$ aralkyl group, $R^2$ is a $C_2$-$C_{12}$ alkylene group in which at least one hydrogen may be substituted by a halogen other than fluorine, or a $C_6$-$C_{10}$ arylene group in which at least one hydrogen may be substituted by a $C_1$-$C_{10}$ alkyl, $C_1$-$C_{10}$ alkoxy, halogen or hydroxyl moiety, $R^3$, $R^4$ and $R^5$ are each independently fluorine, chlorine, bromine, iodine or a $C_1$-$C_{20}$ monovalent hydrocarbon group which may contain a heteroatom, any two of $R^3$, $R^4$ and $R^5$ may bond together to form a ring with the sulfur atom to which they are attached, $R^6$ and $R^7$ are each independently trifluoromethyl or a $C_1$-$C_{20}$ monovalent hydrocarbon group which may contain a heteroatom, $X^1$ is a single bond or a (p+1)-valent $C_1$-$C_{20}$ linking group which may contain an ether bond, carbonyl, ester bond, amide bond, sultone, lactam, carbonate, halogen, hydroxyl or carboxyl moiety, $X^2$ is an ether bond or —$NR^{10}$—, $R^{10}$ is hydrogen or $C_1$-$C_4$ alkyl, m is an integer of 1 to 5, n is an integer of 0 to 3, m+n is 1 to 5, and p is an integer of 1 to 3, wherein the base polymer comprises recurring units of at least one type selected from the formulae (f1) to (f3):

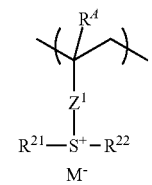

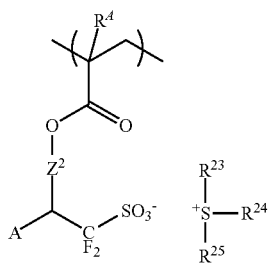

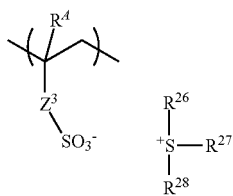

(f3)

wherein $R^A$ is each independently hydrogen or methyl, $Z^1$ is a single bond, phenylene group, —O—$Z^{12}$—, or —C(=O)—$Z^{11}$-$Z^{12}$—, $Z''$ is —O— or —NH—, $Z^{12}$ is a $C_1$-$C_6$ alkylene group, $C_2$-$C_6$ alkenylene group, or phenylene group, which may contain a carbonyl, ester bond, ether bond or hydroxyl moiety, $Z^2$ is a single bond, —$Z^{21}$—C(=O)—O—, —$Z^{21}$—O— or —$Z^{21}$—O—C(=O)—, $Z^{21}$ is a $C_1$-$C_{12}$ alkylene group which may contain a carbonyl, ester bond or ether bond, $Z^3$ is a single bond, methylene, ethylene, phenylene, fluorinated phenylene, —O—$Z^{32}$—, or —C(=O)—$Z^{31}$-$Z^{32}$—, $Z^{31}$ is —O— or —NH—, $Z^{32}$ is a $C_1$-$C_6$ alkylene group, phenylene group, fluorinated phenylene group, trifluoromethyl-substituted phenylene group, or $C_2$-$C_6$ alkenylene group, which may contain a carbonyl, ester bond, ether bond or hydroxyl moiety, $R^{21}$ to $R^{28}$ are each independently a $C_1$-$C_{20}$ monovalent hydrocarbon group which may contain a heteroatom, any two of $R^{23}$, $R^{24}$ and $R^{25}$ or any two of $R^{26}$, $R^{27}$ and $R^{28}$ may bond together to form a ring with the sulfur atom to which they are attached, A is hydrogen or trifluoromethyl, and $M^-$ is a non-nucleophilic counter ion.

16. A process for forming a pattern comprising the steps of applying the resist composition of claim 1 onto a substrate, baking to form a resist film, exposing the resist film to high-energy radiation, and developing the exposed film in a developer.

17. The process of claim 16 wherein the high-energy radiation is ArF excimer laser radiation of wavelength 193 nm or KrF excimer laser radiation of wavelength 248 nm.

18. The process of claim 16 wherein the high-energy radiation is EB or EUV of wavelength 3 to 15 nm.

* * * * *